United States Patent
Brinkmann et al.

(10) Patent No.: US 10,806,795 B2
(45) Date of Patent: *Oct. 20, 2020

(54) BISPECIFIC ANTI-HAPTEN/ANTI-BLOOD BRAIN BARRIER RECEPTOR ANTIBODIES, COMPLEXES THEREOF AND THEIR USE AS BLOOD BRAIN BARRIER SHUTTLES

(71) Applicant: Hoffmann-La Roche Inc., Little Falls, NJ (US)

(72) Inventors: Ulrich Brinkmann, Weilheim (DE); Guy Georges, Habach (DE); Olaf Mundigl, Weilheim (DE); Jens Niewoehner, Munich (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/289,803

(22) Filed: Mar. 1, 2019

(65) Prior Publication Data
US 2020/0000929 A1 Jan. 2, 2020

Related U.S. Application Data

(63) Continuation of application No. 15/109,619, filed as application No. PCT/EP2014/079351 on Dec. 29, 2014.

(30) Foreign Application Priority Data

Jan. 3, 2014 (EP) .................................. 14150092
Jun. 26, 2014 (EP) .................................. 14174045

(51) Int. Cl.
| | | |
|---|---|---|
| *A61K 47/54* | (2017.01) | |
| *C07K 16/28* | (2006.01) | |
| *C07K 16/44* | (2006.01) | |
| *C07K 16/46* | (2006.01) | |
| *C07K 16/40* | (2006.01) | |
| *C07K 16/16* | (2006.01) | |
| *C07K 16/26* | (2006.01) | |
| *A61K 47/60* | (2017.01) | |
| *A61K 47/68* | (2017.01) | |
| *A61K 47/64* | (2017.01) | |

(52) U.S. Cl.
CPC .......... *A61K 47/557* (2017.08); *A61K 47/546* (2017.08); *A61K 47/60* (2017.08); *A61K 47/64* (2017.08); *A61K 47/6879* (2017.08); *C07K 16/16* (2013.01); *C07K 16/26* (2013.01); *C07K 16/2881* (2013.01); *C07K 16/40* (2013.01); *C07K 16/44* (2013.01); *C07K 16/468* (2013.01); *C07K 2299/00* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/567* (2013.01); *C07K 2317/624* (2013.01); *C07K 2317/92* (2013.01); *C07K 2317/94* (2013.01)

(58) Field of Classification Search
CPC .... A61K 47/60; A61K 47/64; A61K 47/6849; A61K 47/557; A61K 47/546; C07K 2317/565; C07K 2317/567; C07K 2317/624; C07K 16/40; C07K 16/16; C07K 16/26; C07K 16/44; C07K 16/468; C07K 2299/00; C07K 2317/24; C07K 2317/31; C07K 2317/55; C07K 2317/56; C07K 2317/92; C07K 2317/94; C07K 16/2881
See application file for complete search history.

(56) References Cited

FOREIGN PATENT DOCUMENTS

| | | |
|---|---|---|
| EP | 1870459 A1 | 12/2007 |
| EP | 1798240 B1 | 4/2011 |
| EP | 2319529 A1 | 5/2011 |
| WO | 03097105 A1 | 11/2003 |
| WO | 2004065569 A2 | 8/2004 |
| WO | 2008002064 A1 | 1/2008 |
| WO | 2009007750 A1 | 1/2009 |
| WO | 2009118324 A1 | 10/2009 |
| WO | 2011003557 A1 | 1/2011 |
| WO | 2012093068 A1 | 7/2012 |

OTHER PUBLICATIONS

The English translation of the Russian Decision, dated Apr. 24, 2019, in the related Russian Application No. 2016129894/10(046496).
Hoffmann E. et al., "PK Modulation of Haptenylated Peptides Via Non-Covalent Antibody Complexation," Journal of Controlled Release, 2013, V. 171, N. 1, p. 48-56.
Deev, S.M., "Modern Technologies for Creating Synthetic Antibodies for Clinical application," Acta Naturae. Apr. 2009; 1(1): 32-50.
Rudikoff S. et al., "Single Amino Acid Substitution Altering Antigen-Binding Specificity," Proceedings of the National Academy of Sciences, 1982, V. 79, N. 6, p. 1979-1983.
Colman P. M., "Effects of Amino Acid Sequence Changes on Antibody-Antigen Interactions," Research in Immunology, 1994, V. 145, N. 1, p. 33-36.
Chen C. et al., "Enhancement and Destruction of Antibody Function by Somatic Mutation: Unequal Occurrence Is Controlled by V Gene Combinatorial Associations," The EMBO Journal, 1995, V. 14, N. 12, p. 2784-2794.
Li et al., "Screening and Affinity Maturation of Hapten-specific Antibody," China Biotechnology, 2010, 30(2), 105-108. (English abstract included).

(Continued)

*Primary Examiner* — Gregory S Emch

(57) ABSTRACT

Herein is reported a bispecific antibody comprising a first binding specificity that specifically binds to a haptenylated payload and a second binding specificity that specifically binds to a blood brain barrier receptor.

17 Claims, 69 Drawing Sheets

Specification includes a Sequence Listing.

(56) References Cited

OTHER PUBLICATIONS

The U.S. Office Action, dated Jan. 19, 2019, in the related U.S. Appl. No. 14/577,084.
Gilarov M. S. Encyclopaedical Dictionary, Moscow "Soviet Encycopaedia" 1986, p. 70.
Polya Gideon, "Biochemical targets of plant bioactive compounds: a pharmacological reference guide to sites of action and biological effects," CRC press, 2003, pp. 42, 160.
The Chinese Office Action, dated Mar. 11, 2019, in the related Chinese Appl. No. 201480070147.6.
The English translation of the Japanese Office Action, dated Mar. 20, 2019, in the corresponding Japanese Application No. 2016-575149.
Gratzner HG, "Monoclonal antibody to 5-bromo- and 5-iododeoxyuridine: A new reagent for detection of DNA replication," Science. Oct. 29, 1982;218(4571):474-5.
Magaud et al., "Double immunocytochemical labeling of cell and tissue samples with monoclonal anti-bromodeoxyuridine," The Journal of Histochemistry and Cytochemistry, 1989, vol. 37, No. 10, p. 1517-1527.
Almagro, J.C., "Humanization of antibodies," Frontiers in Bioscience, 2008, vol. 13, pp. 1619-1633.
The English translation of the Russian Office Action, dated Jan. 16, 2019, in the related Russian Appl. No. 2015103460.
Sun, Wei-Chuan et al, "Synthesis of fluorinated fluoresceins", The Journal of Organic Chemistry 1997, vol. 62 (19), pp. 6469-6475 (see p. 6469).
Kabat, E. A. et al, Sequences of proteins of immunological interest, DIANE publishing, 5th ed., 1991, vol. 1, p. 310.
Yarilin A.A. Principles of immunology: Textbook (Study materials for medical students). M. Medicina, 1999, pp. 172-174.
The English translation of the Chinese Office Action, dated Oct. 15, 2019, in the related Chinese Appl. No. 201580034058.0.
The European Communication, dated Mar. 25, 2020, in the related European Appl. No. 18 150 996.9.
David Gareth Williams et al: "Humanising Antibodies by CDR Grafting" In: "Antibody Engineering", Jan. 1, 2010 (Jan. 1, 2010), Springer Berlin Heidelberg, XP055369742, vol. 1, pp. 319-339.
Olivier Leger et al: Antibody Drug Discovery Chapter 1: "Humanization of Antibodies" In: "Molecular Medicine and Medicinal Chemistry", Jan. 1, 2011 (Jan. 1, 2011), XP055119233, pp. 1-23.
Akinc, A. et al.(Jul. 2010, e-pub. May 11, 2010). "Targeted Delivery of RNAi Therapeutics With Endogenous and xogenous Ligand-Based Mechanisms," Mol. Ther. 18(7):1357-1364.
Akinc, A. et al. (May 11, 2010). "Development of Lipidoid-siRNA Formulations for Systemic Delivery to the Liver," Mol. Ther. 17(5):872-879.
Beck, A. et al. (May 2010). "Strategies and Challenges for the Next Generation of Therapeutic Antibodies," Nat. Rev.Immunol. 10(5):345-352.
Bhattarai, S.R. et al. (Dec. 2010, e-pub. Aug. 21, 2010). "Enhanced Gene and siRNA Delivery by Polycation-Modified Mesoporous Silica Nanoparticles Loaded With Chloroquine," Pharm. Res. 27(12):2556-2568. 26 Sages.
Brinkmann, U. et al. (Oct. 1, 1991). "B3(Fv)-PE38KDEL, A Single-Chain Immunotoxin That Causes Complete Regression of a Human Carcinoma in Mice," Proc. Natl. Acad. Sci. USA 88(19):8616-8620.
Burris, T.P. et al. (Mar. 1999). "A Novel Method for Analysis of Nuclear Receptor Function At Natural Promoters: Peroxisome Proliferator-Activated Receptor y Agonist Actions on aP2 Gene Expression Detected Using Branched DNA Messenger RNA Quantitation," Mol. Endocrinol. 13(3):410-417.
Chan, D.P. et al. (Nov. 2013, e-pub. Aug. 7, 2013). "Click Conjugated Polymeric Immuno-Nanoparticles for Targeted siRNA and Antisense Oligonucleotide Delivery," Biomaterials 34(33):8408-8415.
Chitnis, M.M. et al. (Oct. 15, 2008). "The Type 1 Insulin-Like Growth Factor Receptor Pathway," Clin. Cancer Res. 14(20):6364-6370.
Collins, M.L. et al. (Aug. 1, 1997). "A Branched DNA Signal Amplification Assay for Quantification of Nucleic Acid Targets Below 100 Molecules/ml," Nucleic Acids Res. 25(15):2979-2984.
Jhaveri, A.M. et al. (Apr. 25, 2014, e-pub. Apr. 25, 2014), "Multifunctional Polymeric Micelles for Delivery of Drugs and siRNA," Front Pharmacol. 5:77, 26 pages.
Malhotra, M. et al. (2013, e-pub. May 21, 2013). "Development and Characterization of Chitosan-PEG-TAT Nanoparticles for the Intracellular Delivery of siRNA.Int," J. Nanomedicine 8:2041-2052.
Mansfield, E. et al. (Sep. 1, 1997). "Recombinant RFB4 Immunotoxins Exhibit Potent Cytotoxic Activity for CD22-Bearing Cells and Tumors," Blood 90(5):2020-2026.
Miele, E et al. (2012, e-pub. Jul. 20, 2012). "Nanoparticle-Based Delivery of Small Interfering RNA: Challenges for Cancer Therapy," Int. J. Nanomedicine 7:3637-3657.
Molina, M.A. et al. (Jun. 15, 2011). "Trastuzumab (herceptin), A Humanized Anti-Hei2 Receptor Monoclonal Antibody, Inhibits Basal and Activated Her2 Ectodomain Cleavage in Breast Cancer Cells," Cancer Res. 61 (12):4744-4749.
Pastan, I. et al. (Jul. 15, 1991). "Characterization of Monoclonal Antibodies B1 and B3 That React With Mucinous Adenocarcinomas," Cancer Res. 51(14):3781-3787.
Schneider, B. et al. (2012, e-pub. Sep. 18, 2012). "Targeted siRNA Delivery and mRNA Knockdown Mediated by Bispecific Digoxigenin-binding Antibodies," Mo. Ther. Nucleic Acids 1:e46, 11 pages.
Semple, S.C. et al. (Feb. 2010, e-pub. Jan. 17, 2010). "Rational Design of Cationic Lipids for siRNA Delivery," Nat. Biotechnol. 28(2):172-176.
Tao, W. et al. (Sep. 2010, e-pub. Jul. 13, 2010). "Noninvasive Imaging of Lipid Nanoparticle-Mediated Systemic Delivery of Small-Interfering RNA to the Liver," Mol. Ther. 18(9):1657-1666.
Weidle, U.H. et al. (Jan.-Feb. 2013). "The Intriguing Options of Multispecific Antibody Formats for Treatment of Cancer," Cancer Genomics Proteomics 10(1):1-18.
Wolff, J.A. et al. (Jan. 2008, e-pub. Oct. 23, 2007). "Breaking the Bonds: Non-Viral Vectors Become Chemically Dynamic," Mol. Ther. 16(1):8-15.
Wong, S.C. et al. (Dec. 2012). "Co-Injection of a Targeted, Reversibly Masked Endosomolytic Polymer Dramatically Improves the Efficacy of Cholesterol-Conjugated Small Interfering RNAs In Vivo," Nucleic Acid Ther. 22:380-390.
Yu, B. et al. (Mar. 2009, e-pub. Mar. 19: 2009). "Targeted Delivery Systems for Oligonucleotide Therapeutics," AAPS J 11(1):195-203.
Aigner, A. (2008). "Cellular Delivery In Vivo of Sirna-Based Therapeutics." Curr. Pharm. Des. 14(34):3603-3619.
Baselga, J. (Sep. 2001). "The EGFR As a Target for Anticancer Therapy—Focus on Cetuximab," Eur. J. Cancer 37(Suppl. 4):S16-S22.
Grote, M. et al. (2012). "Bispecific Antibody Derivatives Based on Full-Length IgG Formats," Methods Mol. Biol. 901:247-263.
Haas, A.K. et al. (2012). "Chapter 17: Generation of Fluorescent IgG Fusion Proteins in Mammalian Cells," Methods Mol. Biol. 901:265-276.
Jung, S.H. et al. (May 1994). "Design of Interchain Disulfide Bonds in the Framework Region of the Fv Fragment of the Monoclonal Antibody 83," Proteins 19(1):35-47.
Kabat, E.A. (1991). Sequences of Proteins of Immunological Interest, 5th ed., Public Health Service, National Institutes of Health, Bethesda, MD, pp. 647-723.
Kies, M.S. et al. (Jul. 2002). "Cetuximab (Imcione/Merck/Bristol-Myers Squibb)," Curr. Opin. Investig. Drugs 3 (7):1092-1100.
Lee, S.K. et al. (2012). "Cell-Specific siRNA Delivery by Peptides and Antibodies," Meth. Enzymol. 502:91-122.
Leucuta, S.E. (Apr. 2013). "Systemic and Biophase Bioavailability and Pharmacokinetics of Nanoparticulate Drug Delivery Systems," Curr. Drug. Deily. 10(2):208-240.
Leus, N. G. et al. (Jan. 1.2014, e-pub. Nov. 12, 2013). "Effective siRNA Delivery to Inflamed Primary Vascular Endothelial Cells by Anti-E-Selectin and Anti-VCAM-1 PEGylated Saint-Based Lipoplexes," Int. J. Pharm. 459(1-2):40-50.
Reiter, Y. et al. (Dec. 1995). "Disulfide Stabilization of Antibody Fv: Computer Predictions and Experimental Evaluation," Protein Eng. 8(12):1323-1331.

(56) References Cited

OTHER PUBLICATIONS

Robbins, M. et al. (Jun. 2009). "siRNA and Innate Immunity," Oligonucleotides 19(2):89-102.
Sou, K. et al. (May-Jun. 2000, e-pub. Apr. 14, 2000). "Poly(ethylene glycol)-Modification of the Phospholipid Vesicles by Using the Spontaneous Incorporation of Poly(ethylene glycol)-Lipid Into the Vesicles," Bioconjug. Chem. 11(3)372-379.
Soutschek, J. et al. (Nov. 11, 2004). "Therapeutic Silencing of an Endogenous Gene by Systemic Administration of Modified siRNAs," Nature 432(7014):173-178.
Tiera, M.J. et al. (Oct. 2013). "Polymeric Systems As Nanodevices for siRNA Delivery," Curr. Gene Ther. 13 (5):358-369.
Toloue, M.M. et al. (2011). "Chapter 8: Antibody Targeted siRNA Delivery," Methods Mol. Biol. 764:123-139.
Zimmermann, T.S. et al. (Mary 4, 2006, e-pub. Mar. 26, 2006). "RNAi-Mediated Gene Silencing in Non-Human Primates." Nature 441(7089)111-114, 18 pages.

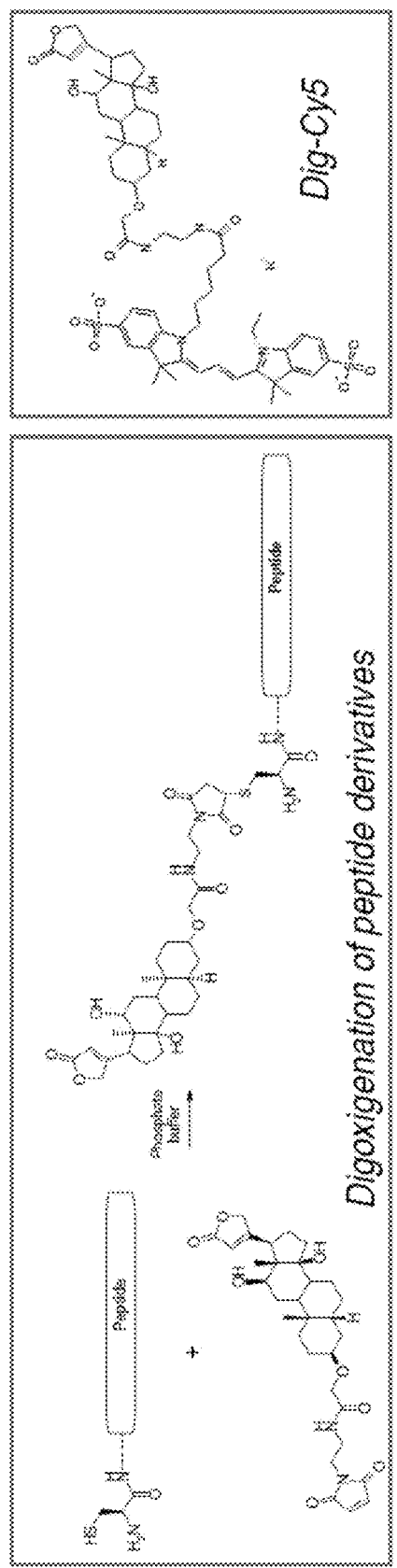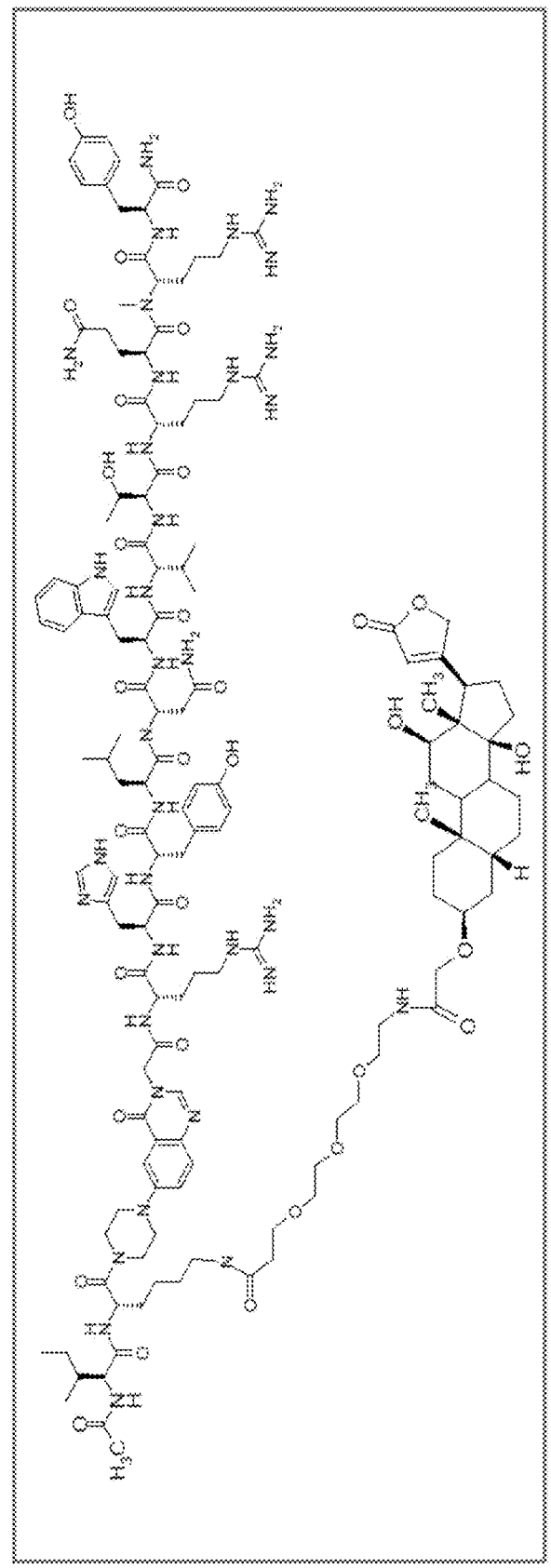
FIG. 1A
FIG. 1B
FIG. 1C

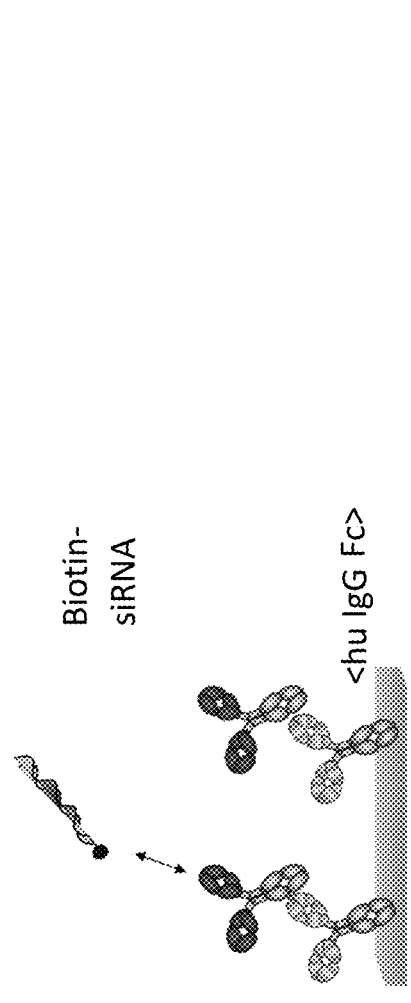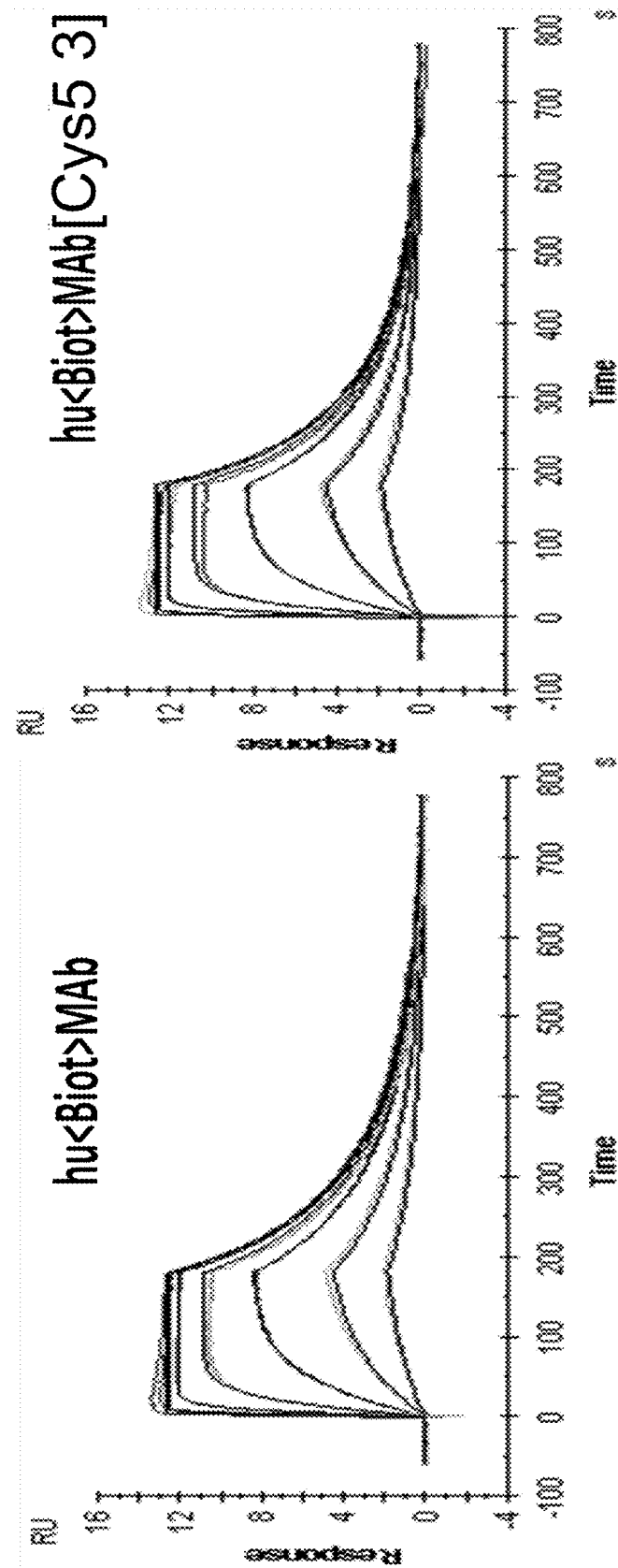
FIG. 5A
FIG. 5B

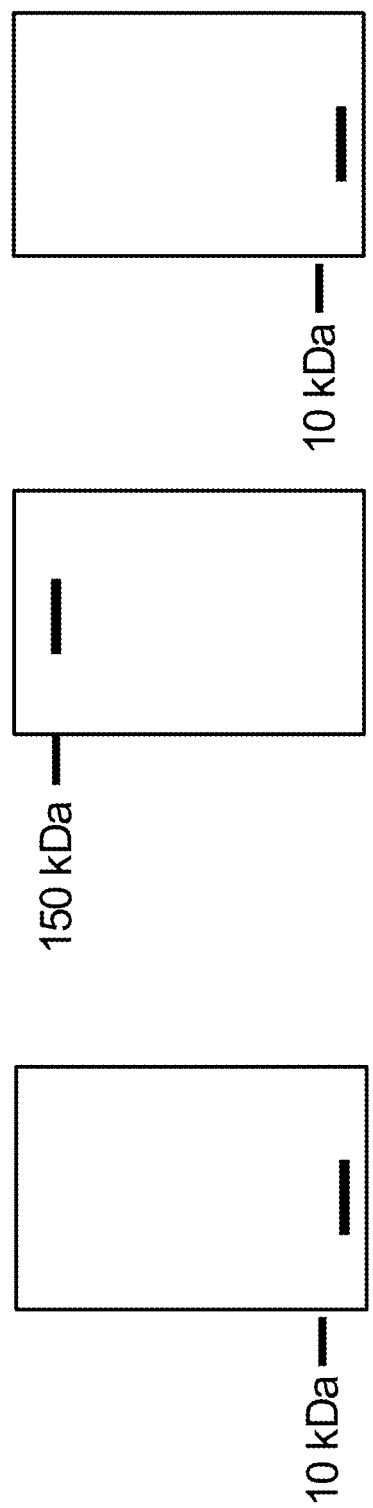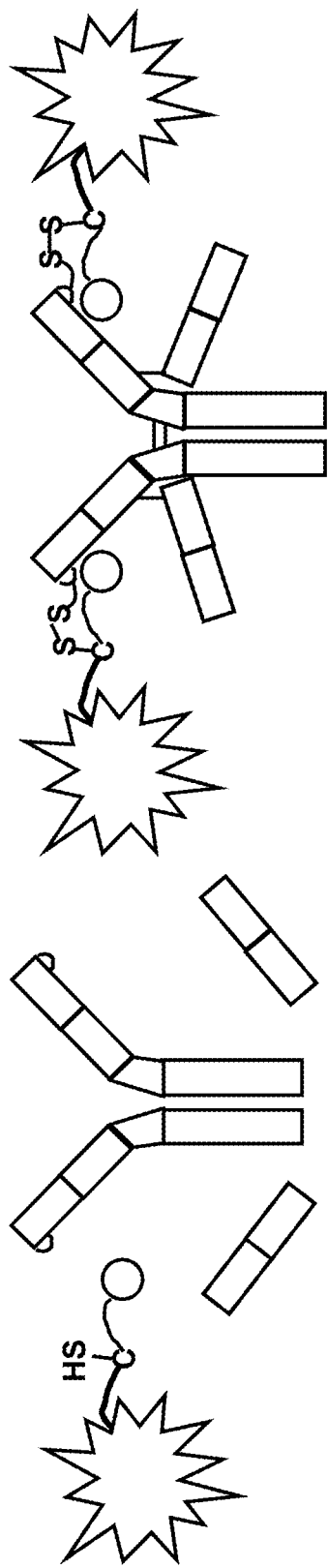
FIG. 7B
FIG. 7A

FIG. 56

SEQUENCE LISTING

```
<160> NUMBER OF SEQ ID NOS: 292

<210> SEQ ID NO 1
<211> LENGTH: 5
<212> TYPE: PRT
<213> ORGANISM: Mus musculus

<400> SEQUENCE: 1

Asp Tyr Ala Met Ser
1               5

<210> SEQ ID NO 2
<211> LENGTH: 17
<212> TYPE: PRT
<213> ORGANISM: Mus musculus

<400> SEQUENCE: 2

Ser Ile Asn Ile Gly Ala Thr Tyr Ala Tyr Tyr Pro Asp Ser Val Lys
1               5                   10                  15

Gly

<210> SEQ ID NO 3
<211> LENGTH: 16
<212> TYPE: PRT
<213> ORGANISM: Mus musculus

<400> SEQUENCE: 3

Pro Gly Ser Pro Tyr Glu Tyr Asp Lys Ala Tyr Tyr Ser Met Ala Tyr
1               5                   10                  15

<210> SEQ ID NO 4
<211> LENGTH: 125
<212> TYPE: PRT
<213> ORGANISM: Mus musculus

<400> SEQUENCE: 4

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asp Tyr
            20                  25                  30

Ala Met Ser Trp Ile Arg Gln Thr Pro Glu Asn Arg Leu Glu Trp Val
        35                  40                  45

Ala Ser Ile Asn Ile Gly Ala Thr Tyr Ala Tyr Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Gly Ser Glu Asp Thr Ala Met Tyr Tyr Cys
                85                  90                  95
```

```
Ala Arg Pro Gly Ser Pro Tyr Glu Tyr Asp Lys Ala Tyr Tyr Ser Met
                100                 105                 110

Ala Tyr Trp Gly Pro Gly Thr Ser Val Thr Val Ser Ser
        115                 120                 125

<210> SEQ ID NO 5
<211> LENGTH: 11
<212> TYPE: PRT
<213> ORGANISM: Mus musculus

<400> SEQUENCE: 5

Arg Ala Ser Gly Asn Ile His Asn Tyr Leu Ser
1               5                   10

<210> SEQ ID NO 6
<211> LENGTH: 7
<212> TYPE: PRT
<213> ORGANISM: Mus musculus

<400> SEQUENCE: 6

Ser Ala Lys Thr Leu Ala Asp
1               5

<210> SEQ ID NO 7
<211> LENGTH: 9
<212> TYPE: PRT
<213> ORGANISM: Mus musculus

<400> SEQUENCE: 7

Gln His Phe Trp Ser Ser Ile Tyr Thr
1               5

<210> SEQ ID NO 8
<211> LENGTH: 107
<212> TYPE: PRT
<213> ORGANISM: Mus musculus

<400> SEQUENCE: 8

Asp Val Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Lys Asn Tyr
                20                  25                  30

Leu Asn Trp Tyr Gln Gln Lys Pro Gly Gly Thr Val Lys Leu Leu Ile
            35                  40                  45

Tyr Tyr Ser Ser Thr Leu Leu Ser Gly Val Pro Ser Arg Phe Ser Gly
    50                  55                  60

Arg Gly Ser Gly Thr Asp Phe Ser Leu Thr Ile Thr Asn Leu Glu Arg
65                  70                  75                  80

Glu Asp Ile Ala Thr Tyr Phe Cys Gln Gln Ser Ile Thr Leu Pro Pro
                85                  90                  95

Thr Phe Gly Gly Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: humanized anti-digoxigenin antibody HVR-H1

<400> SEQUENCE: 9

Asp Tyr Ala Met Ser
```

```
<210> SEQ ID NO 10
<211> LENGTH: 17
<212> TYPE: PRT
<213> ORGANISM: Artificial Sequence
<220> FEATURE:
<223> OTHER INFORMATION: humanized anti-digoxigenin antibody HVR-H2

<400> SEQUENCE: 10

Ser Ile Asn Ile Gly Ala Thr Tyr Ile Tyr Tyr Ala Asp Ser Val Lys
1               5                   10                  15
Gly

<210> SEQ ID NO 11
<211> LENGTH: 16
<212> TYPE: PRT
<213> ORGANISM: Artificial Sequence
<220> FEATURE:
<223> OTHER INFORMATION: humanized anti-digoxigenin antibody HVR-H3

<400> SEQUENCE: 11

Pro Gly Ser Pro Tyr Glu Tyr Asp Lys Ala Tyr Tyr Ser Met Ala Tyr
1               5                   10                  15

<210> SEQ ID NO 12
<211> LENGTH: 125
<212> TYPE: PRT
<213> ORGANISM: Artificial Sequence
<220> FEATURE:
<223> OTHER INFORMATION: humanized anti-digoxigenin antibody VH

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 13
<211> LENGTH: 11
<212> TYPE: PRT
<213> ORGANISM: Artificial Sequence
<220> FEATURE:
<223> OTHER INFORMATION: humanized anti-digoxigenin antibody HVR-L1

<400> SEQUENCE: 13

Arg Ala Ser Gln Asp Ile Lys Asn Tyr Leu Asn
1               5                   10

<210> SEQ ID NO 14
```

```
<211> LENGTH: 7
<212> TYPE: PRT
<213> ORGANISM: Artificial Sequence
<220> FEATURE:
<223> OTHER INFORMATION: humanized anti-digoxigenin antibody HVR-L2

<400> SEQUENCE: 14

Tyr Ser Ser Thr Leu Leu Ser
1               5

<210> SEQ ID NO 15
<211> LENGTH: 9
<212> TYPE: PRT
<213> ORGANISM: Artificial Sequence
<220> FEATURE:
<223> OTHER INFORMATION: humanized anti-digoxigenin antibody HVR-L3

<400> SEQUENCE: 15

Gln Gln Ser Ile Thr Leu Pro Pro Thr
1               5

<210> SEQ ID NO 16
<211> LENGTH: 108
<212> TYPE: PRT
<213> ORGANISM: Artificial Sequence
<220> FEATURE:
<223> OTHER INFORMATION: humanized anti-digoxigenin antibody VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg
            100                 105

<210> SEQ ID NO 17
<211> LENGTH: 5
<212> TYPE: PRT
<213> ORGANISM: Mus musculus

<400> SEQUENCE: 17

Asp Tyr Ala Met Ser
1               5

<210> SEQ ID NO 18
<211> LENGTH: 17
<212> TYPE: PRT
<213> ORGANISM: Artificial Sequence
<220> FEATURE:
<223> OTHER INFORMATION: murine anti-digoxigenin antibody VH52bC HVR-H2

<400> SEQUENCE: 18

Ser Ile Asn Ile Cys Ala Thr Tyr Ala Tyr Tyr Pro Asp Ser Val Lys
1               5                   10                  15
```

Gly

<210> SEQ ID NO 19
<211> LENGTH: 16
<212> TYPE: PRT
<213> ORGANISM: Mus musculus

<400> SEQUENCE: 19

Pro Gly Ser Pro Tyr Glu Tyr Asp Lys Ala Tyr Tyr Ser Met Ala Tyr
1               5                   10                  15

<210> SEQ ID NO 20
<211> LENGTH: 125
<212> TYPE: PRT
<213> ORGANISM: Artificial Sequence
<220> FEATURE:
<223> OTHER INFORMATION: murine anti-digoxigenin antibody VH52bC VH

<400> SEQUENCE: 20

Glu Val Gln Leu Val Glu Ser Gly Gly Leu Val Lys Pro Gly Gly
1               5                   10                  15

Ser Leu Lys Leu Ser Cys Ala Val Ser Gly Phe Thr Phe Ser Asp Tyr
            20                  25                  30

Ala Met Ser Trp Ile Arg Gln Thr Pro Glu Asn Arg Leu Glu Trp Val
        35                  40                  45

Ala Ser Ile Asn Ile Cys Ala Thr Tyr Ala Tyr Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Gly Ser Glu Asp Thr Ala Met Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Pro Gly Thr Ser Val Thr Val Ser Ser
        115                 120                 125

<210> SEQ ID NO 21
<211> LENGTH: 11
<212> TYPE: PRT
<213> ORGANISM: Mus musculus

<400> SEQUENCE: 21

Arg Ala Ser Gly Asn Ile His Asn Tyr Leu Ser
1               5                   10

<210> SEQ ID NO 22
<211> LENGTH: 7
<212> TYPE: PRT
<213> ORGANISM: Mus musculus

<400> SEQUENCE: 22

Ser Ala Lys Thr Leu Ala Asp
1               5

<210> SEQ ID NO 23
<211> LENGTH: 9
<212> TYPE: PRT
<213> ORGANISM: Mus musculus

<400> SEQUENCE: 23

Gln His Phe Trp Ser Ser Ile Tyr Thr
1               5

<210> SEQ ID NO 24
<211> LENGTH: 107
<212> TYPE: PRT
<213> ORGANISM: Mus musculus

<400> SEQUENCE: 24

Asp Val Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Gly Gly Thr Val Lys Leu Leu Ile
        35                  40                  45

Tyr Tyr Ser Ser Thr Leu Leu Ser Gly Val Pro Ser Arg Phe Ser Gly
50                  55                  60

Arg Gly Ser Gly Thr Asp Phe Ser Leu Thr Ile Thr Asn Leu Glu Arg
65                  70                  75                  80

Glu Asp Ile Ala Thr Tyr Phe Cys Gln Gln Ser Ile Thr Leu Pro Pro
                85                  90                  95

Thr Phe Gly Gly Gly Thr Lys Leu Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: humanized anti-digoxigenin antibody VH52bC
      HVR-H1

<400> SEQUENCE: 25

Asp Tyr Ala Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: humanized anti-digoxigenin antibody VH52bC
      HVR-H2

<400> SEQUENCE: 26

Ser Ile Asn Ile Cys Ala Thr Tyr Ile Tyr Tyr Ala Asp Ser Val Lys
1               5                   10                  15
Gly

<210> SEQ ID NO 27
<211> LENGTH: 16
<212> TYPE: PRT
<213> ORGANISM: Artificial Sequence
<220> FEATURE:
<223> OTHER INFORMATION: humanized anti-digoxigenin antibody VH52bC
      HVR-H3

<400> SEQUENCE: 27

Pro Gly Ser Pro Tyr Glu Tyr Asp Lys Ala Tyr Tyr Ser Met Ala Tyr
1               5                   10                  15

<210> SEQ ID NO 28
<211> LENGTH: 125
<212> TYPE: PRT
<213> ORGANISM: Artificial Sequence

```
<220> FEATURE:
<223> OTHER INFORMATION: humanized anti-digoxigenin antibody VH52bC VH

<400> SEQUENCE: 28

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Cys Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 29
<211> LENGTH: 11
<212> TYPE: PRT
<213> ORGANISM: Artificial Sequence
<220> FEATURE:
<223> OTHER INFORMATION: humanized anti-digoxigenin antibody VH52bC
      HVR-L1

<400> SEQUENCE: 29

Arg Ala Ser Gln Asp Ile Lys Asn Tyr Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: humanized anti-digoxigenin antibody VH52bC
      HVR-L2

<400> SEQUENCE: 30

Tyr Ser Ser Thr Leu Leu Ser
1               5

<210> SEQ ID NO 31
<211> LENGTH: 9
<212> TYPE: PRT
<213> ORGANISM: Artificial Sequence
<220> FEATURE:
<223> OTHER INFORMATION: humanized anti-digoxigenin antibody VH52bC
      HVR-L3

<400> SEQUENCE: 31

Gln Gln Ser Ile Thr Leu Pro Pro Thr
1               5

<210> SEQ ID NO 32
<211> LENGTH: 107
<212> TYPE: PRT
<213> ORGANISM: Artificial Sequence
<220> FEATURE:
<223> OTHER INFORMATION: humanized anti-digoxigenin antibody VH52bC VL
```

-continued

<400> SEQUENCE: 32

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Cys Gly Thr Lys Val Glu Ile Lys
            100                 105

<210> SEQ ID NO 33
<211> LENGTH: 5
<212> TYPE: PRT
<213> ORGANISM: Mus musculus

<400> SEQUENCE: 33

Asp Thr Phe Phe Gln
1               5

<210> SEQ ID NO 34
<211> LENGTH: 17
<212> TYPE: PRT
<213> ORGANISM: Mus musculus

<400> SEQUENCE: 34

Arg Ile Asp Pro Ala Asn Gly Phe Thr Lys Tyr Asp Pro Lys Phe Gln
1               5                   10                  15

Gly

<210> SEQ ID NO 35
<211> LENGTH: 11
<212> TYPE: PRT
<213> ORGANISM: Mus musculus

<400> SEQUENCE: 35

Trp Asp Thr Tyr Gly Ala Ala Trp Phe Ala Tyr
1               5                   10

<210> SEQ ID NO 36
<211> LENGTH: 120
<212> TYPE: PRT
<213> ORGANISM: Mus musculus

<400> SEQUENCE: 36

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Asn Lys Asp Thr
            20                  25                  30

Phe Phe Gln Trp Val Lys Gln Arg Pro Glu Glu Cys Leu Glu Trp Ile
        35                  40                  45

Gly Arg Ile Asp Pro Ala Asn Gly Phe Thr Lys Tyr Asp Pro Lys Phe
50                  55                  60

Gln Gly Lys Ala Thr Ile Thr Val Asp Thr Ser Ser Asn Thr Ala Tyr

```
                    65                   70                   75                   80
Leu Gln Leu Asn Ser Leu Thr Ser Glu Asp Thr Ala Leu Tyr Tyr Cys
                    85                   90                   95

Thr Arg Trp Asp Thr Tyr Gly Ala Ala Trp Phe Ala Tyr Trp Gly Gln
                   100                  105                  110

Gly Thr Leu Val Thr Val Ser Ala
                   115                  120

<210> SEQ ID NO 37
<211> LENGTH: 11
<212> TYPE: PRT
<213> ORGANISM: Mus musculus

<400> SEQUENCE: 37

Arg Ala Ser Gly Asn Ile His Asn Tyr Leu Ser
1               5                   10

<210> SEQ ID NO 38
<211> LENGTH: 7
<212> TYPE: PRT
<213> ORGANISM: Mus musculus

<400> SEQUENCE: 38

Ser Ala Lys Thr Leu Ala Asp
1               5

<210> SEQ ID NO 39
<211> LENGTH: 9
<212> TYPE: PRT
<213> ORGANISM: Mus musculus

<400> SEQUENCE: 39

Gln His Phe Trp Ser Ser Ile Tyr Thr
1               5

<210> SEQ ID NO 40
<211> LENGTH: 107
<212> TYPE: PRT
<213> ORGANISM: Mus musculus

<400> SEQUENCE: 40

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ser Trp Phe Gln Gln Lys Gln Gly Lys Ser Pro Gln Leu Leu Val
            35                  40                  45

Tyr Ser Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Ile Tyr
                85                  90                  95

Thr Phe Gly Cys Gly Thr Lys Leu Glu Ile Lys
            100                 105

<210> SEQ ID NO 41
<211> LENGTH: 5
<212> TYPE: PRT
<213> ORGANISM: Artificial Sequence
<220> FEATURE:
```

<223> OTHER INFORMATION: humanized anti-biotin antibody HVR-H1

<400> SEQUENCE: 41

Asp Thr Phe Phe Gln
1               5

<210> SEQ ID NO 42
<211> LENGTH: 17
<212> TYPE: PRT
<213> ORGANISM: Artificial Sequence
<220> FEATURE:
<223> OTHER INFORMATION: humanized anti-biotin antibody HVR-H2

<400> SEQUENCE: 42

Arg Ile Asp Pro Ala Asn Gly Phe Thr Lys Tyr Ala Gln Lys Phe Gln
1               5                   10                  15

Gly

<210> SEQ ID NO 43
<211> LENGTH: 11
<212> TYPE: PRT
<213> ORGANISM: Artificial Sequence
<220> FEATURE:
<223> OTHER INFORMATION: humanized anti-biotin antibody HVR-H3

<400> SEQUENCE: 43

Trp Asp Thr Tyr Gly Ala Ala Trp Phe Ala Tyr
1               5                   10

<210> SEQ ID NO 44
<211> LENGTH: 120
<212> TYPE: PRT
<213> ORGANISM: Artificial Sequence
<220> FEATURE:
<223> OTHER INFORMATION: humanized anti-biotin antibody VH

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120

<210> SEQ ID NO 45
<211> LENGTH: 11
<212> TYPE: PRT
<213> ORGANISM: Artificial Sequence
<220> FEATURE:
<223> OTHER INFORMATION: humanized anti-biotin antibody HVR-L1

<400> SEQUENCE: 45

Arg Ala Ser Gly Asn Ile His Asn Tyr Leu Ser
1               5                   10

<210> SEQ ID NO 46
<211> LENGTH: 7
<212> TYPE: PRT
<213> ORGANISM: Artificial Sequence
<220> FEATURE:
<223> OTHER INFORMATION: humanized anti-biotin antibody HVR-L2

<400> SEQUENCE: 46

Ser Ala Lys Thr Leu Ala Asp
1               5

<210> SEQ ID NO 47
<211> LENGTH: 9
<212> TYPE: PRT
<213> ORGANISM: Artificial Sequence
<220> FEATURE:
<223> OTHER INFORMATION: humanized anti-biotin antibody HVR-L3

<400> SEQUENCE: 47

Gln His Phe Trp Ser Ser Ile Tyr Thr
1               5

<210> SEQ ID NO 48
<211> LENGTH: 107
<212> TYPE: PRT
<213> ORGANISM: Artificial Sequence
<220> FEATURE:
<223> OTHER INFORMATION: humanized anti-biotin antibody VL

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
            100                 105

<210> SEQ ID NO 49
<211> LENGTH: 5
<212> TYPE: PRT
<213> ORGANISM: Mus musculus

<400> SEQUENCE: 49

Asp Thr Phe Phe Gln
1               5

<210> SEQ ID NO 50
<211> LENGTH: 17
<212> TYPE: PRT
<213> ORGANISM: Artificial Sequence
<220> FEATURE:
<223> OTHER INFORMATION: murine anti-biotin antibody VH53C HVR-H2

```
<400> SEQUENCE: 50

Arg Ile Asp Pro Cys Asn Gly Phe Thr Lys Tyr Asp Pro Lys Phe Gln
1               5                   10                  15

Gly

<210> SEQ ID NO 51
<211> LENGTH: 11
<212> TYPE: PRT
<213> ORGANISM: Mus musculus

<400> SEQUENCE: 51

Trp Asp Thr Tyr Gly Ala Ala Trp Phe Ala Tyr
1               5                   10

<210> SEQ ID NO 52
<211> LENGTH: 120
<212> TYPE: PRT
<213> ORGANISM: Artificial Sequence
<220> FEATURE:
<223> OTHER INFORMATION: murine anti-biotin antibody VH53C VH

<400> SEQUENCE: 52

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Asn Lys Asp Thr
            20                  25                  30

Phe Phe Gln Trp Val Lys Gln Arg Pro Glu Glu Cys Leu Glu Trp Ile
        35                  40                  45

Gly Arg Ile Asp Pro Cys Asn Gly Phe Thr Lys Tyr Asp Pro Lys Phe
    50                  55                  60

Gln Gly Lys Ala Thr Ile Thr Val Asp Thr Ser Ser Asn Thr Ala Tyr
65                  70                  75                  80

Leu Gln Leu Asn Ser Leu Thr Ser Glu Asp Thr Ala Leu Tyr Tyr Cys
                85                  90                  95

Thr Arg Trp Asp Thr Tyr Gly Ala Ala Trp Phe Ala Tyr Trp Gly Gln
            100                 105                 110

Gly Thr Leu Val Thr Val Ser Ala
        115                 120

<210> SEQ ID NO 53
<211> LENGTH: 11
<212> TYPE: PRT
<213> ORGANISM: Mus musculus

<400> SEQUENCE: 53

Arg Ala Ser Gly Asn Ile His Asn Tyr Leu Ser
1               5                   10

<210> SEQ ID NO 54
<211> LENGTH: 7
<212> TYPE: PRT
<213> ORGANISM: Mus musculus

<400> SEQUENCE: 54

Ser Ala Lys Thr Leu Ala Asp
1               5

<210> SEQ ID NO 55
<211> LENGTH: 9
<212> TYPE: PRT
<213> ORGANISM: Mus musculus
```

-continued

<400> SEQUENCE: 55

Gln His Phe Trp Ser Ser Ile Tyr Thr
1               5

<210> SEQ ID NO 56
<211> LENGTH: 107
<212> TYPE: PRT
<213> ORGANISM: Mus musculus

<400> SEQUENCE: 56

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Phe Gln Gln Lys Gln Gly Lys Ser Pro Gln Leu Leu Val
        35                  40                  45

Tyr Ser Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Ile Tyr
                85                  90                  95

Thr Phe Gly Cys Gly Thr Lys Leu Glu Ile Lys
            100                 105

<210> SEQ ID NO 57
<211> LENGTH: 5
<212> TYPE: PRT
<213> ORGANISM: Artificial Sequence
<220> FEATURE:
<223> OTHER INFORMATION: humanized anti-biotin antibody VH53C HVR-H1

<400> SEQUENCE: 57

Asp Thr Phe Phe Gln
1               5

<210> SEQ ID NO 58
<211> LENGTH: 17
<212> TYPE: PRT
<213> ORGANISM: Artificial Sequence
<220> FEATURE:
<223> OTHER INFORMATION: humanized anti-biotin antibody VH53C HVR-H2

<400> SEQUENCE: 58

Arg Ile Asp Pro Cys Asn Gly Phe Thr Lys Tyr Ala Gln Lys Phe Gln
1               5                   10                  15

Gly

<210> SEQ ID NO 59
<211> LENGTH: 11
<212> TYPE: PRT
<213> ORGANISM: Artificial Sequence
<220> FEATURE:
<223> OTHER INFORMATION: humanized anti-biotin antibody VH53C HVR-H3

<400> SEQUENCE: 59

Trp Asp Thr Tyr Gly Ala Ala Trp Phe Ala Tyr
1               5                   10

<210> SEQ ID NO 60
<211> LENGTH: 120

-continued

```
<212> TYPE: PRT
<213> ORGANISM: Artificial Sequence
<220> FEATURE:
<223> OTHER INFORMATION: humanized anti-biotin antibody VH53C VH

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ser Gly Phe Asn Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Cys Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120

<210> SEQ ID NO 61
<211> LENGTH: 11
<212> TYPE: PRT
<213> ORGANISM: Artificial Sequence
<220> FEATURE:
<223> OTHER INFORMATION: humanized anti-biotin antibody VH53C HVR-L1

<400> SEQUENCE: 61

Arg Ala Ser Gly Asn Ile His Asn Tyr Leu Ser
1               5                   10

<210> SEQ ID NO 62
<211> LENGTH: 7
<212> TYPE: PRT
<213> ORGANISM: Artificial Sequence
<220> FEATURE:
<223> OTHER INFORMATION: humanized anti-biotin antibody VH53C HVR-L2

<400> SEQUENCE: 62

Ser Ala Lys Thr Leu Ala Asp
1               5

<210> SEQ ID NO 63
<211> LENGTH: 9
<212> TYPE: PRT
<213> ORGANISM: Artificial Sequence
<220> FEATURE:
<223> OTHER INFORMATION: humanized anti-biotin antibody VH53C HVR-L3

<400> SEQUENCE: 63

Gln His Phe Trp Ser Ser Ile Tyr Thr
1               5

<210> SEQ ID NO 64
<211> LENGTH: 107
<212> TYPE: PRT
<213> ORGANISM: Artificial Sequence
<220> FEATURE:
<223> OTHER INFORMATION: humanized anti-biotin antibody VH53C VL

<400> SEQUENCE: 64
```

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gly Asn Ile His Asn Tyr
            20                  25                 30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Val Ala Thr Tyr Tyr Cys Gln His Phe Trp Ser Ile Tyr
                85                  90                  95

Thr Phe Gly Gln Gly Thr Lys Leu Glu Ile Lys
            100                 105
```

<210> SEQ ID NO 65
<211> LENGTH: 6
<212> TYPE: PRT
<213> ORGANISM: Mus musculus

<400> SEQUENCE: 65

```
Ser Asp Tyr Ala Trp Asn
1               5
```

<210> SEQ ID NO 66
<211> LENGTH: 16
<212> TYPE: PRT
<213> ORGANISM: Mus musculus

<400> SEQUENCE: 66

```
Tyr Ile Arg Tyr Ser Gly His Thr Gly Tyr Asn Pro Ser Leu Lys Ser
1               5                   10                  15
```

<210> SEQ ID NO 67
<211> LENGTH: 7
<212> TYPE: PRT
<213> ORGANISM: Mus musculus

<400> SEQUENCE: 67

```
Trp Val Asp Tyr Phe Asp Tyr
1               5
```

<210> SEQ ID NO 68
<211> LENGTH: 116
<212> TYPE: PRT
<213> ORGANISM: Mus musculus

<400> SEQUENCE: 68

```
Asp Val Gln Leu Gln Glu Ser Gly Pro Gly Leu Val Lys Pro Ser Gln
1               5                   10                  15

Ser Leu Ser Leu Thr Cys Ala Val Thr Gly Tyr Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Arg Tyr Ser Gly His Thr Gly Tyr Asn Pro Ser Leu
    50                  55                  60

Lys Ser Arg Ile Ser Ile Thr Arg Asp Thr Phe Lys Asn Gln Phe Phe
65                  70                  75                  80

Leu Gln Phe Asn Ser Val Thr Thr Glu Asp Thr Ala Thr Tyr Tyr Cys
```

-continued

```
                    85                  90                  95
Ala Arg Trp Val Asp Tyr Phe Asp Tyr Trp Gly Gln Gly Thr Thr Leu
                100                 105                 110

Thr Val Ser Ser
            115

<210> SEQ ID NO 69
<211> LENGTH: 16
<212> TYPE: PRT
<213> ORGANISM: Mus musculus

<400> SEQUENCE: 69

Arg Ser Ser Gln Ser Ile Val Tyr Asn Asn Arg Tyr Thr Tyr Leu Glu
1               5                   10                  15

<210> SEQ ID NO 70
<211> LENGTH: 7
<212> TYPE: PRT
<213> ORGANISM: Mus musculus

<400> SEQUENCE: 70

Gly Val Ser Asn Arg Phe Ser
1               5

<210> SEQ ID NO 71
<211> LENGTH: 9
<212> TYPE: PRT
<213> ORGANISM: Mus musculus

<400> SEQUENCE: 71

Tyr Gln Gly Thr His Ala Pro Tyr Thr
1               5

<210> SEQ ID NO 72
<211> LENGTH: 112
<212> TYPE: PRT
<213> ORGANISM: Mus musculus

<400> SEQUENCE: 72

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val Tyr Asn
            20                  25                  30

Asn Arg Tyr Thr Tyr Leu Glu Trp Phe Val Gln Lys Pro Gly Gln Ser
        35                  40                  45

Leu Lys Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Tyr Gln Gly
                85                  90                  95

Thr His Ala Pro Tyr Thr Phe Gly Gly Gly Thr Lys Leu Glu Ile Lys
            100                 105                 110

<210> SEQ ID NO 73
<211> LENGTH: 6
<212> TYPE: PRT
<213> ORGANISM: Artificial Sequence
<220> FEATURE:
<223> OTHER INFORMATION: humanized anti-theophylline antibody HVR-H1

<400> SEQUENCE: 73
```

```
Ser Asp Tyr Ala Trp Asn
1               5

<210> SEQ ID NO 74
<211> LENGTH: 16
<212> TYPE: PRT
<213> ORGANISM: Artificial Sequence
<220> FEATURE:
<223> OTHER INFORMATION: humanized anti-theophylline antibody HVR-H2

<400> SEQUENCE: 74

Tyr Ile Arg Tyr Ser Gly His Thr Gly Tyr Asn Pro Ser Leu Lys Ser
1               5                   10                  15

<210> SEQ ID NO 75
<211> LENGTH: 7
<212> TYPE: PRT
<213> ORGANISM: Artificial Sequence
<220> FEATURE:
<223> OTHER INFORMATION: humanized anti-theophylline antibody HVR-H3

<400> SEQUENCE: 75

Trp Val Asp Tyr Phe Asp Tyr
1               5

<210> SEQ ID NO 76
<211> LENGTH: 116
<212> TYPE: PRT
<213> ORGANISM: Artificial Sequence
<220> FEATURE:
<223> OTHER INFORMATION: humanized anti-theophylline antibody VH

<400> SEQUENCE: 76

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Arg Tyr Ser Gly His Thr Gly Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Val Asp Tyr Phe Asp Tyr Trp Gly Gln Gly Thr Leu Val
            100                 105                 110

Thr Val Ser Ser
        115

<210> SEQ ID NO 77
<211> LENGTH: 16
<212> TYPE: PRT
<213> ORGANISM: Artificial Sequence
<220> FEATURE:
<223> OTHER INFORMATION: humanized anti-theophylline antibody HVR-L1

<400> SEQUENCE: 77

Arg Ser Ser Gln Ser Ile Val Tyr Asn Asn Arg Tyr Thr Tyr Leu Glu
1               5                   10                  15

<210> SEQ ID NO 78
```

```
<211> LENGTH: 7
<212> TYPE: PRT
<213> ORGANISM: Artificial Sequence
<220> FEATURE:
<223> OTHER INFORMATION: humanized anti-theophylline antibody HVR-L2

<400> SEQUENCE: 78

Gly Val Ser Asn Arg Phe Ser
1               5

<210> SEQ ID NO 79
<211> LENGTH: 9
<212> TYPE: PRT
<213> ORGANISM: Artificial Sequence
<220> FEATURE:
<223> OTHER INFORMATION: humanized anti-theophylline antibody HVR-L3

<400> SEQUENCE: 79

Tyr Gln Gly Thr His Ala Pro Tyr Thr
1               5

<210> SEQ ID NO 80
<211> LENGTH: 112
<212> TYPE: PRT
<213> ORGANISM: Artificial Sequence
<220> FEATURE:
<223> OTHER INFORMATION: humanized anti-theophylline antibody VL

<400> SEQUENCE: 80

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Asn
            20                  25                  30

Asn Arg Tyr Thr Tyr Leu Glu Trp Phe Gln Gln Arg Pro Gly Gln Ser
        35                  40                  45

Pro Arg Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Gly
                85                  90                  95

Thr His Ala Pro Tyr Thr Phe Gly Gln Gly Thr Lys Leu Glu Ile Lys
            100                 105                 110

<210> SEQ ID NO 81
<211> LENGTH: 6
<212> TYPE: PRT
<213> ORGANISM: Mus musculus

<400> SEQUENCE: 81

Ser Asp Tyr Ala Trp Asn
1               5

<210> SEQ ID NO 82
<211> LENGTH: 16
<212> TYPE: PRT
<213> ORGANISM: Artificial Sequence
<220> FEATURE:
<223> OTHER INFORMATION: murine anti-theophylline antibody VH53C HVR-H2

<400> SEQUENCE: 82

Tyr Ile Arg Cys Ser Gly His Thr Gly Tyr Asn Pro Ser Leu Lys Ser
1               5                   10                  15
```

<210> SEQ ID NO 83
<211> LENGTH: 7
<212> TYPE: PRT
<213> ORGANISM: Mus musculus

<400> SEQUENCE: 83

Trp Val Asp Tyr Phe Asp Tyr
1               5

<210> SEQ ID NO 84
<211> LENGTH: 116
<212> TYPE: PRT
<213> ORGANISM: Artificial Sequence
<220> FEATURE:
<223> OTHER INFORMATION: murine anti-theophylline antibody VH53C VH

<400> SEQUENCE: 84

Asp Val Gln Leu Gln Glu Ser Gly Pro Gly Leu Val Lys Pro Ser Gln
1               5                   10                  15

Ser Leu Ser Leu Thr Cys Ala Val Thr Gly Tyr Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Arg Cys Ser Gly His Thr Gly Tyr Asn Pro Ser Leu
    50                  55                  60

Lys Ser Arg Ile Ser Ile Thr Arg Asp Thr Phe Lys Asn Gln Phe Phe
65                  70                  75                  80

Leu Gln Phe Asn Ser Val Thr Thr Glu Asp Thr Ala Thr Tyr Tyr Cys
                85                  90                  95

Ala Arg Trp Val Asp Tyr Phe Asp Tyr Trp Gly Gln Gly Thr Thr Leu
            100                 105                 110

Thr Val Ser Ser
        115

<210> SEQ ID NO 85
<211> LENGTH: 16
<212> TYPE: PRT
<213> ORGANISM: Mus musculus

<400> SEQUENCE: 85

Arg Ser Ser Gln Ser Ile Val Tyr Asn Asn Arg Tyr Thr Tyr Leu Glu
1               5                   10                  15

<210> SEQ ID NO 86
<211> LENGTH: 7
<212> TYPE: PRT
<213> ORGANISM: Mus musculus

<400> SEQUENCE: 86

Gly Val Ser Asn Arg Phe Ser
1               5

<210> SEQ ID NO 87
<211> LENGTH: 9
<212> TYPE: PRT
<213> ORGANISM: Mus musculus

<400> SEQUENCE: 87

Tyr Gln Gly Thr His Ala Pro Tyr Thr
1               5

```
<210> SEQ ID NO 88
<211> LENGTH: 112
<212> TYPE: PRT
<213> ORGANISM: Mus musculus

<400> SEQUENCE: 88

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val Tyr Asn
            20                  25                  30

Asn Arg Tyr Thr Tyr Leu Glu Trp Phe Val Gln Lys Pro Gly Gln Ser
        35                  40                  45

Leu Lys Leu Leu Ile Tyr Gly Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Tyr Gln Gly
                85                  90                  95

Thr His Ala Pro Tyr Thr Phe Gly Gly Gly Thr Lys Leu Glu Ile Lys
            100                 105                 110

<210> SEQ ID NO 89
<211> LENGTH: 6
<212> TYPE: PRT
<213> ORGANISM: Artificial Sequence
<220> FEATURE:
<223> OTHER INFORMATION: humanized anti-theophylline antibody VH53C
      HVR-H1

<400> SEQUENCE: 89

Ser Asp Tyr Ala Trp Asn
1               5

<210> SEQ ID NO 90
<211> LENGTH: 16
<212> TYPE: PRT
<213> ORGANISM: Artificial Sequence
<220> FEATURE:
<223> OTHER INFORMATION: humanized anti-theophylline antibody VH53C
      HVR-H2

<400> SEQUENCE: 90

Tyr Ile Arg Cys Ser Gly His Thr Gly Tyr Asn Pro Ser Leu Lys Ser
1               5                   10                  15

<210> SEQ ID NO 91
<211> LENGTH: 7
<212> TYPE: PRT
<213> ORGANISM: Artificial Sequence
<220> FEATURE:
<223> OTHER INFORMATION: humanized anti-theophylline antibody VH53C
      HVR-H3

<400> SEQUENCE: 91

Trp Val Asp Tyr Phe Asp Tyr
1               5

<210> SEQ ID NO 92
<211> LENGTH: 116
<212> TYPE: PRT
<213> ORGANISM: Artificial Sequence
<220> FEATURE:
<223> OTHER INFORMATION: humanized anti-theophylline antibody VH53C VH

<400> SEQUENCE: 92
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Lys Gly Leu Glu Trp
            35                  40                  45

Ile Gly Tyr Ile Arg Cys Ser Gly His Thr Gly Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Val Asp Tyr Phe Asp Tyr Trp Gly Gln Gly Thr Leu Val
            100                 105                 110

Thr Val Ser Ser
        115

<210> SEQ ID NO 93
<211> LENGTH: 16
<212> TYPE: PRT
<213> ORGANISM: Artificial Sequence
<220> FEATURE:
<223> OTHER INFORMATION: humanized anti-theophylline antibody VH53C
      HVR-L1

<400> SEQUENCE: 93

Arg Ser Ser Gln Ser Ile Val Tyr Asn Asn Arg Tyr Thr Tyr Leu Glu
1               5                   10                  15

<210> SEQ ID NO 94
<211> LENGTH: 7
<212> TYPE: PRT
<213> ORGANISM: Artificial Sequence
<220> FEATURE:
<223> OTHER INFORMATION: humanized anti-theophylline antibody VH53C
      HVR-L2

<400> SEQUENCE: 94

Gly Val Ser Asn Arg Phe Ser
1               5

<210> SEQ ID NO 95
<211> LENGTH: 9
<212> TYPE: PRT
<213> ORGANISM: Artificial Sequence
<220> FEATURE:
<223> OTHER INFORMATION: humanized anti-theophylline antibody VH53C
      HVR-L3

<400> SEQUENCE: 95

Tyr Gln Gly Thr His Ala Pro Tyr Thr
1               5

<210> SEQ ID NO 96
<211> LENGTH: 112
<212> TYPE: PRT
<213> ORGANISM: Artificial Sequence
<220> FEATURE:
<223> OTHER INFORMATION: humanized anti-theophylline antibody VH53C VL

<400> SEQUENCE: 96

Asp Val Val Met Thr Gln Ser Pro Leu Ser Leu Pro Val Thr Leu Gly
1               5                   10                  15

-continued

Gln Pro Ala Ser Ile Ser Cys Arg Ser Ser Gln Ser Ile Val Tyr Asn
                20                  25                  30

Asn Arg Tyr Thr Tyr Leu Glu Trp Phe Gln Gln Arg Pro Gly Gln Ser
            35                  40                  45

Pro Arg Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Gly
                85                  90                  95

Thr His Ala Pro Tyr Thr Phe Gly Gln Gly Thr Lys Leu Glu Ile Lys
            100                 105                 110

<210> SEQ ID NO 97
<211> LENGTH: 5
<212> TYPE: PRT
<213> ORGANISM: Mus musculus

<400> SEQUENCE: 97

His Tyr Trp Met Asn
1               5

<210> SEQ ID NO 98
<211> LENGTH: 19
<212> TYPE: PRT
<213> ORGANISM: Mus musculus

<400> SEQUENCE: 98

Gln Phe Arg Asn Lys Pro Tyr Asn Tyr Glu Thr Tyr Tyr Ser Asp Ser
1               5                   10                  15

Val Lys Gly

<210> SEQ ID NO 99
<211> LENGTH: 7
<212> TYPE: PRT
<213> ORGANISM: Mus musculus

<400> SEQUENCE: 99

Ala Ser Tyr Gly Met Glu Tyr
1               5

<210> SEQ ID NO 100
<211> LENGTH: 118
<212> TYPE: PRT
<213> ORGANISM: Mus musculus

<400> SEQUENCE: 100

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
                20                  25                  30

Trp Met Asn Trp Val Arg Gln Ser Pro Glu Lys Gly Leu Glu Trp Val
            35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

```
Tyr Cys Thr Gly Ala Ser Tyr Gly Met Glu Tyr Leu Gly Gln Gly Thr
            100                 105                 110

Ser Val Thr Val Ser Ser
        115
```

<210> SEQ ID NO 101
<211> LENGTH: 16
<212> TYPE: PRT
<213> ORGANISM: Mus musculus

<400> SEQUENCE: 101

```
Arg Ser Ser Gln Ser Leu Val His Ser Asn Gly Asn Thr Tyr Leu Arg
1               5                   10                  15
```

<210> SEQ ID NO 102
<211> LENGTH: 7
<212> TYPE: PRT
<213> ORGANISM: Mus musculus

<400> SEQUENCE: 102

```
Lys Val Ser Asn Arg Val Ser
1               5
```

<210> SEQ ID NO 103
<211> LENGTH: 9
<212> TYPE: PRT
<213> ORGANISM: Mus musculus

<400> SEQUENCE: 103

```
Ser Gln Ser Thr His Val Pro Trp Thr
1               5
```

<210> SEQ ID NO 104
<211> LENGTH: 120
<212> TYPE: PRT
<213> ORGANISM: Mus musculus

<400> SEQUENCE: 104

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val
        115                 120
```

<210> SEQ ID NO 105
<211> LENGTH: 5
<212> TYPE: PRT
<213> ORGANISM: Mus musculus

<400> SEQUENCE: 105

His Tyr Trp Met Asn
1               5

<210> SEQ ID NO 106
<211> LENGTH: 19
<212> TYPE: PRT
<213> ORGANISM: Artificial Sequence
<220> FEATURE:
<223> OTHER INFORMATION: murine anti-fluorescein antibody VH53C HVR-H2

<400> SEQUENCE: 106

Gln Phe Arg Asn Cys Pro Tyr Asn Tyr Glu Thr Tyr Tyr Ser Asp Ser
1               5                   10                  15

Val Lys Gly

<210> SEQ ID NO 107
<211> LENGTH: 7
<212> TYPE: PRT
<213> ORGANISM: Mus musculus

<400> SEQUENCE: 107

Ala Ser Tyr Gly Met Glu Tyr
1               5

<210> SEQ ID NO 108
<211> LENGTH: 118
<212> TYPE: PRT
<213> ORGANISM: Artificial Sequence
<220> FEATURE:
<223> OTHER INFORMATION: murine anti-fluorescein antibody VH53C VH

<400> SEQUENCE: 108

Gly Val Lys Leu Asp Glu Thr Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Cys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser
        115

<210> SEQ ID NO 109
<211> LENGTH: 16
<212> TYPE: PRT
<213> ORGANISM: Mus musculus

<400> SEQUENCE: 109

Arg Ser Ser Gln Ser Leu Val His Ser Asn Gly Asn Thr Tyr Leu Arg
1               5                   10                  15

<210> SEQ ID NO 110
<211> LENGTH: 7
<212> TYPE: PRT

<213> ORGANISM: Mus musculus

<400> SEQUENCE: 110

Lys Val Ser Asn Arg Val Ser
1               5

<210> SEQ ID NO 111
<211> LENGTH: 9
<212> TYPE: PRT
<213> ORGANISM: Mus musculus

<400> SEQUENCE: 111

Ser Gln Ser Thr His Val Pro Trp Thr
1               5

<210> SEQ ID NO 112
<211> LENGTH: 112
<212> TYPE: PRT
<213> ORGANISM: Mus musculus

<400> SEQUENCE: 112

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 113
<211> LENGTH: 5
<212> TYPE: PRT
<213> ORGANISM: Mus musculus

<400> SEQUENCE: 113

His Tyr Trp Met Asn
1               5

<210> SEQ ID NO 114
<211> LENGTH: 19
<212> TYPE: PRT
<213> ORGANISM: Mus musculus

<400> SEQUENCE: 114

Gln Phe Arg Asn Lys Pro Tyr Asn Tyr Glu Thr Tyr Tyr Ser Asp Ser
1               5                   10                  15

Val Lys Gly

<210> SEQ ID NO 115
<211> LENGTH: 7
<212> TYPE: PRT
<213> ORGANISM: Mus musculus

<400> SEQUENCE: 115

Ala Ser Tyr Gly Met Glu Tyr
1               5

<210> SEQ ID NO 116
<211> LENGTH: 118
<212> TYPE: PRT
<213> ORGANISM: Artificial Sequence
<220> FEATURE:
<223> OTHER INFORMATION: murine anti-fluorescein antibody VH28C VH

<400> SEQUENCE: 116

Gly Val Lys Leu Asp Glu Thr Gly Gly Leu Val Gln Pro Gly Gly
1               5                   10                  15

Ala Met Lys Leu Ser Cys Val Thr Ser Gly Phe Cys Phe Gly His Tyr
            20                  25                  30

Trp Met Asn Trp Val Arg Gln Ser Pro Glu Lys Gly Leu Glu Trp Val
            35                  40                  45

Ala Gln Phe Arg Asn Lys Pro Tyr Asn Tyr Glu Thr Tyr Tyr Ser Asp
50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser
        115

<210> SEQ ID NO 117
<211> LENGTH: 16
<212> TYPE: PRT
<213> ORGANISM: Mus musculus

<400> SEQUENCE: 117

Arg Ser Ser Gln Ser Leu Val His Ser Asn Gly Asn Thr Tyr Leu Arg
1               5                   10                  15

<210> SEQ ID NO 118
<211> LENGTH: 7
<212> TYPE: PRT
<213> ORGANISM: Mus musculus

<400> SEQUENCE: 118

Lys Val Ser Asn Arg Val Ser
1               5

<210> SEQ ID NO 119
<211> LENGTH: 9
<212> TYPE: PRT
<213> ORGANISM: Mus musculus

<400> SEQUENCE: 119

Ser Gln Ser Thr His Val Pro Trp Thr
1               5

<210> SEQ ID NO 120
<211> LENGTH: 112
<212> TYPE: PRT
<213> ORGANISM: Mus musculus

<400> SEQUENCE: 120

Asp Val Val Met Thr Gln Thr Pro Leu Ser Leu Pro Val Ser Leu Gly

```
                1               5                  10                  15
Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Val Ser Gly Val Pro
        50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 121
<211> LENGTH: 5
<212> TYPE: PRT
<213> ORGANISM: Mus musculus

<400> SEQUENCE: 121

```
Asp Tyr Ala Met Ser
1               5
```

<210> SEQ ID NO 122
<211> LENGTH: 17
<212> TYPE: PRT
<213> ORGANISM: Mus musculus

<400> SEQUENCE: 122

```
Ser Ile Asn Ile Gly Ala Thr Tyr Ala Tyr Tyr Pro Asp Ser Val Lys
1               5                   10                  15

Gly
```

<210> SEQ ID NO 123
<211> LENGTH: 16
<212> TYPE: PRT
<213> ORGANISM: Mus musculus

<400> SEQUENCE: 123

```
Pro Gly Ser Pro Tyr Glu Tyr Asp Lys Ala Tyr Tyr Ser Met Ala Tyr
1               5                   10                  15
```

<210> SEQ ID NO 124
<211> LENGTH: 125
<212> TYPE: PRT
<213> ORGANISM: Artificial Sequence
<220> FEATURE:
<223> OTHER INFORMATION: murine anti-digoxigenin antibody VH28C VH

<400> SEQUENCE: 124

```
Glu Val Gln Leu Val Glu Ser Gly Gly Gly Leu Val Lys Pro Gly Gly
1               5                   10                  15

Ser Leu Lys Leu Ser Cys Ala Val Ser Gly Phe Cys Phe Ser Asp Tyr
            20                  25                  30

Ala Met Ser Trp Ile Arg Gln Thr Pro Glu Asn Arg Leu Glu Trp Val
        35                  40                  45

Ala Ser Ile Asn Ile Gly Ala Thr Tyr Ala Tyr Tyr Pro Asp Ser Val
    50                  55                  60

Lys Gly Arg Phe Thr Ile Ser Arg Asp Asn Ala Lys Asn Thr Leu Phe
65                  70                  75                  80
```

Leu Gln Met Ser Ser Leu Gly Ser Glu Asp Thr Ala Met Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Pro Gly Thr Ser Val Thr Val Ser Ser
        115                 120                 125

<210> SEQ ID NO 125
<211> LENGTH: 11
<212> TYPE: PRT
<213> ORGANISM: Mus musculus

<400> SEQUENCE: 125

Arg Ala Ser Gln Asp Ile Lys Asn Tyr Leu Asn
1               5                   10

<210> SEQ ID NO 126
<211> LENGTH: 7
<212> TYPE: PRT
<213> ORGANISM: Mus musculus

<400> SEQUENCE: 126

Tyr Ser Ser Thr Leu Leu Ser
1               5

<210> SEQ ID NO 127
<211> LENGTH: 9
<212> TYPE: PRT
<213> ORGANISM: Mus musculus

<400> SEQUENCE: 127

Gln Gln Ser Ile Thr Leu Pro Pro Thr
1               5

<210> SEQ ID NO 128
<211> LENGTH: 107
<212> TYPE: PRT
<213> ORGANISM: Mus musculus

<400> SEQUENCE: 128

Asp Val Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Gly Gly Thr Val Lys Leu Leu Ile
        35                  40                  45

Tyr Tyr Ser Ser Thr Leu Leu Ser Gly Val Pro Ser Arg Phe Ser Gly
    50                  55                  60

Arg Gly Ser Gly Thr Asp Phe Ser Leu Thr Ile Thr Asn Leu Glu Arg
65                  70                  75                  80

Glu Asp Ile Ala Thr Tyr Phe Cys Gln Gln Ser Ile Thr Leu Pro Pro
                85                  90                  95

Thr Phe Gly Gly Gly Thr Lys Leu Glu Ile Lys
            100                 105

<210> SEQ ID NO 129
<211> LENGTH: 5
<212> TYPE: PRT
<213> ORGANISM: Artificial Sequence
<220> FEATURE:
<223> OTHER INFORMATION: humanized anti-digoxigenin antibody VH28C

```
       HVR-H1

<400> SEQUENCE: 129

Asp Tyr Ala Met Ser
1               5

<210> SEQ ID NO 130
<211> LENGTH: 17
<212> TYPE: PRT
<213> ORGANISM: Artificial Sequence
<220> FEATURE:
<223> OTHER INFORMATION: humanized anti-digoxigenin antibody VH28C
      HVR-H2

<400> SEQUENCE: 130

Ser Ile Asn Ile Gly Ala Thr Tyr Ile Tyr Tyr Ala Asp Ser Val Lys
1               5                   10                  15

Gly

<210> SEQ ID NO 131
<211> LENGTH: 16
<212> TYPE: PRT
<213> ORGANISM: Artificial Sequence
<220> FEATURE:
<223> OTHER INFORMATION: humanized anti-digoxigenin antibody VH28C
      HVR-H3

<400> SEQUENCE: 131

Pro Gly Ser Pro Tyr Glu Tyr Asp Lys Ala Tyr Tyr Ser Met Ala Tyr
1               5                   10                  15

<210> SEQ ID NO 132
<211> LENGTH: 125
<212> TYPE: PRT
<213> ORGANISM: Artificial Sequence
<220> FEATURE:
<223> OTHER INFORMATION: humanized anti-digoxigenin antibody VH28C VH

<400> SEQUENCE: 132

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Cys Phe Ser Asp Tyr
                20                  25                  30

Ala Met Ser Trp Ile Arg Gln Ala Pro Gly Lys Gly Leu Glu Trp Val
            35                  40                  45

Ser Ser Ile Asn Ile Gly Ala Thr Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 133
<211> LENGTH: 11
<212> TYPE: PRT
<213> ORGANISM: Artificial Sequence
<220> FEATURE:
<223> OTHER INFORMATION: humanized anti-digoxigenin antibody VH28C
      HVR-L1
```

<400> SEQUENCE: 133

Arg Ala Ser Gln Asp Ile Lys Asn Tyr Leu Asn
1               5                   10

<210> SEQ ID NO 134
<211> LENGTH: 7
<212> TYPE: PRT
<213> ORGANISM: Artificial Sequence
<220> FEATURE:
<223> OTHER INFORMATION: humanized anti-digoxigenin antibody VH28C
      HVR-L2

<400> SEQUENCE: 134

Tyr Ser Ser Thr Leu Leu Ser
1               5

<210> SEQ ID NO 135
<211> LENGTH: 9
<212> TYPE: PRT
<213> ORGANISM: Artificial Sequence
<220> FEATURE:
<223> OTHER INFORMATION: humanized anti-digoxigenin antibody VH28C
      HVR-L3

<400> SEQUENCE: 135

Gln Gln Ser Ile Thr Leu Pro Pro Thr
1               5

<210> SEQ ID NO 136
<211> LENGTH: 108
<212> TYPE: PRT
<213> ORGANISM: Artificial Sequence
<220> FEATURE:
<223> OTHER INFORMATION: humanized anti-digoxigenin antibody VH28C VL

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg
            100                 105

<210> SEQ ID NO 137
<211> LENGTH: 5
<212> TYPE: PRT
<213> ORGANISM: Mus musculus

<400> SEQUENCE: 137

Asp Thr Phe Phe Gln
1               5

<210> SEQ ID NO 138
<211> LENGTH: 17

```
<212> TYPE: PRT
<213> ORGANISM: Mus musculus

<400> SEQUENCE: 138

Arg Ile Asp Pro Ala Asn Gly Phe Thr Lys Tyr Asp Pro Lys Phe Gln
1               5                   10                  15

Gly

<210> SEQ ID NO 139
<211> LENGTH: 11
<212> TYPE: PRT
<213> ORGANISM: Mus musculus

<400> SEQUENCE: 139

Trp Asp Thr Tyr Gly Ala Ala Trp Phe Ala Tyr
1               5                   10

<210> SEQ ID NO 140
<211> LENGTH: 120
<212> TYPE: PRT
<213> ORGANISM: Artificial Sequence
<220> FEATURE:
<223> OTHER INFORMATION: murine anti-biotin antibody VH28C VH

<400> SEQUENCE: 140

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Cys Asn Lys Asp Thr
            20                  25                  30

Phe Phe Gln Trp Val Lys Gln Arg Pro Glu Glu Cys Leu Glu Trp Ile
        35                  40                  45

Gly Arg Ile Asp Pro Ala Asn Gly Phe Thr Lys Tyr Asp Pro Lys Phe
    50                  55                  60

Gln Gly Lys Ala Thr Ile Thr Val Asp Thr Ser Ser Asn Thr Ala Tyr
65                  70                  75                  80

Leu Gln Leu Asn Ser Leu Thr Ser Glu Asp Thr Ala Leu Tyr Tyr Cys
                85                  90                  95

Thr Arg Trp Asp Thr Tyr Gly Ala Ala Trp Phe Ala Tyr Trp Gly Gln
            100                 105                 110

Gly Thr Leu Val Thr Val Ser Ala
        115                 120

<210> SEQ ID NO 141
<211> LENGTH: 11
<212> TYPE: PRT
<213> ORGANISM: Mus musculus

<400> SEQUENCE: 141

Arg Ala Ser Gly Asn Ile His Asn Tyr Leu Ser
1               5                   10

<210> SEQ ID NO 142
<211> LENGTH: 7
<212> TYPE: PRT
<213> ORGANISM: Mus musculus

<400> SEQUENCE: 142

Ser Ala Lys Thr Leu Ala Asp
1               5

<210> SEQ ID NO 143
```

```
<211> LENGTH: 9
<212> TYPE: PRT
<213> ORGANISM: Mus musculus

<400> SEQUENCE: 143

Gln His Phe Trp Ser Ser Ile Tyr Thr
1               5

<210> SEQ ID NO 144
<211> LENGTH: 107
<212> TYPE: PRT
<213> ORGANISM: Mus musculus

<400> SEQUENCE: 144

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Phe Gln Gln Lys Gln Gly Lys Ser Pro Gln Leu Leu Val
        35                  40                  45

Tyr Ser Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Ile Tyr
                85                  90                  95

Thr Phe Gly Cys Gly Thr Lys Leu Glu Ile Lys
            100                 105

<210> SEQ ID NO 145
<211> LENGTH: 5
<212> TYPE: PRT
<213> ORGANISM: Artificial Sequence
<220> FEATURE:
<223> OTHER INFORMATION: humanized anti-biotin antibody VH28C HVR-H1

<400> SEQUENCE: 145

Asp Thr Phe Phe Gln
1               5

<210> SEQ ID NO 146
<211> LENGTH: 17
<212> TYPE: PRT
<213> ORGANISM: Artificial Sequence
<220> FEATURE:
<223> OTHER INFORMATION: humanized anti-biotin antibody VH28C HVR-H2

<400> SEQUENCE: 146

Arg Ile Asp Pro Ala Asn Gly Phe Thr Lys Tyr Ala Gln Lys Phe Gln
1               5                   10                  15

Gly

<210> SEQ ID NO 147
<211> LENGTH: 11
<212> TYPE: PRT
<213> ORGANISM: Artificial Sequence
<220> FEATURE:
<223> OTHER INFORMATION: humanized anti-biotin antibody VH28C HVR-H3

<400> SEQUENCE: 147

Trp Asp Thr Tyr Gly Ala Ala Trp Phe Ala Tyr
1               5                   10
```

<210> SEQ ID NO 148
<211> LENGTH: 120
<212> TYPE: PRT
<213> ORGANISM: Artificial Sequence
<220> FEATURE:
<223> OTHER INFORMATION: humanized anti-biotin antibody VH28C VH

<400> SEQUENCE: 148

```
Gln Val Gln Leu Val Gln Ser Gly Ala Glu Val Lys Lys Pro Gly Ser
1               5                   10                  15

Ser Val Lys Val Ser Cys Lys Ser Ser Gly Phe Cys Asn Lys Asp Thr
            20                  25                  30

Phe Phe Gln Trp Val Arg Gln Ala Pro Gly Gln Gly Leu Glu Trp Met
        35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120
```

<210> SEQ ID NO 149
<211> LENGTH: 11
<212> TYPE: PRT
<213> ORGANISM: Artificial Sequence
<220> FEATURE:
<223> OTHER INFORMATION: humanized anti-biotin antibody VH28C HVR-L1

<400> SEQUENCE: 149

```
Arg Ala Ser Gly Asn Ile His Asn Tyr Leu Ser
1               5                   10
```

<210> SEQ ID NO 150
<211> LENGTH: 7
<212> TYPE: PRT
<213> ORGANISM: Artificial Sequence
<220> FEATURE:
<223> OTHER INFORMATION: humanized anti-biotin antibody VH28C HVR-L2

<400> SEQUENCE: 150

```
Ser Ala Lys Thr Leu Ala Asp
1               5
```

<210> SEQ ID NO 151
<211> LENGTH: 9
<212> TYPE: PRT
<213> ORGANISM: Artificial Sequence
<220> FEATURE:
<223> OTHER INFORMATION: humanized anti-biotin antibody VH28C HVR-L3

<400> SEQUENCE: 151

```
Gln His Phe Trp Ser Ser Ile Tyr Thr
1               5
```

<210> SEQ ID NO 152
<211> LENGTH: 107
<212> TYPE: PRT
<213> ORGANISM: Artificial Sequence
<220> FEATURE:

<223> OTHER INFORMATION: humanized anti-biotin antibody VH28C VL

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
            100                 105

<210> SEQ ID NO 153
<211> LENGTH: 6
<212> TYPE: PRT
<213> ORGANISM: Mus musculus

<400> SEQUENCE: 153

Ser Asp Tyr Ala Trp Asn
1               5

<210> SEQ ID NO 154
<211> LENGTH: 16
<212> TYPE: PRT
<213> ORGANISM: Mus musculus

<400> SEQUENCE: 154

Tyr Ile Arg Tyr Ser Gly His Thr Gly Tyr Asn Pro Ser Leu Lys Ser
1               5                   10                  15

<210> SEQ ID NO 155
<211> LENGTH: 7
<212> TYPE: PRT
<213> ORGANISM: Mus musculus

<400> SEQUENCE: 155

Trp Val Asp Tyr Phe Asp Tyr
1               5

<210> SEQ ID NO 156
<211> LENGTH: 116
<212> TYPE: PRT
<213> ORGANISM: Artificial Sequence
<220> FEATURE:
<223> OTHER INFORMATION: murine anti-theophylline antibody VH28C VH

<400> SEQUENCE: 156

Asp Val Gln Leu Gln Glu Ser Gly Pro Gly Leu Val Lys Pro Ser Gln
1               5                   10                  15

Ser Leu Ser Leu Thr Cys Ala Val Thr Gly Tyr Cys Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Arg Tyr Ser Gly His Thr Gly Tyr Asn Pro Ser Leu
    50                  55                  60

```
Lys Ser Arg Ile Ser Ile Thr Arg Asp Thr Phe Lys Asn Gln Phe Phe
65                  70                  75                  80

Leu Gln Phe Asn Ser Val Thr Thr Glu Asp Thr Ala Thr Tyr Tyr Cys
                85                  90                  95

Ala Arg Trp Val Asp Tyr Phe Asp Tyr Trp Gly Gln Gly Thr Thr Leu
            100                 105                 110

Thr Val Ser Ser
        115

<210> SEQ ID NO 157
<211> LENGTH: 16
<212> TYPE: PRT
<213> ORGANISM: Mus musculus

<400> SEQUENCE: 157

Arg Ser Ser Gln Ser Ile Val Tyr Asn Asn Arg Tyr Thr Tyr Leu Glu
1               5                   10                  15

<210> SEQ ID NO 158
<211> LENGTH: 7
<212> TYPE: PRT
<213> ORGANISM: Mus musculus

<400> SEQUENCE: 158

Gly Val Ser Asn Arg Phe Ser
1               5

<210> SEQ ID NO 159
<211> LENGTH: 9
<212> TYPE: PRT
<213> ORGANISM: Mus musculus

<400> SEQUENCE: 159

Tyr Gln Gly Thr His Ala Pro Tyr Thr
1               5

<210> SEQ ID NO 160
<211> LENGTH: 112
<212> TYPE: PRT
<213> ORGANISM: Mus musculus

<400> SEQUENCE: 160

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val Tyr Asn
            20                  25                  30

Asn Arg Tyr Thr Tyr Leu Glu Trp Phe Val Gln Lys Pro Gly Gln Ser
        35                  40                  45

Leu Lys Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Tyr Gln Gly
                85                  90                  95

Thr His Ala Pro Tyr Thr Phe Gly Gly Gly Thr Lys Leu Glu Ile Lys
            100                 105                 110

<210> SEQ ID NO 161
<211> LENGTH: 6
<212> TYPE: PRT
```

```
<213> ORGANISM: Artificial Sequence
<220> FEATURE:
<223> OTHER INFORMATION: humanized anti-theophylline antibody VH28C
      HVR-H1

<400> SEQUENCE: 161

Ser Asp Tyr Ala Trp Asn
1               5

<210> SEQ ID NO 162
<211> LENGTH: 16
<212> TYPE: PRT
<213> ORGANISM: Artificial Sequence
<220> FEATURE:
<223> OTHER INFORMATION: humanized anti-theophylline antibody VH28C
      HVR-H2

<400> SEQUENCE: 162

Tyr Ile Arg Tyr Ser Gly His Thr Gly Tyr Asn Pro Ser Leu Lys Ser
1               5                   10                  15

<210> SEQ ID NO 163
<211> LENGTH: 7
<212> TYPE: PRT
<213> ORGANISM: Artificial Sequence
<220> FEATURE:
<223> OTHER INFORMATION: humanized anti-theophylline antibody VH28C
      HVR-H3

<400> SEQUENCE: 163

Trp Val Asp Tyr Phe Asp Tyr
1               5

<210> SEQ ID NO 164
<211> LENGTH: 116
<212> TYPE: PRT
<213> ORGANISM: Artificial Sequence
<220> FEATURE:
<223> OTHER INFORMATION: humanized anti-theophylline antibody VH28C VH

<400> SEQUENCE: 164

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Cys Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Arg Tyr Ser Gly His Thr Gly Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Val Asp Tyr Phe Asp Tyr Trp Gly Gln Gly Thr Leu Val
            100                 105                 110

Thr Val Ser Ser
        115

<210> SEQ ID NO 165
<211> LENGTH: 16
<212> TYPE: PRT
<213> ORGANISM: Artificial Sequence
<220> FEATURE:
<223> OTHER INFORMATION: humanized anti-theophylline antibody VH28C
```

```
        HVR-L1

<400> SEQUENCE: 165

Arg Ser Ser Gln Ser Ile Val Tyr Asn Asn Arg Tyr Thr Tyr Leu Glu
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: humanized anti-theophylline antibody VH28C
      HVR-L2

<400> SEQUENCE: 166

Gly Val Ser Asn Arg Phe Ser
1               5

<210> SEQ ID NO 167
<211> LENGTH: 9
<212> TYPE: PRT
<213> ORGANISM: Artificial Sequence
<220> FEATURE:
<223> OTHER INFORMATION: humanized anti-theophylline antibody VH28C
      HVR-L3

<400> SEQUENCE: 167

Tyr Gln Gly Thr His Ala Pro Tyr Thr
1               5

<210> SEQ ID NO 168
<211> LENGTH: 112
<212> TYPE: PRT
<213> ORGANISM: Artificial Sequence
<220> FEATURE:
<223> OTHER INFORMATION: humanized anti-theophylline antibody VH28C VL

<400> SEQUENCE: 168

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Asn
            20                  25                  30

Asn Arg Tyr Thr Tyr Leu Glu Trp Phe Gln Gln Arg Pro Gly Gln Ser
        35                  40                  45

Pro Arg Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Gly
                85                  90                  95

Thr His Ala Pro Tyr Thr Phe Gly Gln Gly Thr Lys Leu Glu Ile Lys
            100                 105                 110

<210> SEQ ID NO 169
<211> LENGTH: 330
<212> TYPE: PRT
<213> ORGANISM: Homo sapiens

<400> SEQUENCE: 169

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 170
<211> LENGTH: 330
<212> TYPE: PRT
<213> ORGANISM: Homo sapiens

<400> SEQUENCE: 170

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 171
<211> LENGTH: 330
<212> TYPE: PRT
<213> ORGANISM: Homo sapiens

<400> SEQUENCE: 171

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
```

```
Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 172
<211> LENGTH: 330
<212> TYPE: PRT
<213> ORGANISM: Homo sapiens

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 173
<211> LENGTH: 327
<212> TYPE: PRT
<213> ORGANISM: Homo sapiens

<400> SEQUENCE: 173

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
            195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 174
<211> LENGTH: 327
<212> TYPE: PRT
<213> ORGANISM: Homo sapiens

<400> SEQUENCE: 174

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

-continued

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 175
<211> LENGTH: 327
<212> TYPE: PRT
<213> ORGANISM: Homo sapiens

<400> SEQUENCE: 175

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Gly Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

```
Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 176
<211> LENGTH: 15
<212> TYPE: PRT
<213> ORGANISM: Artificial Sequence
<220> FEATURE:
<223> OTHER INFORMATION: haptenylated polypeptide 01 - Ac IK Pqa
      R(Pbf)H(Trt)Y(tBu)LN(Trt)W(Boc)VT(But)R(Pbf)Q(Trt)-MeArg(Mtr)-Y(t
      Bu)
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 176

Ile Lys Xaa Arg His Tyr Leu Asn Trp Val Thr Arg Gln Xaa Tyr
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: haptenylated polypeptide 02
<220> FEATURE:
<221> NAME/KEY: MISC_FEATURE
<222> LOCATION: (2)..(2)
<223> OTHER INFORMATION: -PEG3-dig
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 177

Ile Lys Xaa Arg His Tyr Leu Asn Trp Val Thr Arg Gln Xaa Tyr
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: haptenylated polypeptide 03
<220> FEATURE:
<221> NAME/KEY: MISC_FEATURE
<222> LOCATION: (2)..(2)
<223> OTHER INFORMATION: -PEG3-Cys-4Abu-NH2
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 178
```

```
Ile Lys Xaa Arg His Tyr Leu Asn Trp Val Thr Arg Gln Xaa Tyr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: haptenylated polypeptide 04
<220> FEATURE:
<221> NAME/KEY: MISC_FEATURE
<222> LOCATION: (2)..(2)
<223> OTHER INFORMATION: -PEG3-Cys-4Abu-dig
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(24)
<223> OTHER INFORMATION: X=Me-ARG

<400> SEQUENCE: 179

Ile Lys Xaa Arg His Tyr Leu Asn Trp Val Thr Arg Gln Xaa Tyr
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: haptenylated polypeptide 05
<220> FEATURE:
<221> NAME/KEY: MISC_FEATURE
<222> LOCATION: (2)..(2)
<223> OTHER INFORMATION: -PEG3-Cys-4Abu-NH2
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 180

Ile Lys Xaa Arg His Tyr Leu Asn Trp Val Thr Arg Gln Xaa Tyr
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: haptenylated polypeptide 06 -
      PEG2-IK(ivDde)-Pqa-R(Pbf)H(Trt)Y(tBu)LN(Trt)W(Boc)VT(tBu)R(Pbf)Q(
      Trt)-MeArg(Mtr)-Y(tBu)
<220> FEATURE:
<221> NAME/KEY: MISC_FEATURE
<222> LOCATION: (1)..(1)
<223> OTHER INFORMATION: X=PEG2
<220> FEATURE:
<221> NAME/KEY: MISC_FEATURE
<222> LOCATION: (3)..(3)
<223> OTHER INFORMATION: -ivDde
<220> FEATURE:
<221> NAME/KEY: MISC_FEATURE
<222> LOCATION: (4)..(4)
<223> OTHER INFORMATION: X=PQA
<220> FEATURE:
<221> NAME/KEY: MISC_FEATURE
<222> LOCATION: (15)..(15)
<223> OTHER INFORMATION: X=Me-ARG
```

<400> SEQUENCE: 181

Xaa Ile Lys Xaa Arg His Tyr Leu Asn Trp Val Thr Arg Gln Xaa Tyr
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: haptenylated polypeptide 07
<220> FEATURE:
<221> NAME/KEY: MISC_FEATURE
<222> LOCATION: (1)..(1)
<223> OTHER INFORMATION: X=PEG2
<220> FEATURE:
<221> NAME/KEY: MISC_FEATURE
<222> LOCATION: (3)..(3)
<223> OTHER INFORMATION: -PEG3-Cys-Abu-NH2
<220> FEATURE:
<221> NAME/KEY: MISC_FEATURE
<222> LOCATION: (4)..(4)
<223> OTHER INFORMATION: X=PQA
<220> FEATURE:
<221> NAME/KEY: MISC_FEATURE
<222> LOCATION: (15)..(15)
<223> OTHER INFORMATION: X=Me-ARG

<400> SEQUENCE: 182

Xaa Ile Lys Xaa Arg His Tyr Leu Asn Trp Val Thr Arg Gln Xaa Tyr
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: haptenylated polypeptide 08
<220> FEATURE:
<221> NAME/KEY: MISC_FEATURE
<222> LOCATION: (1)..(1)
<223> OTHER INFORMATION: X=PEG2
<220> FEATURE:
<221> NAME/KEY: MISC_FEATURE
<222> LOCATION: (3)..(3)
<223> OTHER INFORMATION: -PEG3-Cys-4Abu-dig
<220> FEATURE:
<221> NAME/KEY: MISC_FEATURE
<222> LOCATION: (4)..(4)
<223> OTHER INFORMATION: X=PQA
<220> FEATURE:
<221> NAME/KEY: MISC_FEATURE
<222> LOCATION: (15)..(15)
<223> OTHER INFORMATION: X=Me-ARG

<400> SEQUENCE: 183

Xaa Ile Lys Xaa Arg His Tyr Leu Asn Trp Val Thr Arg Gln Xaa Tyr
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: haptenylated polypeptide 09
<220> FEATURE:
<221> NAME/KEY: MISC_FEATURE
<222> LOCATION: (2)..(2)
<223> OTHER INFORMATION: -PEG2-biotin
<220> FEATURE:
<221> NAME/KEY: MISC_FEATURE
<222> LOCATION: (3)..(3)
<223> OTHER INFORMATION: X=PQA

```
<220> FEATURE:
<221> NAME/KEY: MISC_FEATURE
<222> LOCATION: (14)..(14)
<223> OTHER INFORMATION: X=Me-ARG

<400> SEQUENCE: 184

Ile Lys Xaa Arg His Tyr Leu Asn Trp Val Thr Arg Gln Xaa Tyr
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: haptenylated polypeptide 10
<220> FEATURE:
<221> NAME/KEY: MISC_FEATURE
<222> LOCATION: (2)..(2)
<223> OTHER INFORMATION: -PEG3-Cys--Ala-biotin
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 185

Ile Lys Xaa Arg His Tyr Leu Asn Trp Val Thr Arg Gln Xaa Tyr
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: haptenylated polypeptide 11
<220> FEATURE:
<221> NAME/KEY: MISC_FEATURE
<222> LOCATION: (2)..(2)
<223> OTHER INFORMATION: -PEG3-Cys-PEG2-biotin
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 186

Ile Lys Xaa Arg His Tyr Leu Asn Trp Val Thr Arg Gln Xaa Tyr
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: haptenylated polypeptide 12
<220> FEATURE:
<221> NAME/KEY: MISC_FEATURE
<222> LOCATION: (2)..(2)
<223> OTHER INFORMATION: -PEG3-Cys-4-Abu-5-Fluo
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG
```

<400> SEQUENCE: 187

Ile Lys Xaa Arg His Tyr Leu Asn Trp Val Thr Arg Gln Xaa Tyr
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: haptenylated polypeptide 13
<220> FEATURE:
<221> NAME/KEY: MISC_FEATURE
<222> LOCATION: (2)..(2)
<223> OTHER INFORMATION: -PEG3-Cys-PEG2-5-Fluo
<220> FEATURE:
<221> NAME/KEY: MISC_FEATURE
<222> LOCATION: (3)..(3)
<223> OTHER INFORMATION: X=PQA
<220> FEATURE:
<221> NAME/KEY: MISC_FEATURE
<222> LOCATION: (14)..(14)
<223> OTHER INFORMATION: X=Me-ARG

<400> SEQUENCE: 188

Ile Lys Xaa Arg His Tyr Leu Asn Trp Val Thr Arg Gln Xaa Tyr
1               5                   10                  15

<210> SEQ ID NO 189
<211> LENGTH: 107
<212> TYPE: PRT
<213> ORGANISM: Artificial Sequence
<220> FEATURE:
<223> OTHER INFORMATION: anti-digoxigenin scdsFv VL

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Cys Gly Thr Lys Val Glu Ile Lys
            100                 105

<210> SEQ ID NO 190
<211> LENGTH: 125
<212> TYPE: PRT
<213> ORGANISM: Artificial Sequence
<220> FEATURE:
<223> OTHER INFORMATION: anti-digoxigenin scdsFv VH

<400> SEQUENCE: 190

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Cys Leu Glu Trp Val

```
            35                  40                  45
Ser Ser Ile Asn Ile Cys Ala Thr Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Gly Ser Pro Tyr Gly Tyr Asp Lys Ala Tyr Tyr Ser Met
                100                 105                 110

Ala Tyr Trp Gly Gln Gly Thr Thr Val Thr Val Ser Ser
            115                 120                 125
```

<210> SEQ ID NO 191
<211> LENGTH: 219
<212> TYPE: PRT
<213> ORGANISM: Artificial Sequence
<220> FEATURE:
<223> OTHER INFORMATION: anti-LeY antibody kappa light chain

<400> SEQUENCE: 191

```
Asp Val Leu Met Thr Gln Ser Pro Leu Ser Leu Pro Val Ser Leu Gly
  1               5                  10                  15

Asp Gln Ala Ser Ile Ser Cys Arg Ser Ser Gln Ile Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 192
<211> LENGTH: 706
<212> TYPE: PRT
<213> ORGANISM: Artificial Sequence
<220> FEATURE:
<223> OTHER INFORMATION: anti-LeY antibody heavy chain_ds44-100scFvDig-
      Cys53

<400> SEQUENCE: 192

-continued

Asp Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Ser Ser Ala Tyr Ser Asp Thr Val
50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
            85                  90                  95

Ala Arg Gly Leu Ala Trp Gly Ala Trp Phe Ala Tyr Trp Gly Gln Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gln Val Gln Leu Val
            450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Asp Tyr Ala Met Ser Trp Ile
                485                 490                 495

Arg Gln Ala Pro Gly Lys Cys Leu Glu Trp Val Ser Ser Ile Asn Ile
            500                 505                 510

Cys Ala Thr Tyr Ile Tyr Tyr Ala Asp Ser Val Lys Gly Arg Phe Thr
            515                 520                 525

Ile Ser Arg Asp Asn Ala Lys Asn Ser Leu Tyr Leu Gln Met Asn Ser
            530                 535                 540

Leu Arg Ala Glu Asp Thr Ala Val Tyr Tyr Cys Ala Arg Pro Gly Ser
545                 550                 555                 560

Pro Tyr Glu Tyr Asp Lys Ala Tyr Tyr Ser Met Ala Tyr Trp Gly Gln
                565                 570                 575

Gly Thr Thr Val Thr Val Ser Ser Gly Gly Gly Ser Gly Gly Gly
            580                 585                 590

Gly Ser Gly Gly Gly Ser Asp Ile Gln Met Thr Gln Ser Pro Ser
            595                 600                 605

Ser Leu Ser Ala Ser Val Gly Asp Arg Val Thr Ile Thr Cys Arg Ala
            610                 615                 620

Ser Gln Asp Ile Lys Asn Tyr Leu Asn Trp Tyr Gln Gln Lys Pro Gly
625                 630                 635                 640

Lys Ala Pro Lys Leu Leu Ile Tyr Tyr Ser Thr Leu Leu Ser Gly
                645                 650                 655

Val Pro Ser Arg Phe Ser Gly Ser Gly Thr Asp Phe Thr Leu
            660                 665                 670

Thr Ile Ser Ser Leu Gln Pro Glu Asp Phe Ala Thr Tyr Tyr Cys Gln
            675                 680                 685

Gln Ser Ile Thr Leu Pro Pro Thr Phe Gly Cys Gly Thr Lys Val Glu
            690                 695                 700

Ile Lys
705

<210> SEQ ID NO 193
<211> LENGTH: 213
<212> TYPE: PRT
<213> ORGANISM: Artificial Sequence
<220> FEATURE:
<223> OTHER INFORMATION: LC anti-TfR1 antibody

<400> SEQUENCE: 193

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Arg Tyr Ile
                20                  25                  30

His Trp Tyr Gln Gln Arg Pro Gly Thr Ser Pro Lys Arg Trp Ile Tyr
            35                  40                  45

Asp Thr Ser Asn Leu Ala Ser Gly Val Pro Ala Arg Phe Ser Gly Ser
        50                  55                  60
```

```
Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Asn Ser Tyr Pro Trp Thr
                 85                  90                  95

Phe Gly Gly Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 194
<211> LENGTH: 705
<212> TYPE: PRT
<213> ORGANISM: Artificial Sequence
<220> FEATURE:
<223> OTHER INFORMATION: HC anti-TfR1 antibody conjugated to scFv anti-
      digoxigenin antibody fragment

<400> SEQUENCE: 194

Glu Val Gln Leu Gln Gln Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
             20                  25                  30

Thr Met Asn Trp Val Lys Gln Ser His Gly Glu Asn Leu Glu Trp Ile
         35                  40                  45

Gly Arg Ile Asn Pro His Asn Gly Gly Thr Asp Tyr Asn Gln Lys Phe
     50                  55                  60

Lys Asp Lys Ala Pro Leu Thr Val Asp Lys Ser Ser Asn Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Tyr Tyr Tyr Tyr Ser Leu Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gln Val Gln Leu Val Glu
        450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Asp Tyr Ala Met Ser Trp Ile Arg
                485                 490                 495

Gln Ala Pro Gly Lys Cys Leu Glu Trp Val Ser Ser Ile Asn Ile Gly
                500                 505                 510

Ala Thr Tyr Ile Tyr Tyr Ala Asp Ser Val Lys Gly Arg Phe Thr Ile
            515                 520                 525

Ser Arg Asp Asn Ala Lys Asn Ser Leu Tyr Leu Gln Met Asn Ser Leu
530                 535                 540

Arg Ala Glu Asp Thr Ala Val Tyr Tyr Cys Ala Arg Pro Gly Ser Pro
545                 550                 555                 560

Tyr Glu Tyr Asp Lys Ala Tyr Tyr Ser Met Ala Tyr Trp Gly Gln Gly
                565                 570                 575

Thr Thr Val Thr Val Ser Ser Gly Gly Gly Ser Gly Gly Gly Gly
                580                 585                 590

Ser Gly Gly Gly Gly Ser Asp Ile Gln Met Thr Gln Ser Pro Ser Ser
            595                 600                 605

Leu Ser Ala Ser Val Gly Asp Arg Val Thr Ile Thr Cys Arg Ala Ser
        610                 615                 620
```

```
Gln Asp Ile Lys Asn Tyr Leu Asn Trp Tyr Gln Gln Lys Pro Gly Lys
625                 630                 635                 640

Ala Pro Lys Leu Leu Ile Tyr Tyr Ser Ser Thr Leu Leu Ser Gly Val
                645                 650                 655

Pro Ser Arg Phe Ser Gly Ser Gly Ser Gly Thr Asp Phe Thr Leu Thr
            660                 665                 670

Ile Ser Ser Leu Gln Pro Glu Asp Phe Ala Thr Tyr Tyr Cys Gln Gln
        675                 680                 685

Ser Ile Thr Leu Pro Pro Thr Phe Gly Cys Gly Thr Lys Val Glu Ile
        690                 695                 700

Lys
705

<210> SEQ ID NO 195
<211> LENGTH: 706
<212> TYPE: PRT
<213> ORGANISM: Artificial Sequence
<220> FEATURE:
<223> OTHER INFORMATION: HC anti-TfR1 antibody conjugated to scFv anti-
      biotin antibody fragment

<400> SEQUENCE: 195

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Glu Asn Leu Glu Trp Ile
            35                  40                  45

Gly Arg Ile Asn Pro His Asn Gly Gly Thr Asp Tyr Asn Gln Lys Phe
        50                  55                  60

Lys Asp Lys Ala Pro Leu Thr Val Asp Lys Ser Ser Asn Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Tyr Tyr Tyr Tyr Ser Leu Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

-continued

Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Ser Asp Ile Gln Met Thr Gln
    450                 455                 460
Ser Pro Ser Ser Leu Ser Ala Ser Val Gly Asp Arg Val Thr Ile Thr
465                 470                 475                 480
Cys Arg Ala Ser Gly Asn Ile His Asn Tyr Leu Ser Trp Tyr Gln Gln
                485                 490                 495
Lys Pro Gly Lys Val Pro Lys Leu Leu Ile Tyr Ser Ala Lys Thr Leu
            500                 505                 510
Ala Asp Gly Val Pro Ser Arg Phe Ser Gly Ser Gly Ser Gly Thr Asp
        515                 520                 525
Phe Thr Leu Thr Ile Ser Ser Leu Gln Pro Glu Asp Val Ala Thr Tyr
    530                 535                 540
Tyr Cys Gln His Phe Trp Ser Ser Ile Tyr Thr Phe Gly Cys Gly Thr
545                 550                 555                 560
Lys Leu Glu Ile Lys Arg Gly Gly Gly Ser Gly Gly Gly Gly Ser
                565                 570                 575
Gly Gly Gly Gly Ser Gly Gly Gly Ser Gln Val Gln Leu Val Gln
            580                 585                 590
Ser Gly Ala Glu Val Lys Lys Pro Gly Ser Ser Val Lys Val Ser Cys
        595                 600                 605
Lys Ser Ser Gly Phe Asn Asn Lys Asp Thr Phe Phe Gln Trp Val Arg
    610                 615                 620
Gln Ala Pro Gly Gln Cys Leu Glu Trp Met Gly Arg Ile Asp Pro Ala
625                 630                 635                 640
Asn Gly Phe Thr Lys Tyr Ala Gln Lys Phe Gln Gly Arg Val Thr Ile
                645                 650                 655
Thr Ala Asp Thr Ser Thr Ser Thr Ala Tyr Met Glu Leu Ser Ser Leu
            660                 665                 670
Arg Ser Glu Asp Thr Ala Val Tyr Tyr Cys Ala Arg Trp Asp Thr Tyr
        675                 680                 685

```
Gly Ala Ala Trp Phe Ala Tyr Trp Gly Gln Gly Thr Leu Val Thr Val
            690                 695                 700

Ser Ser
705

<210> SEQ ID NO 196
<211> LENGTH: 213
<212> TYPE: PRT
<213> ORGANISM: Artificial Sequence
<220> FEATURE:
<223> OTHER INFORMATION: LC anti-TfR2 antibody

<400> SEQUENCE: 196

Gln Ile Val Leu Thr Gln Ser Pro Ala Ile Met Ser Ala Ser Pro Gly
1               5                   10                  15

Glu Lys Val Thr Val Thr Cys Ser Ala Ser Ser Ser Ile Arg Tyr Met
            20                  25                  30

His Trp Tyr Gln Gln Lys Pro Gly Thr Ser Pro Lys Arg Trp Ile Tyr
        35                  40                  45

Asp Thr Ser Glu Leu Ala Ser Gly Val Pro Ala Arg Phe Ser Gly Ser
    50                  55                  60

Gly Ser Gly Thr Ser Tyr Ser Leu Thr Ile Asn Ser Met Glu Ala Glu
65                  70                  75                  80

Asp Ala Ala Thr Tyr Tyr Cys His Gln Arg Ser Ser Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 197
<211> LENGTH: 705
<212> TYPE: PRT
<213> ORGANISM: Artificial Sequence
<220> FEATURE:
<223> OTHER INFORMATION: HC anti-TfR2 antibody conjugated to scFv anti-
      digoxigenin antibody fragment

<400> SEQUENCE: 197

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Val Asn Pro Tyr Asn Asp Asp Thr Lys Tyr Asn Glu Lys Phe
```

```
                50                  55                  60
Arg Gly Lys Ala Thr Leu Thr Ser Asp Lys Ser Ser Thr Ala Tyr
65                  70                  75                  80
Met Glu Leu Ser Ser Leu Thr Ser Glu Asp Ser Ala Val Tyr Tyr Cys
                    85                  90                  95
Ala Arg Ser Tyr Tyr Tyr Ser Met Asp Asn Trp Gly Gln Gly Thr
                100                 105                 110
Ser Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
Gly Gly Gly Gly Ser Gly Gly Gly Ser Gln Val Gln Leu Val Glu
                450                 455                 460
Ser Gly Gly Gly Leu Val Lys Pro Gly Gly Ser Leu Arg Leu Ser Cys
465                 470                 475                 480
```

```
Ala Ala Ser Gly Phe Thr Phe Ser Asp Tyr Ala Met Ser Trp Ile Arg
            485                 490                 495

Gln Ala Pro Gly Lys Cys Leu Glu Trp Val Ser Ser Ile Asn Ile Gly
        500                 505                 510

Ala Thr Tyr Ile Tyr Tyr Ala Asp Ser Val Lys Gly Arg Phe Thr Ile
    515                 520                 525

Ser Arg Asp Asn Ala Lys Asn Ser Leu Tyr Leu Gln Met Asn Ser Leu
530                 535                 540

Arg Ala Glu Asp Thr Ala Val Tyr Tyr Cys Ala Arg Pro Gly Ser Pro
545                 550                 555                 560

Tyr Glu Tyr Asp Lys Ala Tyr Tyr Ser Met Ala Tyr Trp Gly Gln Gly
                565                 570                 575

Thr Thr Val Thr Val Ser Ser Gly Gly Gly Gly Ser Gly Gly Gly Gly
            580                 585                 590

Ser Gly Gly Gly Gly Ser Asp Ile Gln Met Thr Gln Ser Pro Ser Ser
        595                 600                 605

Leu Ser Ala Ser Val Gly Asp Arg Val Thr Ile Thr Cys Arg Ala Ser
    610                 615                 620

Gln Asp Ile Lys Asn Tyr Leu Asn Trp Tyr Gln Gln Lys Pro Gly Lys
625                 630                 635                 640

Ala Pro Lys Leu Leu Ile Tyr Tyr Ser Ser Thr Leu Leu Ser Gly Val
                645                 650                 655

Pro Ser Arg Phe Ser Gly Ser Gly Ser Gly Thr Asp Phe Thr Leu Thr
            660                 665                 670

Ile Ser Ser Leu Gln Pro Glu Asp Phe Ala Thr Tyr Tyr Cys Gln Gln
        675                 680                 685

Ser Ile Thr Leu Pro Pro Thr Phe Gly Cys Gly Thr Lys Val Glu Ile
    690                 695                 700

Lys
705

<210> SEQ ID NO 198
<211> LENGTH: 725
<212> TYPE: PRT
<213> ORGANISM: Artificial Sequence
<220> FEATURE:
<223> OTHER INFORMATION: HC anti-TfR2 antibody conjugated to scFv anti-
      biotin antibody fragment

<400> SEQUENCE: 198

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Val Asn Pro Tyr Asn Asp Asp Thr Lys Tyr Asn
65                  70                  75                  80

Glu Lys Phe Arg Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Ser Tyr Tyr Tyr Tyr Ser Met Asp Asn Trp Gly
```

```
            115                 120                 125
Gln Gly Thr Ser Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys Gly Gly Gly Gly Ser Gly Gly Gly Gly Ser Asp Ile Gln
465                 470                 475                 480
Met Thr Gln Ser Pro Ser Ser Leu Ser Ala Ser Val Gly Asp Arg Val
                485                 490                 495
Thr Ile Thr Cys Arg Ala Ser Gly Asn Ile His Asn Tyr Leu Ser Trp
            500                 505                 510
Tyr Gln Gln Lys Pro Gly Lys Val Pro Lys Leu Leu Ile Tyr Ser Ala
        515                 520                 525
Lys Thr Leu Ala Asp Gly Val Pro Ser Arg Phe Ser Gly Ser Gly Ser
530                 535                 540
```

```
Gly Thr Asp Phe Thr Leu Thr Ile Ser Ser Leu Gln Pro Glu Asp Val
545                 550                 555                 560

Ala Thr Tyr Tyr Cys Gln His Phe Trp Ser Ser Ile Tyr Thr Phe Gly
                565                 570                 575

Cys Gly Thr Lys Leu Glu Ile Lys Arg Gly Gly Gly Gly Ser Gly Gly
            580                 585                 590

Gly Gly Ser Gly Gly Gly Gly Ser Gly Gly Gly Gly Ser Gln Val Gln
            595                 600                 605

Leu Val Gln Ser Gly Ala Glu Val Lys Lys Pro Gly Ser Ser Val Lys
        610                 615                 620

Val Ser Cys Lys Ser Ser Gly Phe Asn Asn Lys Asp Thr Phe Phe Gln
625                 630                 635                 640

Trp Val Arg Gln Ala Pro Gly Gln Cys Leu Glu Trp Met Gly Arg Ile
                645                 650                 655

Asp Pro Ala Asn Gly Phe Thr Lys Tyr Ala Gln Lys Phe Gln Gly Arg
            660                 665                 670

Val Thr Ile Thr Ala Asp Thr Ser Thr Ser Thr Ala Tyr Met Glu Leu
        675                 680                 685

Ser Ser Leu Arg Ser Glu Asp Thr Ala Val Tyr Tyr Cys Ala Arg Trp
    690                 695                 700

Asp Thr Tyr Gly Ala Ala Trp Phe Ala Tyr Trp Gly Gln Gly Thr Leu
705                 710                 715                 720

Val Thr Val Ser Ser
                725
```

```
<210> SEQ ID NO 199
<211> LENGTH: 51
<212> TYPE: DNA
<213> ORGANISM: Artificial Sequence
<220> FEATURE:
<223> OTHER INFORMATION: terminally mono-biotinylated or mono-
      digoxigeninylated double-stranded DNA 50 mer payload
<220> FEATURE:
<221> NAME/KEY: misc_structure
<222> LOCATION: (1)..(1)
<223> OTHER INFORMATION: n=biotin or digoxigenin
<220> FEATURE:
<221> NAME/KEY: misc_feature
<222> LOCATION: (1)..(1)
<223> OTHER INFORMATION: n is a, c, g, or t

<400> SEQUENCE: 199
naccaagcct agagaggagc aatacaacag tacatatcgc gtggtaagcg t          51

<210> SEQ ID NO 200
<211> LENGTH: 20
<212> TYPE: DNA
<213> ORGANISM: Artificial Sequence
<220> FEATURE:
<223> OTHER INFORMATION: PrFor

<400> SEQUENCE: 200
accaagccta gagaggagca                                              20

<210> SEQ ID NO 201
<211> LENGTH: 20
<212> TYPE: DNA
<213> ORGANISM: Artificial Sequence
<220> FEATURE:
<223> OTHER INFORMATION: PrRev

<400> SEQUENCE: 201
```

```
acgcttacca cgcgatatgt                                              20
```

<210> SEQ ID NO 202
<211> LENGTH: 12
<212> TYPE: PRT
<213> ORGANISM: Saccharomyces cerevisiae

<400> SEQUENCE: 202

Ala His Leu Glu Asn Glu Val Ala Arg Leu Lys Lys
1               5                   10

<210> SEQ ID NO 203
<211> LENGTH: 12
<212> TYPE: PRT
<213> ORGANISM: Artificial Sequence
<220> FEATURE:
<223> OTHER INFORMATION: helicar motif variant 1

<400> SEQUENCE: 203

Ala His Leu Glu Asn Glu Val Ala Arg Cys Lys Lys
1               5                   10

<210> SEQ ID NO 204
<211> LENGTH: 12
<212> TYPE: PRT
<213> ORGANISM: Artificial Sequence
<220> FEATURE:
<223> OTHER INFORMATION: helicar motif variant 2

<400> SEQUENCE: 204

Ala His Leu Glu Asn Glu Val Ala Arg Leu Cys Lys
1               5                   10

<210> SEQ ID NO 205
<211> LENGTH: 109
<212> TYPE: PRT
<213> ORGANISM: Artificial Sequence
<220> FEATURE:
<223> OTHER INFORMATION: anti-helicar antibody VH

<400> SEQUENCE: 205

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Phe Thr Gly
        35                  40                  45

Leu Ile Gly Gly Thr Asn Asn Arg Ala Pro Trp Thr Pro Ala Arg Phe
    50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 206
<211> LENGTH: 109
<212> TYPE: PRT
<213> ORGANISM: Artificial Sequence
<220> FEATURE:
<223> OTHER INFORMATION: anti-helicar antibody VL -continued

```
<400> SEQUENCE: 206

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 207
<211> LENGTH: 109
<212> TYPE: PRT
<213> ORGANISM: Artificial Sequence
<220> FEATURE:
<223> OTHER INFORMATION: anti-helicar antibody VL55C

<400> SEQUENCE: 207

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Cys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 208
<211> LENGTH: 109
<212> TYPE: PRT
<213> ORGANISM: Artificial Sequence
<220> FEATURE:
<223> OTHER INFORMATION: anti-helicar antibody VL51C

<400> SEQUENCE: 208

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Cys Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80
```

Gln Thr Glu Asp Glu Ala Ile Tyr Phe Cys Ala Leu Trp Tyr Ser Asn
            85                  90                  95

His Trp Val Phe Gly Gly Gly Thr Lys Leu Thr Val Leu
            100                 105

<210> SEQ ID NO 209
<211> LENGTH: 107
<212> TYPE: PRT
<213> ORGANISM: Homo sapiens

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 210
<211> LENGTH: 106
<212> TYPE: PRT
<213> ORGANISM: Homo sapiens

<400> SEQUENCE: 210

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 211
<211> LENGTH: 34
<212> TYPE: PRT
<213> ORGANISM: Homo sapiens
<220> FEATURE:
<221> NAME/KEY: MISC_FEATURE
<222> LOCATION: (34)..(34)
<223> OTHER INFORMATION: X=tyrosine amide

<400> SEQUENCE: 211

Ile Lys Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Leu Val Thr Arg Gln
                20                  25                  30

Arg Xaa

<210> SEQ ID NO 212
<211> LENGTH: 34
<212> TYPE: PRT
<213> ORGANISM: Artificial Sequence
<220> FEATURE:
<223> OTHER INFORMATION: PYY3-36 helicar
<220> FEATURE:
<221> NAME/KEY: MISC_FEATURE
<222> LOCATION: (34)..(34)
<223> OTHER INFORMATION: X=thyrosine amide

<400> SEQUENCE: 212

Ile Lys Pro Glu Ala Pro Gly Glu Asp Ala Ser Pro Glu Ala His Leu
1               5                   10                  15

Ala Asn Glu Val Ala Arg Leu His Tyr Leu Asn Leu Val Thr Arg Gln
                20                  25                  30

Arg Xaa

<210> SEQ ID NO 213
<211> LENGTH: 244
<212> TYPE: PRT
<213> ORGANISM: Artificial Sequence
<220> FEATURE:
<223> OTHER INFORMATION: helicar motif amino acid sequence cystein
      variant 1 fused to pseudomonas exotoxin LR8M with a GGG-peptidic
      linker and the C-terminal K deleted

<400> SEQUENCE: 213

Ala His Leu Glu Asn Glu Val Ala Arg Leu Cys Lys Gly Gly Gly Arg
1               5                   10                  15

His Arg Gln Pro Arg Gly Trp Glu Gln Leu Pro Thr Gly Ala Glu Phe
                20                  25                  30

Leu Gly Asp Gly Gly Ala Val Ser Phe Ser Thr Arg Gly Thr Gln Asn
            35                  40                  45

Trp Thr Val Glu Arg Leu Leu Gln Ala His Arg Gln Leu Glu Glu Gly
    50                  55                  60

Gly Tyr Val Phe Val Gly Tyr His Gly Thr Phe Leu Glu Ala Ala Gln
65                  70                  75                  80

Ser Ile Val Phe Gly Gly Val Arg Ala Arg Ser Gln Asp Leu Asp Ala
                85                  90                  95

Ile Trp Ala Gly Phe Tyr Ile Ala Gly Asp Pro Ala Leu Ala Tyr Gly
            100                 105                 110

Tyr Ala Gln Asp Gln Glu Pro Asp Ala Ala Gly Arg Ile Arg Asn Gly
        115                 120                 125

Ala Leu Leu Arg Val Tyr Val Pro Arg Ser Ser Leu Pro Gly Phe Tyr
    130                 135                 140

Ala Thr Ser Leu Thr Leu Ala Ala Pro Glu Ala Ala Gly Glu Val Glu
145                 150                 155                 160

Arg Leu Ile Gly His Pro Leu Pro Leu Arg Leu Asp Ala Ile Thr Gly
                165                 170                 175

Pro Glu Glu Ser Gly Gly Arg Leu Glu Thr Ile Leu Gly Trp Pro Leu
            180                 185                 190

Ala Glu Arg Thr Val Val Ile Pro Ser Ala Ile Pro Thr Asp Pro Arg
        195                 200                 205

Asn Val Gly Gly Asp Leu Asp Pro Ser Ser Ile Pro Asp Ser Glu Ala
```

```
                210                 215                 220
Ala Ile Ser Ala Leu Pro Asp Tyr Ala Ser Gln Pro Gly Lys Pro Pro
225                 230                 235                 240

Arg Glu Asp Leu

<210> SEQ ID NO 214
<211> LENGTH: 5
<212> TYPE: PRT
<213> ORGANISM: Mus musculus

<400> SEQUENCE: 214

Glu Tyr Pro Ile His
1               5

<210> SEQ ID NO 215
<211> LENGTH: 10
<212> TYPE: PRT
<213> ORGANISM: Mus musculus

<400> SEQUENCE: 215

Gly Tyr Thr Phe Pro Glu Tyr Pro Ile His
1               5                   10

<210> SEQ ID NO 216
<211> LENGTH: 17
<212> TYPE: PRT
<213> ORGANISM: Artificial Sequence
<220> FEATURE:
<223> OTHER INFORMATION: humanized CDR-H2

<400> SEQUENCE: 216

Gly Ile Val Pro Asn Asn Gly Phe Thr Phe Tyr Ala Gln Lys Leu Gln
1               5                   10                  15

Gly

<210> SEQ ID NO 217
<211> LENGTH: 6
<212> TYPE: PRT
<213> ORGANISM: Mus musculus

<400> SEQUENCE: 217

Val Pro Asn Asn Gly Phe
1               5

<210> SEQ ID NO 218
<211> LENGTH: 10
<212> TYPE: PRT
<213> ORGANISM: Mus musculus

<400> SEQUENCE: 218

Lys Asn Leu Gly Ser Ser Pro Leu Asp Tyr
1               5                   10

<210> SEQ ID NO 219
<211> LENGTH: 11
<212> TYPE: PRT
<213> ORGANISM: Mus musculus

<400> SEQUENCE: 219

Arg Ala Ser Gln Ser Ile Gly Thr Ser Ile His
1               5                   10

<210> SEQ ID NO 220
```

```
<211> LENGTH: 7
<212> TYPE: PRT
<213> ORGANISM: Mus musculus

<400> SEQUENCE: 220

Tyr Ala Ser Glu Ser Ile Ser
1               5

<210> SEQ ID NO 221
<211> LENGTH: 9
<212> TYPE: PRT
<213> ORGANISM: Mus musculus

<400> SEQUENCE: 221

Gln Gln Ser Asn Arg Trp Pro Leu Thr
1               5

<210> SEQ ID NO 222
<211> LENGTH: 119
<212> TYPE: PRT
<213> ORGANISM: Artificial Sequence
<220> FEATURE:
<223> OTHER INFORMATION: humanized heavy chain variable domain

<400> SEQUENCE: 222

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Glu Tyr
                20                  25                  30

Pro Ile His Trp Val Arg Gln Ala Pro Gly Gln Gly Leu Glu Trp Met
            35                  40                  45

Gly Gly Ile Val Pro Asn Asn Gly Phe Thr Phe Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Asn Leu Gly Ser Ser Pro Leu Asp Tyr Trp Gly Gln Gly
            100                 105                 110

Thr Thr Val Thr Val Ser Ser
        115

<210> SEQ ID NO 223
<211> LENGTH: 107
<212> TYPE: PRT
<213> ORGANISM: Artificial Sequence
<220> FEATURE:
<223> OTHER INFORMATION: humanized light chain variable domain

<400> SEQUENCE: 223

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
                20                  25                  30

Ile His Trp Tyr Gln Gln Lys Pro Gly Gln Ala Pro Arg Leu Leu Ile
            35                  40                  45

Lys Tyr Ala Ser Glu Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80
```

Glu Asp Phe Ala Val Tyr Tyr Cys Gln Gln Ser Asn Arg Trp Pro Leu
            85                  90                  95

Thr Leu Gly Gln Gly Thr Lys Leu Glu Ile Lys
        100                 105

<210> SEQ ID NO 224
<211> LENGTH: 119
<212> TYPE: PRT
<213> ORGANISM: Mus musculus

<400> SEQUENCE: 224

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Pro Glu Tyr
            20                  25                  30

Pro Ile His Trp Val Lys Gln Ser His Gly Lys Ser Leu Glu Trp Ile
        35                  40                  45

Gly Gly Ile Val Pro Asn Asn Gly Phe Thr Phe Tyr Asn Gln Lys Phe
    50                  55                  60

Lys Gly Lys Ala Ser Leu Thr Val Asp Lys Ser Ser Ser Thr Ala Tyr
65                  70                  75                  80

Val Glu Val Arg Ser Leu Thr Ser Asp Asp Ser Ala Val Tyr Tyr Cys
                85                  90                  95

Ala Arg Lys Asn Leu Gly Ser Ser Pro Leu Asp Tyr Trp Gly Gln Gly
            100                 105                 110

Thr Thr Leu Thr Val Ser Ser
        115

<210> SEQ ID NO 225
<211> LENGTH: 107
<212> TYPE: PRT
<213> ORGANISM: Mus musculus

<400> SEQUENCE: 225

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln His Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Arg Trp Pro Leu
                85                  90                  95

Thr Leu Gly Ala Gly Thr Lys Leu Glu Leu Lys
            100                 105

<210> SEQ ID NO 226
<211> LENGTH: 119
<212> TYPE: PRT
<213> ORGANISM: Artificial Sequence
<220> FEATURE:
<223> OTHER INFORMATION: VH variant with cysteine at position 52b/53
      according to Kabat

<400> SEQUENCE: 226

Gln Val Gln Leu Val Gln Ser Gly Ala Glu Val Lys Lys Pro Gly Ala

```
                 1               5                  10                  15
            Ser Val Lys Val Ser Cys Lys Ala Ser Gly Tyr Thr Phe Pro Glu Tyr
                             20                  25                  30

Pro Ile His Trp Val Arg Gln Ala Pro Gly Gln Gly Leu Glu Trp Met
                         35                  40                  45

Gly Gly Ile Val Pro Cys Asn Gly Phe Thr Phe Tyr Ala Gln Lys Leu
                     50                  55                  60

Gln Gly Arg Val Thr Met Thr Thr Asp Thr Ser Thr Ser Thr Ala Tyr
             65                  70                  75                  80

Met Glu Leu Arg Ser Leu Arg Ser Asp Asp Thr Ala Val Tyr Tyr Cys
                             85                  90                  95

Ala Arg Lys Asn Leu Gly Ser Ser Pro Leu Asp Tyr Trp Gly Gln Gly
                         100                 105                 110

Thr Thr Val Thr Val Ser Ser
                         115

<210> SEQ ID NO 227
<211> LENGTH: 119
<212> TYPE: PRT
<213> ORGANISM: Artificial Sequence
<220> FEATURE:
<223> OTHER INFORMATION: VH sequence with cysteine at position 28

<400> SEQUENCE: 227

Gln Val Gln Leu Val Gln Ser Gly Ala Glu Val Lys Lys Pro Gly Ala
             1               5                  10                  15

Ser Val Lys Val Ser Cys Lys Ala Ser Gly Tyr Cys Phe Pro Glu Tyr
                             20                  25                  30

Pro Ile His Trp Val Arg Gln Ala Pro Gly Gln Gly Leu Glu Trp Met
                         35                  40                  45

Gly Gly Ile Val Pro Asn Asn Gly Phe Thr Phe Tyr Ala Gln Lys Leu
                     50                  55                  60

Gln Gly Arg Val Thr Met Thr Thr Asp Thr Ser Thr Ser Thr Ala Tyr
             65                  70                  75                  80

Met Glu Leu Arg Ser Leu Arg Ser Asp Asp Thr Ala Val Tyr Tyr Cys
                             85                  90                  95

Ala Arg Lys Asn Leu Gly Ser Ser Pro Leu Asp Tyr Trp Gly Gln Gly
                         100                 105                 110

Thr Thr Val Thr Val Ser Ser
                         115

<210> SEQ ID NO 228
<211> LENGTH: 51
<212> TYPE: DNA
<213> ORGANISM: Artificial Sequence
<220> FEATURE:
<223> OTHER INFORMATION: BRDU-DNA conjugate
<220> FEATURE:
<221> NAME/KEY: misc_RNA
<222> LOCATION: (1)..(1)
<223> OTHER INFORMATION: BRDU
<220> FEATURE:
<221> NAME/KEY: misc_feature
<222> LOCATION: (1)..(1)
<223> OTHER INFORMATION: n is a, c, g, or t

<400> SEQUENCE: 228
naccaagcct agagaggagc aatacaacag tacatatcgc gtggtaagcg t          51

<210> SEQ ID NO 229
```

-continued

```
<211> LENGTH: 7
<212> TYPE: PRT
<213> ORGANISM: Oryctolagus cuniculus

<400> SEQUENCE: 229

Ser Ala Ser Thr Leu Asp Phe
1               5

<210> SEQ ID NO 230
<211> LENGTH: 5
<212> TYPE: PRT
<213> ORGANISM: Oryctolagus cuniculus

<400> SEQUENCE: 230

Ser Asn Ala Ile Asn
1               5

<210> SEQ ID NO 231
<211> LENGTH: 16
<212> TYPE: PRT
<213> ORGANISM: Oryctolagus cuniculus

<400> SEQUENCE: 231

Tyr Ile Ala Val Ser Gly Asn Thr Tyr Tyr Ala Ser Trp Ala Lys Gly
1               5                   10                  15

<210> SEQ ID NO 232
<211> LENGTH: 3
<212> TYPE: PRT
<213> ORGANISM: Oryctolagus cuniculus

<400> SEQUENCE: 232

Ser Asn Ile
1

<210> SEQ ID NO 233
<211> LENGTH: 12
<212> TYPE: PRT
<213> ORGANISM: Artificial Sequence
<220> FEATURE:
<223> OTHER INFORMATION: humanized sequence

<400> SEQUENCE: 233

Arg Ser Ser Gln Ser Val Arg Thr Asn Lys Leu Ala
1               5                   10

<210> SEQ ID NO 234
<211> LENGTH: 12
<212> TYPE: PRT
<213> ORGANISM: Artificial Sequence
<220> FEATURE:
<223> OTHER INFORMATION: humanized sequence

<400> SEQUENCE: 234

Arg Ser Ser Gln Ser Val Arg Thr Asn Arg Leu Ala
1               5                   10

<210> SEQ ID NO 235
<211> LENGTH: 7
<212> TYPE: PRT
<213> ORGANISM: Artificial Sequence
<220> FEATURE:
<223> OTHER INFORMATION: humanized sequence

<400> SEQUENCE: 235

Ser Ala Ser Thr Leu Asp Tyr
```

```
<210> SEQ ID NO 236
<211> LENGTH: 12
<212> TYPE: PRT
<213> ORGANISM: Artificial Sequence
<220> FEATURE:
<223> OTHER INFORMATION: humanized sequence

<400> SEQUENCE: 236

Leu Gly Tyr Phe Asp Ser Ser Ala Asp Ile Val Ala
1               5                   10

<210> SEQ ID NO 237
<211> LENGTH: 111
<212> TYPE: PRT
<213> ORGANISM: Artificial Sequence
<220> FEATURE:
<223> OTHER INFORMATION: humanized sequence

<400> SEQUENCE: 237

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 238
<211> LENGTH: 111
<212> TYPE: PRT
<213> ORGANISM: Artificial Sequence
<220> FEATURE:
<223> OTHER INFORMATION: humanized sequence

<400> SEQUENCE: 238

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 239
```

```
<211> LENGTH: 16
<212> TYPE: PRT
<213> ORGANISM: Artificial Sequence
<220> FEATURE:
<223> OTHER INFORMATION: humanized sequence

<400> SEQUENCE: 239

Tyr Ile Ala Val Ser Gly Asn Thr Tyr Tyr Ala Asp Ser Val Lys Gly
1               5                   10                  15

<210> SEQ ID NO 240
<211> LENGTH: 111
<212> TYPE: PRT
<213> ORGANISM: Artificial Sequence
<220> FEATURE:
<223> OTHER INFORMATION: humanized sequence

<400> SEQUENCE: 240

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
                20                  25                  30

Ala Ile Asn Trp Val Arg Gln Ala Pro Gly Lys Gly Leu Glu Trp Val
            35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 241
<211> LENGTH: 112
<212> TYPE: PRT
<213> ORGANISM: Artificial Sequence
<220> FEATURE:
<223> OTHER INFORMATION: humanized sequence

<400> SEQUENCE: 241

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
                20                  25                  30

Lys Leu Ala Trp Phe Gln Gln Lys Pro Gly Gln Pro Pro Lys Arg Leu
            35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 242
<211> LENGTH: 112
<212> TYPE: PRT
<213> ORGANISM: Artificial Sequence
<220> FEATURE:
```

<223> OTHER INFORMATION: humanizes sequence

<400> SEQUENCE: 242

Ala Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 243
<211> LENGTH: 4
<212> TYPE: PRT
<213> ORGANISM: Artificial Sequence
<220> FEATURE:
<223> OTHER INFORMATION: CDRH1

<400> SEQUENCE: 243

Tyr Ala Met Ile
1

<210> SEQ ID NO 244
<211> LENGTH: 9
<212> TYPE: PRT
<213> ORGANISM: Artificial Sequence
<220> FEATURE:
<223> OTHER INFORMATION: CDRH2

<400> SEQUENCE: 244

Pro Ser Gly Asn Thr Tyr Tyr Ala Asn
1               5

<210> SEQ ID NO 245
<211> LENGTH: 10
<212> TYPE: PRT
<213> ORGANISM: Artificial Sequence
<220> FEATURE:
<223> OTHER INFORMATION: CDRH3

<400> SEQUENCE: 245

Arg Asp Gly Thr Asp Lys Thr Phe Asn Ile
1               5                   10

<210> SEQ ID NO 246
<211> LENGTH: 6
<212> TYPE: PRT
<213> ORGANISM: Artificial Sequence
<220> FEATURE:
<223> OTHER INFORMATION: CDRL1

<400> SEQUENCE: 246

Asn Val Tyr Gly Asp Asn
1               5

<210> SEQ ID NO 247

```
<211> LENGTH: 6
<212> TYPE: PRT
<213> ORGANISM: Artificial Sequence
<220> FEATURE:
<223> OTHER INFORMATION: CDRL2

<400> SEQUENCE: 247

Glu Ala Ser Lys Leu Ala
1               5

<210> SEQ ID NO 248
<211> LENGTH: 10
<212> TYPE: PRT
<213> ORGANISM: Artificial Sequence
<220> FEATURE:
<223> OTHER INFORMATION: CDRL3

<400> SEQUENCE: 248

Gly Glu Phe Leu Cys Thr Thr Ser Asp Cys
1               5                   10

<210> SEQ ID NO 249
<211> LENGTH: 5
<212> TYPE: PRT
<213> ORGANISM: Artificial Sequence
<220> FEATURE:
<223> OTHER INFORMATION: CDRH1

<400> SEQUENCE: 249

Ser Tyr Ala Met Ile
1               5

<210> SEQ ID NO 250
<211> LENGTH: 16
<212> TYPE: PRT
<213> ORGANISM: Artificial Sequence
<220> FEATURE:
<223> OTHER INFORMATION: CDRH2

<400> SEQUENCE: 250

Val Ile Tyr Pro Ser Gly Asn Thr Tyr Tyr Ala Asn Trp Ala Lys Gly
1               5                   10                  15

<210> SEQ ID NO 251
<211> LENGTH: 13
<212> TYPE: PRT
<213> ORGANISM: Artificial Sequence
<220> FEATURE:
<223> OTHER INFORMATION: CDRL1

<400> SEQUENCE: 251

Gln Ala Ser Gln Asn Val Tyr Gly Asp Asn Tyr Leu Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: CDRL2

<400> SEQUENCE: 252

Glu Ala Ser Lys Leu Ala Ser
1               5

<210> SEQ ID NO 253
<211> LENGTH: 13
```

<212> TYPE: PRT
<213> ORGANISM: Artificial Sequence
<220> FEATURE:
<223> OTHER INFORMATION: CDRL3

<400> SEQUENCE: 253

Gln Gly Glu Phe Leu Cys Thr Thr Ser Asp Cys Phe Thr
1               5                   10

<210> SEQ ID NO 254
<211> LENGTH: 115
<212> TYPE: PRT
<213> ORGANISM: Artificial Sequence
<220> FEATURE:
<223> OTHER INFORMATION: heavy chain variable domain

<400> SEQUENCE: 254

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Ile Asn Ser Tyr Ala
            20                  25                  30

Met Ile Trp Val Arg Gln Ala Pro Gly Glu Gly Leu Glu Trp Ile Gly
        35                  40                  45

Val Ile Tyr Pro Ser Gly Asn Thr Tyr Tyr Ala Asn Trp Ala Lys Gly
    50                  55                  60

Arg Phe Thr Val Ser Arg Thr Ser Thr Val Asp Leu Lys Ile Thr
65                  70                  75                  80

Ser Pro Thr Thr Glu Asp Thr Ala Thr Tyr Phe Cys Ala Arg Arg Asp
                85                  90                  95

Gly Thr Asp Lys Thr Phe Asn Ile Trp Gly Pro Gly Thr Leu Val Thr
            100                 105                 110

Val Ser Leu
        115

<210> SEQ ID NO 255
<211> LENGTH: 112
<212> TYPE: PRT
<213> ORGANISM: Artificial Sequence
<220> FEATURE:
<223> OTHER INFORMATION: light chain variable domain

<400> SEQUENCE: 255

Gln Val Leu Thr Gln Thr Pro Ser Pro Val Ser Ala Ala Val Gly Gly
1               5                   10                  15

Thr Val Thr Ile Asn Cys Gln Ala Ser Gln Asn Val Tyr Gly Asp Asn
            20                  25                  30

Tyr Leu Ala Trp Tyr Gln Gln Lys Pro Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Glu Phe Leu Cys Thr
                85                  90                  95

Thr Ser Asp Cys Phe Thr Phe Gly Gly Gly Thr Gly Val Val Val Arg
            100                 105                 110

<210> SEQ ID NO 256
<211> LENGTH: 3
<212> TYPE: PRT

```
<213> ORGANISM: Artificial Sequence
<220> FEATURE:
<223> OTHER INFORMATION: CDRH1

<400> SEQUENCE: 256

Arg Tyr Ala
1

<210> SEQ ID NO 257
<211> LENGTH: 5
<212> TYPE: PRT
<213> ORGANISM: Artificial Sequence
<220> FEATURE:
<223> OTHER INFORMATION: CDRH2

<400> SEQUENCE: 257

Asn Ser Ser Gly Ala
1               5

<210> SEQ ID NO 258
<211> LENGTH: 14
<212> TYPE: PRT
<213> ORGANISM: Artificial Sequence
<220> FEATURE:
<223> OTHER INFORMATION: CDRH3

<400> SEQUENCE: 258

Trp Thr Tyr Asp Asp Tyr Gly Asp Phe Gln Gly Phe Asn Ile
1               5                   10

<210> SEQ ID NO 259
<211> LENGTH: 9
<212> TYPE: PRT
<213> ORGANISM: Artificial Sequence
<220> FEATURE:
<223> OTHER INFORMATION: CDRL1

<400> SEQUENCE: 259

Ser Val Tyr Asn Asn Asn Asp Leu Ala
1               5

<210> SEQ ID NO 260
<211> LENGTH: 6
<212> TYPE: PRT
<213> ORGANISM: Artificial Sequence
<220> FEATURE:
<223> OTHER INFORMATION: CDRL2

<400> SEQUENCE: 260

Arg Ala Ser Lys Leu Ala
1               5

<210> SEQ ID NO 261
<211> LENGTH: 11
<212> TYPE: PRT
<213> ORGANISM: Artificial Sequence
<220> FEATURE:
<223> OTHER INFORMATION: CDRL3

<400> SEQUENCE: 261

Gly Gly Tyr Asp Asp Ala Asp Met Gly Ala
1               5                   10

<210> SEQ ID NO 262
<211> LENGTH: 5
<212> TYPE: PRT
<213> ORGANISM: Artificial Sequence
```

-continued

```
<220> FEATURE:
<223> OTHER INFORMATION: CDRH1

<400> SEQUENCE: 262

Arg Tyr Ala Met Ser
1               5

<210> SEQ ID NO 263
<211> LENGTH: 16
<212> TYPE: PRT
<213> ORGANISM: Artificial Sequence
<220> FEATURE:
<223> OTHER INFORMATION: CDRH2

<400> SEQUENCE: 263

Val Ile Asn Ser Ser Gly Ala Thr Tyr Tyr Ala Ser Trp Ala Lys Gly
1               5                   10                  15

<210> SEQ ID NO 264
<211> LENGTH: 13
<212> TYPE: PRT
<213> ORGANISM: Artificial Sequence
<220> FEATURE:
<223> OTHER INFORMATION: CDRL1

<400> SEQUENCE: 264

Gln Ser Ser Gln Ser Val Tyr Asn Asn Asn Asp Leu Ala
1               5                   10

<210> SEQ ID NO 265
<211> LENGTH: 7
<212> TYPE: PRT
<213> ORGANISM: Artificial Sequence
<220> FEATURE:
<223> OTHER INFORMATION: CDRL2

<400> SEQUENCE: 265

Arg Ala Ser Lys Leu Ala Ser
1               5

<210> SEQ ID NO 266
<211> LENGTH: 12
<212> TYPE: PRT
<213> ORGANISM: Artificial Sequence
<220> FEATURE:
<223> OTHER INFORMATION: CDRL3

<400> SEQUENCE: 266

Leu Gly Gly Tyr Asp Asp Asp Ala Asp Met Gly Ala
1               5                   10

<210> SEQ ID NO 267
<211> LENGTH: 119
<212> TYPE: PRT
<213> ORGANISM: Artificial Sequence
<220> FEATURE:
<223> OTHER INFORMATION: heavy chain variable domain

<400> SEQUENCE: 267

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Tyr Ala
                20                  25                  30

Met Ser Trp Val Arg Gln Ala Pro Gly Lys Gly Leu Glu Trp Ile Gly
            35                  40                  45
```

Val Ile Asn Ser Ser Gly Ala Thr Tyr Tyr Ala Ser Trp Ala Lys Gly
            50                  55                  60

Arg Phe Thr Ile Ser Glu Thr Ser Thr Thr Val Glu Leu Lys Ile Thr
65                  70                  75                  80

Ser Pro Thr Thr Glu Asp Thr Ala Thr Tyr Phe Cys Ala Arg Trp Thr
                85                  90                  95

Tyr Asp Asp Tyr Gly Asp Phe Gln Gly Phe Asn Ile Trp Gly Pro Gly
                100                 105                 110

Thr Leu Val Thr Val Ser Leu
            115

<210> SEQ ID NO 268
<211> LENGTH: 111
<212> TYPE: PRT
<213> ORGANISM: Artificial Sequence
<220> FEATURE:
<223> OTHER INFORMATION: light chain variable domain

<400> SEQUENCE: 268

Ala Val Leu Thr Gln Thr Pro Ser Pro Val Ser Ala Ala Val Gly Gly
1               5                   10                  15

Thr Val Thr Ile Ser Cys Gln Ser Ser Gln Ser Val Tyr Asn Asn Asn
            20                  25                  30

Asp Leu Ala Trp Tyr Gln Gln Lys Pro Gly Gln Pro Pro Lys Leu Leu
        35                  40                  45

Ile Tyr Arg Ala Ser Lys Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Gly Tyr Asp Asp Asp
                85                  90                  95

Ala Asp Met Gly Ala Phe Gly Gly Gly Thr Glu Val Val Val Lys
                100                 105                 110

<210> SEQ ID NO 269
<211> LENGTH: 5
<212> TYPE: PRT
<213> ORGANISM: Artificial Sequence
<220> FEATURE:
<223> OTHER INFORMATION: CDRH1

<400> SEQUENCE: 269

Arg Asp Thr Met Ile
1               5

<210> SEQ ID NO 270
<211> LENGTH: 10
<212> TYPE: PRT
<213> ORGANISM: Artificial Sequence
<220> FEATURE:
<223> OTHER INFORMATION: CDRH2

<400> SEQUENCE: 270

Ser Ile Tyr Thr Asp Ser Gly Asn Thr Trp
1               5                   10

<210> SEQ ID NO 271
<211> LENGTH: 4
<212> TYPE: PRT
<213> ORGANISM: Artificial Sequence
<220> FEATURE:
<223> OTHER INFORMATION: CDRH3

<400> SEQUENCE: 271

Asn Phe Ser Val
1

<210> SEQ ID NO 272
<211> LENGTH: 6
<212> TYPE: PRT
<213> ORGANISM: Artificial Sequence
<220> FEATURE:
<223> OTHER INFORMATION: CDRL1

<400> SEQUENCE: 272

Val Tyr Asn Ser Asp Arg
1               5

<210> SEQ ID NO 273
<211> LENGTH: 5
<212> TYPE: PRT
<213> ORGANISM: Artificial Sequence
<220> FEATURE:
<223> OTHER INFORMATION: CDRL2

<400> SEQUENCE: 273

Val Ser Lys Leu Ala
1               5

<210> SEQ ID NO 274
<211> LENGTH: 11
<212> TYPE: PRT
<213> ORGANISM: Artificial Sequence
<220> FEATURE:
<223> OTHER INFORMATION: CDRL3

<400> SEQUENCE: 274

Leu Gly Gly Tyr Asp Cys Ser Ser Ala Glu Cys
1               5                   10

<210> SEQ ID NO 275
<211> LENGTH: 17
<212> TYPE: PRT
<213> ORGANISM: Artificial Sequence
<220> FEATURE:
<223> OTHER INFORMATION: CDRH2

<400> SEQUENCE: 275

Ser Ile Tyr Thr Asp Ser Gly Asn Thr Trp Tyr Ala Ser Trp Val Lys
1               5                   10                  15

Gly

<210> SEQ ID NO 276
<211> LENGTH: 13
<212> TYPE: PRT
<213> ORGANISM: Artificial Sequence
<220> FEATURE:
<223> OTHER INFORMATION: CDRL1

<400> SEQUENCE: 276

Gln Ala Ser Gln Ser Val Tyr Asn Ser Asp Arg Leu Ala
1               5                   10

<210> SEQ ID NO 277
<211> LENGTH: 7
<212> TYPE: PRT
<213> ORGANISM: Artificial Sequence
<220> FEATURE:

<223> OTHER INFORMATION: CDRL2

<400> SEQUENCE: 277

Asp Val Ser Lys Leu Ala Ser
1               5

<210> SEQ ID NO 278
<211> LENGTH: 13
<212> TYPE: PRT
<213> ORGANISM: Artificial Sequence
<220> FEATURE:
<223> OTHER INFORMATION: CDRL3

<400> SEQUENCE: 278

Leu Gly Gly Tyr Asp Cys Ser Ser Ala Glu Cys Asn Val
1               5                   10

<210> SEQ ID NO 279
<211> LENGTH: 111
<212> TYPE: PRT
<213> ORGANISM: Artificial Sequence
<220> FEATURE:
<223> OTHER INFORMATION: heavy chain variable domain

<400> SEQUENCE: 279

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asp Thr
            20                  25                  30

Met Ile Trp Val Arg Gln Ala Pro Gly Glu Gly Leu Glu Trp Ile Gly
        35                  40                  45

Ser Ile Tyr Thr Asp Ser Gly Asn Thr Trp Tyr Ala Ser Trp Val Lys
    50                  55                  60

Gly Arg Phe Thr Ile Ser Lys Thr Ser Thr Thr Val Asp Leu Arg
65                  70                  75                  80

Ile Thr Ser Pro Thr Thr Glu Asp Thr Ala Thr Tyr Phe Cys Ala Arg
                85                  90                  95

Asn Phe Ser Val Trp Gly Pro Gly Thr Leu Val Thr Val Ser Leu
            100                 105                 110

<210> SEQ ID NO 280
<211> LENGTH: 112
<212> TYPE: PRT
<213> ORGANISM: Artificial Sequence
<220> FEATURE:
<223> OTHER INFORMATION: light chain variable domain

<400> SEQUENCE: 280

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Ser Asp
            20                  25                  30

Arg Leu Ala Trp Phe Gln Gln Met Arg Gly Gln Pro Pro Lys Leu Leu
        35                  40                  45

Ile Tyr Asp Val Ser Lys Leu Ala Ser Gly Val Pro Ser Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Cys Ser
                85                  90                  95

```
Ser Ala Glu Cys Asn Val Phe Gly Gly Gly Thr Glu Val Val Val Lys
            100                 105                 110

<210> SEQ ID NO 281
<211> LENGTH: 13
<212> TYPE: PRT
<213> ORGANISM: Artificial
<220> FEATURE:
<223> OTHER INFORMATION: VH CDR3

<400> SEQUENCE: 281

Leu Thr His Tyr Ala Arg Tyr Tyr Arg Tyr Phe Asp Val
1               5                   10

<210> SEQ ID NO 282
<211> LENGTH: 17
<212> TYPE: PRT
<213> ORGANISM: Artificial
<220> FEATURE:
<223> OTHER INFORMATION: VH CDR3

<400> SEQUENCE: 282

Gly Lys Gly Asn Thr His Lys Pro Tyr Gly Tyr Val Arg Tyr Phe Asp
1               5                   10                  15

Val

<210> SEQ ID NO 283
<211> LENGTH: 15
<212> TYPE: PRT
<213> ORGANISM: Artificial
<220> FEATURE:
<223> OTHER INFORMATION: VH CDR3

<400> SEQUENCE: 283

Leu Leu Ser Arg Gly Tyr Asn Gly Tyr Tyr His Lys Phe Asp Val
1               5                   10                  15

<210> SEQ ID NO 284
<211> LENGTH: 8
<212> TYPE: PRT
<213> ORGANISM: Artificial
<220> FEATURE:
<223> OTHER INFORMATION: VL-CDR3

<400> SEQUENCE: 284

Gln Gln Val Tyr Asn Pro Pro Val
1               5

<210> SEQ ID NO 285
<211> LENGTH: 8
<212> TYPE: PRT
<213> ORGANISM: Artificial
<220> FEATURE:
<223> OTHER INFORMATION: VL-CDR3

<400> SEQUENCE: 285

Phe Gln Leu Tyr Ser Asp Pro Phe
1               5

<210> SEQ ID NO 286
<211> LENGTH: 8
<212> TYPE: PRT
<213> ORGANISM: Artificial
<220> FEATURE:
<223> OTHER INFORMATION: VL-CDR3

<400> SEQUENCE: 286
```

Gln Gln Leu Ser Ser Phe Pro Pro
1               5

<210> SEQ ID NO 287
<211> LENGTH: 122
<212> TYPE: PRT
<213> ORGANISM: Artificial
<220> FEATURE:
<223> OTHER INFORMATION: VH

<400> SEQUENCE: 287

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr His Tyr Ala Arg Tyr Tyr Arg Tyr Phe Asp Val Trp
            100                 105                 110

Gly Gln Gly Thr Leu Val Thr Val Ser Ser
        115                 120

<210> SEQ ID NO 288
<211> LENGTH: 126
<212> TYPE: PRT
<213> ORGANISM: Artificial
<220> FEATURE:
<223> OTHER INFORMATION: VH

<400> SEQUENCE: 288

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
        115                 120                 125

<210> SEQ ID NO 289
<211> LENGTH: 124
<212> TYPE: PRT
<213> ORGANISM: Artificial
<220> FEATURE:
<223> OTHER INFORMATION: VH

<400> SEQUENCE: 289

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ser Arg Gly Tyr Asn Gly Tyr Tyr His Lys Phe Asp
            100                 105                 110

Val Trp Gly Gln Gly Thr Leu Val Thr Val Ser Ser
        115                 120
```

<210> SEQ ID NO 290
<211> LENGTH: 110
<212> TYPE: PRT
<213> ORGANISM: Artificial
<220> FEATURE:
<223> OTHER INFORMATION: VL

<400> SEQUENCE: 290

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Val Tyr Asn Pro Pro
                85                  90                  95

Val Thr Phe Gly Gln Gly Thr Lys Val Glu Ile Lys Arg Thr
            100                 105                 110
```

<210> SEQ ID NO 291
<211> LENGTH: 110
<212> TYPE: PRT
<213> ORGANISM: Artificial
<220> FEATURE:
<223> OTHER INFORMATION: VL

<400> SEQUENCE: 291

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60
```

-continued

```
Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Phe Gln Leu Tyr Ser Asp Pro
                85                  90                  95

Phe Thr Phe Gly Gln Gly Thr Lys Val Glu Ile Lys Arg Thr
            100                 105                 110

<210> SEQ ID NO 292
<211> LENGTH: 110
<212> TYPE: PRT
<213> ORGANISM: Artificial
<220> FEATURE:
<223> OTHER INFORMATION: VL

<400> SEQUENCE: 292

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Leu Ser Ser Phe Pro
                85                  90                  95

Pro Thr Phe Gly Gln Gly Thr Lys Val Glu Ile Lys Arg Thr
            100                 105                 110
```

BISPECIFIC ANTI-HAPTEN/ANTI-BLOOD BRAIN BARRIER RECEPTOR ANTIBODIES, COMPLEXES THEREOF AND THEIR USE AS BLOOD BRAIN BARRIER SHUTTLES

CROSS-REFERENCE TO RELATED APPLICATION

This application claims priority to and is a continuation of pending U.S. patent application Ser. No. 15/109,619, filed Jul. 1, 2016, which in turn claims priority to National Stage Application of PCT/EP2014/079351, filed Dec. 29, 2014, which in turn claims priority from European Application No. 14150092.6, filed on Jan. 3, 2014 and European Application No. 14174045.6, filed on Jun. 26, 2014. Each of these applications is hereby incorporated by reference herein in its entirety.

Herein are reported bispecific anti-hapten/anti-blood brain barrier receptor antibodies, non-covalent as well as covalent complexes thereof with haptenylated payloads and the use of the antibodies as well as of their complexes as blood brain barrier shuttles.

REFERENCE TO AN ELECTRONIC SEQUENCE LISTING

The instant application contains a Sequence Listing which has been submitted electronically in ASCII format and is herein incorporated by reference in its entirety. Said ASCII copy, created on Sep. 11, 2019, is named SequenceListing.txt and is 179 KB in size.

BACKGROUND OF THE INVENTION

Major bottlenecks for therapeutic application of polypeptides are their limited solubility, in vivo stability, short serum half-life and fast clearance from the bloodstream.

Different approaches are reported to address this. One approach to improve PK/stability and biophysical behavior of therapeutic polypeptides is to fuse them to entities which stabilized the polypeptide, keep it in solution, and extend its half-life. Examples of such entities are human serum albumin or human immunoglobulin Fc-regions. Another approach to improve PK/stability and biophysical behavior of therapeutic polypeptides, is the chemical or enzymatic conjugation to polymers, for example by PEGylation or HESylation.

U.S. Pat. No. 5,804,371 reports hapten-labeled peptides and their use in an immunological method of detection. A digoxigenin-labeled peptide (Bradykinin) and its application to chemiluminoenzyme immunoassay of Bradykinin in inflamed tissues are reported by Decarie A., et al. (Peptides 15 (1994) 511-518).

In WO 2004/065569 multi-functional antibodies are reported.

In WO 2011/003780 bi-specific digoxigenin binding antibodies are reported.

In WO 2012/093068 a pharmaceutical composition of a complex of an anti-DIG antibody and digoxigenin that is conjugated to a peptide is reported.

In WO 2014/006124 covalent complexes of anti-hapten antibodies and a haptenylated payload are reported.

Monoclonal antibodies have vast therapeutic potential for treatment of neurological or central nervous system (CNS) diseases, but their passage into the brain is restricted by the blood-brain-barrier (BBB). Past studies have shown that a very small percentage (approximately 0.1%) of an IgG circulating in the bloodstream crosses through the BBB into the CNS (Felgenhauer, K., Klin. Wschr. 52 (1974) 1158-1164), where the CNS concentration of the antibody may be insufficient to permit a robust effect.

It has been reported that by defining the binding mode of an antibody or antibody fragment that specifically binds to a blood-brain-barrier receptor (BBBR) to be monovalent a BBB-shuttle module with BBB transcytosis properties can be obtained WO 2014/033074.

It has been reported that by using an antibody or antibody fragment that specifically binds to a BBBR with medium affinity a BBB-shuttle module with BBB transcytosis properties can be obtained WO 2012/075037.

It has been reported that by using an antibody or antibody fragment that has a specific ratio of EC50 values determined at different pH values a BBB-shuttle module with BBB transcytosis properties can be obtained WO 2012/143379.

Pardridge, W. M., reports the re-engineering of biopharmaceuticals for delivery to brain with molecular Trojan horses (Bioconjug. Chem. 19 (2008) 1327-1338). Receptor-mediated transport of drugs across the BBB is reported by Feng Ji-Ming et al. (Neurometh. 45 (2010) 15-34). Zhou, Q.-H., et al. report the delivery of a peptide radiopharmaceutical to brain with an IgG-avidin fusion protein (Bioconjug. Chem. 22 (2011) 1611-1618). The study of the transcytosis of an anti-transferrin receptor antibody with a Fab' cargo across the blood-brain barrier in mice is reported by Manich, G., et al. (Eur. J. Pharm. Sci. 49 (2013) 556-564).

SUMMARY OF THE INVENTION

Herein is reported a blood brain barrier-shuttle module (BBB-shuttle module) that is a bispecific antibody with a first binding specificity for a hapten and a second binding specificity for a blood brain barrier receptor (BBBR). Such a BBB-shuttle module recognizes a transcytoseable cell surface target on the blood brain barrier (such as TfR, LRPs or other targets, BBBR) and simultaneously binds to haptenylated payloads.

It has been found that no further requirements with respect to binding valency, antibody format, BBBR binding affinities have to be met.

It has further been found that it is not required that the bispecific antibody-based shuttle module as reported herein is released from the endothelial cells of the blood brain barrier in order to mediate transcytosis of the haptenylated payload. Instead, the haptenylated payload, which is complexed by/bound to the bispecific antibody-based shuttle module upon binding to the BBBR, is released from the bispecific antibody-based shuttle module within the BBB cell, i.e. in the intracellular vesicular system, is separated from the shuttle module, and subsequently is exocytosed from the BBB cell into the brain leaving the bispecific antibody behind in the BBB cell. This is also applicable when a covalent complex is used.

The bispecific antibody-based shuttle module as reported herein is very variable in terms of binding specificity valency as well as affinity of the BBBR binding specificity. Simultaneously it enables payload release from the shuttle module.

One aspect as reported herein is a bispecific antibody comprising a first binding specificity that specifically binds to a haptenylated payload and a second binding specificity that specifically binds to a blood brain barrier receptor.

One aspect as reported herein is a non-covalent complex comprising a bispecific antibody, which has a first binding specificity that specifically binds to a haptenylated payload and a second binding specificity that specifically binds to a blood brain barrier receptor and a haptenylated payload, wherein the haptenylated payload is specifically bound by the first binding specificity.

One aspect as reported herein is a covalent conjugate comprising i) a bispecific antibody, which has a first binding specificity that specifically binds to a haptenylated payload and a second binding specificity that specifically binds to a blood brain barrier receptor and ii) a haptenylated payload, wherein the haptenylated payload is specifically bound by the first binding specificity, and which has a covalent bond between the haptenylated payload and the first binding specificity that specifically binds to the haptenylated payload.

In one embodiment the haptenylated payload is selected from the group comprising biotinylated payloads, theophyllinylated payloads, digoxigenylated payloads, carboranylated payloads, fluoresceinylated payloads, helicarylated payloads and bromodeoxyuridinylated payloads.

One aspect as reported herein is a covalent conjugate comprising
  i) a bispecific antibody, which has a first binding specificity, which specifically binds to a haptenylated payload, and a second binding specificity, which specifically binds to a blood brain barrier receptor, and
  ii) a haptenylated payload, wherein the haptenylated payload is specifically bound by the first binding specificity, wherein the covalent conjugate has a covalent bond between the haptenylated payload and the first binding specificity that specifically binds to the haptenylated payload, and wherein the haptenylated payload is selected from the group consisting of biotinylated payloads, theophyllinylated payloads, digoxigenylated payloads, carboranylated payloads, fluoresceinylated payloads, helicarylated payloads and bromodeoxyuridinylated payloads.

In one embodiment of all aspects the covalent conjugate is a non-permanent covalent conjugate. In one embodiment the covalent conjugate is an intracellularly cleavable covalent conjugate.

In one embodiment the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

In one embodiment the bispecific antibody is free of effector function.

In one embodiment the bispecific antibody comprises
  a) one binding site for the haptenylated payload and one binding site for the blood brain barrier receptor, or
  b) two binding sites for the haptenylated payload and one binding site for the blood brain barrier receptor, or
  c) one binding site for the haptenylated payload and two binding sites for the blood brain barrier receptor, or
  d) two binding sites for the haptenylated payload and two binding sites for the blood brain barrier receptor.

In one embodiment the bispecific antibody comprises a cysteine residue at an amino acid residue in the CDR2 of the antibody, whereby the CDR2 is determined according to Kabat.

In one embodiment the covalent bond is between a cysteine residue in the CDR2 of the antibody and a thiol group in the haptenylated payload.

One aspect as reported herein is a covalent conjugate comprising
  i) a bispecific antibody, which has a first binding specificity, which specifically binds to a haptenylated payload, and a second binding specificity, which specifically binds to the transferrin receptor, and
  ii) a haptenylated payload,
  wherein the haptenylated payload is specifically bound by the first binding specificity,
  wherein the covalent conjugate has a disulfide bond between the haptenylated payload and a cysteine residue at position 52b or 53 in the heavy chain CDR2 of the first binding specificity whereby the numbering is according to Kabat,
  wherein the haptenylated payload is selected from the group consisting of biotinylated payloads, theophyllinylated payloads, digoxigenylated payloads, carboranylated payloads, fluoresceinylated payloads, helicarylated payloads and bromodeoxyuridinylated payloads, and
  wherein the bispecific antibody comprises
  a) one binding site for the haptenylated payload and one binding site for the transferrin receptor, or
  b) two binding sites for the haptenylated payload and one binding site for the transferrin receptor, or
  c) one binding site for the haptenylated payload and two binding sites for the transferrin receptor, or
  d) two binding sites for the haptenylated payload and two binding sites for the transferrin receptor.

In one embodiment the hapten is a derivative or analogue of a nucleotide or a nucleoside. In one embodiment the hapten is a derivative or analogues of an amino acid.

In one embodiment the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

In one embodiment the bispecific antibody is a full length antibody comprising two binding sites.

In one embodiment the bispecific antibody is a full length antibody to which one or two scFvs or scFabs have been fused and that comprises three or four binding sites.

In one embodiment the bispecific antibody is an antibody fragment. In one embodiment the antibody fragment is selected from F(ab')2 and diabodies.

In one embodiment the bispecific antibody is a humanized or a human antibody.

In one embodiment the bispecific antibody is free of effector function. In one embodiment the bispecific antibody has no functional Fc-region. In one embodiment the bispecific antibody has no Fc-region. In one embodiment the bispecific antibody has an Fc-region of the human IgG1 subclass with the mutations L234A, L235A and P329G, wherein the positions are determined according to the Fc-region numbering of Kabat (Kabat EU index). In one embodiment the bispecific antibody has an Fc-region of the human IgG4 subclass with the mutations S228P, L235E and P329G, wherein the positions are determined according to the Fc-region numbering of Kabat (Kabat EU index).

In one embodiment the bispecific antibody comprises
  a) one binding site for the haptenylated payload and one binding site for the blood brain barrier receptor, or
  b) two binding sites for the haptenylated payload and one binding site for the blood brain barrier receptor, or c) one binding site for the haptenylated payload and two binding sites for the blood brain barrier receptor, or
d) two binding sites for the haptenylated payload and two binding sites for the blood brain barrier receptor.

In cases b) and c) of the previous embodiment one heavy chain of the bispecific antibody comprises a hole mutation and the respective other chain comprises a knob mutation.

In one preferred embodiment the bispecific antibody comprises two binding sites for the haptenylated payload and two binding sites for the blood brain barrier receptor.

In one embodiment the haptenylated payload comprises between the hapten and the payload a linker. In one embodiment the linker is a peptidic linker. In one embodiment the linker is a chemical linker (non-peptidic linker).

It has been found that by the covalent coupling of a haptenylated payload to an anti-hapten antibody a stabilization and PK-property improvement of the payload can be achieved.

One aspect as reported herein is the use of a covalent conjugate comprising i) a bispecific antibody, which has a first binding specificity, which specifically binds to a haptenylated payload, and a second binding specificity, which specifically binds to a blood brain barrier receptor, and
ii) a haptenylated payload, wherein the haptenylated payload is specifically bound by the first binding specificity, wherein the covalent conjugate has a covalent bond between the haptenylated payload and the first binding specificity that specifically binds to the haptenylated payload, and wherein the haptenylated payload is selected from the group consisting of biotinylated payloads, theophyllinylated payloads, digoxigenylated payloads, carboranylated payloads, fluoresceinylated payloads, helicarylated payloads and bromodeoxyuridinylated payloads, for targeted delivery of the haptenylated payload across the blood brain barrier.

In one embodiment the use is for the targeted delivery of the free (i.e. isolated) haptenylated payload across the blood brain barrier.

In one embodiment the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

In one embodiment the blood brain barrier receptor is the transferrin receptor or low density lipoprotein receptor-related protein 8.

In one embodiment the bispecific antibody is free of effector function.

In one embodiment the bispecific antibody comprises a) one binding site for the haptenylated payload and one binding site for the blood brain barrier receptor, or
b) two binding sites for the haptenylated payload and one binding site for the blood brain barrier receptor, or
c) one binding site for the haptenylated payload and two binding sites for the blood brain barrier receptor, or
d) two binding sites for the haptenylated payload and two binding sites for the blood brain barrier receptor.

In one embodiment the bispecific antibody comprises a cysteine residue at an amino acid residue in the CDR2 of the antibody, whereby the CDR2 is determined according to Kabat.

In one embodiment the covalent bond is between a cysteine residue in the CDR2 of the antibody and a thiol group in the haptenylated payload.

In one embodiment of all aspects the bispecific antibody and the haptenylated payload each comprise a functional group whereby upon binding of the haptenylated payload by the bispecific antibody a covalent bond is formed between the haptenylated payload and the bispecific antibody.

In one embodiment of all aspects the bispecific antibody comprises a functional group at an amino acid residue in the CDR2 of the antibody, whereby the CDR2 is determined according to Kabat. In one embodiment the functional group at an amino acid residue in the CDR2 of the antibody is a thiol group. In one embodiment the bispecific antibody comprises a cysteine amino acid residue in the CDR2 of the antibody.

In one embodiment of all aspects the haptenylated payload comprises a functional group in the hapten or if present in the linker between the hapten and the payload. In one embodiment the functional group is a thiol, or a maleimide, or a haloacetyl. In one embodiment the functional group in the hapten or if present in the linker is a thiol group.

In one embodiment of all aspects the covalent bond is between a cysteine residue in the CDR2 of the antibody and the thiol group in the haptenylated payload. In one embodiment the covalent bond is a disulfide bond. In one embodiment the covalent bond is a disulfide bond and it is formed without the addition of redox active agents.

In one embodiment of all aspects the CDR2 is the heavy chain CDR2 in case of a haptenylated payload selected from the group consisting of biotinylated payloads, theophyllinylated payloads, digoxigenylated payloads, and fluoresceinylated payloads. In one embodiment the cysteine residue in the heavy chain CDR2 of the antibody is at position 52, or position 52a, or position 52b, or position 52c, or position 52d, or position 53 according to the heavy chain variable domain numbering of Kabat. In one embodiment the cysteine residue in the heavy chain CDR2 of the antibody is at position 52a, or position 52b, or position 52c, or position 53 according to the heavy chain variable domain numbering of Kabat. In one preferred embodiment the cysteine residue in the heavy chain CDR2 of the antibody is at position 52b or at position 53 according to the heavy chain variable domain numbering of Kabat.

It has been found that any payload can be used in the haptenylated payload upon derivatization with a universal linker which comprises the functional group for the formation of the covalent bond between the haptenylated payload and an amino acid residue in the heavy chain CDR2 of the antibody. The location of the functional group in the universal linker has the advantage that it is not necessary to re-engineer the synthesis and the position of the functional group in the heavy chain CDR2 of the antibody if the payload is changed.

In one embodiment of all aspects the CDR2 is the light chain CDR2 in case of a helicarylated payload. In one embodiment the cysteine residue in the light chain CDR2 of the antibody is at position 51 or at position 55 according to the light chain variable domain numbering of Kabat. In one preferred embodiment the cysteine residue in the light chain CDR2 of the antibody is at position 55 according to the light chain variable domain numbering of Kabat.

It has been found that any payload can be used in the helicarylated payload upon derivatization of the helicar amino acid sequence with a cysteine comprising the functional group for the formation of the covalent disulfide bond between the helicarylated payload and the cysteine residue in the light chain CDR2 of the antibody. The location of the cysteine residue (thiol functional group) in the helicar motif amino acid sequence has the advantage that it is not necessary to re-engineer the synthesis and the position of the cysteine residue in the light chain CDR2 of the antibody if the payload is changed.

In one embodiment of all aspects exactly one covalent bond is formed per CDR2.

In one embodiment of all aspects the payload is selected from a binding moiety, a labeling moiety, and a biologically active moiety.

In one embodiment of all aspects the biologically active moiety is selected from the group comprising antibodies, polypeptides, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), locked nucleic acids (LNAs), ribozymes, and small molecules, or active fragments of any of the foregoing.

In one embodiment of all aspects the payload is a nucleic acid or nucleic acid derivative. In one embodiment the nucleic acid is an iRNA or a LNA.

In one embodiment of all aspects the payload is a polypeptide.

In one embodiment of all aspects the payload is a full length antibody or an antibody fragment.

In one embodiment of all aspects the haptenylated payload is a haptenylated full length anti-alpha synuclein antibody.

In one embodiment of all aspects the haptenylated payload is a haptenylated anti-alpha synuclein antibody fragment that specifically binds to alpha-synuclein.

In one embodiment of all aspects the hapten is biotin.

In one embodiment of all aspects the antibody comprises in the heavy chain variable domain the HVRs of SEQ ID NO: 243 to 245 and in the light chain variable domain the HVRs of SEQ ID NO: 246 to 248.

In one embodiment of all aspects the antibody comprises in the heavy chain variable domain the HVRs of SEQ ID NO: 249, 250 and 245 and in the light chain variable domain the HVRs of SEQ ID NO: 251 to 253.

In one embodiment of all aspects the antibody comprises a heavy chain variable domain consisting of SEQ ID NO: 254 and a light chain variable domain consisting of SEQ ID NO: 255.

In one embodiment of all aspects the antibody has been obtained by humanizing an antibody comprising a heavy chain variable domain consisting of SEQ ID NO: 254 and a light chain variable domain consisting of SEQ ID NO: 255.

In one embodiment of all aspects the antibody is a humanized antibody and comprises in the heavy chain variable domain the HVRs of SEQ ID NO: 243 to 245 and in the light chain variable domain the HVRs of SEQ ID NO: 246 to 248, wherein in each HVR up to 3 amino acid residues can be changed.

In one embodiment of all aspects the antibody is a humanized antibody and comprises in the heavy chain variable domain the HVRs of SEQ ID NO: 249, 250 and 245 and in the light chain variable domain the HVRs of SEQ ID NO: 251 to 253, wherein in each HVR up to 3 amino acid residues can be changed.

In one embodiment of all aspects the antibody is a humanized antibody and the heavy chain variable domain is derived from a heavy chain variable domain consisting of SEQ ID NO: 254 and a light chain variable domain is derived from a light chain variable domain consisting of SEQ ID NO: 255.

In one embodiment of all aspects the antibody binds to the same epitope as an antibody comprising in the heavy chain the HVRs of SEQ ID NO: 256 to 258 and in the light chain the HVRs of SEQ ID NO: 259 to 261.

In one embodiment of all aspects the antibody binds to the same epitope as an antibody comprising in the heavy chain the HVRs of SEQ ID NO: 262, 263 and 258 and in the light chain the HVRs of SEQ ID NO: 264 to 266.

In one embodiment of all aspects the antibody comprises a heavy chain variable domain consisting of SEQ ID NO: 267 and a light chain variable domain consisting of SEQ ID NO: 268.

In one embodiment of all aspects the antibody has been obtained by humanizing an antibody comprising a heavy chain variable domain consisting of SEQ ID NO: 267 and a light chain variable domain consisting of SEQ ID NO: 268.

In one embodiment of all aspects the antibody is a humanized antibody and comprises in the heavy chain variable domain the HVRs of SEQ ID NO: 256 to 258 and in the light chain variable domain the HVRs of SEQ ID NO: 259 to 261, wherein in each HVR up to 3 amino acid residues can be changed.

In one embodiment of all aspects the antibody is a humanized antibody and comprises in the heavy chain variable domain the HVRs of SEQ ID NO: 262, 263 and 258 and in the light chain variable domain the HVRs of SEQ ID NO: 264 to 266, wherein in each HVR up to 3 amino acid residues can be changed.

In one embodiment of all aspects the antibody is a humanized antibody and the heavy chain variable domain is derived from a heavy chain variable domain consisting of SEQ ID NO: 267 and a light chain variable domain is derived from a light chain variable domain consisting of SEQ ID NO: 268.

In one embodiment of all aspects the antibody binds to the same epitope as an antibody comprising in the heavy chain the HVRs of SEQ ID NO: 269 to 271 and in the light chain the HVRs of SEQ ID NO: 272 to 274.

In one embodiment of all aspects the antibody binds to the same epitope as an antibody comprising in the heavy chain the HVRs of SEQ ID NO: 269, 275 and 271 and in the light chain the HVRs of SEQ ID NO: 276 to 278.

In one embodiment of all aspects the antibody comprises a heavy chain variable domain consisting of SEQ ID NO: 279 and a light chain variable domain consisting of SEQ ID NO: 280.

In one embodiment of all aspects the antibody has been obtained by humanizing an antibody comprising a heavy chain variable domain consisting of SEQ ID NO: 279 and a light chain variable domain consisting of SEQ ID NO: 280.

In one embodiment of all aspects the antibody is a humanized antibody and comprises in the heavy chain variable domain the HVRs of SEQ ID NO: 269 to 271 and in the light chain variable domain the HVRs of SEQ ID NO: 272 to 274, wherein in each HVR up to 3 amino acid residues can be changed.

In one embodiment of all aspects the antibody is a humanized antibody and comprises in the heavy chain variable domain the HVRs of SEQ ID NO: 269, 275 and 271 and in the light chain variable domain the HVRs of SEQ ID NO: 276 to 278, wherein in each HVR up to 3 amino acid residues can be changed.

In one embodiment of all aspects the antibody is a humanized antibody and the heavy chain variable domain is derived from a heavy chain variable domain consisting of SEQ ID NO: 279 and a light chain variable domain is derived from a light chain variable domain consisting of SEQ ID NO: 280.

In one embodiment of all aspects the haptenylated payload is a haptenylated full length anti-human Tau(pS422) antibody.

In one embodiment of all aspects the haptenylated payload is a haptenylated anti-human Tau(pS422) antibody fragment that specifically binds to human Tau phosphorylated at the serine at position 422.

In one embodiment of all aspects the hapten is biotin.

In one embodiment of all aspects the anti-human Tau (pS422) antibody comprises
- a) in the heavy chain variable domain the HVRs of SEQ ID NO: 230, 239 and 232, or
- b) in the heavy chain variable domain the HVRs of SEQ ID NO: 230, 231 and 232.

In one embodiment of all aspects the antibody further comprises
- a) in the light chain variable domain the HVRs of SEQ ID NO: 234, 235 and 236, or
- b) in the light chain variable domain the HVRs of SEQ ID NO: 233, 229 and 236.

In one embodiment of all aspects the antibody comprises
- a) in the heavy chain variable domain the HVRs of SEQ ID NO: 230, 239 and 232, and in the light chain variable domain the HVRs of SEQ ID NO: 234, 235 and 236, or
- b) in the heavy chain variable domain the HVRs of SEQ ID NO: 230, 231 and 232, and in the light chain variable domain the HVRs of SEQ ID NO: 233, 229 and 236, or
- c) in the heavy chain variable domain the HVRs of SEQ ID NO: 230, 231 and 232, and in the light chain variable domain the HVRs of SEQ ID NO: 234, 235 and 236.

In one embodiment of all aspects the antibody comprises
- a) a heavy chain variable domain of SEQ ID NO: 241 and a light chain variable domain of SEQ ID NO: 238, or
- b) a heavy chain variable domain of SEQ ID NO: 240 and a light chain variable domain of SEQ ID NO: 237, or
- c) a heavy chain variable domain of SEQ ID NO: 240 and a light chain variable domain of SEQ ID NO: 238, or
- d) a heavy chain variable domain of SEQ ID NO: 242 and a light chain variable domain of SEQ ID NO: 238.

In one embodiment of all aspects the haptenylated payload is a haptenylated full length anti-Abeta antibody.

In one embodiment of all aspects the haptenylated payload is a haptenylated anti-Abeta antibody fragment that specifically binds to human Abeta.

In one embodiment of all aspects the hapten is biotin.

In one embodiment of all aspects anti-Abeta antibody comprises in the heavy chain variable domain the HVRs of SEQ ID NO: 281, 282 and 283.

In one embodiment of all aspects the antibody further comprises in the light chain variable domain the HVRs of SEQ ID NO: 284, 285 and 286.

In one embodiment of all aspects the antibody comprises in the heavy chain variable domain the HVRs of SEQ ID NO: 281, 282 and 283 and in the light chain variable domain the HVRs of SEQ ID NO: 284, 285 and 286.

In one embodiment of all aspects the antibody comprises
- a) a heavy chain variable domain of SEQ ID NO: 287 and a light chain variable domain of SEQ ID NO: 290, or
- b) a heavy chain variable domain of SEQ ID NO: 288 and a light chain variable domain of SEQ ID NO: 291, or
- c) a heavy chain variable domain of SEQ ID NO: 289 and a light chain variable domain of SEQ ID NO: 292.

In one embodiment of all aspects the payload is a small molecule (non-polypeptide biologically active moiety).

In one embodiment of all aspects the biologically active moiety is a polypeptide. In one embodiment the polypeptide is consisting of 5 to 500 amino acid residues. In one embodiment the polypeptide comprises 10 to 450 amino acid residues. In one embodiment the polypeptide comprises 15 to 400 amino acid residues. In one embodiment the polypeptide comprises 18 to 350 amino acids residues.

In one embodiment of all aspects the bispecific antibody comprises a first binding specificity that specifically binds to a digoxigenylated payload (anti-digoxigenin binding specificity; anti-DIG binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment of all aspects the bispecific antibody has two binding specificities that specifically bind to the digoxigenylated payload (two anti-digoxigenin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment of all aspects the binding specificity that specifically binds to a digoxigenylated payload is a pair of an antibody heavy chain variable domain and an antibody light chain variable domain comprising (a) a heavy chain CDR1 comprising the amino acid sequence of SEQ ID NO: 01, (b) a heavy chain CDR2 comprising the amino acid sequence of SEQ ID NO: 02, (c) a heavy chain CDR3 comprising the amino acid sequence of SEQ ID NO: 03, (d) a light chain CDR1 comprising the amino acid sequence of SEQ ID NO: 05, (e) a light chain CDR2 comprising the amino acid sequence of SEQ ID NO: 06, and (f) a light chain CDR3 comprising the amino acid sequence of SEQ ID NO: 07.

In one embodiment of all aspects the binding specificity that specifically binds to a digoxigenylated payload is a humanized binding specificity.

In one embodiment of all aspects the binding specificity that specifically binds to a digoxigenylated payload comprises CDRs as in any of the above embodiments and an acceptor human framework (e.g. a human immunoglobulin framework or a human consensus framework).

In one embodiment of all aspects the binding specificity that specifically binds to a digoxigenylated payload is a pair of an antibody heavy chain variable domain and an antibody light chain variable domain comprising (a) a heavy chain CDR1 comprising the amino acid sequence of SEQ ID NO: 09 or 25, (b) a heavy chain CDR2 comprising the amino acid sequence of SEQ ID NO: 10 or 26, (c) a heavy chain CDR3 comprising the amino acid sequence of SEQ ID NO: 11 or 27, (d) a light chain CDR1 comprising the amino acid sequence of SEQ ID NO: 13 or 29, (e) a light chain CDR2 comprising the amino acid sequence of SEQ ID NO: 14 or 30, and (f) a light chain CDR3 comprising the amino acid sequence of SEQ ID NO: 15 or 31.

In one embodiment of all aspects the binding specificity that specifically binds to a digoxigenylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 04 or 12 or 20 or 28. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 01 or 09 or 17 or 25. In certain embodiments, substitutions, insertions, or deletions occur in regions outside the CDRs (i.e., in the FRs). Optionally, the anti-digoxigenin antibody comprises the VH sequence in SEQ ID NO: 01 or 09 or 17 or 25, including post-translational modifications of that sequence.

In one embodiment of all aspects the binding specificity that specifically binds to a digoxigenylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 08 or 16 or 24 or 32. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 08 or 16 or 24 or 32. In certain embodiments, the substitutions, insertions, or deletions occur in regions outside the CDRs (i.e., in the FRs). Optionally, the anti-digoxigenin antibody comprises the VL sequence in SEQ ID NO: 08 or 16 or 24 or 32, including post-translational modifications of that sequence.

In one embodiment of all aspects the bispecific antibody comprises a first binding specificity that specifically binds to a biotinylated payload (anti-biotin binding specificity; anti-BI binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment of all aspects the bispecific antibody has two binding specificities that specifically bind to the biotinylated payload (two anti-biotin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment of all aspects the binding specificity that specifically binds to a biotinylated payload is a pair of an antibody heavy chain variable domain and an antibody light chain variable domain comprising (a) a heavy chain CDR1 comprising the amino acid sequence of SEQ ID NO: 33, (b) a heavy chain CDR2 comprising the amino acid sequence of SEQ ID NO: 34, (c) a heavy chain CDR3 comprising the amino acid sequence of SEQ ID NO: 35, (d) a light chain CDR1 comprising the amino acid sequence of SEQ ID NO: 37, (e) a light chain CDR2 comprising the amino acid sequence of SEQ ID NO: 38, and (f) a light chain CDR3 comprising the amino acid sequence of SEQ ID NO: 39.

In one embodiment of all aspects the binding specificity that specifically binds to a biotinylated payload is a humanized binding specificity.

In one embodiment of all aspects the binding specificity that specifically binds to a biotinylated payload comprises CDRs as in any of the above embodiments and an acceptor human framework (e.g. a human immunoglobulin framework or a human consensus framework).

In one embodiment of all aspects the binding specificity that specifically binds to a biotinylated payload is a pair of an antibody heavy chain variable domain and an antibody light chain variable domain comprising (a) a heavy chain CDR1 comprising the amino acid sequence of SEQ ID NO: 41 or 57, (b) a heavy chain CDR2 comprising the amino acid sequence of SEQ ID NO: 42 or 58, (c) a heavy chain CDR3 comprising the amino acid sequence of SEQ ID NO: 43 or 59, (d) a light chain CDR1 comprising the amino acid sequence of SEQ ID NO: 45 or 61, (e) a light chain CDR2 comprising the amino acid sequence of SEQ ID NO: 46 or 62, and (f) a light chain CDR3 comprising the amino acid sequence of SEQ ID NO: 47 or 63.

In one embodiment of all aspects the binding specificity that specifically binds to a biotinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 36 or 44 or 52 or 60. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 36 or 44 or 52 or 60. In certain embodiments, substitutions, insertions, or deletions occur in regions outside the CDRs (i.e., in the FRs). Optionally, the anti-biotin antibody comprises the VH sequence in SEQ ID NO: 36 or 44 or 52 or 60, including post-translational modifications of that sequence.

In one embodiment of all aspects the binding specificity that specifically binds to a biotinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 40 or 48 or 56 or 64. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 40 or 48 or 56 or 64. In certain embodiments, the substitutions, insertions, or deletions occur in regions outside the CDRs (i.e., in the FRs). Optionally, the anti-biotin antibody comprises the VL sequence in SEQ ID NO: 40 or 48 or 56 or 64, including post-translational modifications of that sequence.

In one embodiment of all aspects the bispecific antibody comprises a first binding specificity that specifically binds to a theophyllinylated payload (anti-theophylline binding specificity; anti-THEO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment of all aspects the bispecific antibody has two binding specificities that specifically bind to the theophyllinylated payload (two anti-theophylline binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment of all aspects the binding specificity that specifically binds to a theophyllinylated payload is a pair of an antibody heavy chain variable domain and an antibody light chain variable domain comprising (a) a heavy chain CDR1 comprising the amino acid sequence of SEQ ID NO: 65, (b) a heavy chain CDR2 comprising the amino acid sequence of SEQ ID NO: 66, (c) a heavy chain CDR3 comprising the amino acid sequence of SEQ ID NO: 67, (d) a light chain CDR1 comprising the amino acid sequence of SEQ ID NO: 69, (e) a light chain CDR2 comprising the amino acid sequence of SEQ ID NO: 70, and (f) a light chain CDR3 comprising the amino acid sequence of SEQ ID NO: 71.

In one embodiment of all aspects the binding specificity that specifically binds to a theophyllinylated payload is a humanized binding specificity.

In one embodiment of all aspects the binding specificity that specifically binds to a theophyllinylated payload comprises CDRs as in any of the above embodiments and an acceptor human framework (e.g. a human immunoglobulin framework or a human consensus framework).

In one embodiment of all aspects the binding specificity that specifically binds to a theophyllinylated payload is a pair of an antibody heavy chain variable domain and an antibody light chain variable domain comprising (a) a heavy chain CDR1 comprising the amino acid sequence of SEQ ID NO: 73 or 89, (b) a heavy chain CDR2 comprising the amino acid sequence of SEQ ID NO: 74 or 90, (c) a heavy chain CDR3 comprising the amino acid sequence of SEQ ID NO: 75 or 91, (d) a light chain CDR1 comprising the amino acid sequence of SEQ ID NO: 77 or 93, (e) a light chain CDR2 comprising the amino acid sequence of SEQ ID NO: 78 or 94, and (f) a light chain CDR3 comprising the amino acid sequence of SEQ ID NO: 79 or 95.

In one embodiment of all aspects the binding specificity that specifically binds to a theophyllinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 76 or 84 or 92. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline. In certain embodiments, a total of 1 to 10 amino acids have been substituted, inserted and/or deleted in SEQ ID NO: 68 or 76 or 84 or 92. In certain embodiments, substitutions, insertions, or deletions occur in regions outside the CDRs (i.e., in the FRs). Optionally, the anti-theophylline antibody comprises the VH sequence in SEQ ID NO: 68 or 76 or 84 or 92 including post-translational modifications of that sequence.

In one embodiment of all aspects the binding specificity that specifically binds to a theophyllinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 72 or 80 or 88 or 96. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline. In certain embodiments, a total of 1 to 10 amino acids have been substituted, inserted and/or deleted in SEQ ID NO: 72 or 80 or 88 or 96. In certain embodiments, the substitutions, insertions, or deletions occur in regions outside the CDRs (i.e., in the FRs). Optionally, the anti-theophylline antibody comprises the VL sequence in SEQ ID NO: 72 or 80 or 88 or 96, including post-translational modifications of that sequence.

In one embodiment of all aspects the bispecific antibody comprises a first binding specificity that specifically binds to a fluoresceinylated payload (anti-fluorescein binding specificity; anti-FLUO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment of all aspects the bispecific antibody has two binding specificities that specifically bind to the fluoresceinylated payload (two anti-fluorescein binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment of all aspects the binding specificity that specifically binds to a fluoresceinylated payload is a pair of an antibody heavy chain variable domain and an antibody light chain variable domain comprising (a) a heavy chain CDR1 comprising the amino acid sequence of SEQ ID NO: 97, (b) a heavy chain CDR2 comprising the amino acid sequence of SEQ ID NO: 98, (c) a heavy chain CDR3 comprising the amino acid sequence of SEQ ID NO: 99, (d) a light chain CDR1 comprising the amino acid sequence of SEQ ID NO: 101, (e) a light chain CDR2 comprising the amino acid sequence of SEQ ID NO: 102, and (f) a light chain CDR3 comprising the amino acid sequence of SEQ ID NO: 103.

In one embodiment of all aspects the binding specificity that specifically binds to a fluoresceinylated payload is a humanized binding specificity.

In one embodiment of all aspects the binding specificity that specifically binds to a fluoresceinylated payload comprises CDRs as in any of the above embodiments and an acceptor human framework (e.g. a human immunoglobulin framework or a human consensus framework).

In one embodiment of all aspects the binding specificity that specifically binds to a fluoresceinylated payload is a pair of an antibody heavy chain variable domain and an antibody light chain variable domain comprising (a) a heavy chain CDR1 comprising the amino acid sequence of SEQ ID NO: 105 or 113, (b) a heavy chain CDR2 comprising the amino acid sequence of SEQ ID NO: 106 or 114, (c) a heavy chain CDR3 comprising the amino acid sequence of SEQ ID NO: 107 or 115, (d) a light chain CDR1 comprising the amino acid sequence of SEQ ID NO: 109 or 117, (e) a light chain CDR2 comprising the amino acid sequence of SEQ ID NO: 110 or 118, and (f) a light chain CDR3 comprising the amino acid sequence of SEQ ID NO: 111 or 119.

In one embodiment of all aspects the binding specificity that specifically binds to a fluoresceinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 108 or 116. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein. In certain embodiments, a total of 1 to 10 amino acids have been substituted, inserted and/or deleted in SEQ ID NO: 108 or 116. In certain embodiments, substitutions, insertions, or deletions occur in regions outside the CDRs (i.e., in the FRs). Optionally, the anti-fluorescein antibody comprises the VH sequence in SEQ ID NO: 108 or 116, including post-translational modifications of that sequence.

In one embodiment of all aspects the binding specificity that specifically binds to a fluoresceinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 112 or 120. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein. In certain embodiments, a total of 1 to 10 amino acids have been substituted, inserted and/or deleted in SEQ ID NO: 112 or 120. In certain embodiments, the substitutions, insertions, or deletions occur in regions outside the CDRs (i.e., in the FRs). Optionally, the anti-fluorescein antibody comprises the VL sequence in SEQ ID NO: 112 or 120, including post-translational modifications of that sequence.

In one embodiment of all aspects the bispecific antibody comprises a first binding specificity that specifically binds to a bromodeoxyuridinylated payload (anti-bromodeoxyuridine binding specificity; anti-BrdU binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment of all aspects the bispecific antibody has two binding specificities that specifically bind to the bromodeoxyuridinylated payload (two anti-bromodeoxyuridine binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment of all aspects the binding specificity that specifically binds to a bromodeoxyuridinylated payload is a pair of an antibody heavy chain variable domain and an antibody light chain variable domain comprising (a) a heavy chain CDR1 comprising the amino acid sequence of SEQ ID NO: 214, (b) a heavy chain CDR2 comprising the amino acid sequence of SEQ ID NO: 216, (c) a heavy chain CDR3 comprising the amino acid sequence of SEQ ID NO: 218, (d) a light chain CDR1 comprising the amino acid sequence of SEQ ID NO: 219, (e) a light chain CDR2 comprising the amino acid sequence of SEQ ID NO: 220, and (f) a light chain CDR3 comprising the amino acid sequence of SEQ ID NO: 221.

In one embodiment of all aspects the binding specificity that specifically binds to a bromodeoxyuridinylated payload is a humanized binding specificity.

In one embodiment of all aspects the binding specificity that specifically binds to a bromodeoxyuridinylated payload comprises CDRs as in any of the above embodiments and an acceptor human framework (e.g. a human immunoglobulin framework or a human consensus framework).

In one embodiment of all aspects the binding specificity that specifically binds to a bromodeoxyuridinylated payload is a pair of an antibody heavy chain variable domain and an antibody light chain variable domain comprising (a) a heavy chain CDR1 comprising the amino acid sequence of SEQ ID NO: 214 or 215, (b) a heavy chain CDR2 comprising the amino acid sequence of SEQ ID NO: 216 or 217, (c) a heavy chain CDR3 comprising the amino acid sequence of SEQ ID NO: 218, (d) a light chain CDR1 comprising the amino acid sequence of SEQ ID NO: 219, (e) a light chain CDR2 comprising the amino acid sequence of SEQ ID NO: 220, and (f) a light chain CDR3 comprising the amino acid sequence of SEQ ID NO: 221.

In one embodiment of all aspects the binding specificity that specifically binds to a bromodeoxyuridinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 222 or 224. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine. In certain embodiments, a total of 1 to 10 amino acids have been substituted, inserted and/or deleted in SEQ ID NO: 222 or 224. In certain embodiments, substitutions, insertions, or deletions occur in regions outside the CDRs (i.e., in the FRs). Optionally, the anti-bromodeoxyuridine antibody comprises the VH sequence in SEQ ID NO: 222 or 224, including post-translational modifications of that sequence.

In one embodiment of all aspects the binding specificity that specifically binds to a bromodeoxyuridinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 223 or 225. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine. In certain embodiments, a total of 1 to 10 amino acids have been substituted, inserted and/or deleted in SEQ ID NO: 223 or 225. In certain embodiments, the substitutions, insertions, or deletions occur in regions outside the CDRs (i.e., in the FRs). Optionally, the anti-bromodeoxyuridine antibody comprises the VL sequence in SEQ ID NO: 223 or 225, including post-translational modifications of that sequence.

One aspect as reported herein is a pharmaceutical formulation comprising the bispecific antibody as reported herein and a pharmaceutically acceptable carrier.

One aspect as reported herein is a pharmaceutical formulation comprising the non-covalent complex as reported herein and a pharmaceutically acceptable carrier.

One aspect as reported herein is a pharmaceutical formulation comprising the covalent conjugate as reported herein and a pharmaceutically acceptable carrier.

One aspect as reported herein is the bispecific antibody as reported herein for use as a medicament.

One aspect as reported herein is the non-covalent complex as reported herein for use as a medicament.

One aspect as reported herein is the covalent conjugate as reported herein for use as a medicament.

One aspect as reported herein is the bispecific antibody as reported herein for the treatment of cancer or a neurological disorder.

One aspect as reported herein is the non-covalent complex as reported herein for the treatment of cancer or a neurological disorder.

One aspect as reported herein is the covalent conjugate as reported herein for the treatment of cancer or a neurological disorder.

One aspect as reported herein is the use of the bispecific antibody as reported herein in the manufacture of a medicament.

One aspect as reported herein is the use of the non-covalent complex as reported herein in the manufacture of a medicament.

One aspect as reported herein is the use of the covalent conjugate as reported herein in the manufacture of a medicament.

In one embodiment the medicament is for the treatment of cancer.

In one embodiment the medicament is for the treatment of a neurological disorder.

In one embodiment the neurological disorder is selected from Alzheimer's disease (AD) (including, but not limited to, mild cognitive impairment and prodromal AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer (e.g. cancer affecting the CNS or brain), and traumatic brain injury.

One aspect as reported herein is the use of the bispecific antibody as reported herein as diagnostic agent.

One aspect as reported herein is the use of the non-covalent complex as reported herein as diagnostic agent.

One aspect as reported herein is the use of the covalent conjugate as reported herein as diagnostic agent.

One aspect as reported herein is the use of the non-covalent complex as reported herein to increase the stability of a payload.

One aspect as reported herein is the use of the covalent conjugate as reported herein to increase the stability of a payload.

One aspect as reported herein is the use of the non-covalent complex as reported herein to increase the activity of a payload.

One aspect as reported herein is the use of the covalent conjugate as reported herein to increase the activity of a payload.

One aspect as reported herein is the use of the non-covalent complex as reported herein to increase the in vivo half-life of a payload.

One aspect as reported herein is the use of the covalent conjugate as reported herein to increase the in vivo half-life of a payload.

One aspect as reported herein is the use of the bispecific antibody as reported herein in the treatment of a disease.

One aspect as reported herein is the use of the non-covalent complex as reported herein in the treatment of a disease.

One aspect as reported herein is the use of the covalent conjugate as reported herein in the treatment of a disease.

One aspect as reported herein is a method of treating an individual having a disease comprising administering to the individual an effective amount of the non-covalent complex as reported herein.

One aspect as reported herein is a method of treating an individual having a disease comprising administering to the individual an effective amount of the covalent conjugate as reported herein.

One aspect as reported herein is a method of treating a disease in an individual comprising administering to the individual an effective amount of the non-covalent complex as reported herein.

One aspect as reported herein is a method of treating a disease in an individual comprising administering to the individual an effective amount of the covalent conjugate as reported herein.

In one embodiment the disease is cancer.

In one embodiment the disease is a neurological disorder.

In one embodiment the neurological disorder is selected from Alzheimer's disease (AD) (including, but not limited to, mild cognitive impairment and prodromal AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer (e.g. cancer affecting the CNS or brain), and traumatic brain injury.

One aspect as reported herein is the use of the bispecific antibody as reported herein for targeted delivery of a haptenylated payload across the blood brain barrier.

One aspect as reported herein is the use of the non-covalent complex as reported herein for targeted delivery of a haptenylated payload across the blood brain barrier.

One aspect as reported herein is the use of the covalent complex as reported herein for targeted delivery of a haptenylated payload across the blood brain barrier.

One aspect as reported herein is the use of the bispecific antibody as reported herein for targeted delivery of a haptenylated payload across the blood brain barrier and release of the haptenylated payload within the blood brain barrier or in the brain.

One aspect as reported herein is the use of the non-covalent complex as reported herein for targeted delivery of a haptenylated payload across the blood brain barrier and release of the haptenylated payload within the blood brain barrier or in the brain.

In one embodiment the delivery of the haptenylated payload is higher compared to the delivery in the absence of the bispecific antibody. In one embodiment the delivery is two-fold higher. In one embodiment the delivery is 10-fold higher.

In one embodiment the haptenylated payload has a higher biological activity in the absence of the bispecific antibody as reported herein than in the presence of the bispecific antibody as reported herein. In one embodiment the biological activity is two-fold higher in the absence of the bispecific antibody. In one embodiment the biological activity is ten-fold higher in the absence of the bispecific antibody.

DESCRIPTION OF THE FIGURES

FIGS. 1A-1C: Procedure for digoxigenylation (conjugation of digoxigenin to) of peptides (FIG. 1A). Examples of a digoxigenylated label (fluorophore Dig-Cy5; FIG. 1B) and of a digoxigenylated polypeptide (PYY-derivative (DIG-PYY); FIG. 1C).

FIG. 4A: Structure model of an anti-digoxigenin Fab (left) showing that digoxigenin (encircled) is captured in a deep pocket which is formed by the CDRs of the VH and VL regions. FIG. 4B: Structure model of an anti-biotin Fab (right) showing that biocytinamid (encircled) is captured in a deep pocket which is formed by the CDRs of the VH and VL regions.

FIGS. 5A-5B: Comparison of the binding of recombinant humanized anti-biotin antibodies with and without introduced VH53C mutation. Binding properties were analyzed by surface plasmon resonance (SPR) technology using a BIAcore T100 or BIAcore 3000 instrument. FIG. 5A: humanized anti-biotin antibody. Binding of biotinylated siRNA to humanized anti-biotin antibody, KD=624 pM; FIG. 5B: humanized Cys53 mutated anti-biotin antibody. Binding of biotinylated siRNA, KD=643 pM; siRNA concentrations: 0.14, 0.41, 1.23, 3.70, 11.1, 33.3, and 100 nM; anti-biotin antibody concentration: 2 nM; Sensor Chip CM3; binding of antibody via anti-human IgG Fc antibody

|  | ka (1/Ms) | kd (1/s) | KD (M) |
|---|---|---|---|
| humanized anti-biotin antibody VH53C | $2.2 * 10^7$ | 0.01 | $6.4 * 10^{-10}$ |
| humanized anti-biotin antibody | $2.0 * 10^7$ | 0.01 | $6.2 * 10^{-10}$ |

Figure 6:
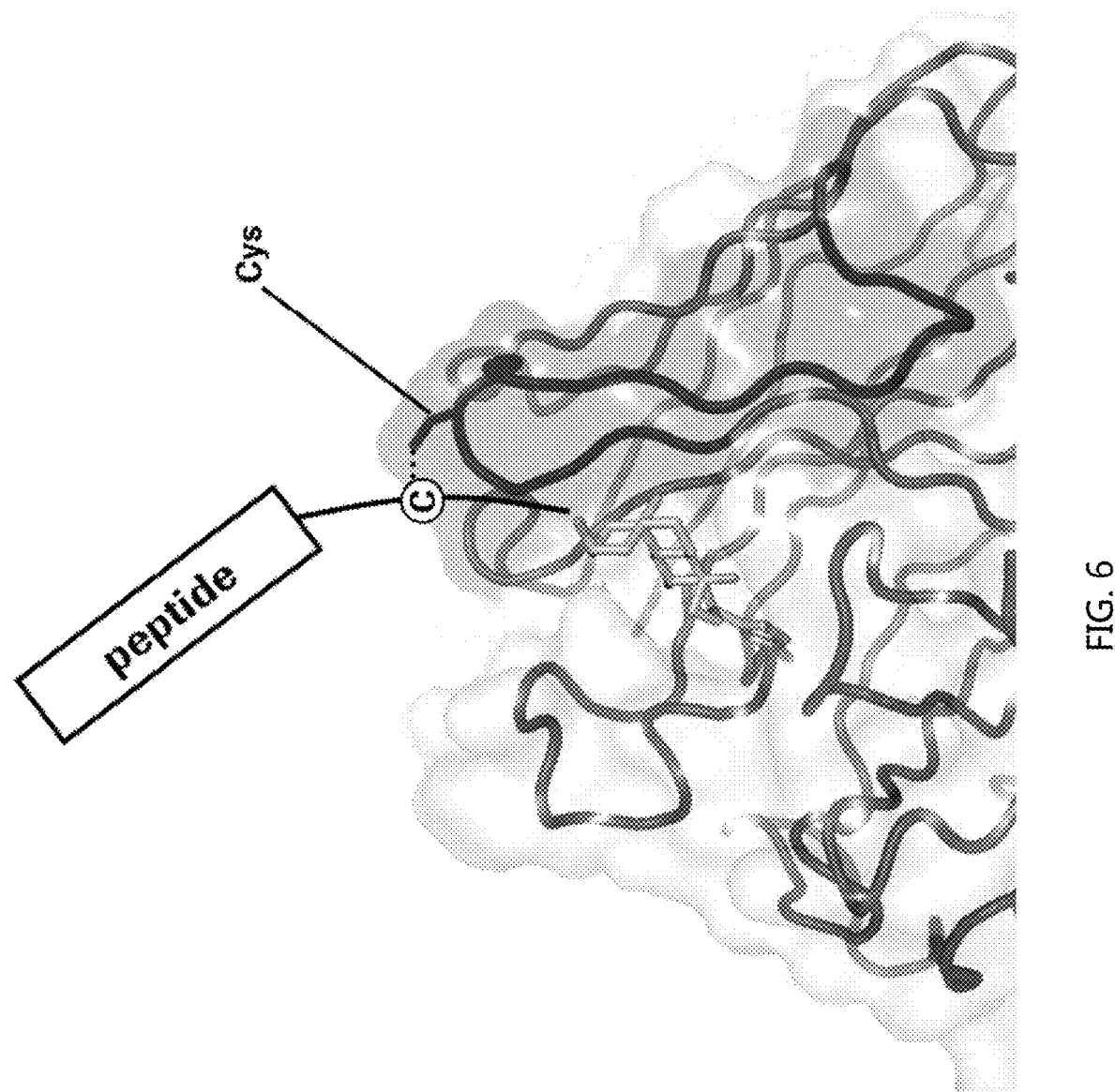

FIG. 6: Introduction of SH functionalities in the hapten as well as in the antibody at appropriate positions allow the antibody and the hapten to form a covalent bond resulting in a conjugate.

FIGS. 7A-7B: Scheme of SDS-PAGE self-fluorescence band pattern (without further staining of the SDS-PAGE gel):

FIG. 7A: If no covalent bond is formed between the antibody and the hapten-fluorophore conjugate both under reducing or non-reducing conditions one self-fluorescent band at the molecular weight of free hapten-fluorophore conjugate can be detected.

FIG. 7B: If a covalent bond is formed between the antibody and the hapten-fluorophore conjugate under non-reducing conditions one self-fluorescent band at the combined molecular weight of the antibody and the hapten-fluorophore conjugate can be detected. Under reducing conditions the disulfide bridges in the conjugate of the antibody and the hapten-fluorophore conjugate (haptenylated compound) are cleaved and one self-fluorescent band at the molecular weight of free hapten-fluorophore conjugate can be detected.

Figure 8:
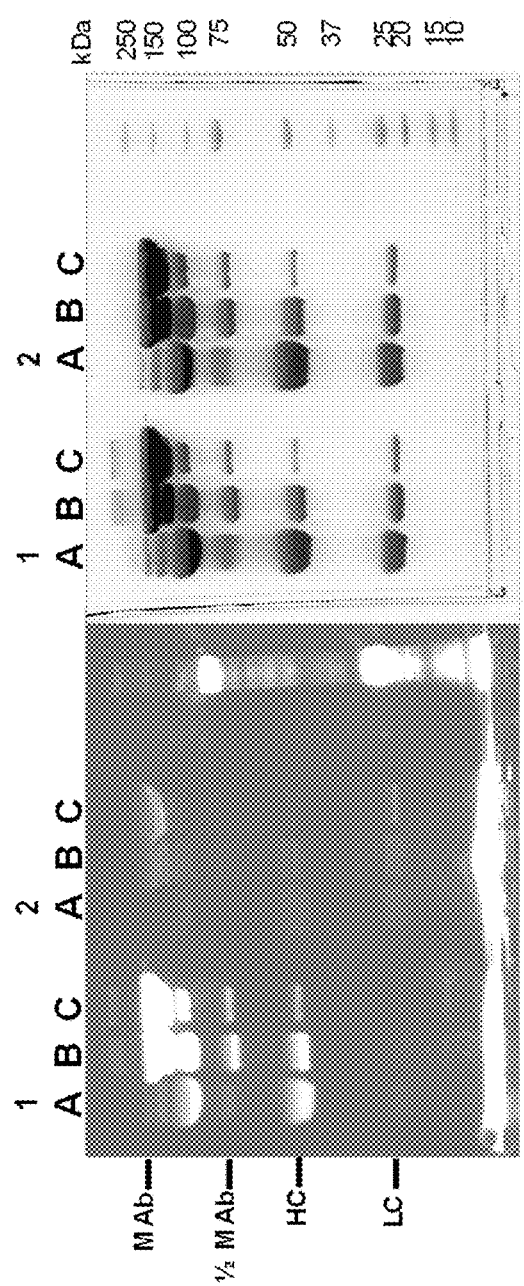
Figure 8:
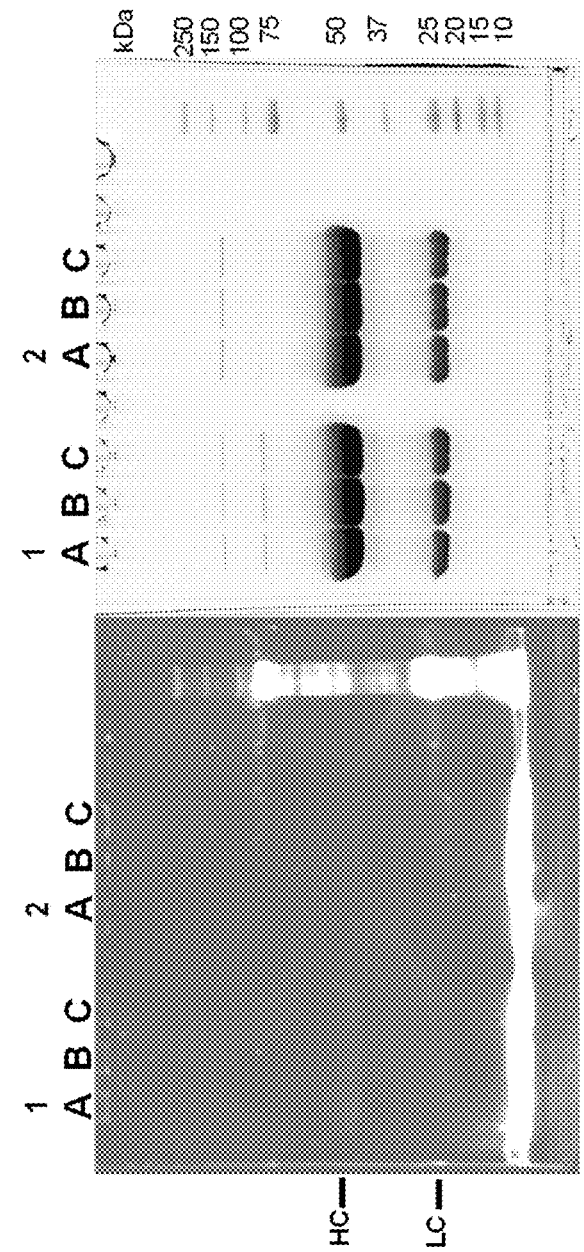

FIG. 8: Conjugate formation of hapten-binding Cys-mutated antibodies with hapten-Cys-fluorescent label conjugates (haptenylated compound) in the presence of redox active agents: oxidation agent (glutathione disulfide, GSSG) and reducing agent (dithioerythritol, DTE): Antibody complexation and subsequent covalent linkage at defined positions is detected by fluorescence signals in SDS PAGE analyses. Non-reducing (upper images) and reducing (lower images) SDS-PAGE analyses were performed as described in Example 11. Covalently antibody linked haptens are detectable as larger sized protein bound signals at the appropriate positions under non-reduced conditions. These signals detach from protein upon reduction and are visible as small entities under reducing conditions.

Left: fluorescence image
Right: Coomassie blue staining
Series 1: anti-digoxigenin antibody with 52bC mutation
Series 2: anti-digoxigenin antibody with wild-type residue at position 52b
(A) covalent coupling with 3 mM DTE and 10 mM GSSG;
(B) covalent coupling with 0.3 mM DTE and 1 mM GSSG;
(C) covalent coupling with 0.03 mM DTE and 0.1 mM GSSG.

Figure 9:
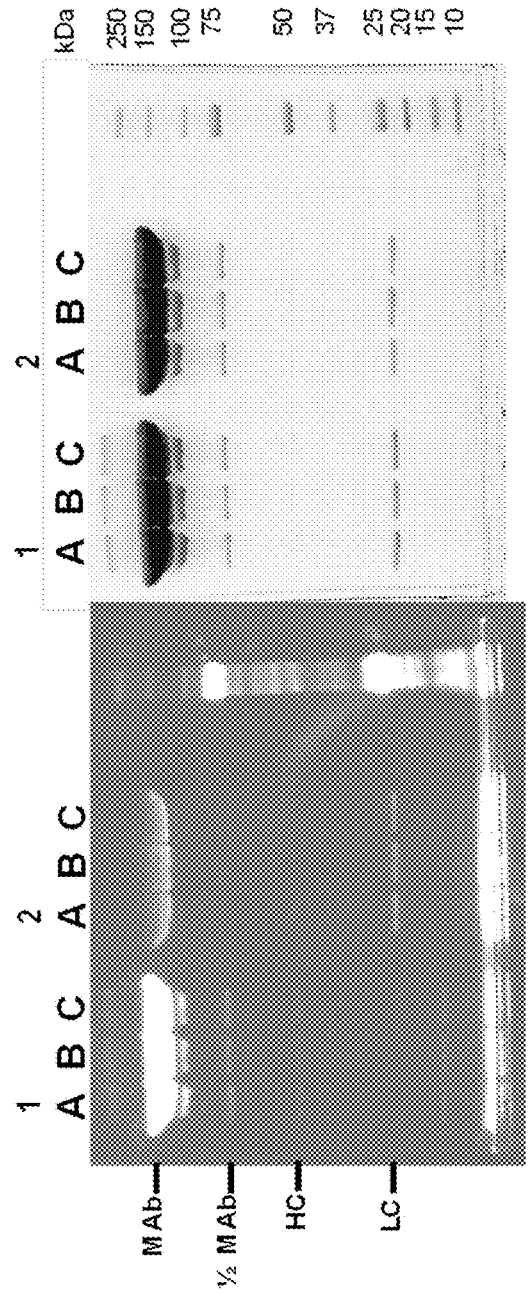
Figure 9:
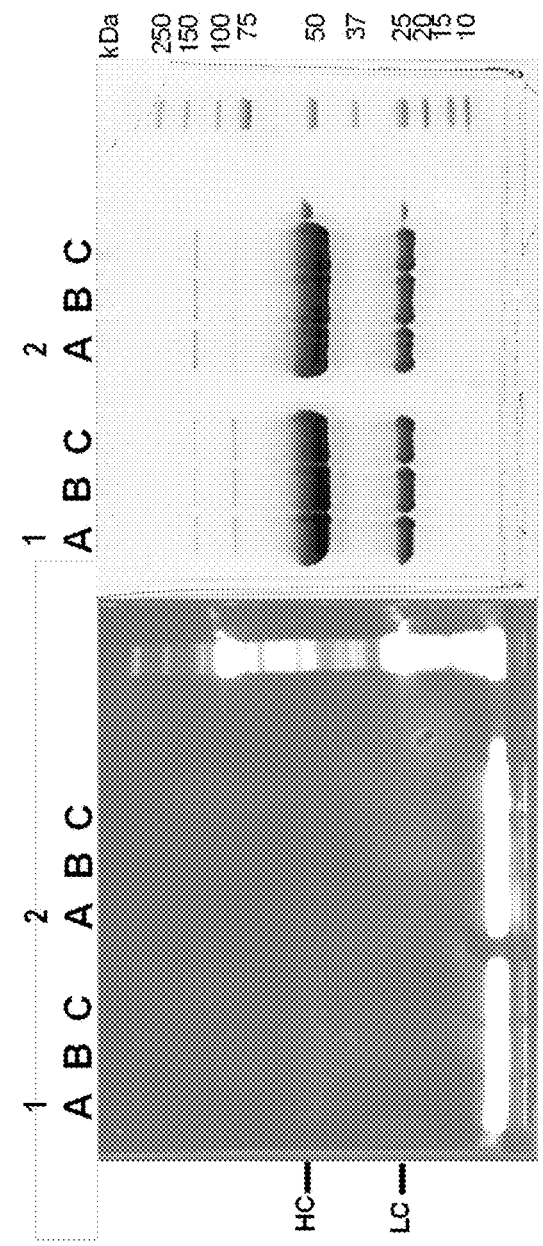

FIG. 9: Complex formation of hapten-binding Cys mutated antibodies with hapten-Cys-fluorescent label conjugates in the presence solely of an oxidation agent (glutathione disulfide, GSSG) but in the absence of reducing agents or in the absence of both: Antibody complexation and subsequent covalent linkage at defined positions is detected by fluorescence signals in SDS PAGE analyses. Non-reducing (upper images) and reducing (lower images) SDS-PAGE analyses were performed as described in Example 12. Covalently antibody linked haptens are detectable as larger sized protein bound signals at the appropriate positions under non-reduced conditions. These signals detach from protein upon reduction and are visible as small entities under reducing conditions.

Figure 10:
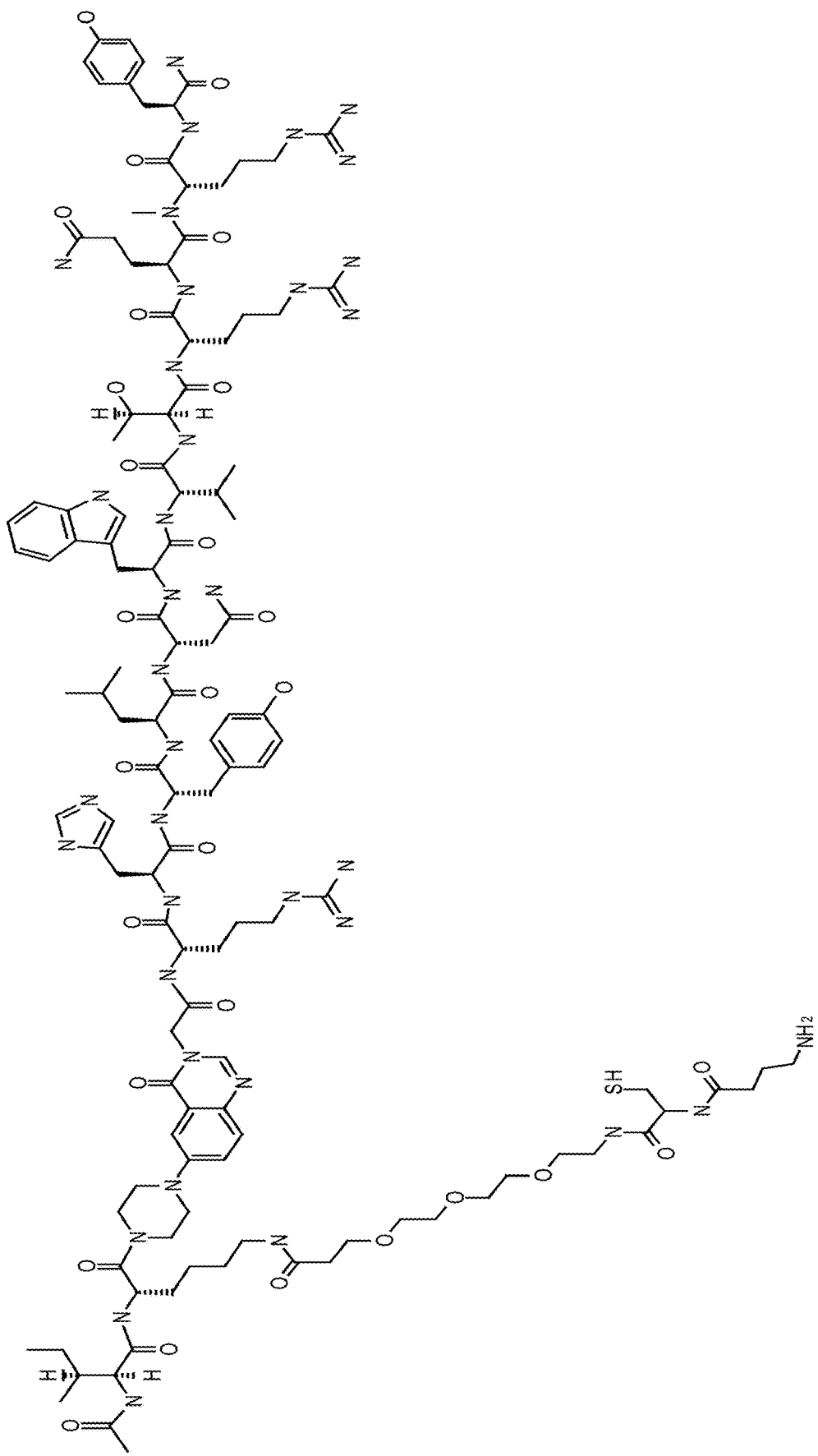
Figure 11:
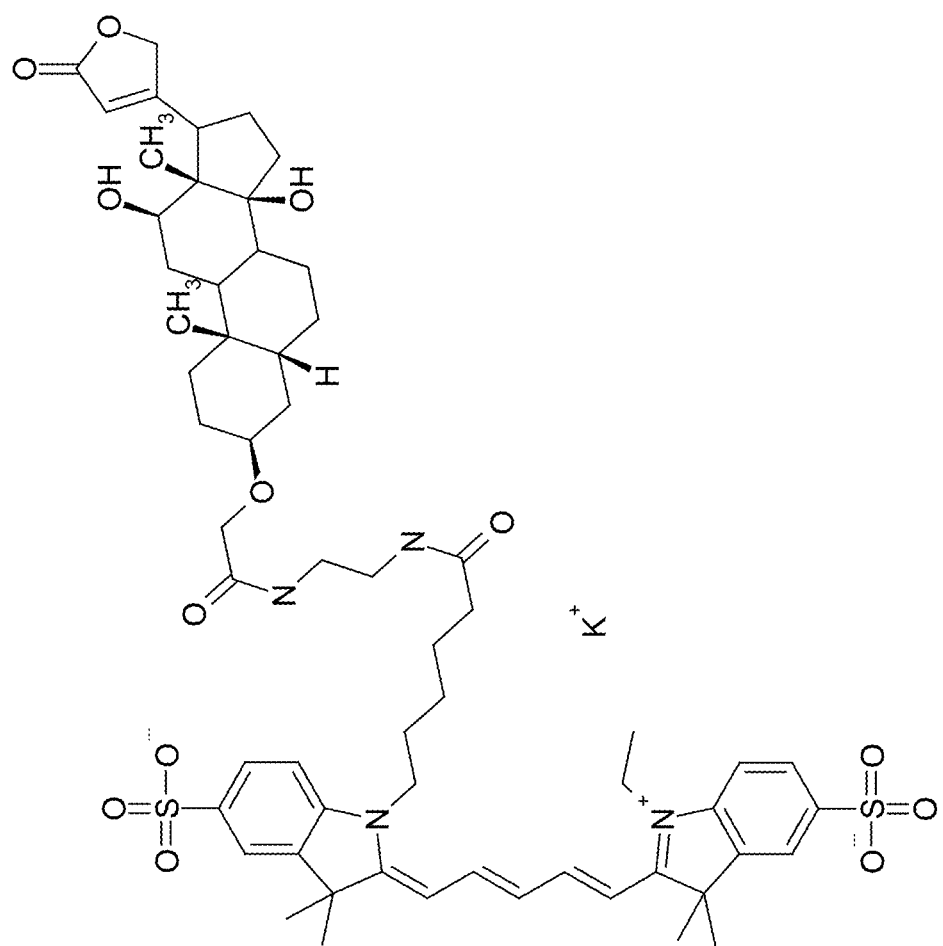

Left: fluorescence image
Right: Coomassie blue staining
Series 1: anti-digoxigenin antibody with 52bC mutation
Series 2: anti-digoxigenin antibody with wild-type residue at position 52b
(A) no additives
(B) covalent coupling with 1 mM GSSG;
(C) covalent coupling with 0.1 mM GSSG.
FIG. 10: Structure of Ac-PYY(PEG3-Cys-4Abu-NH2).
FIG. 11: Structure of DIG-3-cme-eda-Cy5.

Figure 12:
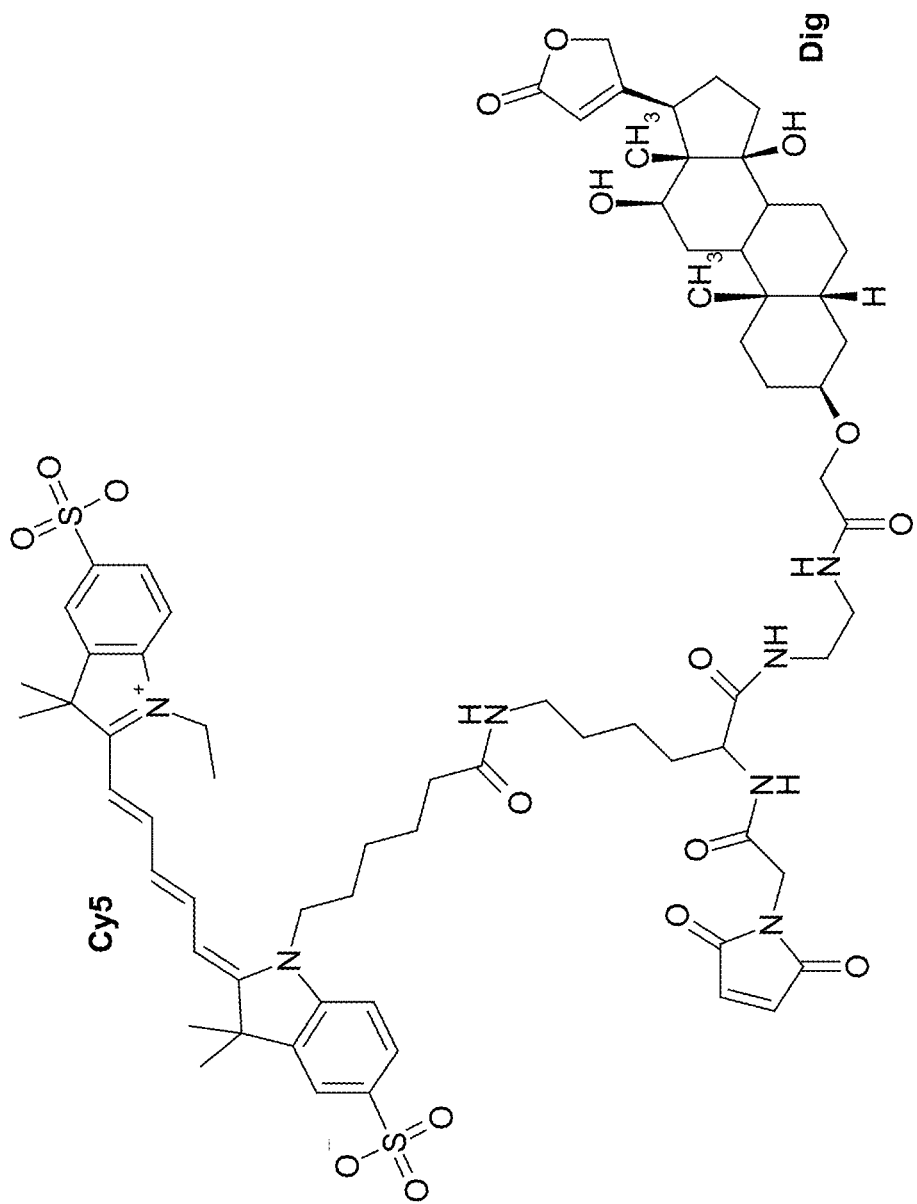
Figure 13:
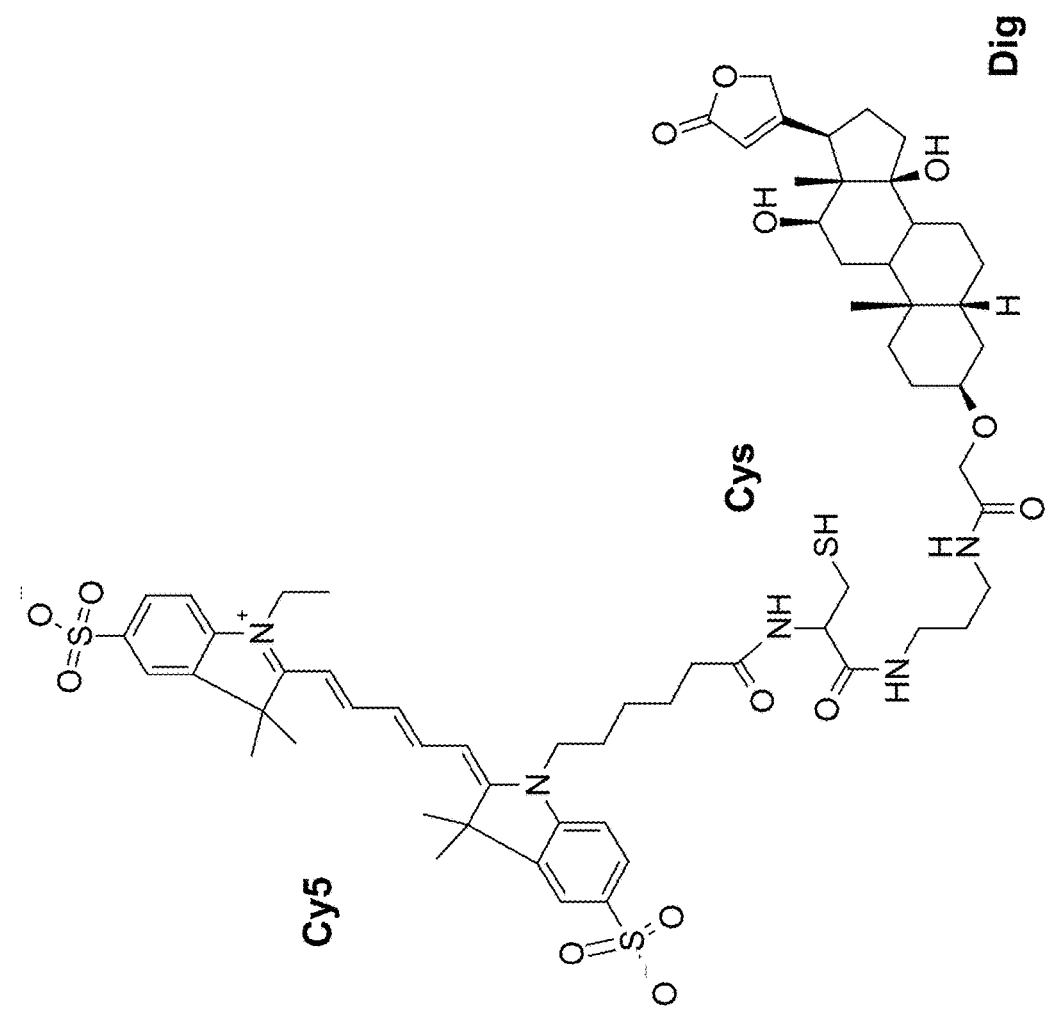
Figure 14:
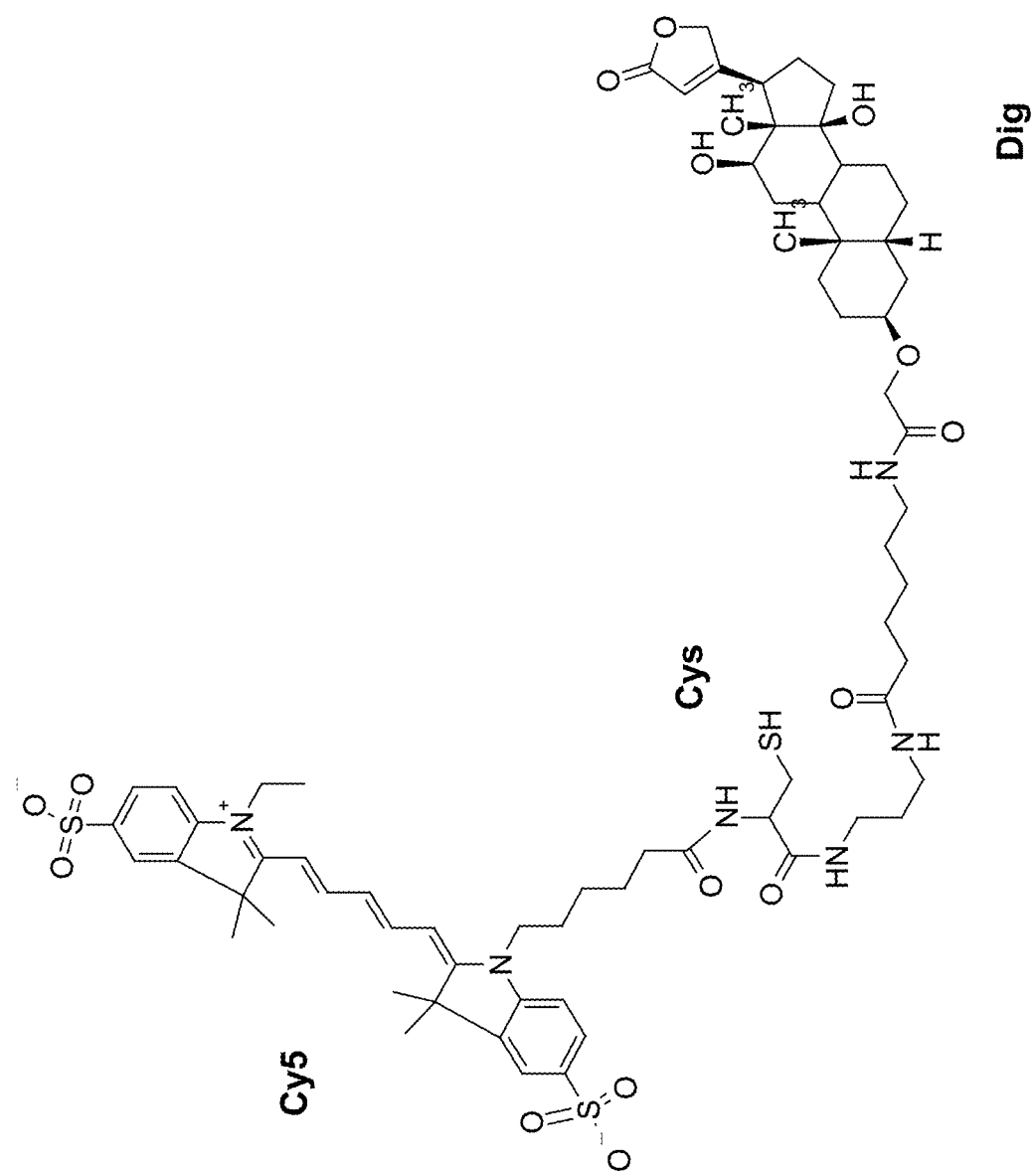
Figure 15:
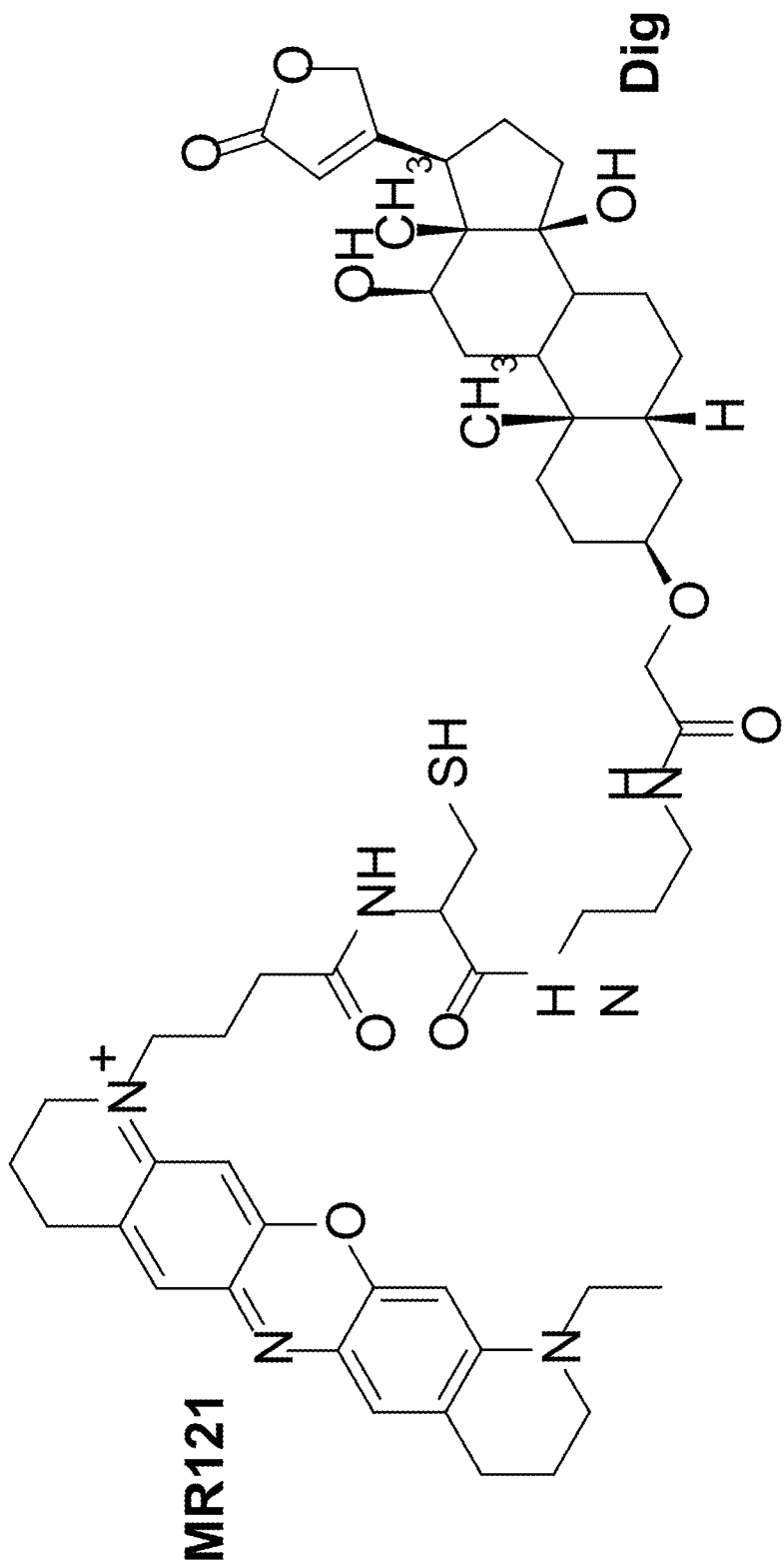
Figure 16:
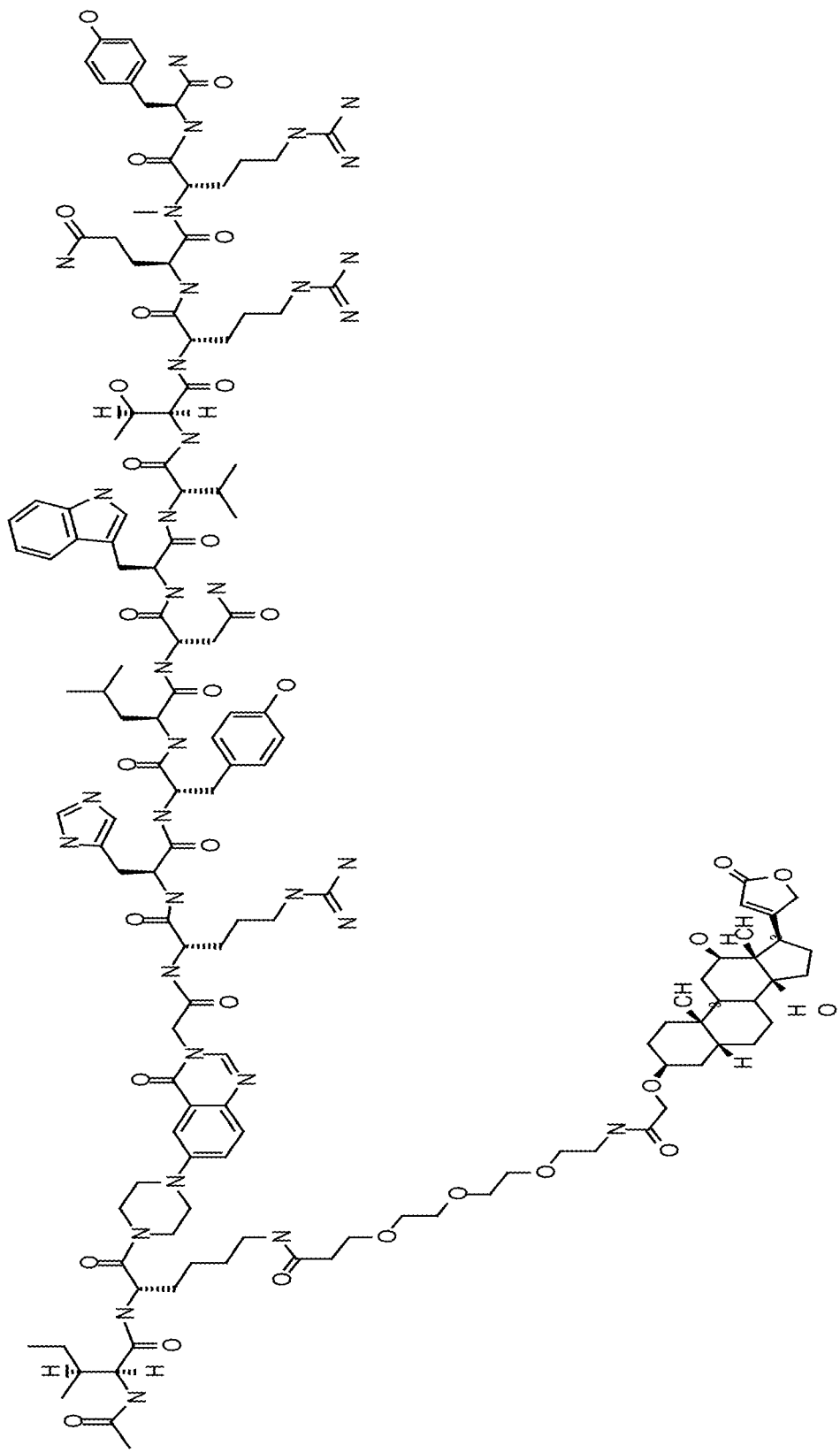
Figure 17:
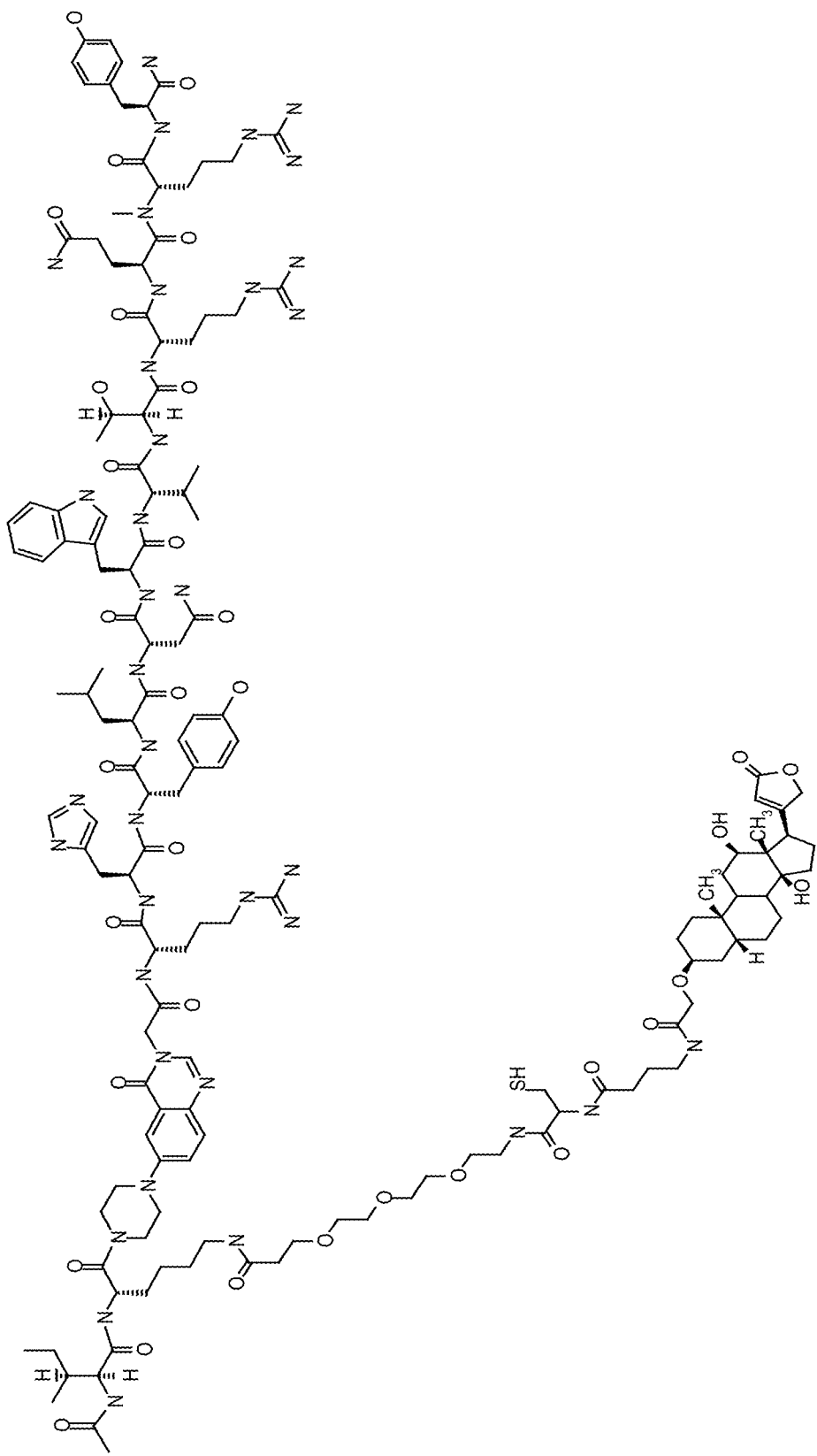
Figure 18:
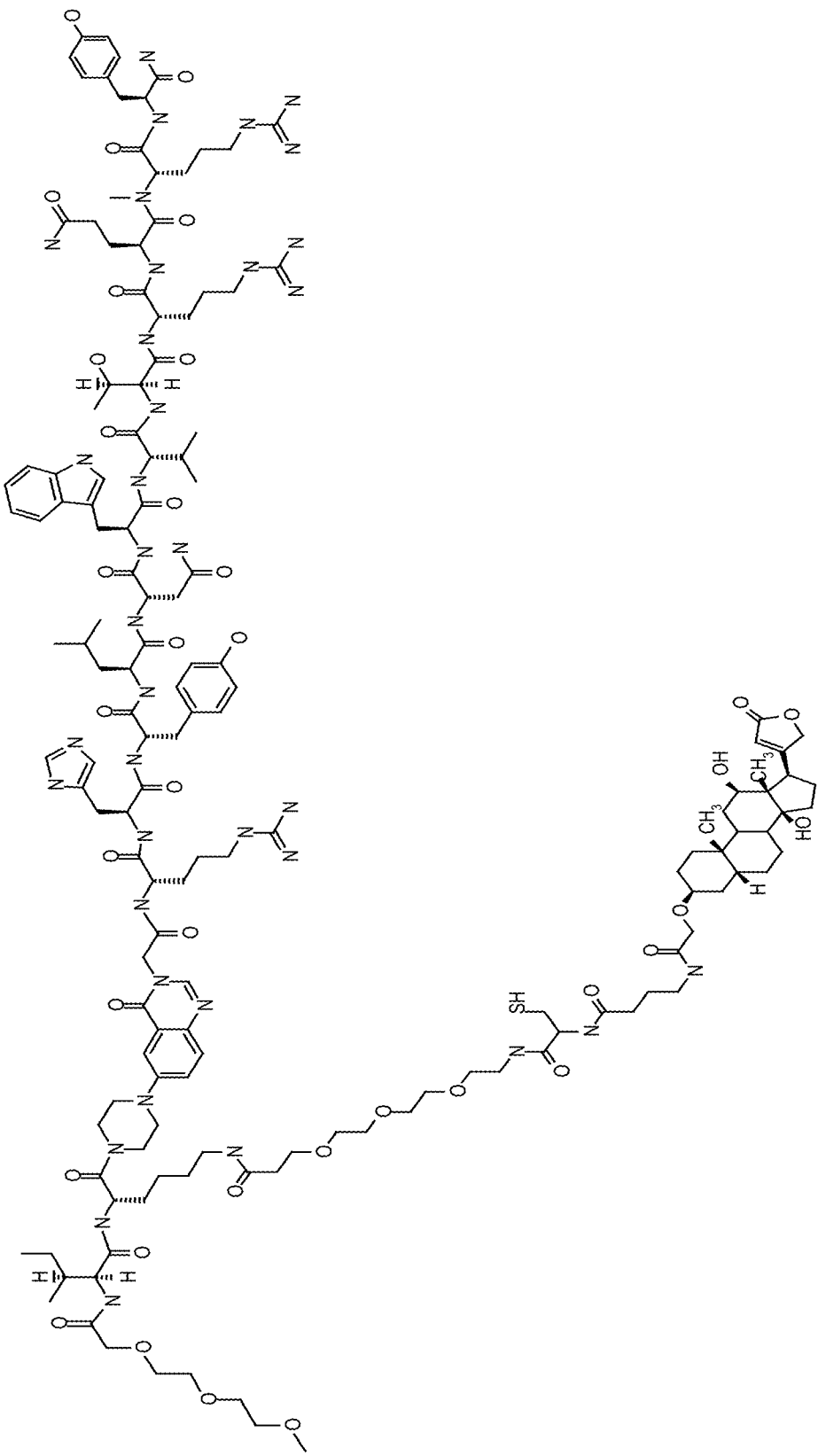
Figure 19:
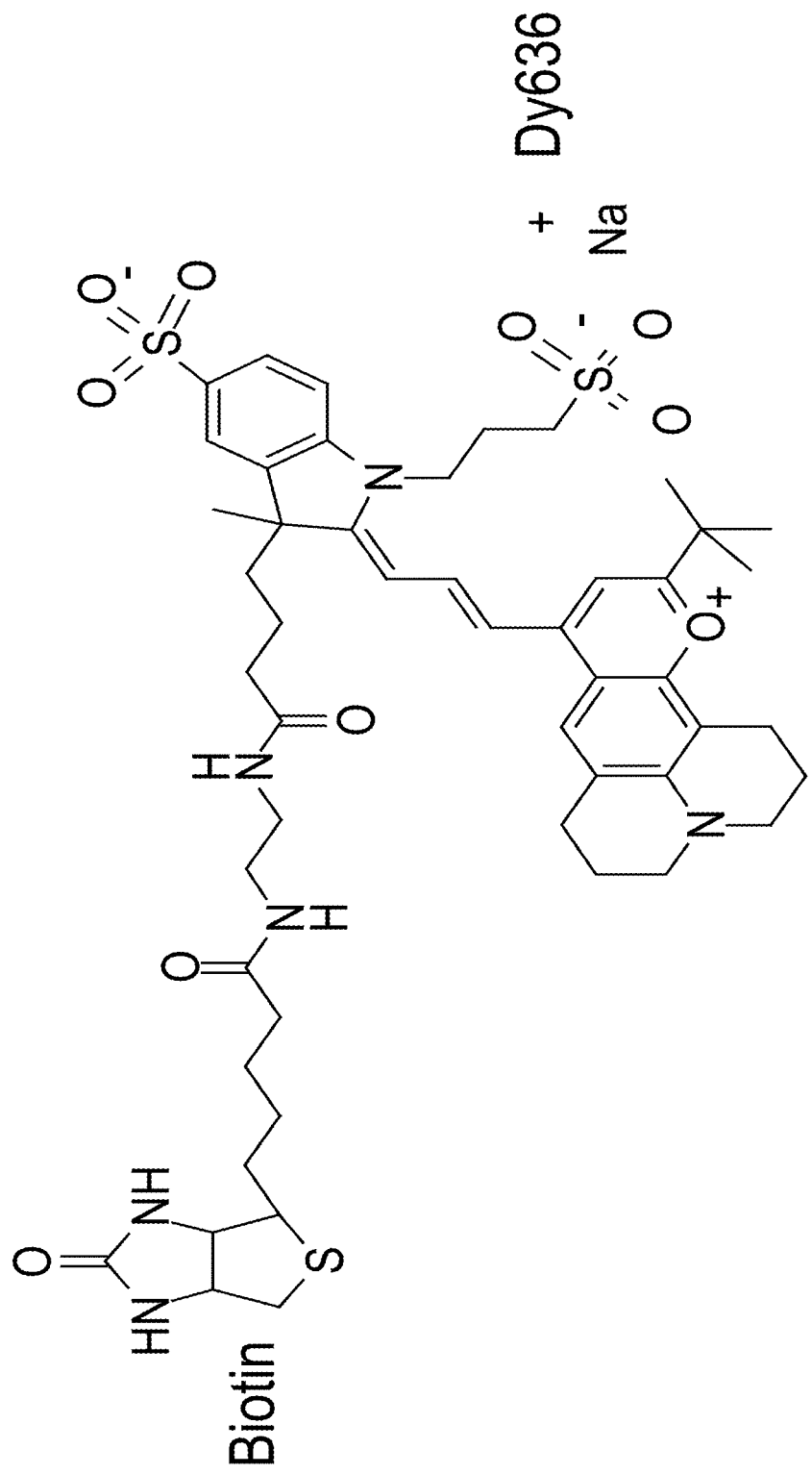
Figure 20:
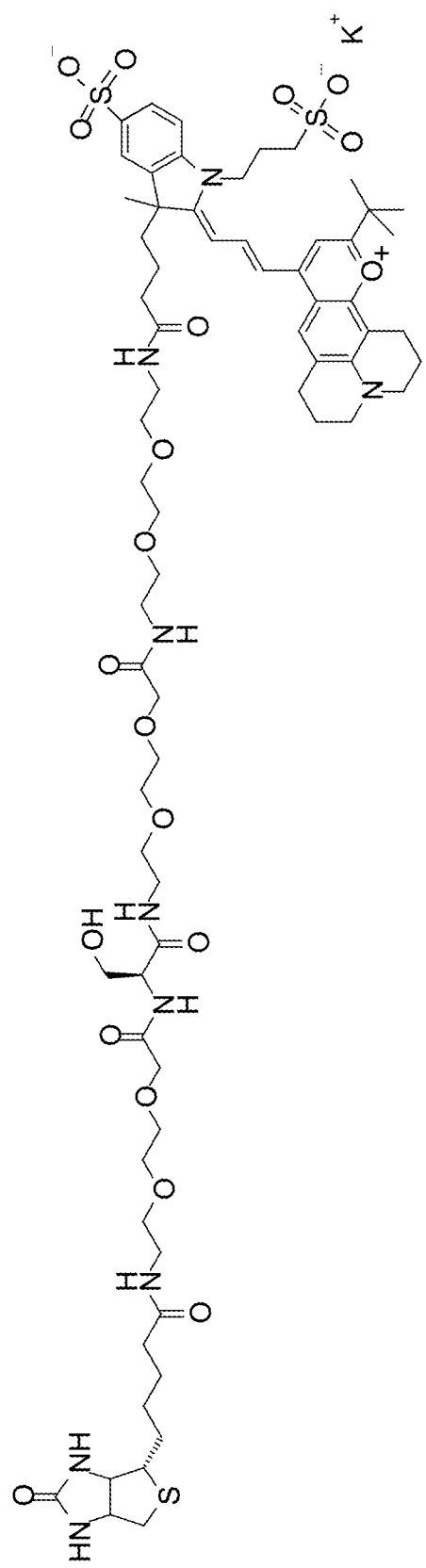
Figure 21:
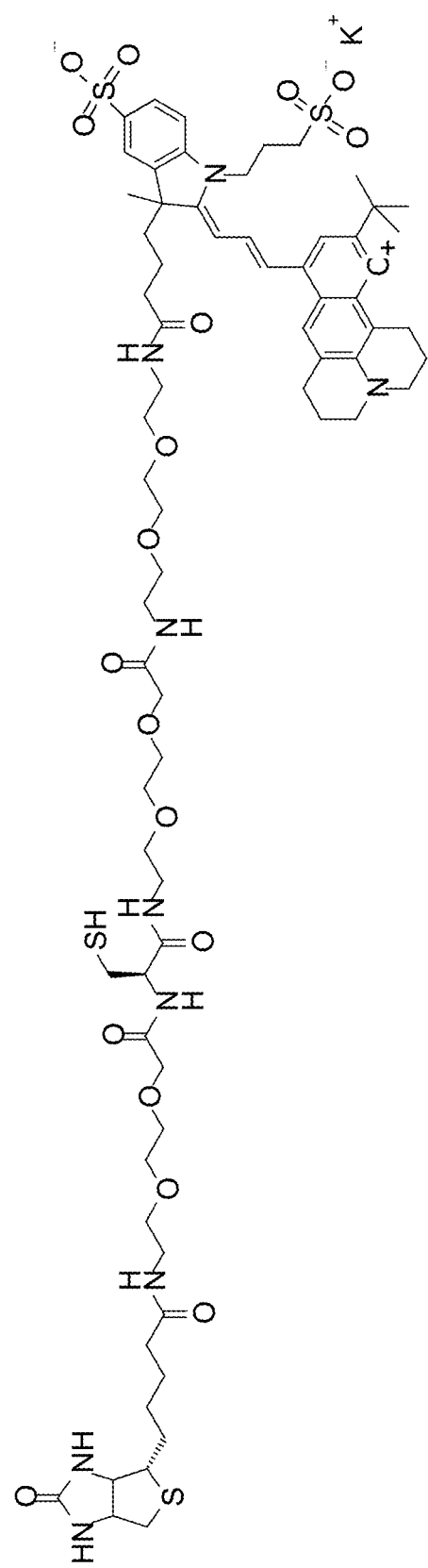
Figure 22:
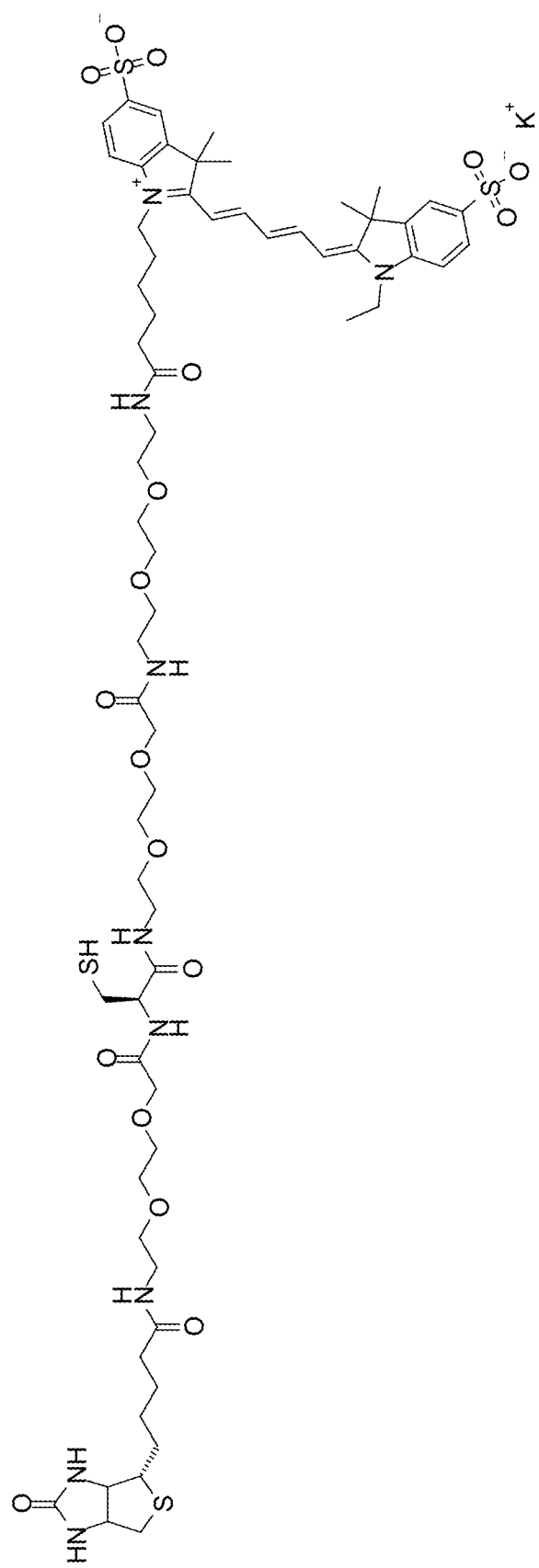
Figure 23:
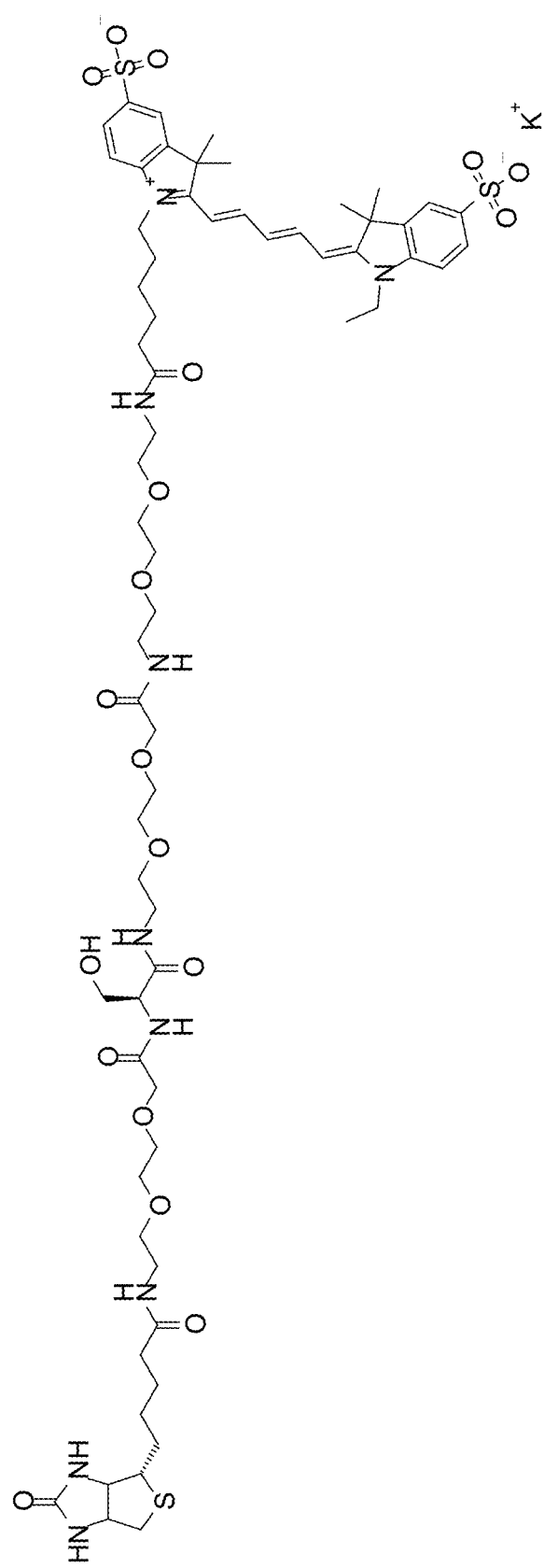
Figure 24:
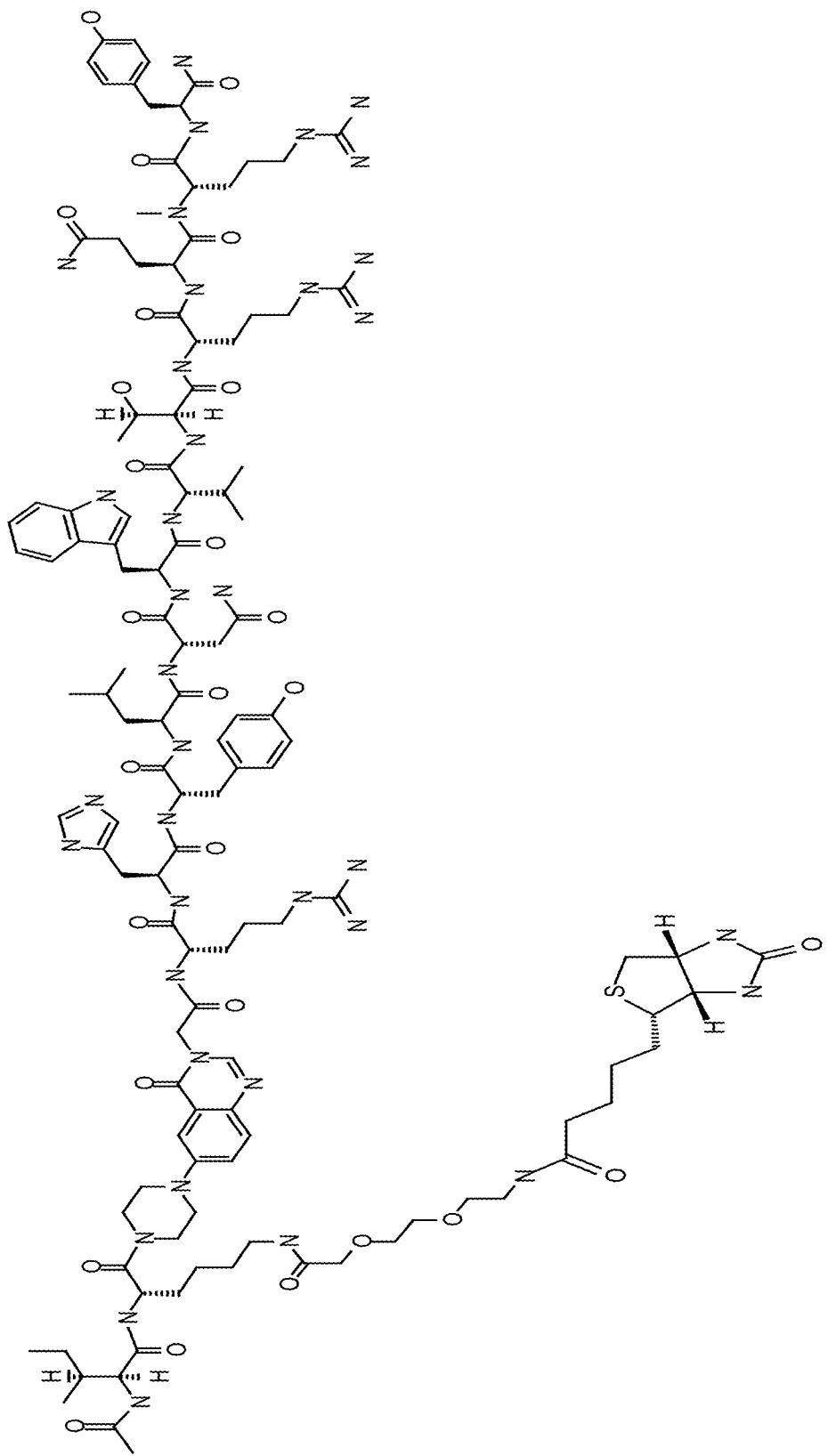
Figure 25:
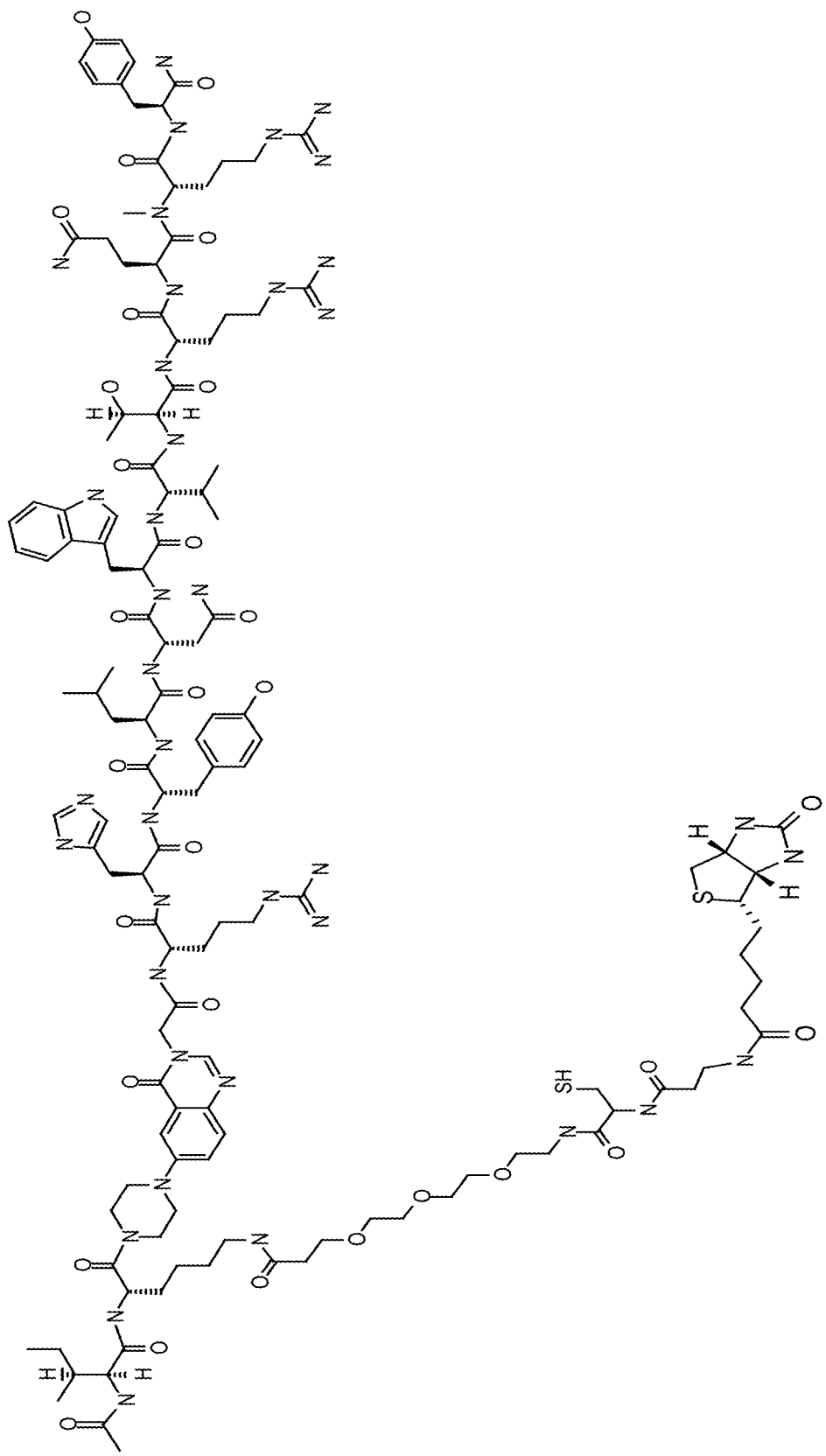
Figure 26:
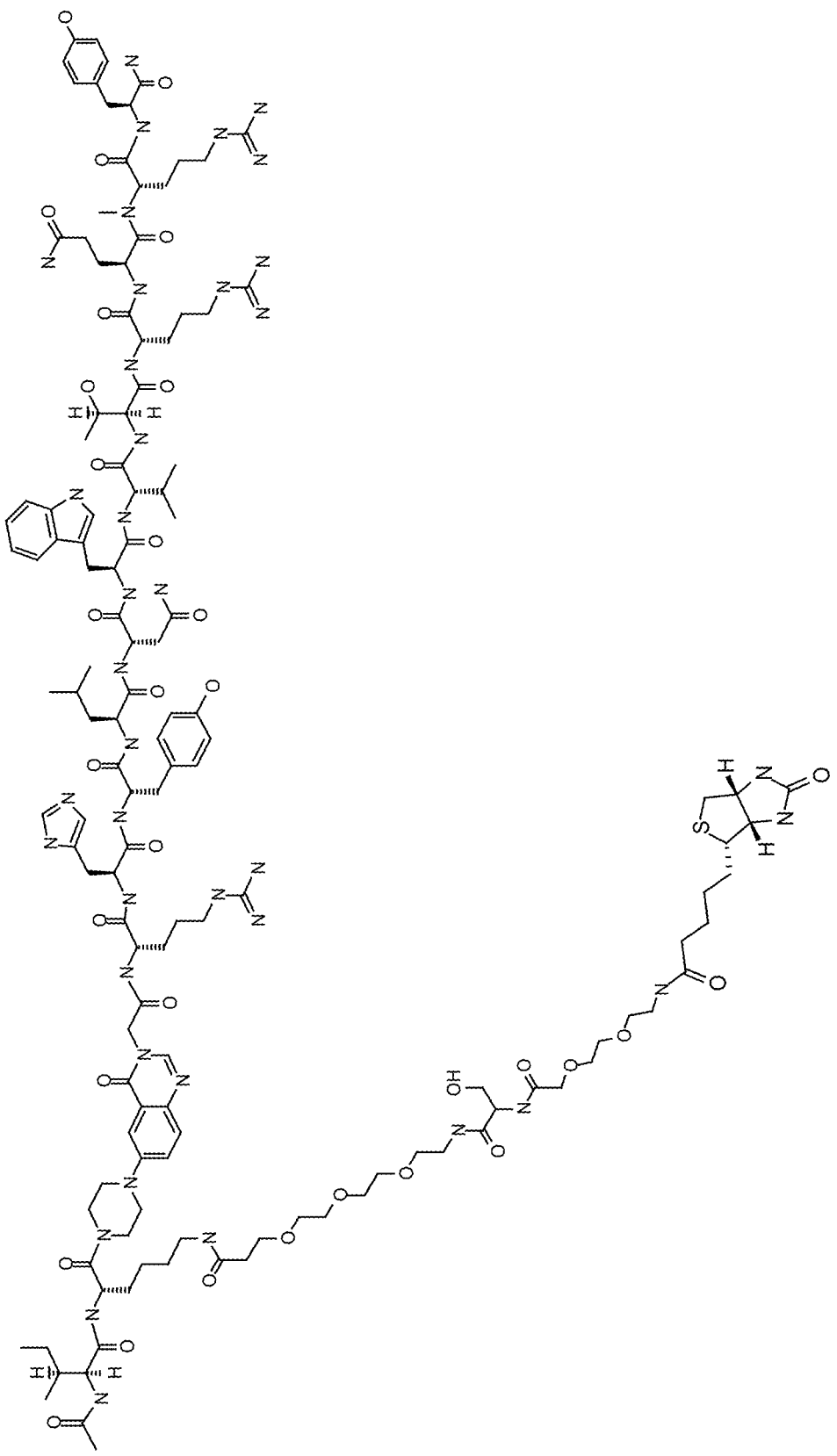
Figure 27:
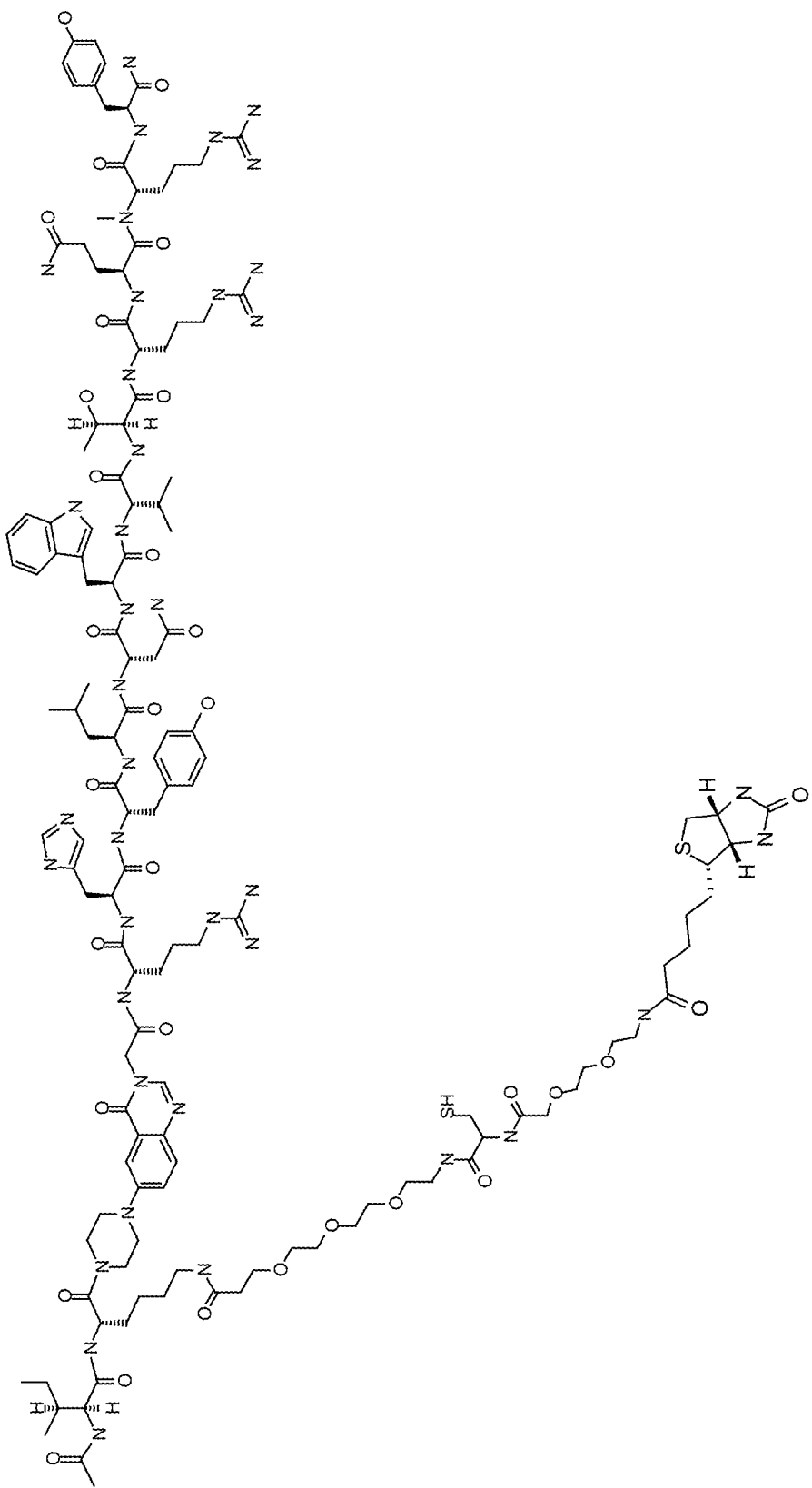
Figure 28:
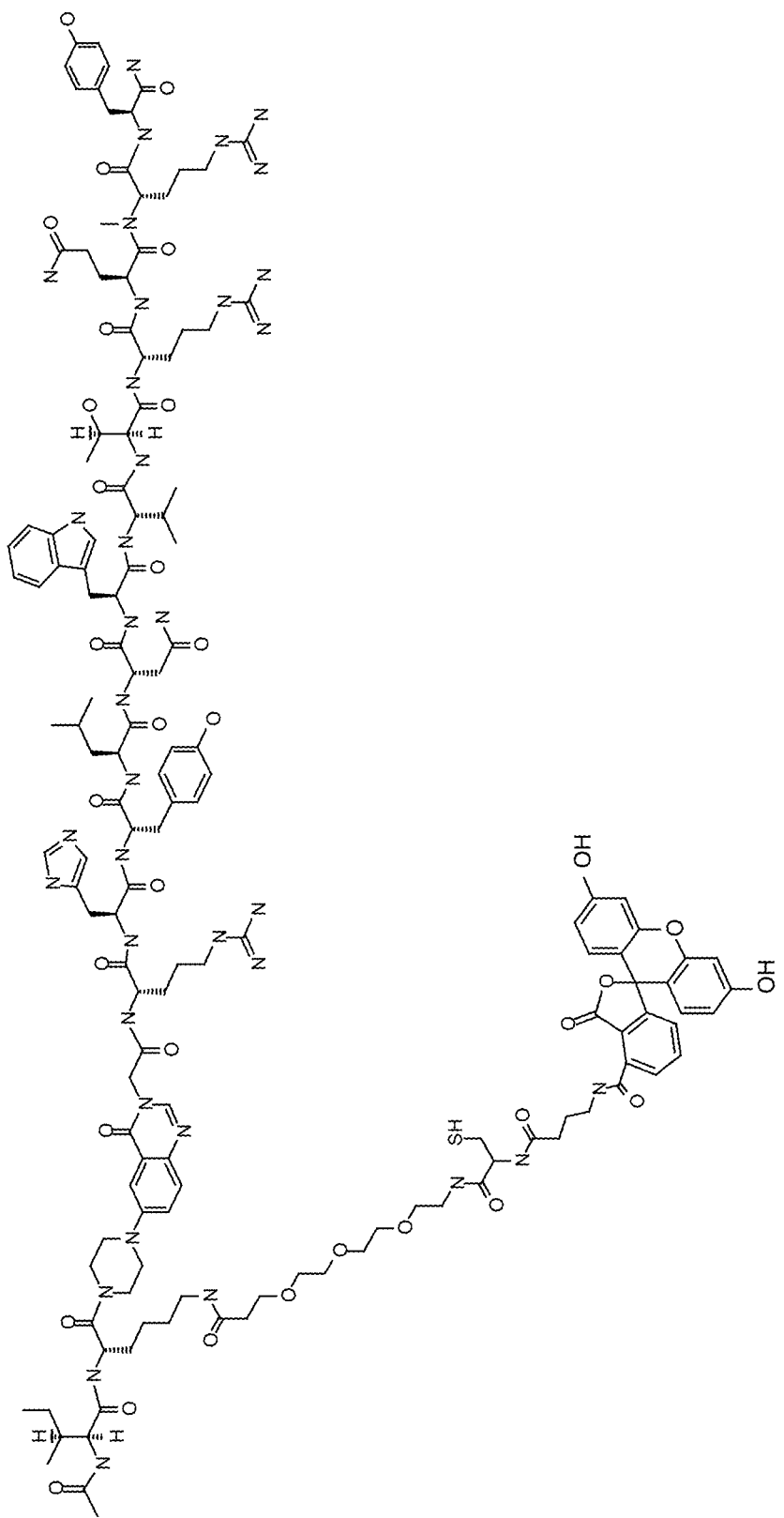
Figure 29:
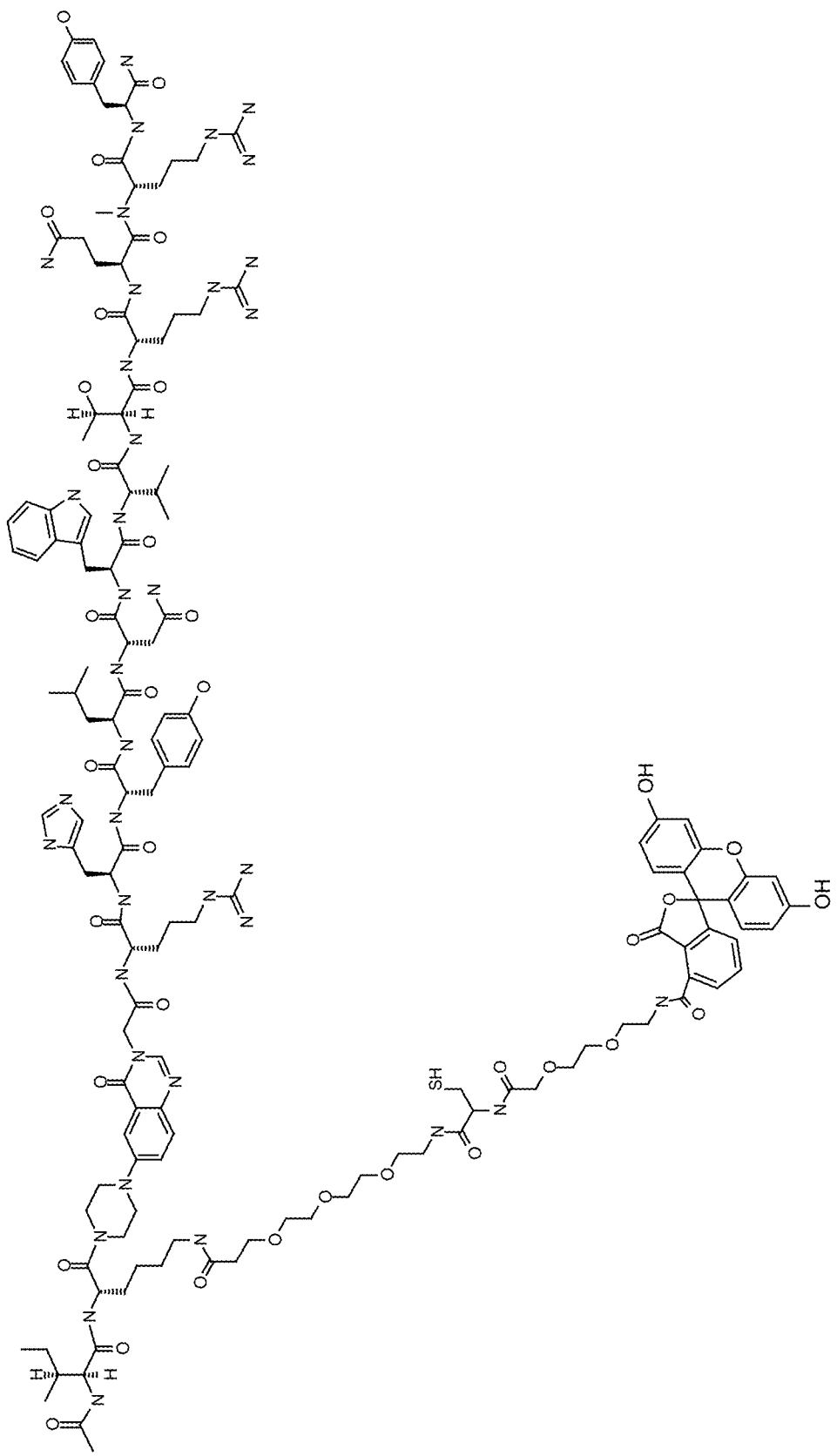
Figure 30:
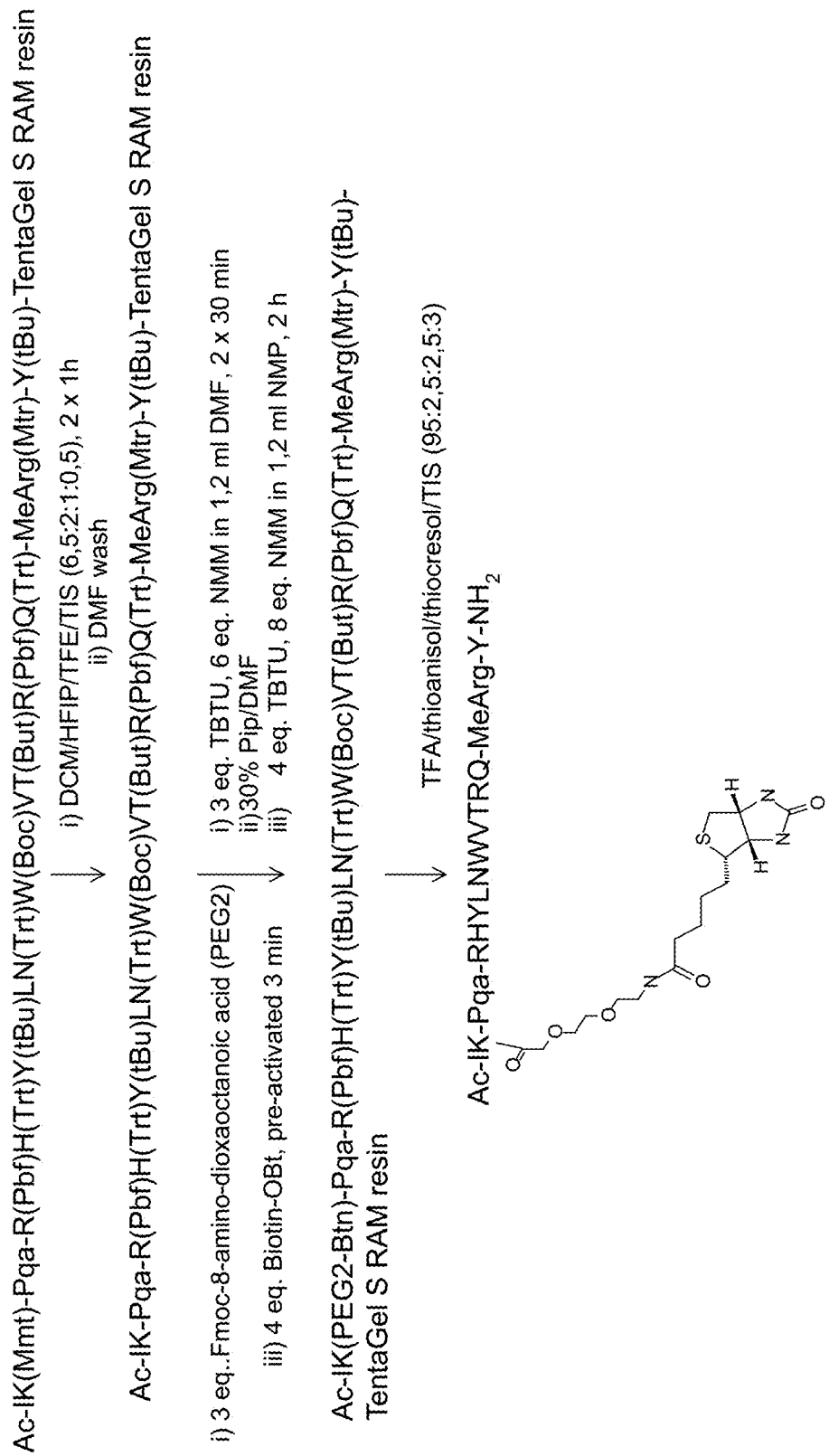
Figure 31:
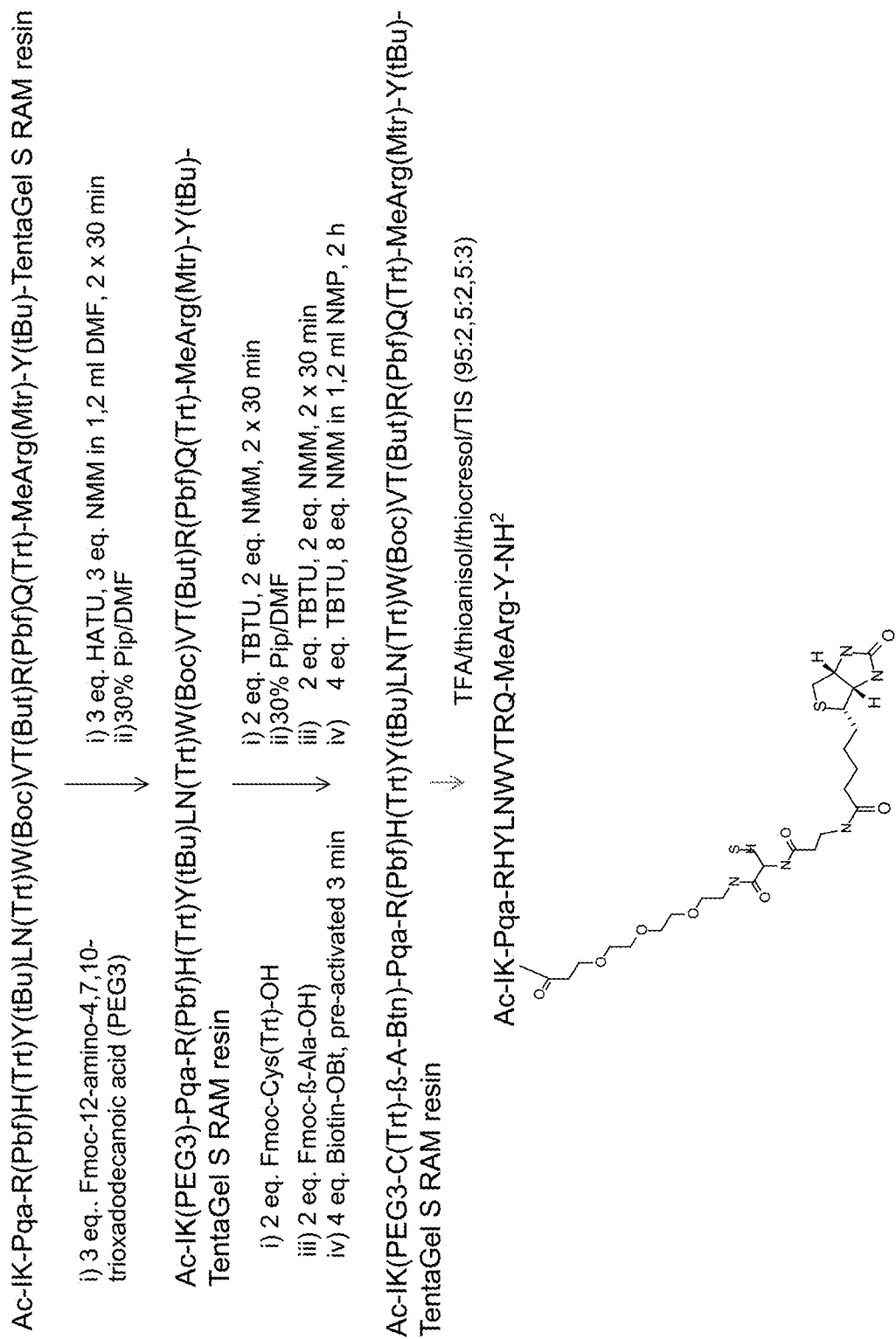
Figure 32:
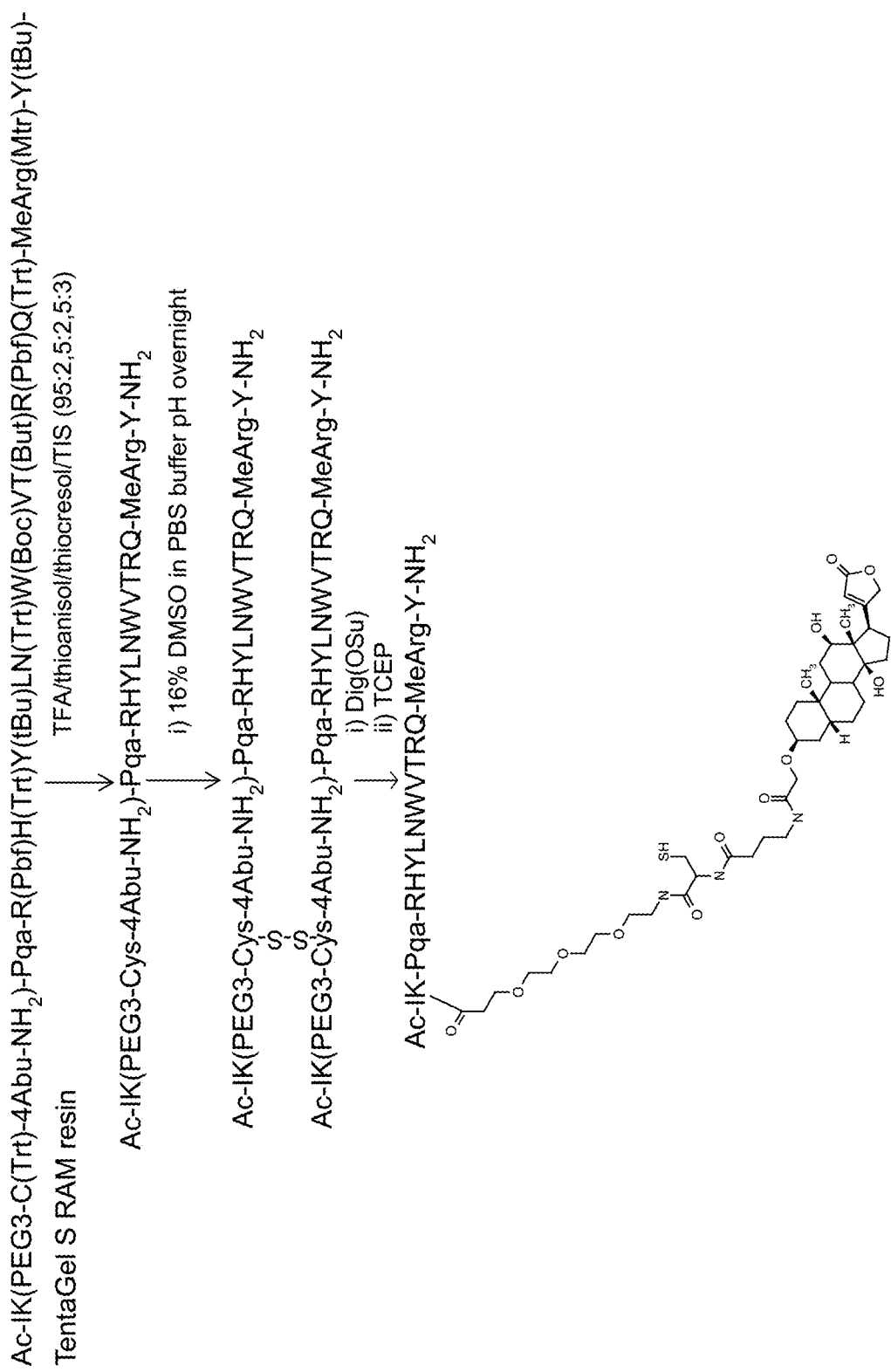
Figure 33:
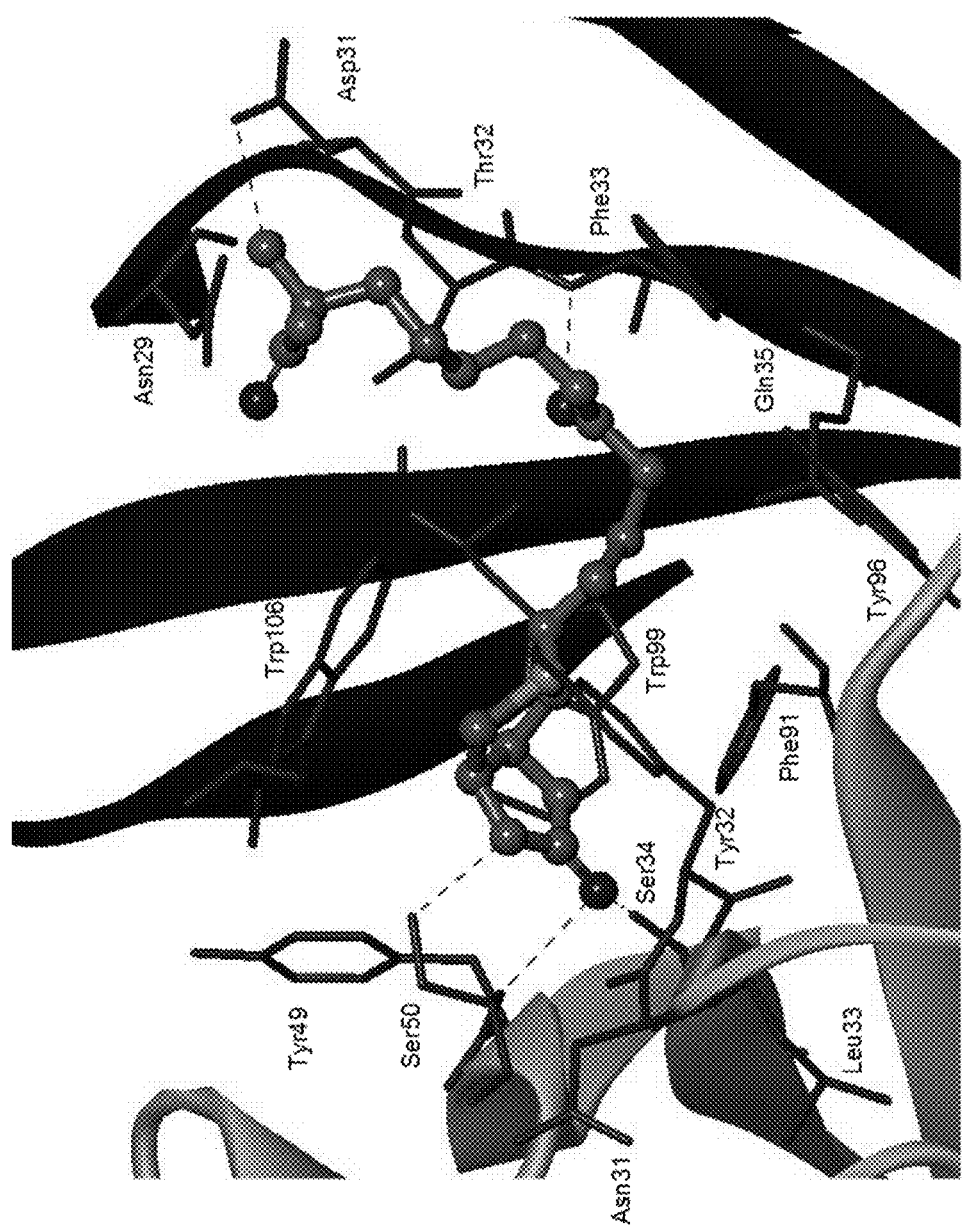
Figure 34A:
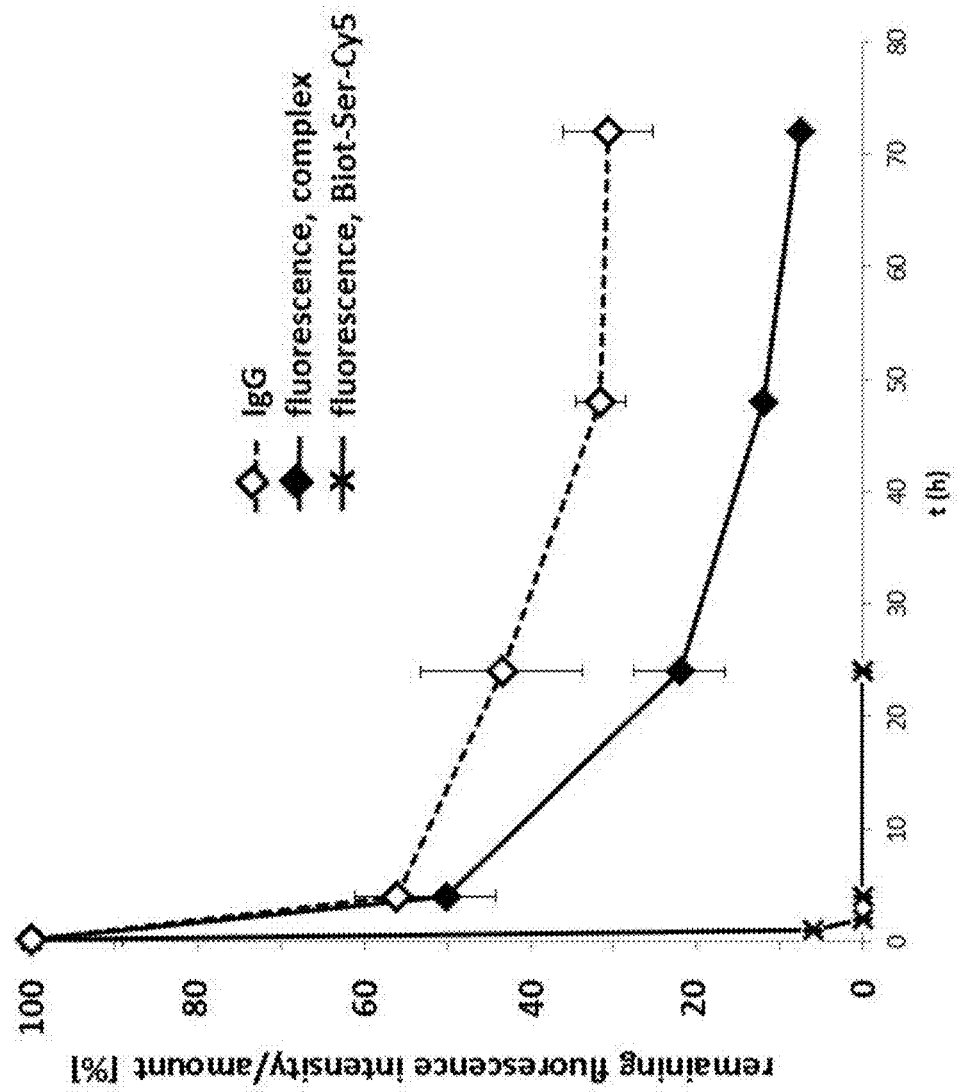
Figure 34B:
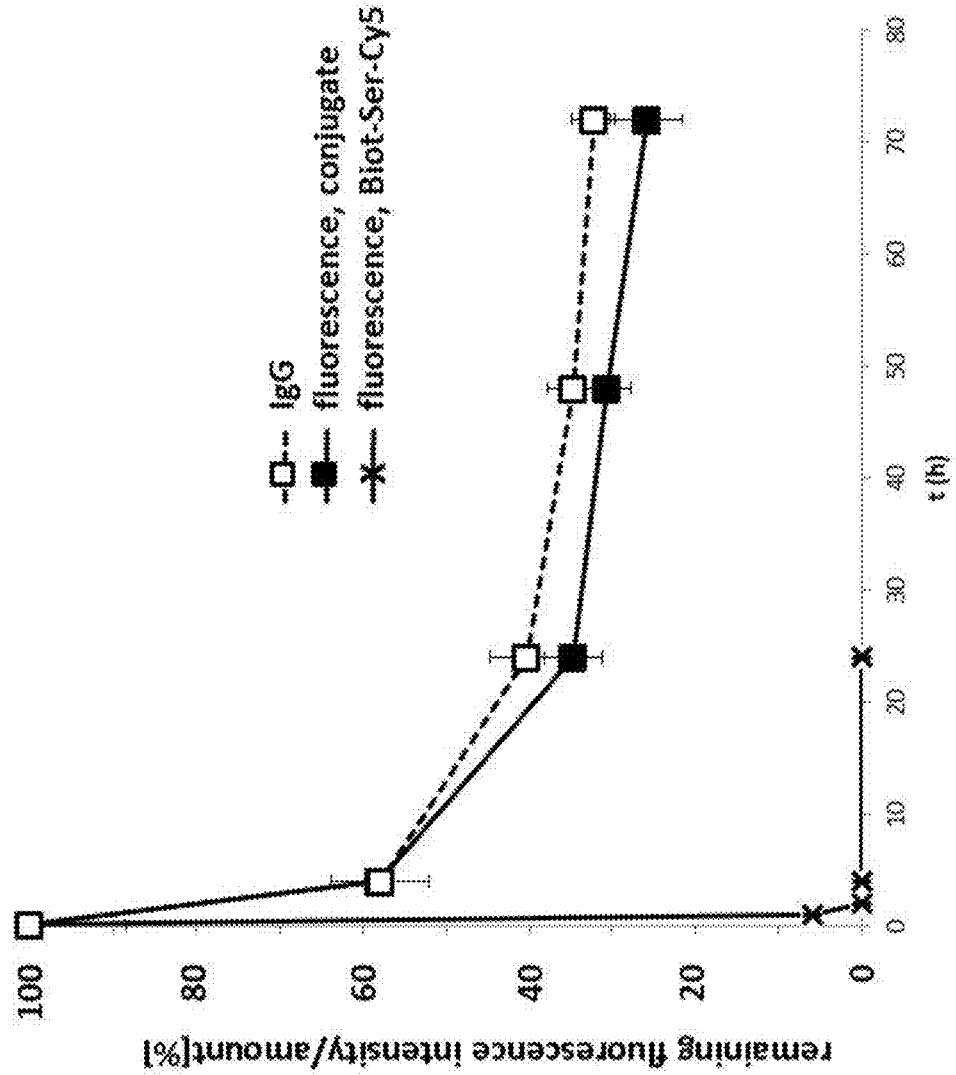
Figure 35:
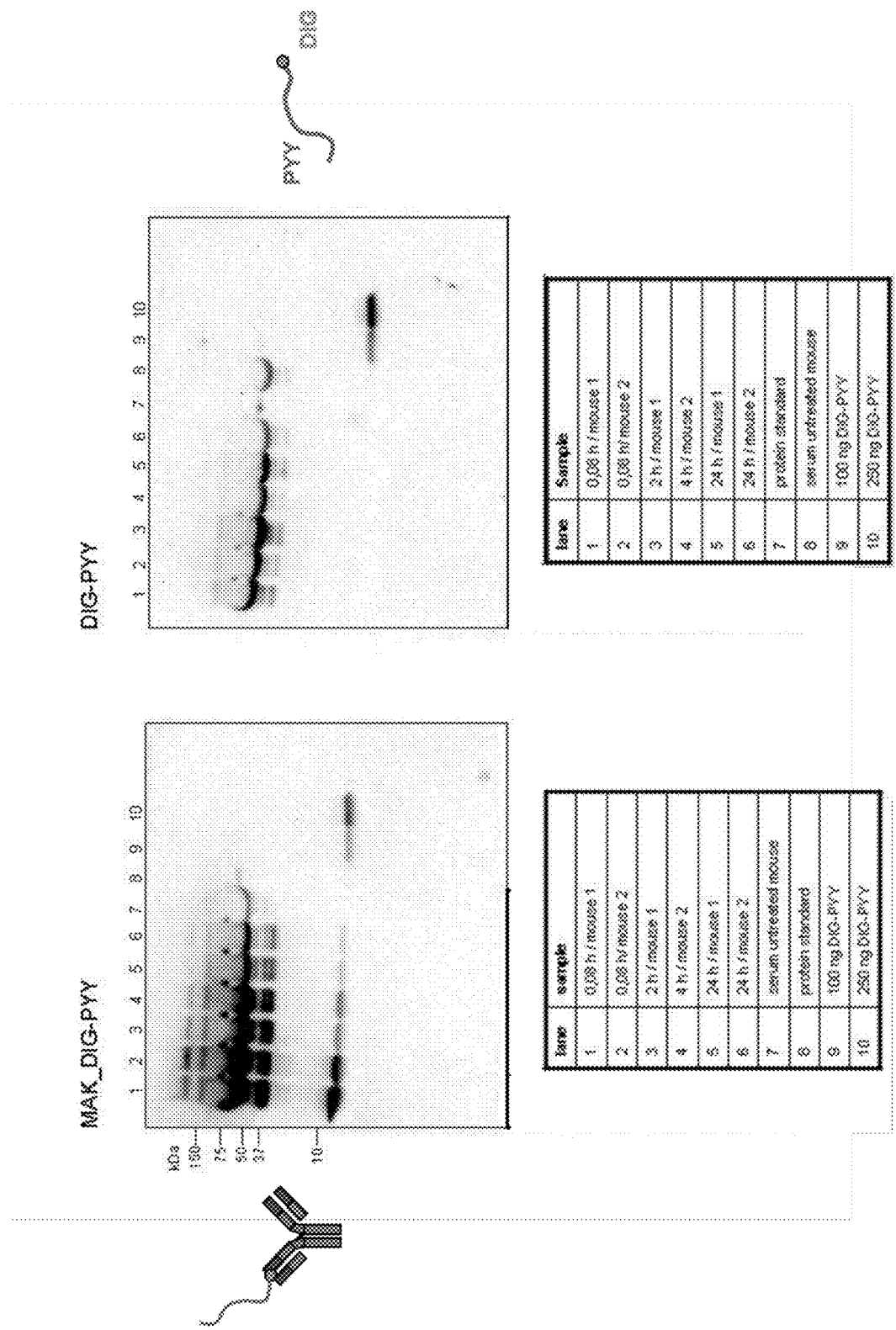
Figure 36:
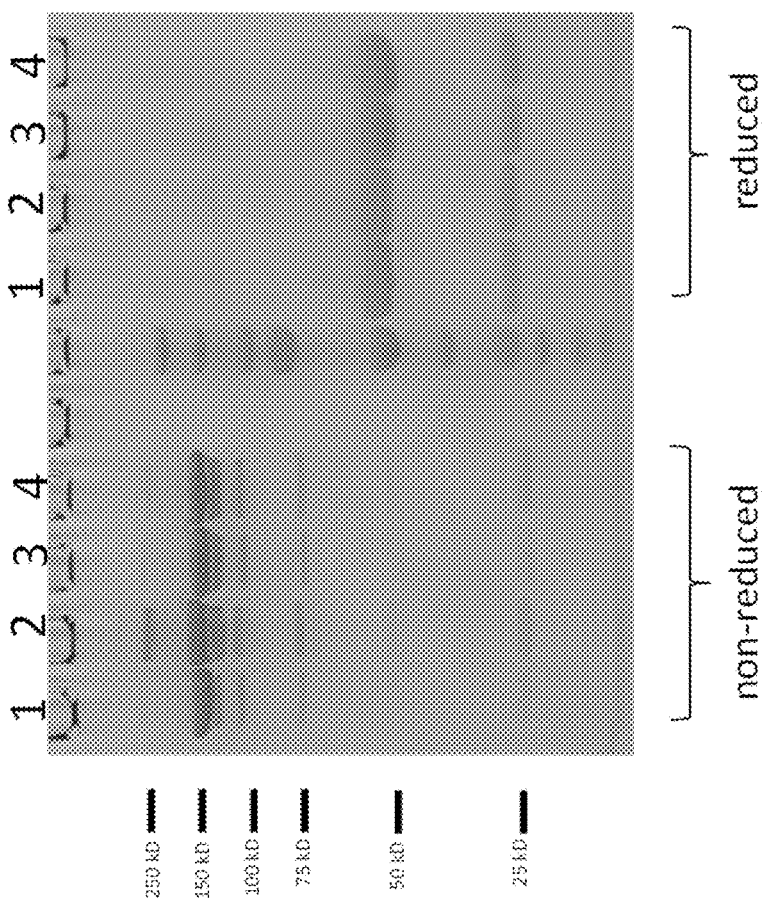
Figure 36:
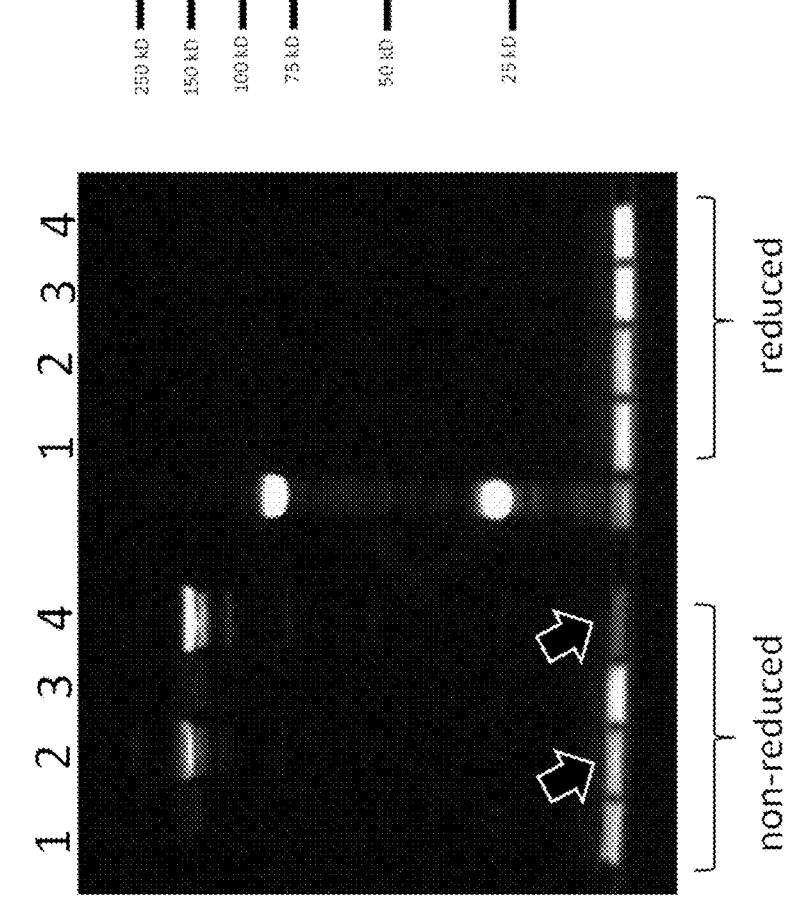
Figure 37:
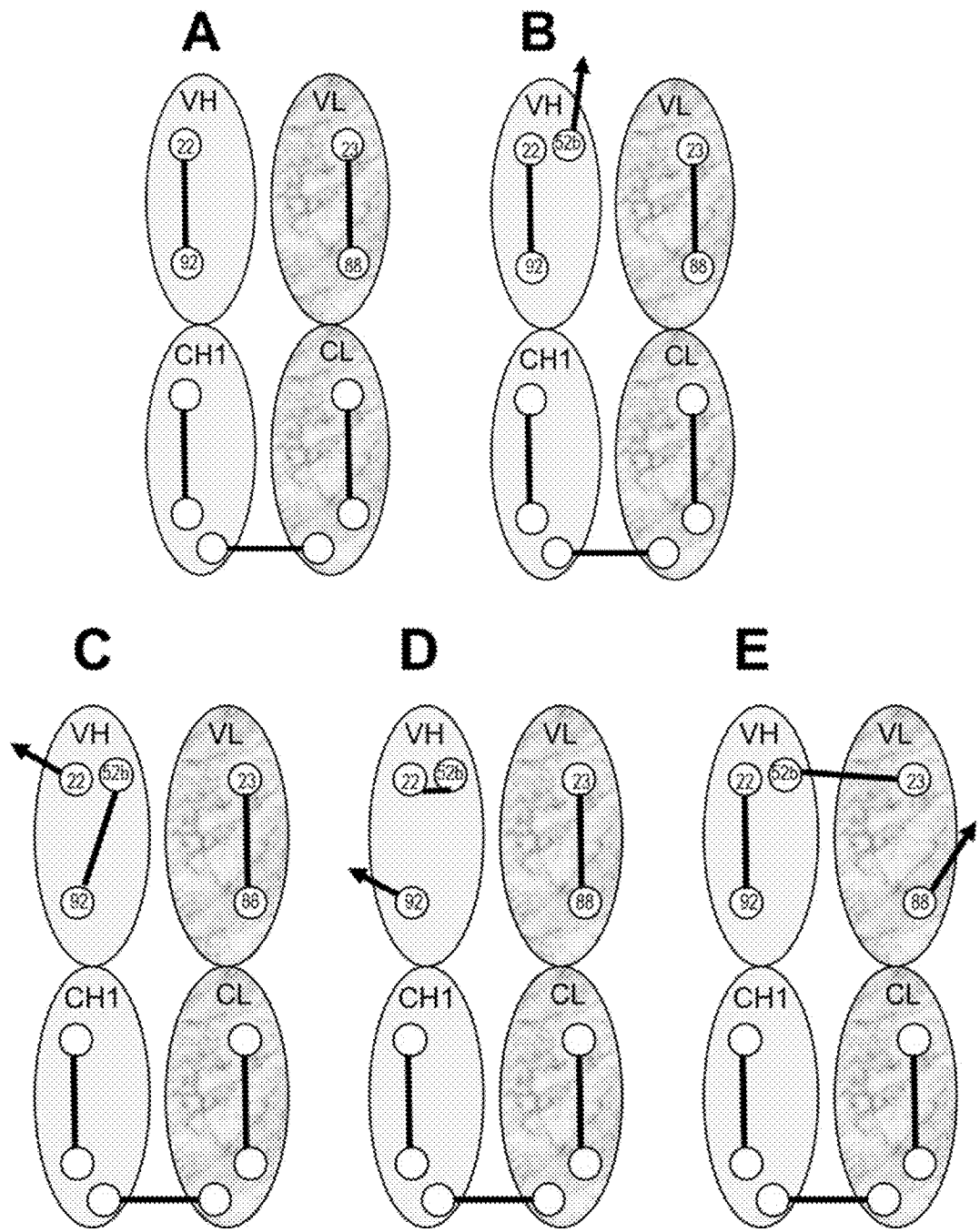

FIG. 12: Structure of DIG-maleiimid-Cy5.
FIG. 13: Structure of DIG-eda-Cys-Cy5.
FIG. 14: Structure of DIG-Ahx-Cys-Cy5.
FIG. 15: Structure of DIG-Cys-MR121.
FIG. 16: Structure of Ac-PYY(PEG3-Dig).
FIG. 17: Structure of Ac-PYY(PEG3-Cys-4Abu-Dig).
FIG. 18: Structure of PEG3-PYY(PEG3-Cys-4Abu-Dig).
FIG. 19: Structure of Dy636-eda-Btn.
FIG. 20: Structure of Dy636-Ser-Btn.
FIG. 21: Structure of Dy636-Cys-Btn.
FIG. 22: Structure of Cy5-Cys-Btn.
FIG. 23: Structure of Cy5-Ser-Btn.
FIG. 24: Structure of Ac-PYY(PEG2-Btn).
FIG. 25: Structure of Ac-PYY-PEG3-Cys-B-Ala-Btn).
FIG. 26: Structure of Ac-PYY-PEG3-Ser-PEG2-Btn).
FIG. 27: Structure of Ac-PYY-PEG3-Cys-PEG2-Btn.
FIG. 28: Structure of Ac-PYY(PEG3-Cys-4-Abu-5-Fluo).
FIG. 29: Structure of Ac-PYY(PEG3-Cys-PEG2-5-Fluo).
FIG. 30: Scheme for the generation of Ac-PYY(PEG2-Btn).
FIG. 31: Scheme for the generation of Ac-PYY(PEG3-Cys-B-Ala-Btn).
FIG. 32: Scheme for the generation of Ac-PYY(PEG3-Cys-4-Abu-Dig).
FIG. 33: X-ray structure of murine anti-biotin antibody in complex with biocytinamid. Amino acid residues that are interacting with biocytinamid are shown in a stick representation.
FIGS. 34A-34B: Results of in vivo blood PK study with covalent conjugates and non-covalent complexes compared to non-complexed antigen/hapten; the relative remaining fluorescence intensity (%, solid marks) of Cy5-mediated fluorescence of Biotin-Cy5 non-covalent complexes (FIG. 34A) and covalent (disulfide-bridged) conjugates (FIG. 34B), as well as of non-complexed Biotin-Ser-Cy5 (asterix) is shown; the fluorescence signal at time point t=0.08 h was set to 100%; additionally, the relative remaining amount of human IgG in the mouse serum samples is shown (open marks); IgG serum concentration (mg/ml) at t=0.08 h was set to 100%.
FIG. 35: Western blot of the determination of the amount of digoxigenylated PYY polypeptide in the serum of mice.
FIG. 36: Analysis of affinity-driven complexation of haptenylated compounds with anti-hapten antibodies.
Antibody complexation and subsequent covalent linkage at defined positions is directed by fluorescence signals in SDS PAGE analyses, which were carried out as described in Example 20.
Left: fluorescent image with non-reduced (left side of gel) and reduced (right side of gel) samples.
Right: Coomassie blue staining.
1: humanized anti-digoxigenin antibody+biotin-Cys-Cy5
2: humanized anti-digoxigenin antibody VH52bC+biotin-Cys-Cy5
3: humanized anti-biotin antibody+biotin-Cys-Cy5
4: humanized anti-biotin antibody VH53C+biotin-Cys-Cy5
The white arrows mark the excess (uncoupled) biotin-Cys-Cy5, which is significantly higher when anti-digoxigenin antibody VH52bC is used, because the conjugation reaction is not affinity driven in this case.
FIG. 37: Cysteine positions and disulfide patterns within the Fab region, required to form a Dig-binding antibody with additional cysteine at position 52b for hapten-mediated site-directed directed covalent payload coupling. (A) Cysteines and disulfide pattern in VH and CH1 domains, and in VL and CL domains that are required to form functional Fab fragments. (B) Cysteines and disulfide pattern in VH and CH1 domains, and in VL and CL domains that are required to form functional Fab fragments with additional cysteine at position 52b for hapten-mediated site-directed directed covalent payload coupling. (C&D) Potential to form incorrect disulfide bonds within the VH domain of the VH52b variant which would result in misfolded nonfunctional antibodies. E) Example for a potential incorrect interdomain disulfide bond within the Fv region of the VH52b variant, which would result in misfolded nonfunctional antibodies.

Figure 38:
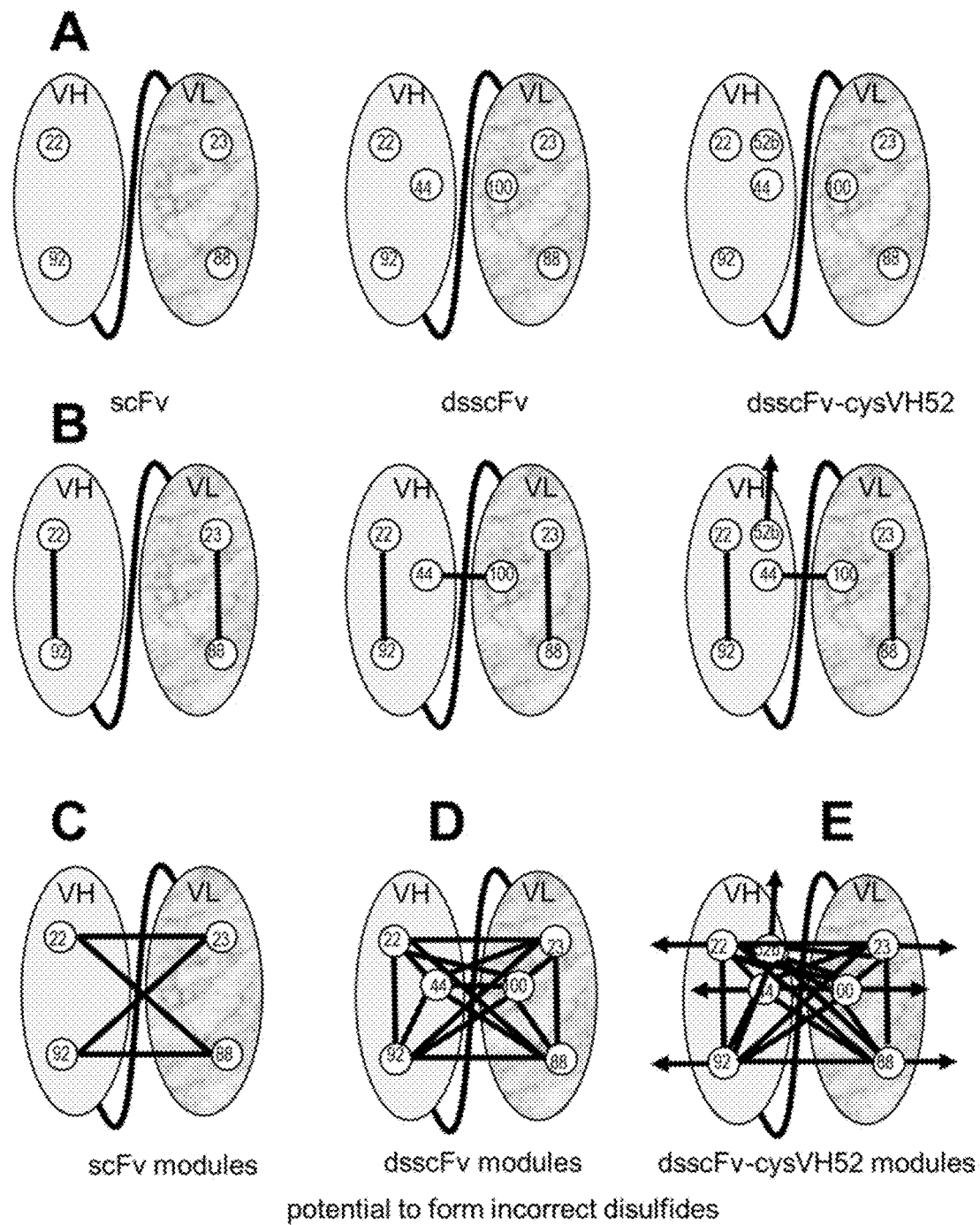

FIG. 38: Cysteine positions and disulfide patterns required to form a Dig-binding disulfide-stabilized single-chain Fv with additional cysteine at position 52b for hapten-mediated site-directed directed covalent payload coupling. (A) Cysteines in VH and VL domains that are required to form functional scFvs, dsscFvs and 52b mutated dsscFvs. (B) correct pattern of disulfide bonds that must be formed to generate functional scFvs, dsscFvs and 52b mutated dss-cFvs. (C) Potential to form incorrect disulfide bonds which would result in misfolded nonfunctional scFvs. (D) Potential to form incorrect disulfide bonds which would result in misfolded nonfunctional dsscFvs. (E) Potential to form incorrect disulfide bonds which would result in misfolded nonfunctional 52b mutated dsscFvs.

Figure 39:
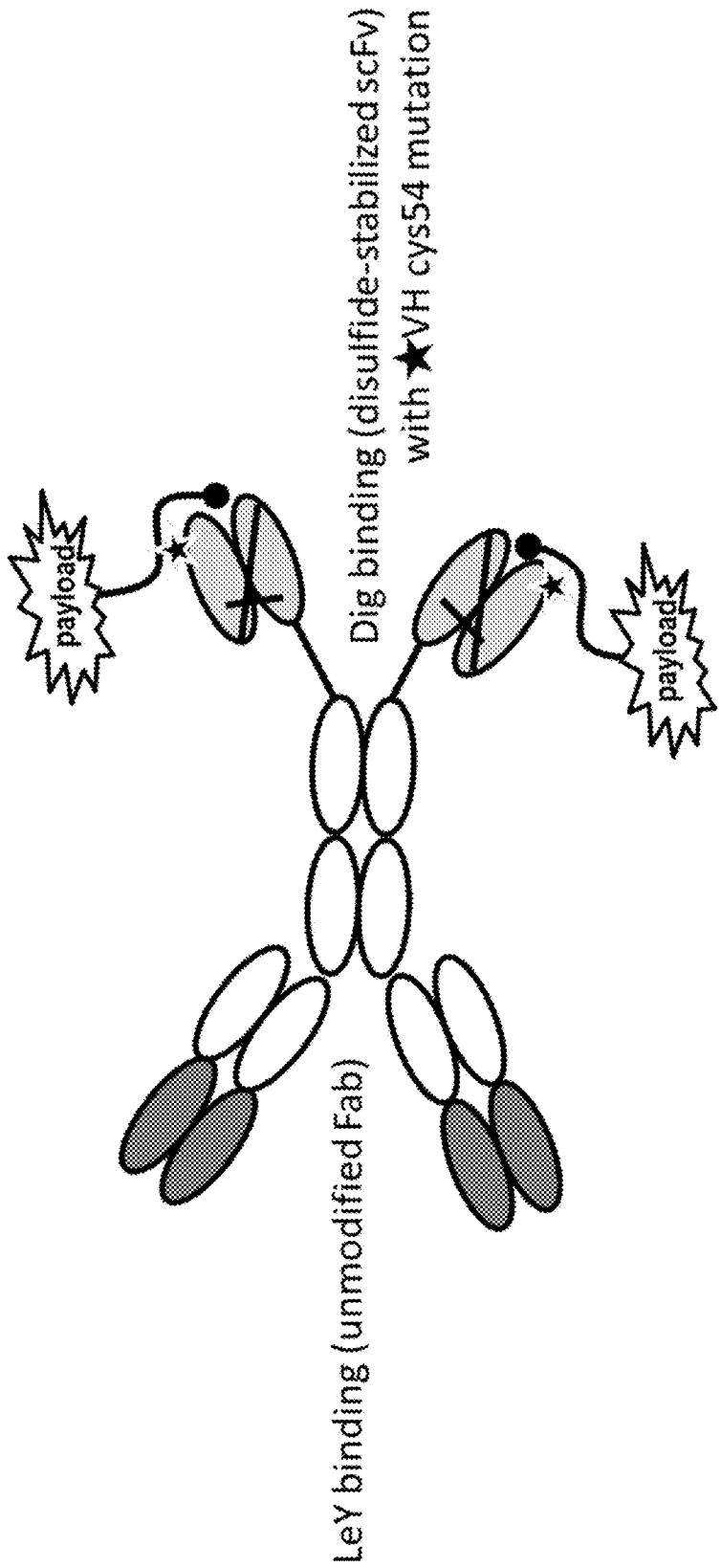

FIG. 39: Composition of a LeY-Dig bispecific antibody derivative as delivery vehicle for covalently coupled payloads.

Figure 40:
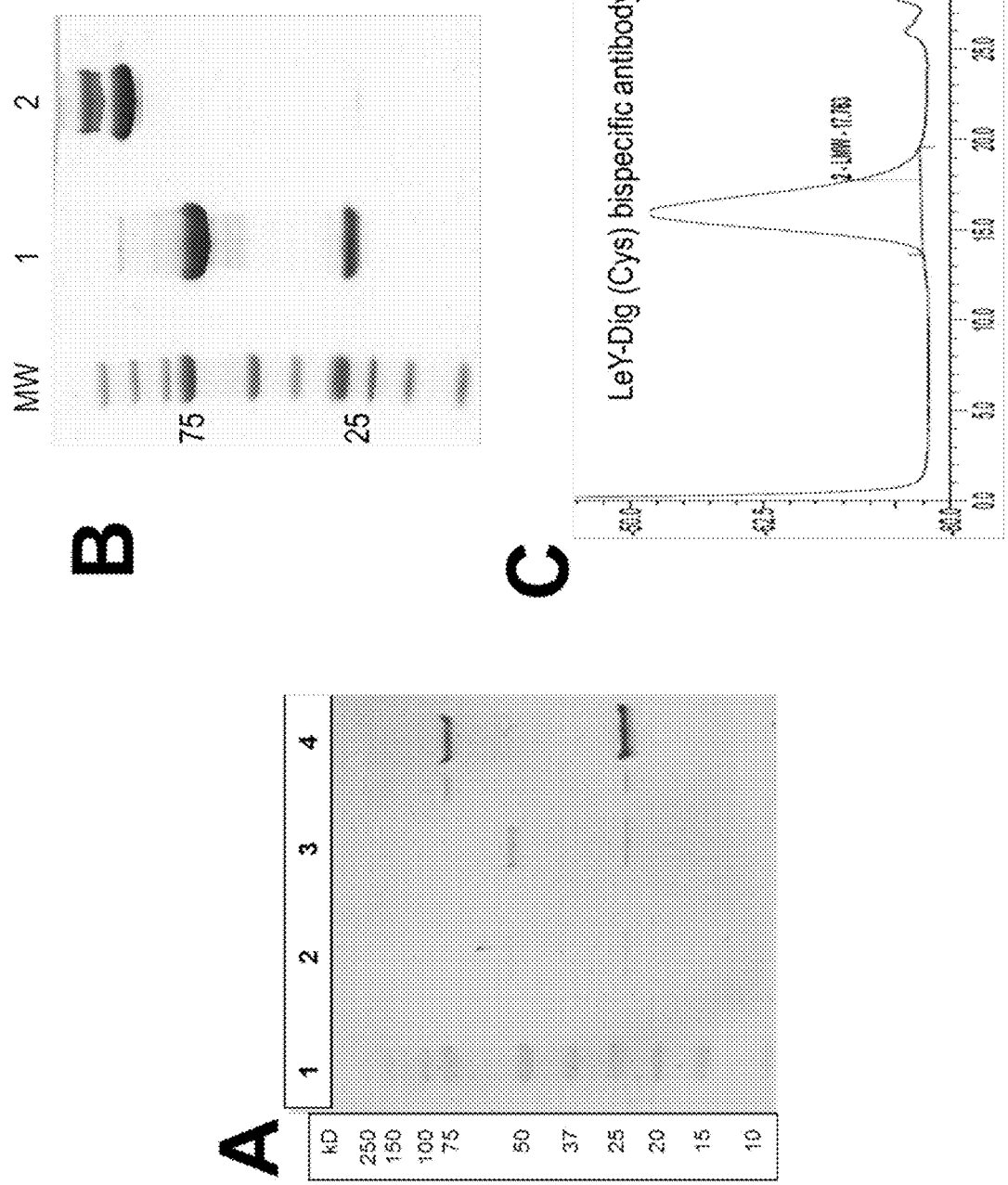

FIG. 40: Expression and Purification of bispecific anti-hapten antibody derivatives for targeted delivery of covalently coupled payloads.
(A) For Western blot analyses, cell culture supernatants were subjected to SDS PAGE (NuPAGE 4-12% Bis-Tris Gel (1.0 mm×12 well) (Invitrogen; Cat. No. NP0322) and proteins were subsequently transferred to Immobilon Transfer Membranes (Immobilon-P) (Millipore; Cat. No. IPVH07850), PVDF with pore Size: 0.45 m. Antibody derivatives were detected by Anti-Human Kappa Light Chain)-Alkaline Phosphatase antibody produced in goat, (affinity purified), Sigma (Cat. No. A3813) at a 1:1000 dilution, and Anti-Human IgG (Fc specific)-Alkaline Phosphatase antibody produced in goat, Sigma (Cat. No. A9544) at a 1:1000 dilution. The substrate BCIP/NBT-Blue Liquid Substrate (Sigma Cat. No. B3804 was applied for the development of the Western blot. Lane 1—molecular weight marker; Lane 2 & 3—control antibody with unmodified heavy-chain; Lane 4 LeY-Dig(52bC) bispecific antibody with extended H-chain.
(B) SDS-PAGE analyses (NuPAGE 4-12% Bis-Tris Gel [Invitrogen] and subsequent staining with Coomassie brilliant blue demonstrates purity of protein preparations and visualizes polypeptide chains related to the IgG with the apparent molecular sizes that correspond to their calculated molecular weights. Lane 1—molecular weight marker; Lane 2—LeY-Dig(52bC) bispecific antibody with extended H-chain reduced, lane 3—LeY-Dig(52bC) bispecific antibody with extended heavy-chain non-reduced;
(C) Size exclusion chromatography (Superdex 200) demonstrates homogeneity and lack of aggregates in the protein preparations of the LeY-Dig(52bC) bispecific antibody derivative after protein A purification.

Figure 41:
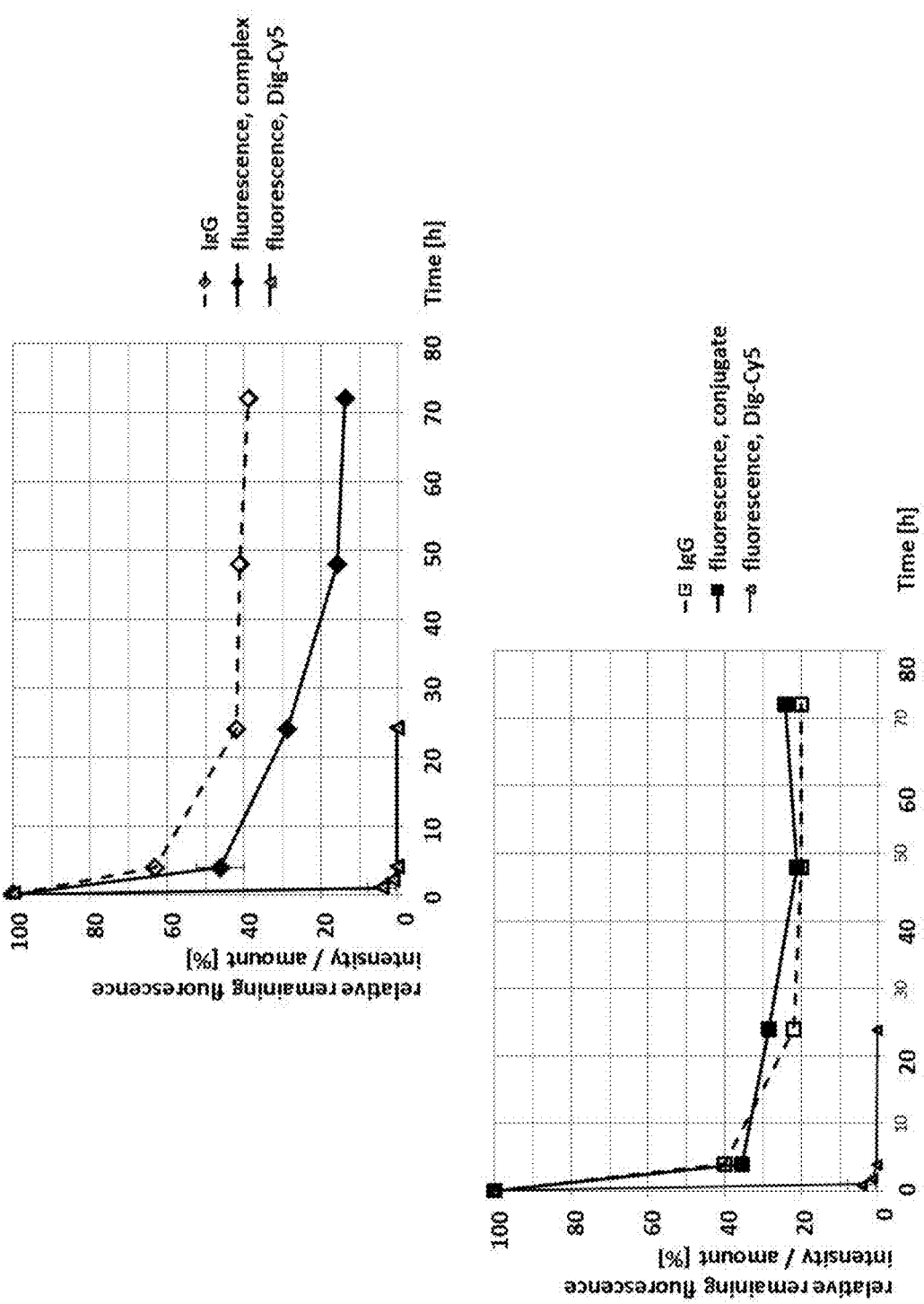

FIG. 41: Results of in vivo blood pharmacokinetic study with covalent conjugates and non-covalent complexes compared to non-complexed hapten compound Dig-Cy5; the relative remaining fluorescence intensity (%) of Dig-Cy5 non-covalent complexes (upper panel), Dig-Cys-Cy5 covalent (disulfide-bridged) conjugates (lower panel), as well as of non-complexed Dig-Cy5 (grey triangles) is shown; the fluorescence signal at time point t=0.08 h was set to 100%; additionally, the relative remaining amount of human IgG in the mouse serum samples is shown; IgG serum concentration (mg/ml) at t=0.08 h was set to 100%.

Figure 42:
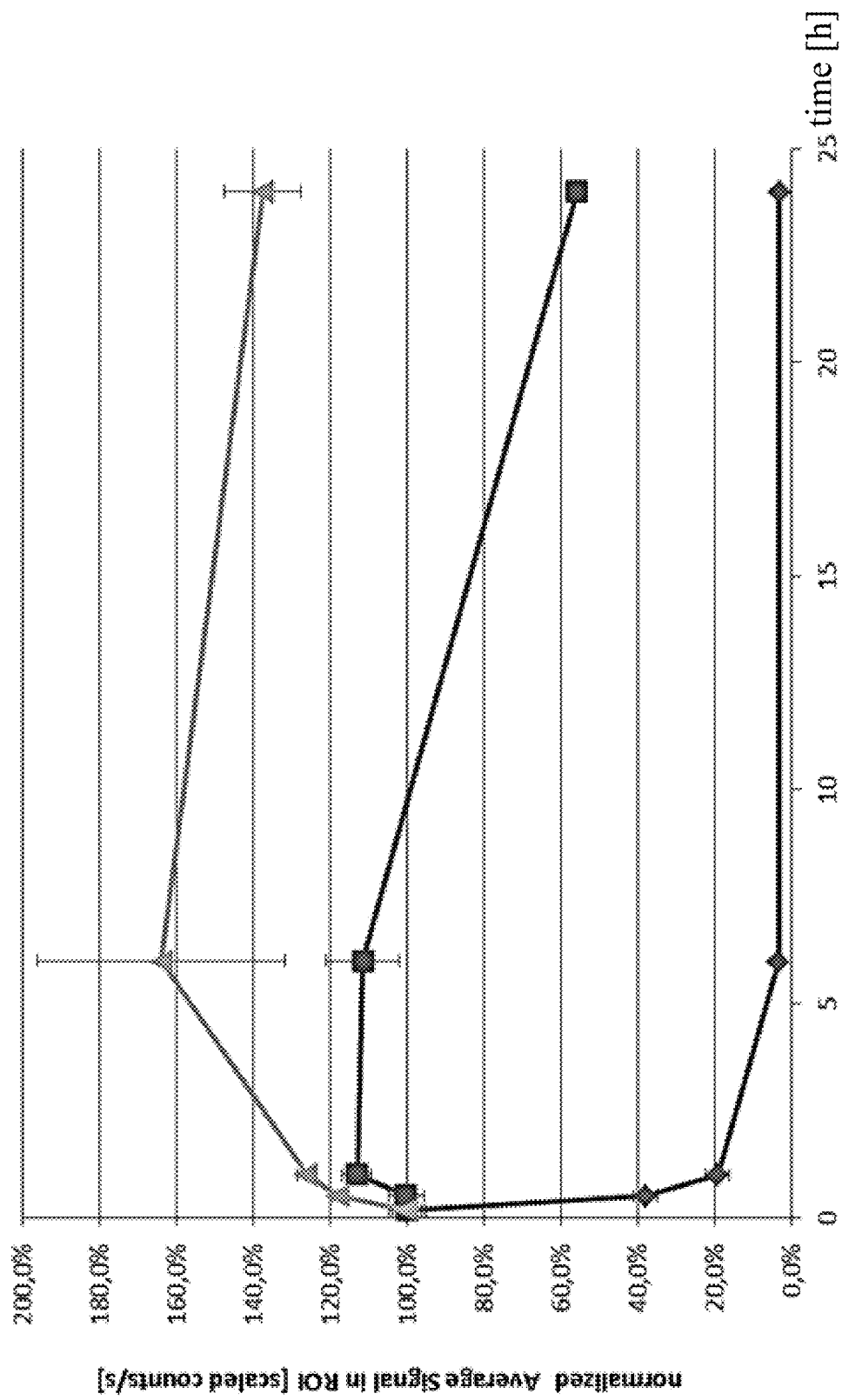

FIG. 42: In vivo pharmacokinetics of Cy5 fluorescence was determined by non-invasive eye imaging after injection of non-covalent complexes or of covalent (disulfide-bridged) conjugates containing Biotin-Cy5 or Biotin-Cys-Cy5, respectively, or of non-complexed Biotin-Cy5; solid diamond: biotin-Cy5; solid square Biotin-Cy5 anti-biotin antibody complex; triangle: Biotin-Cy5 anti-biotin antibody conjugate.

Figure 43A:
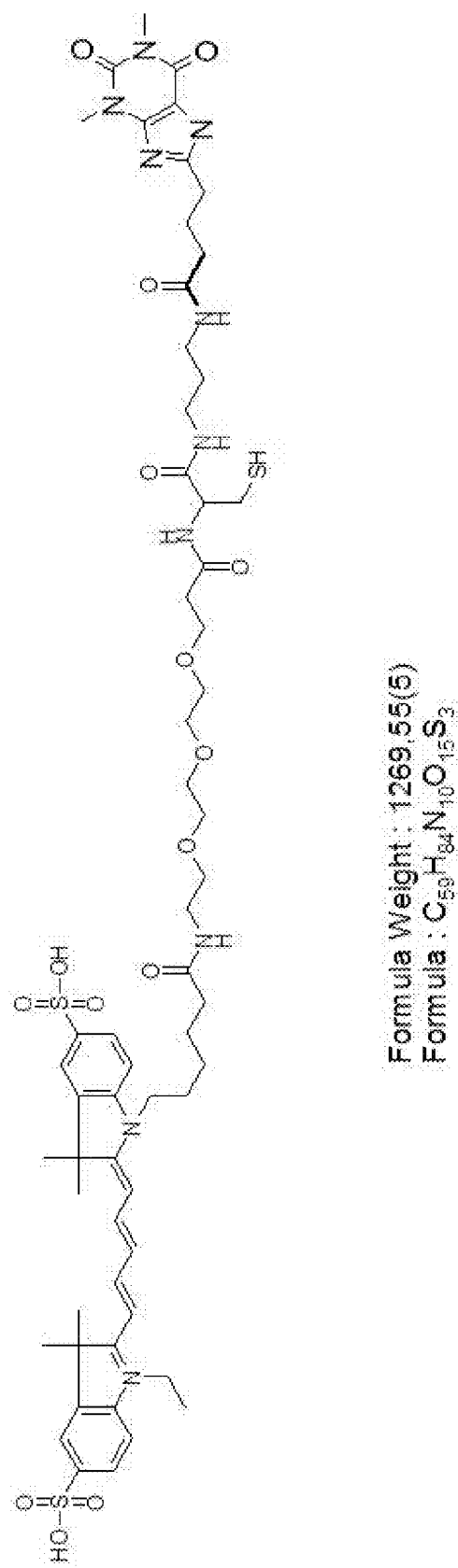
Figure 43B:
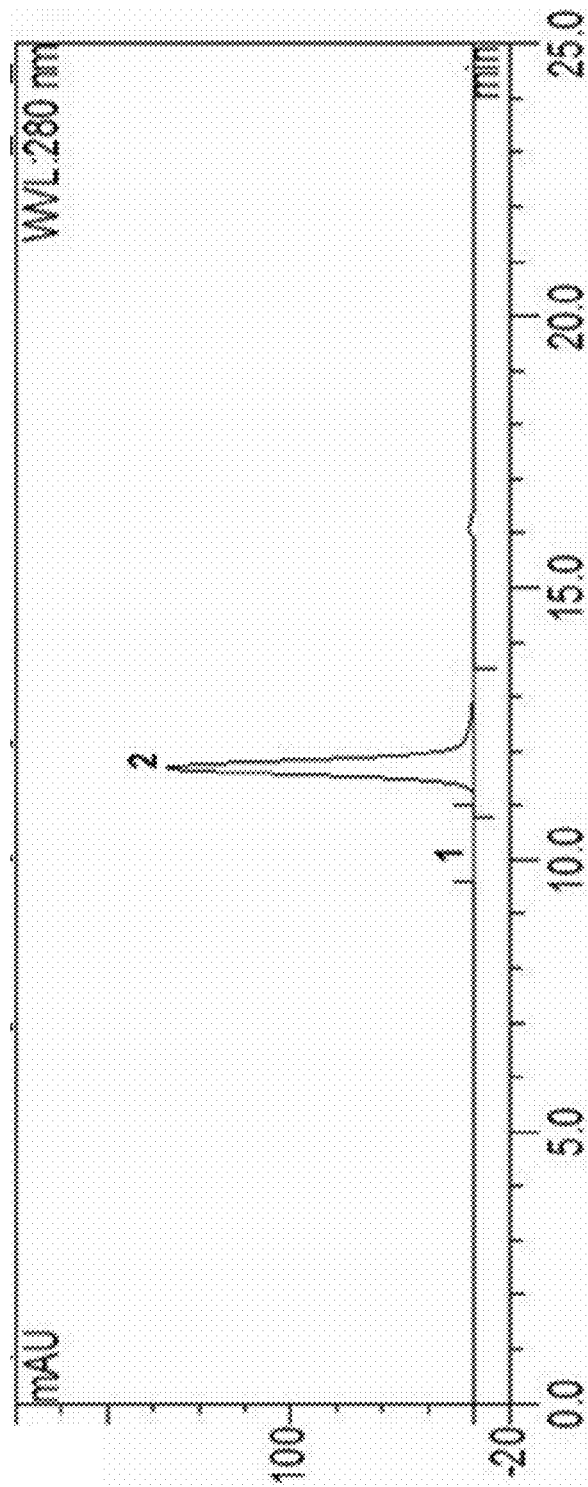
Figure 43C:
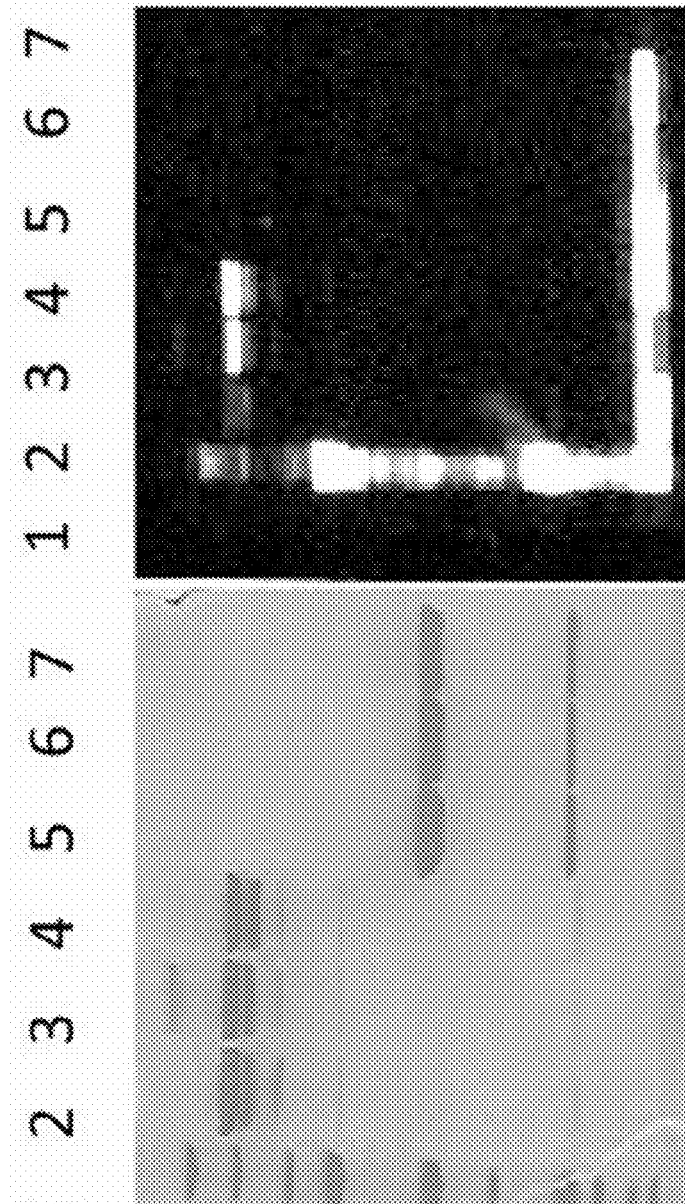

FIGS. 43A-43C: FIG. 43A: Composition, structure and molecular weight of Theophylline-Cys-Cy5; FIG. 43B: Size exclusion chromatography demonstrates purity and homogeneity of purified theophylline-binding antibody variants; peak #2 shows the purified product, lack of peak #1 indicates that such preparations are free of aggregates; FIG. 43C: formation of covalent complexes between theophylline-binding antibodies and Theophylline-Cys-Cy5 as demonstrated by non-reducing (left lanes) and reducing (right lanes) SDS PAGE; Cy5 appears coupled to the H-chain under non-reducing conditions only in samples that contained Theophylline-Cys-Cy5 and Cys-mutated antibody, these covalent conjugates disintegrate upon reduction (right lanes); Lanes 1: Molecular weight marker; 2-4 non-reducing—2: anti-Theophylline antibody (without Cys-mutation)+Theophylline-Cys-Cy5 (complex); 3: anti-Theophylline antibody-cys_55+Theophylline-Cys-Cy5 (conjugate); 4: anti-Theophylline antibody-cys_54+Theophylline-Cys-Cy5 (conjugate); 5-7 reducing—5: anti-Theophylline antibody (without Cys-mutation)+Theophylline-Cys-Cy5 (complex); 6: anti-Theophylline antibody-cys_55+Theophylline-Cys-Cy5 (conjugate); 7: anti-Theophylline antibody-cys_54+Theophylline-Cys-Cy5 (conjugate).

Figure 44:
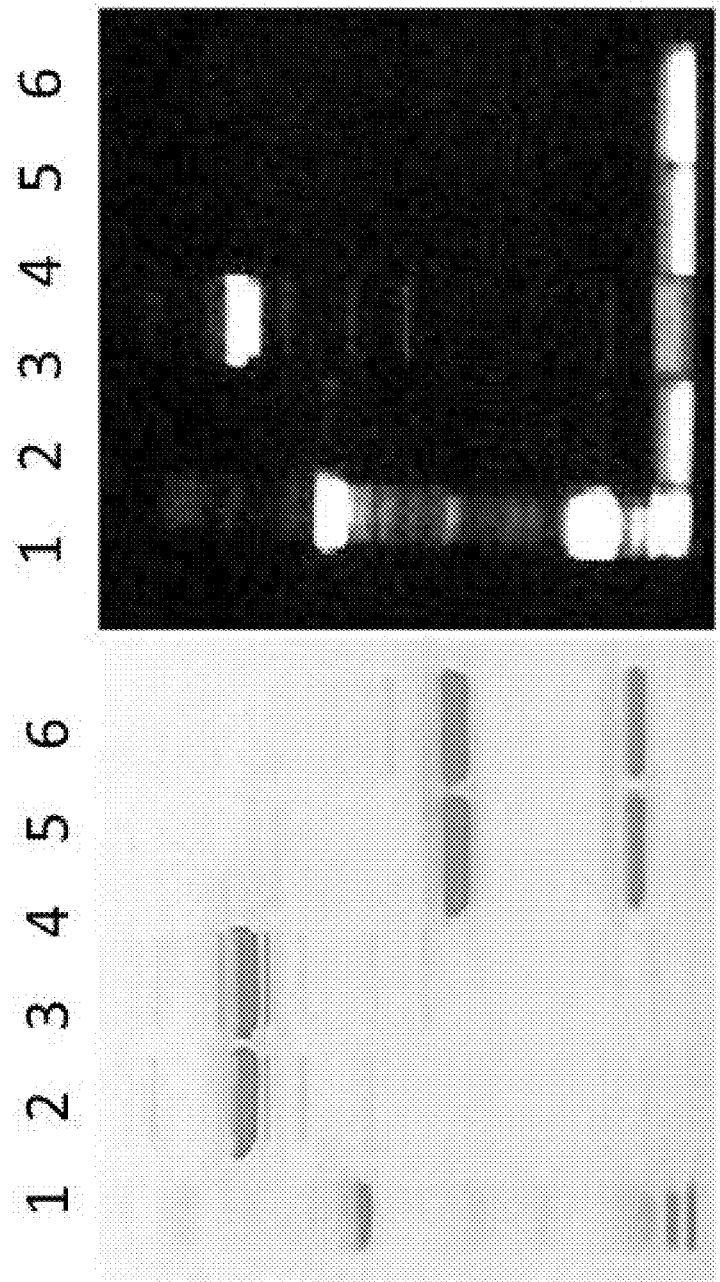

FIG. 44: Formation of covalent complexes between biotin-binding antibodies and Biotin-Cys-Cy5 is demonstrated by non-reducing and reducing SDS PAGE; the coupling reaction was performed in murine serum at 37° C. for 1 hr. Cy5 appears coupled to the H-chain under non-reducing conditions only in samples that contained Biotin-Cys-Cy5 and Cys-mutated antibody; these covalent conjugates disintegrate upon reduction (right lanes); lanes 1: Molecular weight marker; 2-3 non-reducing—2: anti-Biotin antibody (without Cys mutation)+Biotin-Cys-Cy5 (complex); 3: anti-Biotin antibody-Cys+Biotin-Cys-Cy5 (conjugate); 4-5 reducing—5: anti-Biotin antibody (without Cys mutation)+Biotin-Cys-Cy5 (complex); 6: anti-Biotin antibody-Cys+Biotin-Cys-Cy5 (conjugate).

Figure 45:
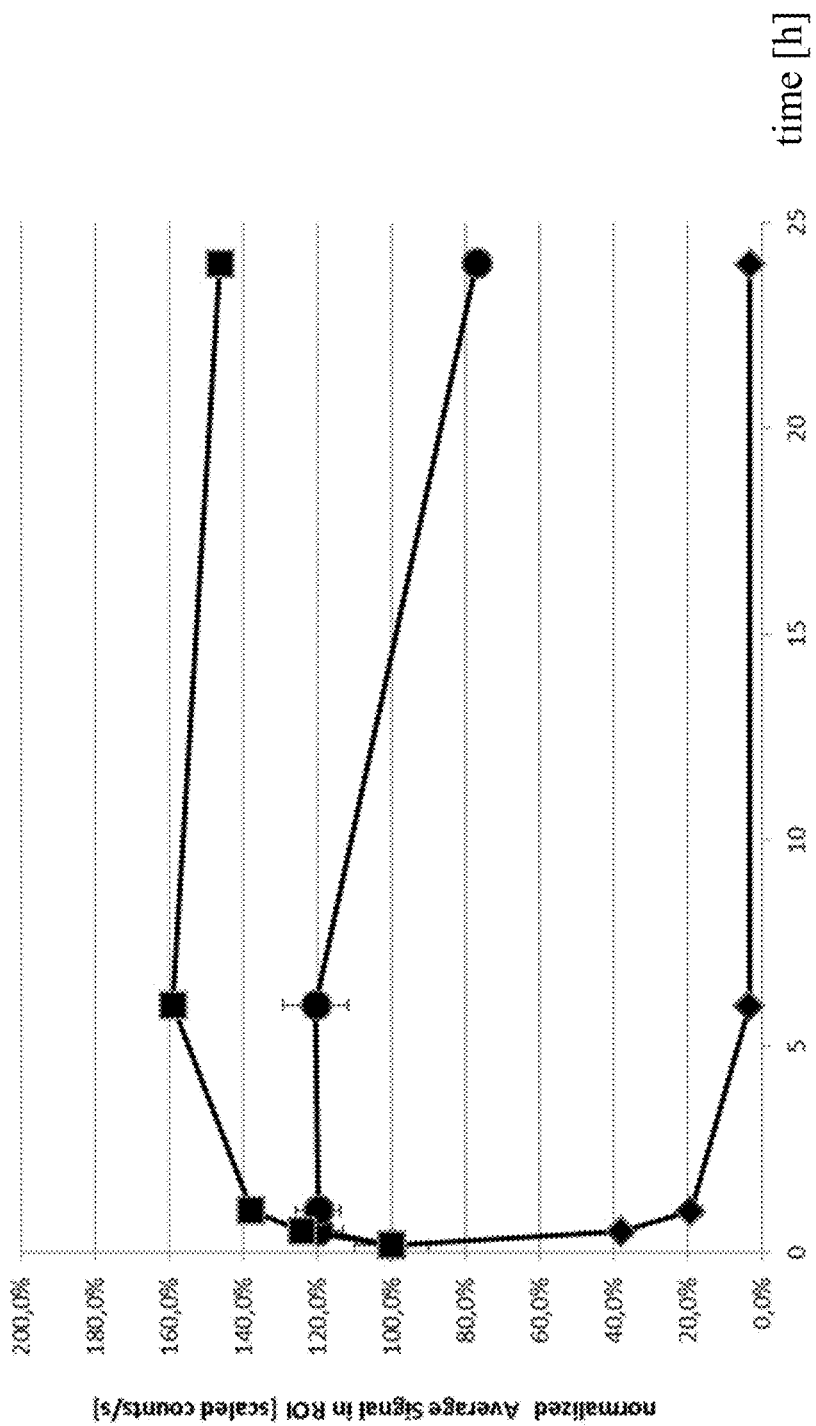

FIG. 45: In vivo pharmacokinetics of Cy5 fluorescence was determined by non-invasive eye imaging after injection of non-covalent complex-forming antibodies or of covalent (disulfide-bridged) conjugate-forming antibodies, followed by injection of Biotin-Cy5; solid diamond: only biotin-Cy5 administered, solid circle: biotin-Cy5 administered 24 hours after administration of anti-biotin antibody (in vivo complex formation); solid square: biotin-Cys-Cy5 administered 24 hours after administration of anti-biotin antibody-Cys (in vivo conjugate formation).

Figure 46:
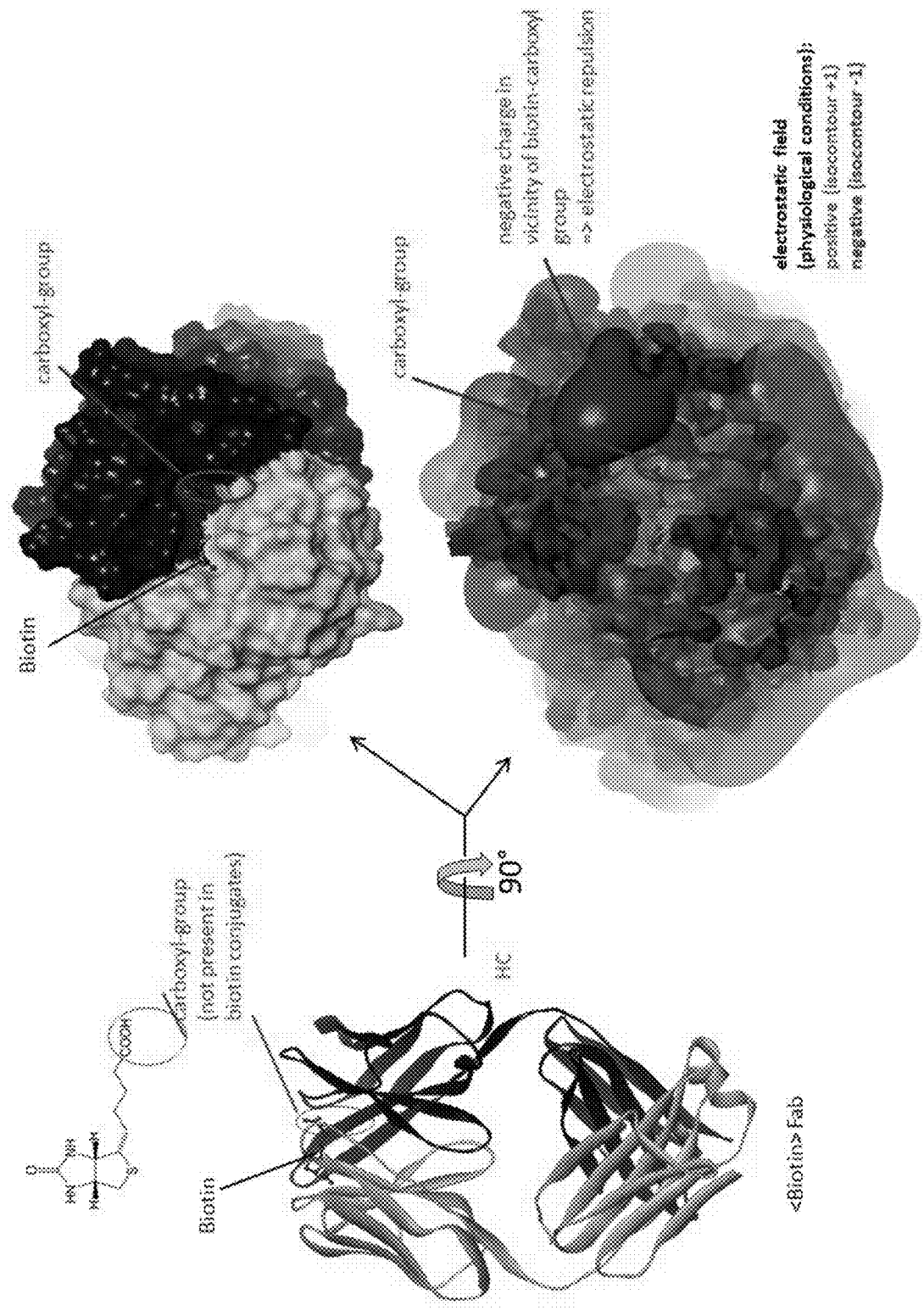

FIG. 46: The protein structure of murine anti-Biotin antibody-Fab-fragment was determined in complex with biocytinamid: the complexed hapten is positioned in close proximity to a negatively charged cluster of amino acids; biotin which—as hapten—is derivatized for payload coupling at its carboxyl group binds with good efficacy as there is no charge repulsion at this position (due to the lack of the COOH group); in contrast, free (normal) biotin cannot bind efficient to the antibody because its carboxyl group would be in close proximity to this negative charge cluster, and hence becomes repulsed.

Figure 47:
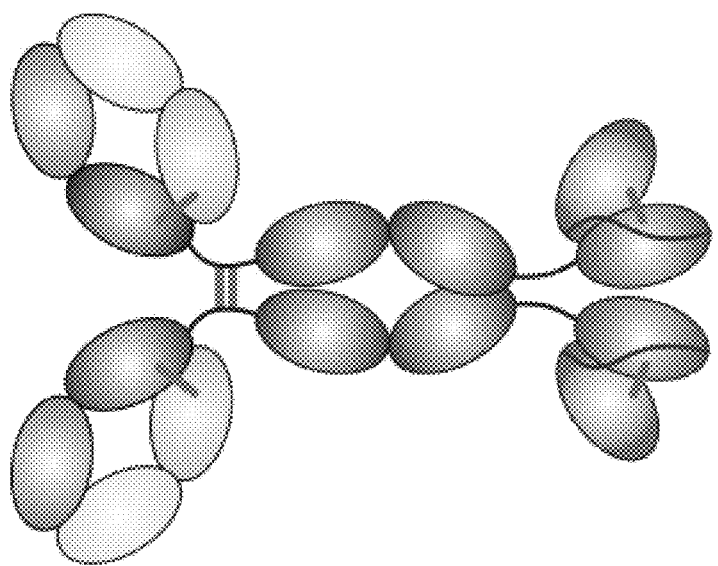

FIG. 47: Scheme of blood brain barrier-shuttle module composition.

Figure 48:
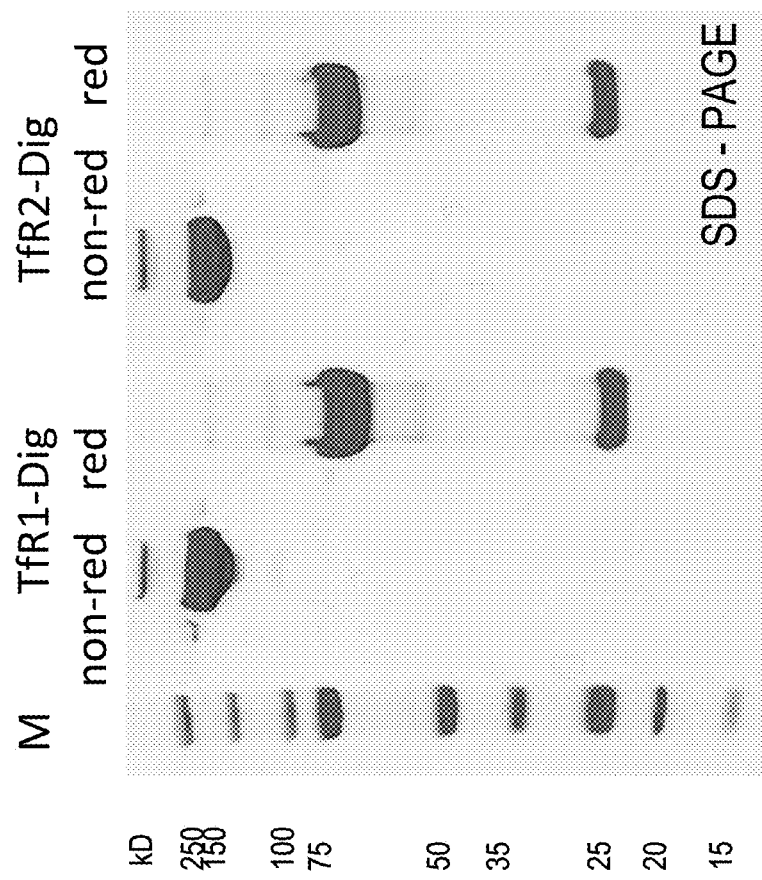

FIG. 48: SEC profiles and SDS PAGE of blood brain barrier-shuttle modules as produced in Example 27.

Figure 49:
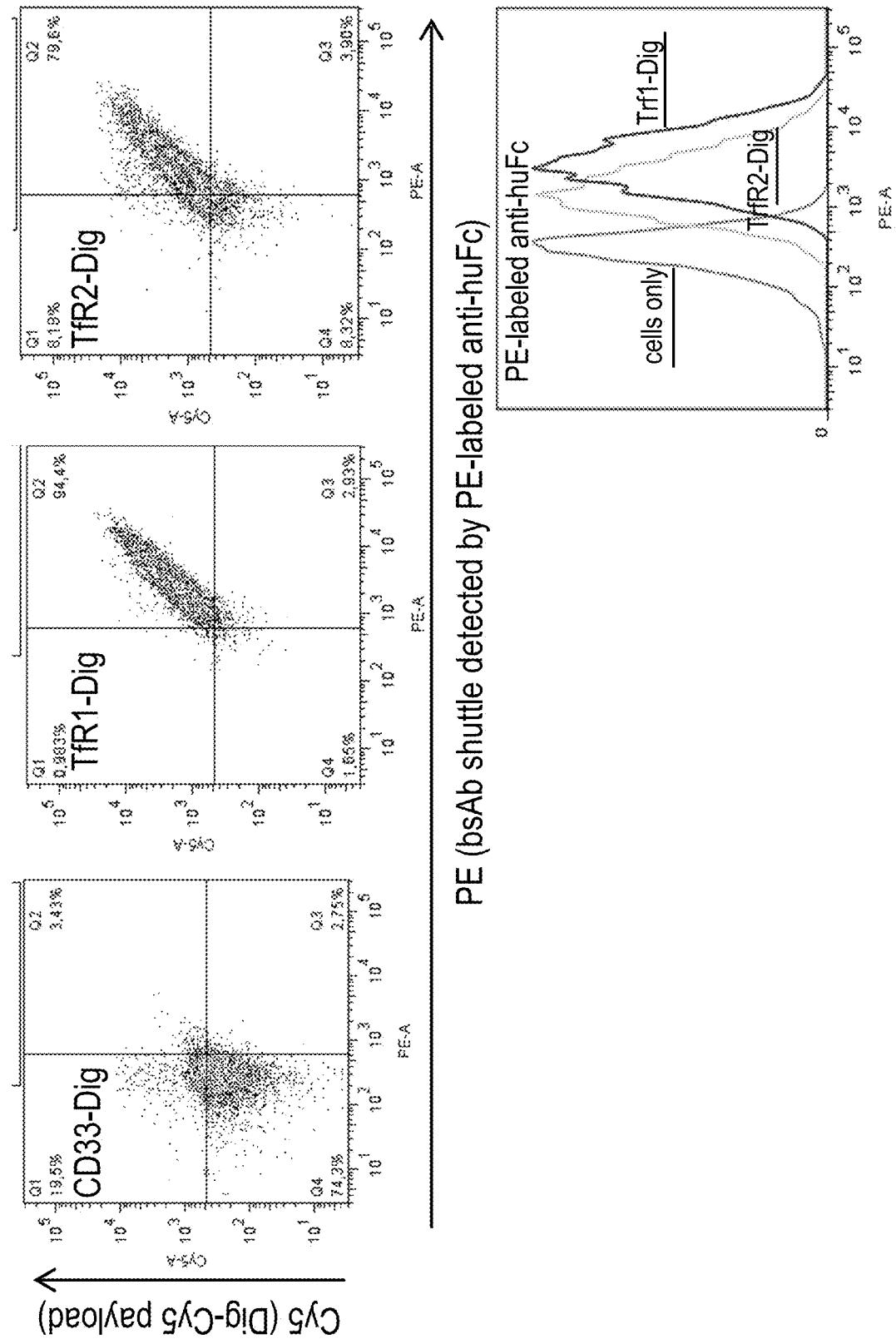

FIG. 49: Results of the FACS analysis, using hCMEC/D3 cells as TfR expressing BBB-derived cell line and Dig-Cy5 as fluorescent payload.

Figure 50:
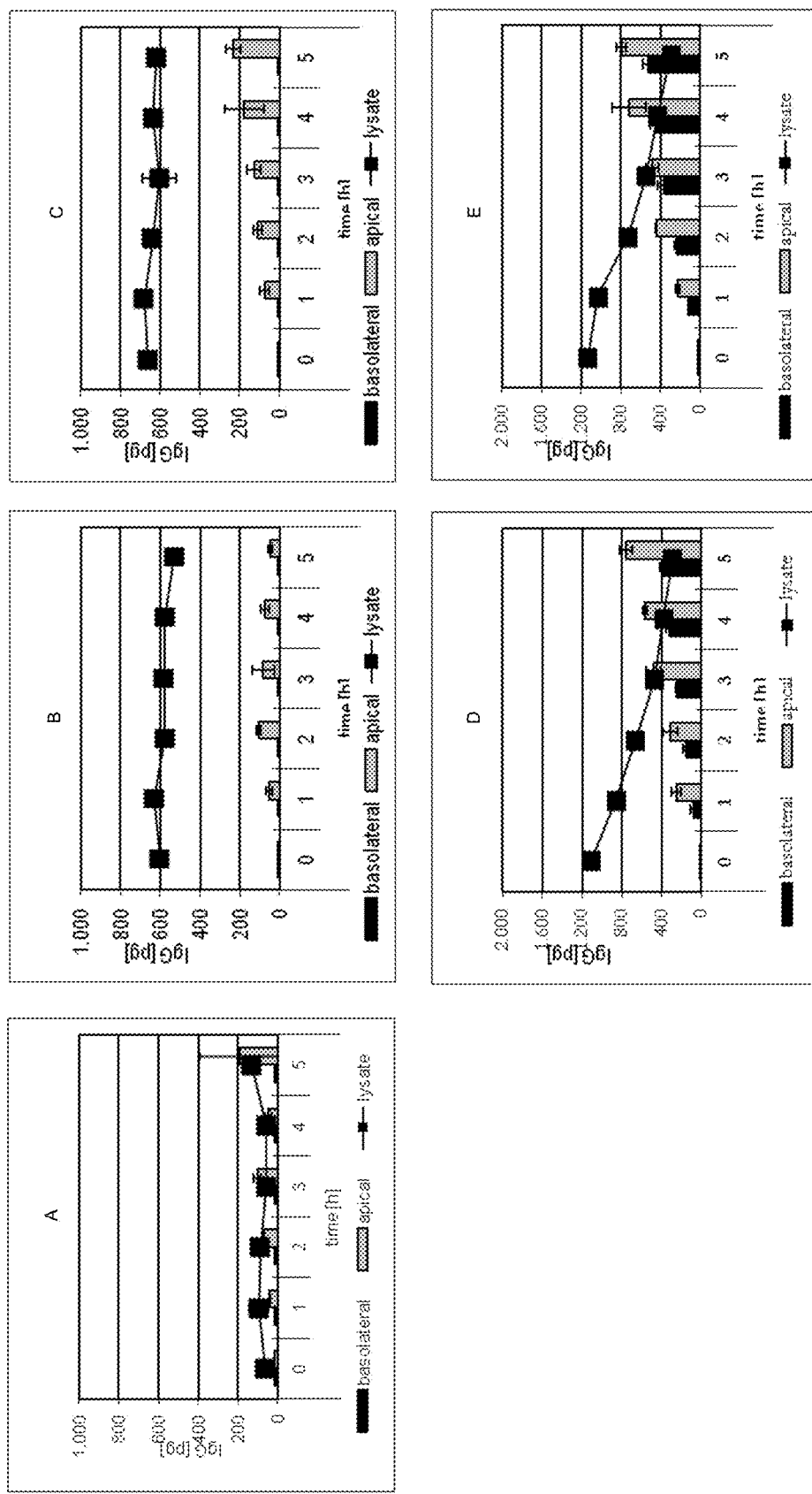

FIG. 50: Transcytosis and release from endothelial cells of hapten-binding bispecific antibody blood brain barrier-shuttle modules; A: anti-CD33-dig antibody transwell assay, huFc ELISA; B: anti-TfR1 antibody transwell assay, huFc ELISA; C: anti-TfR1 antibody-Dig transwell assay, huFc ELISA; D: anti-TfR2 antibody transwell assay, huFc ELISA; E: anti-TfR2-antibody Dig transwell assay, huFc ELISA.

FIG. 51: A: composition and quantification of bispecific antibody-haptenylated payload non-covalent complexes; B: transcytosis and release from endothelial cells of haptenylated payloads using bispecific antibodies with reduced affinity towards TfR (A: anti-CD33-Dig+Dig-DNA transwell assay, qPCR; B: anti-CD33-Bio+Bio-DNA transwell assay, qPCR, C: anti-TfR2-Dig+Dig-DNA transwell assay, qPCR, D: anti-TfR2-Bio+Bio-DNA transwell assay, qPCR).

Figure 52:
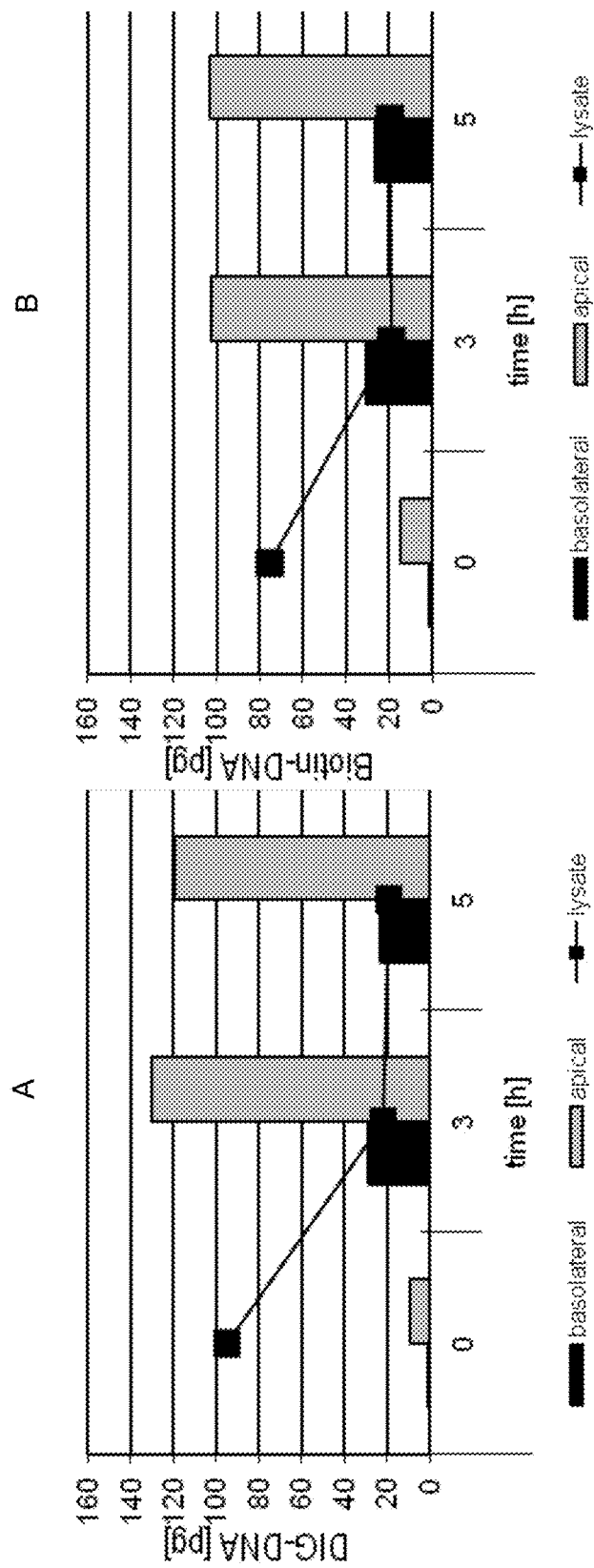

FIG. 52: Transcytosis and release from endothelial cells of haptenylated payloads applying non-releasable blood brain barrier-shuttle modules with high affinity towards TfR; A: anti-TrF1-Dig+Dig-DNA transwell assay, qPCR, B: anti-TfR1 antibody-Bio+Bio-DNA transwell assay, qPCR).

Figure 53:
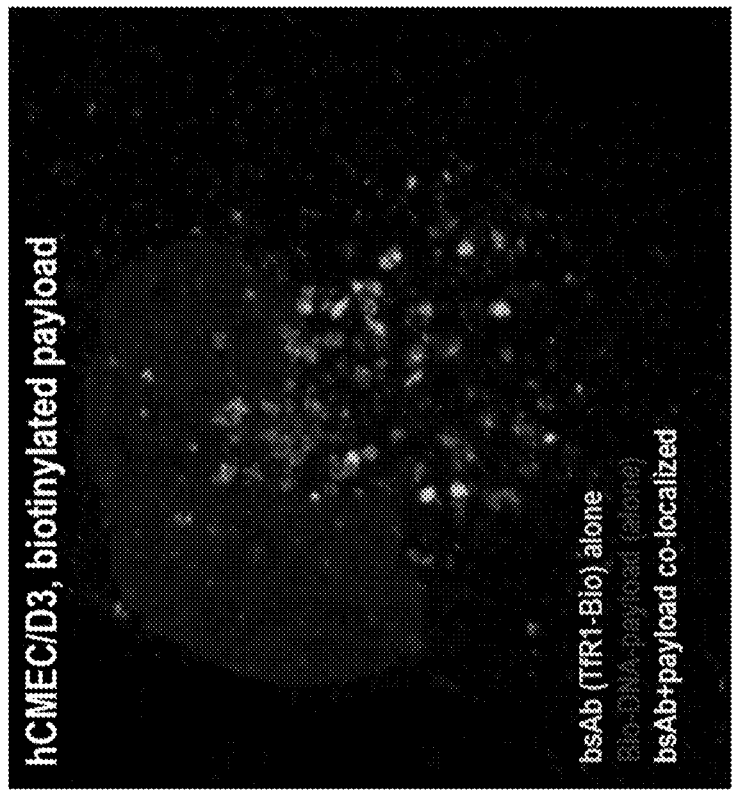
Figure 53:
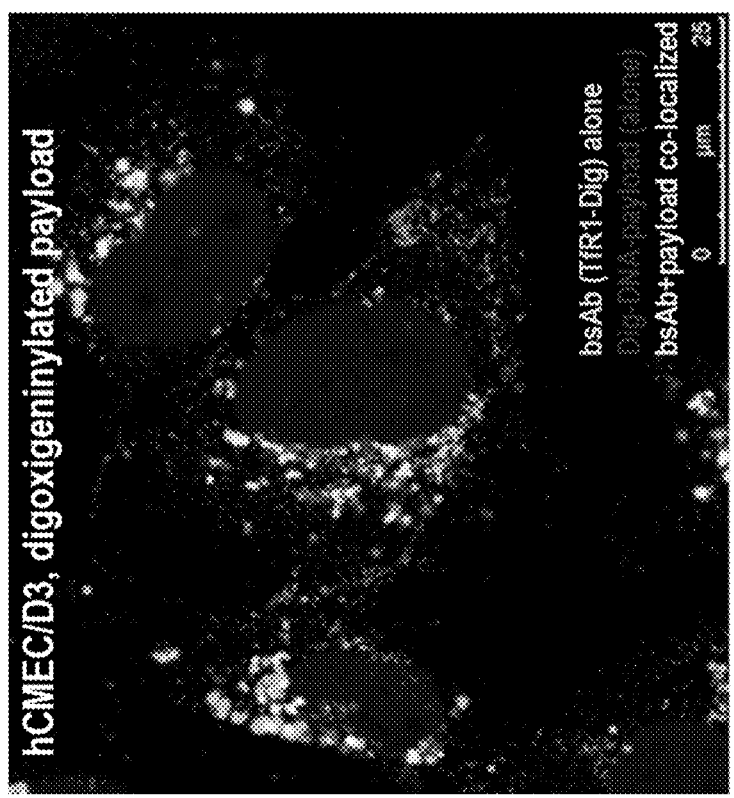

FIG. 53: Binding, uptake and intracellular separation of haptenylated payloads from non-releasable blood brain barrier-shuttle modules with high affinity towards TfR; shown is the subcellular separation of bispecific antibody-complexed haptenylated fluorescent payloads in hCMEC/D3 cells following three hour incubation at 37° C. DIG-DNA-CY5 or Bio-DNA-Cy5 (dark grey) appears in distinct intracellular vesicles not overlapping with internalized anti-digoxigenin- or anti-biotin-binding bispecific antibody (medium grey).

Figure 54:
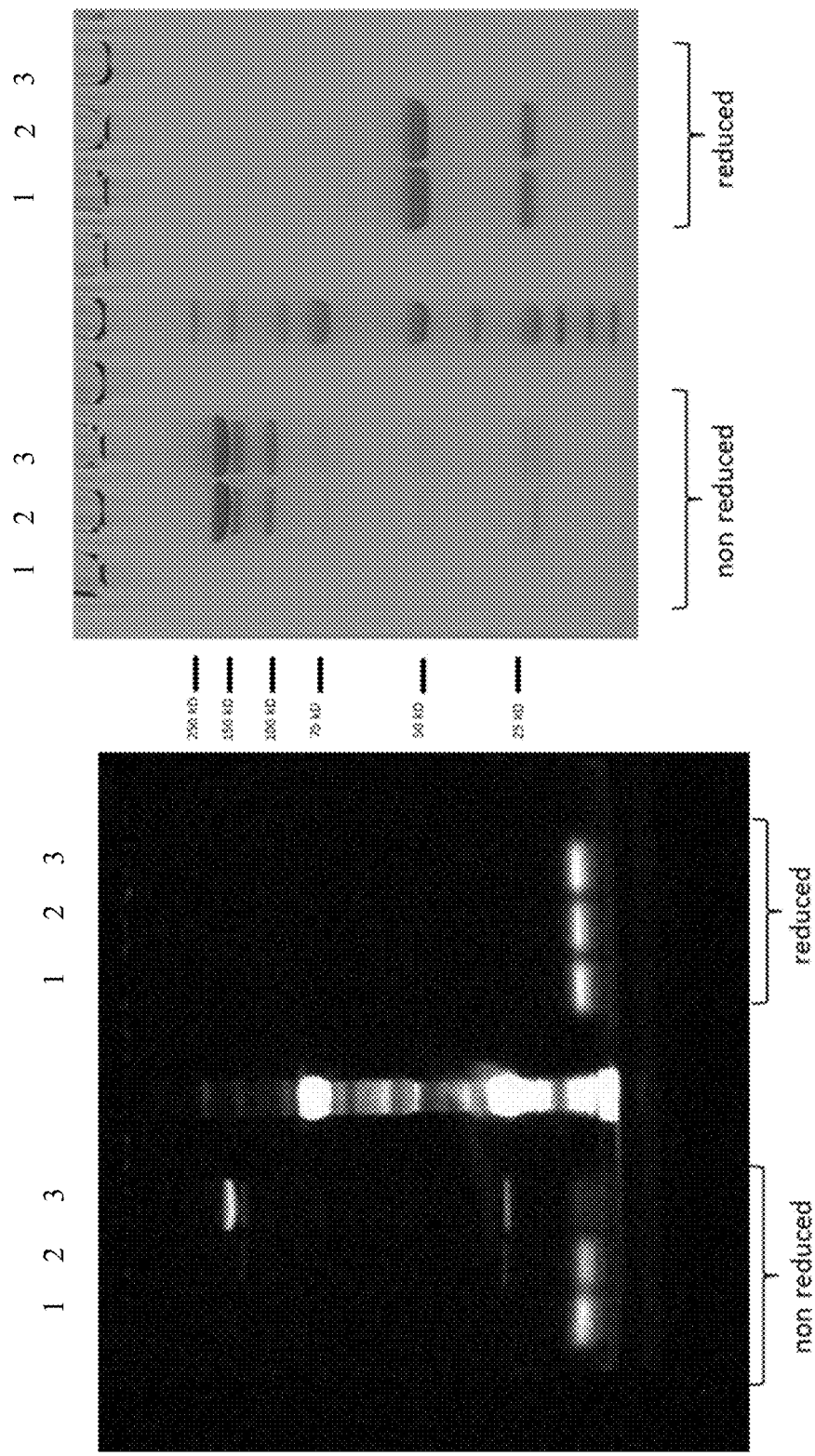

FIG. 54: SDS PAGE gel of the coupling of antibody 0155 with the helicar motif amino acid sequence cysteine variant 2 using a 2.5 molar excess of helicar motif amino acid sequence containing compound form the covalent complex 0156; 1=helicar motif amino acid sequence cysteine variant 2; 2=antibody 0019; 3=antibody 0155.

Figure 55:
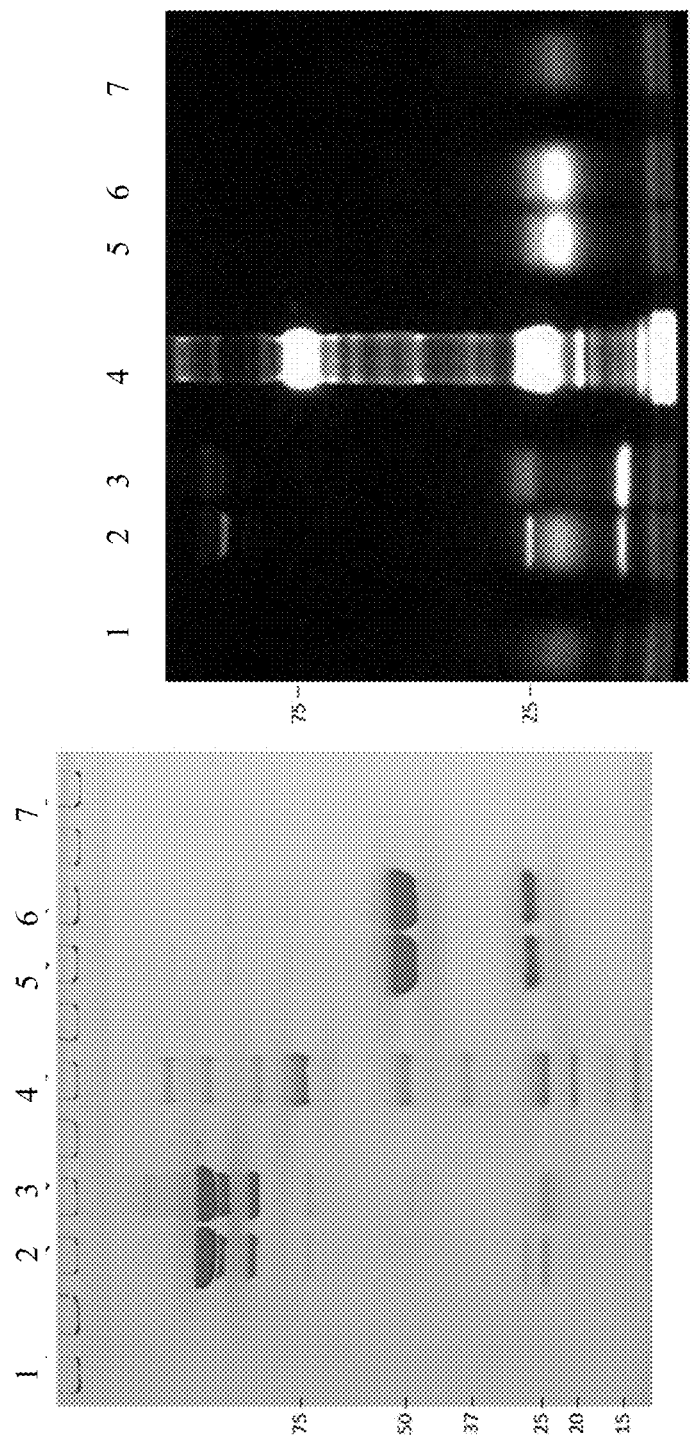

FIG. 55: SDS PAGE gel of the coupling of antibody 0157 with the helicar motif amino acid sequence cysteine variant 1; 1=helicar motif amino acid sequence cysteine variant 1 (oxidized); 2=control coupling (oxidized); 3=covalent conjugate (oxidized); 4=molecular weight marker; 5=covalent conjugate (reduced); 6=control coupling (reduced); 7=helicar motif amino acid sequence cysteine variant 1 (reduced).

Figure 56:
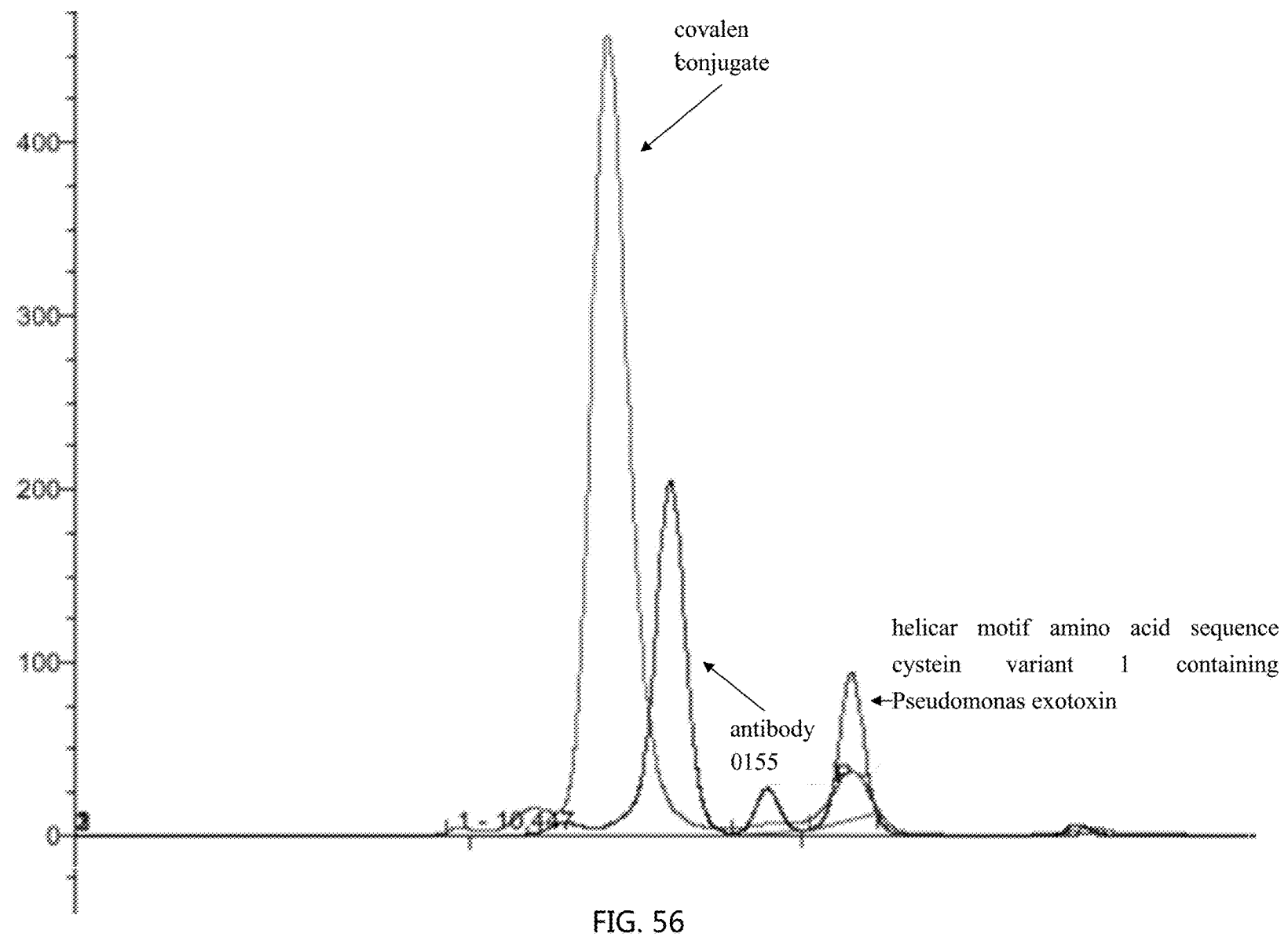

FIG. 56: SEC chromatogram of antibody 0155, the helicar motif amino acid sequence cysteine variant 1 containing Pseudomonas exotoxin molecule LR8M with the C-terminal lysine residue deleted of SEQ ID NO: 28 and the covalent conjugate thereof.

Figure 57:
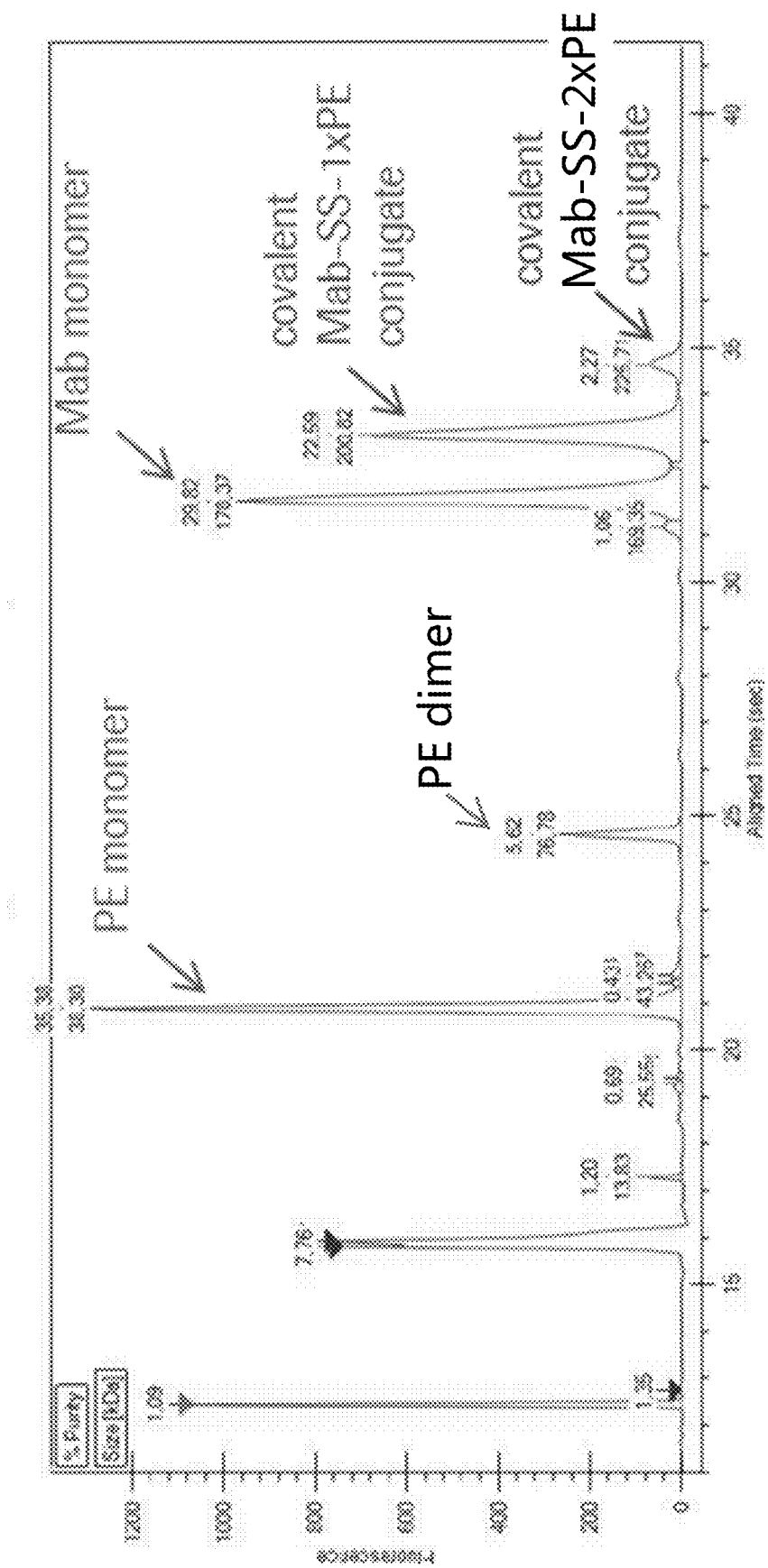

FIG. 57: Analysis of the conjugation efficiency by SDS-CE, Caliper, for the non reduced samples.

Figure 58:
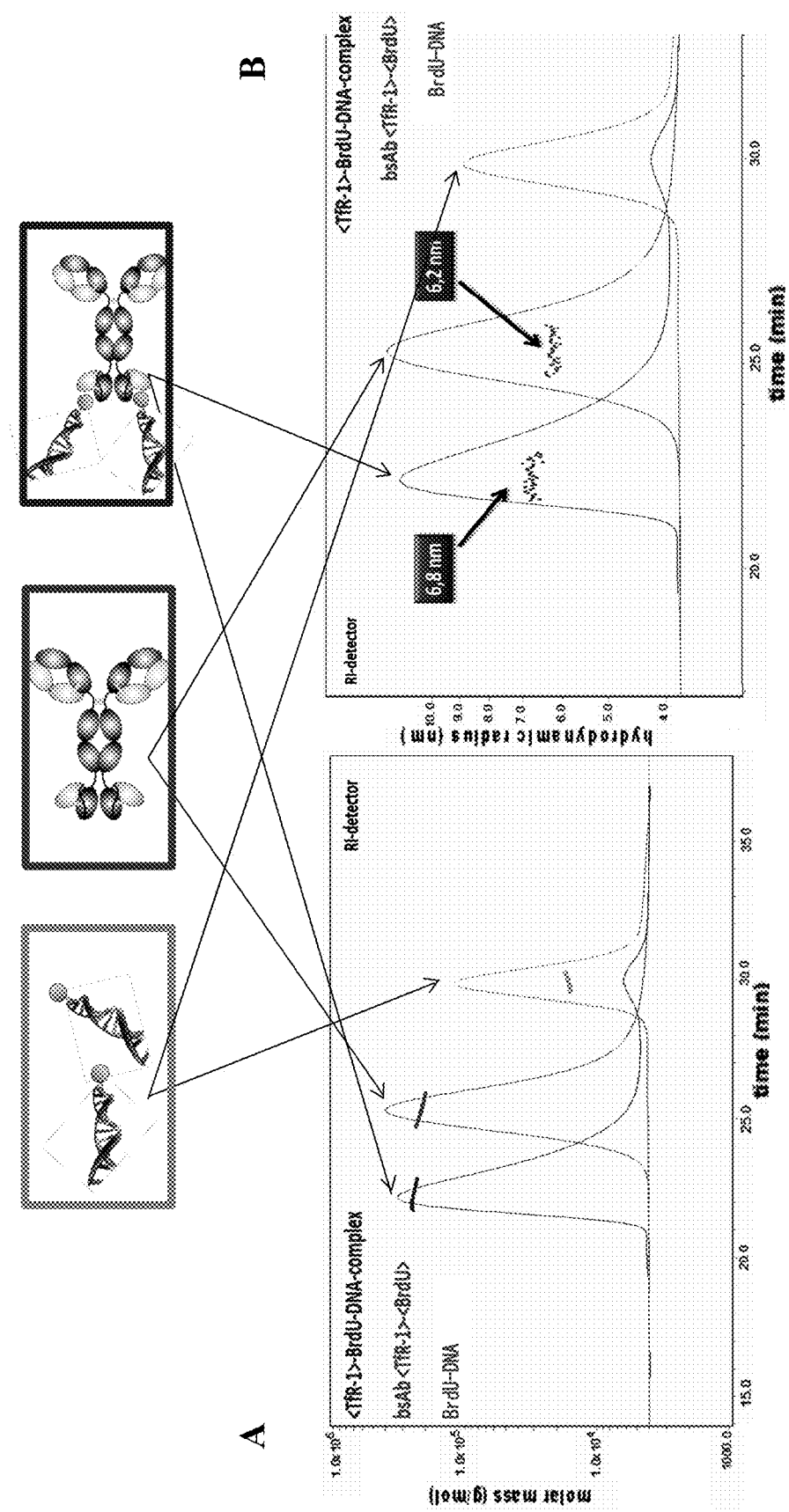

FIG. 58: A: SEC-MALLS analysis was performed to identify and characterize complexes of anti-TfR/BRDU bispecific antibodies with BRDU-labelled DNA as well as free bispecific antibody and free BRDU-DNA. Complexes elute from the column at a MW of 244.9 kDa, free bispecific antibody is detected at a MW of 215.4 kDa and free BRDU-DNA is detected at a MW of 16.4 kDa.

B: SEC-MALLS analysis was performed to identify and characterize complexes of anti-TfR/BRDU bispecific antibodies with BRDU-labelled DNA as well as free bispecific antibody and free BRDU-DNA. Complexes display a hydrodynamic radius of 6.8 nm, whereas free bispecific antibody displays a hydrodynamic radius of 6.2 nm.

Figures 59A, 59B:
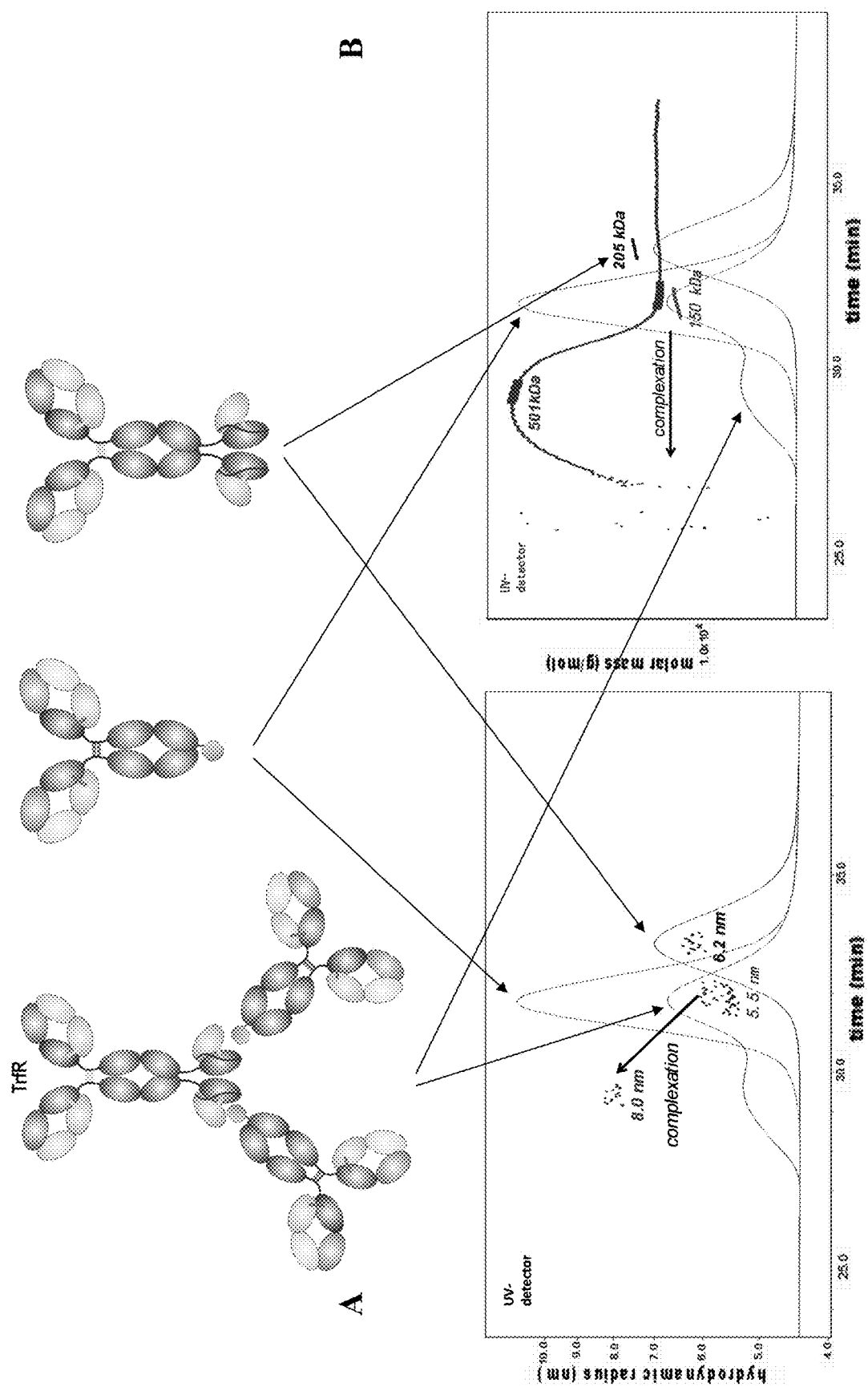
Figure 59C:
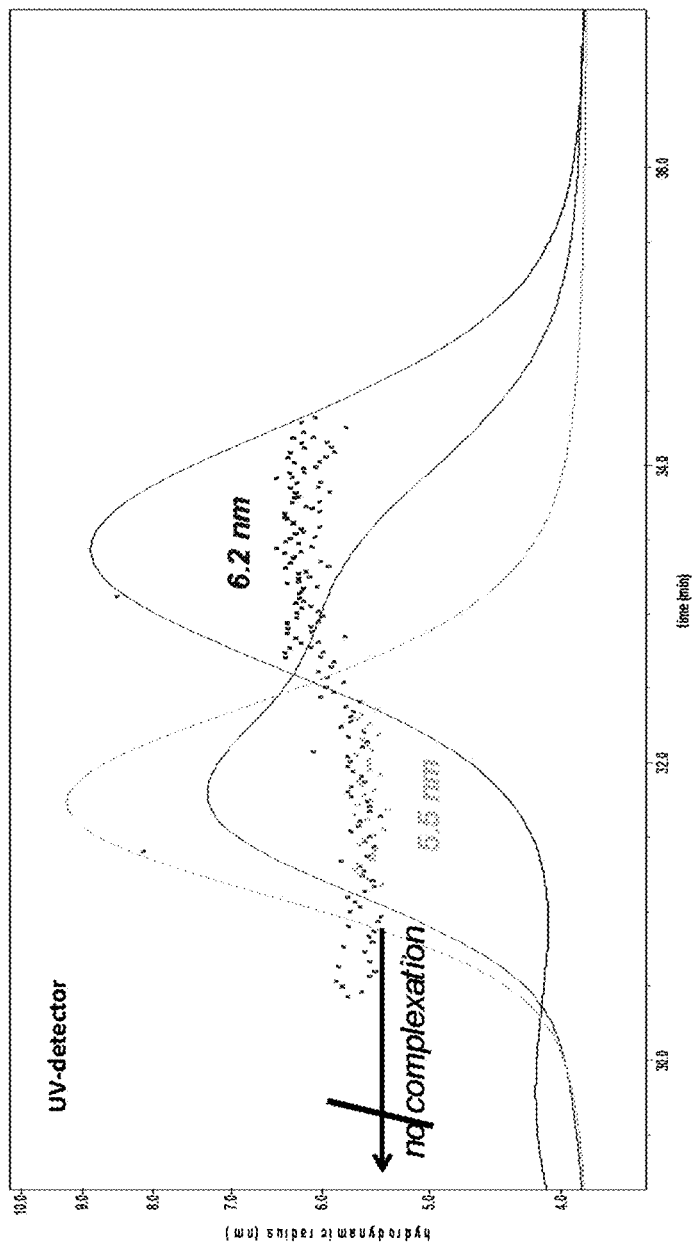

FIGS. 59A-59C: FIG. 59A: SEC-MALLS analysis was performed to identify and characterize complexes of anti-TfR/biotin bispecific antibodies with biotin-labelled anti-pTau antibody as well as free bispecific antibody and free biotin-labelled anti-pTau antibody. Complexes display a hydrodynamic radius of 8.0 nm, whereas free bispecific antibody displays a hydrodynamic radius of 6.2 nm and free biotin-labelled anti-pTau antibody displays a hydrodynamic radius of 5.5 nm.

FIG. 59B: SEC-MALLS analysis was performed to identify and characterize complexes of anti-TfR/biotin bispecific antibodies with biotin-labelled anti-pTau antibody as well as free bispecific antibody and free biotin-labelled anti-pTau antibody. Complexes elute from the column at a MW of 501 kDa, free bispecific antibody is detected at a MW of 205 kDa and free biotin-labelled anti-pTau antibody is detected at a MW of 150 kDa.

FIG. 59C: No complexes are formed if the wrong combination of hapten and anti-hapten antibody are used.

Figure 60:
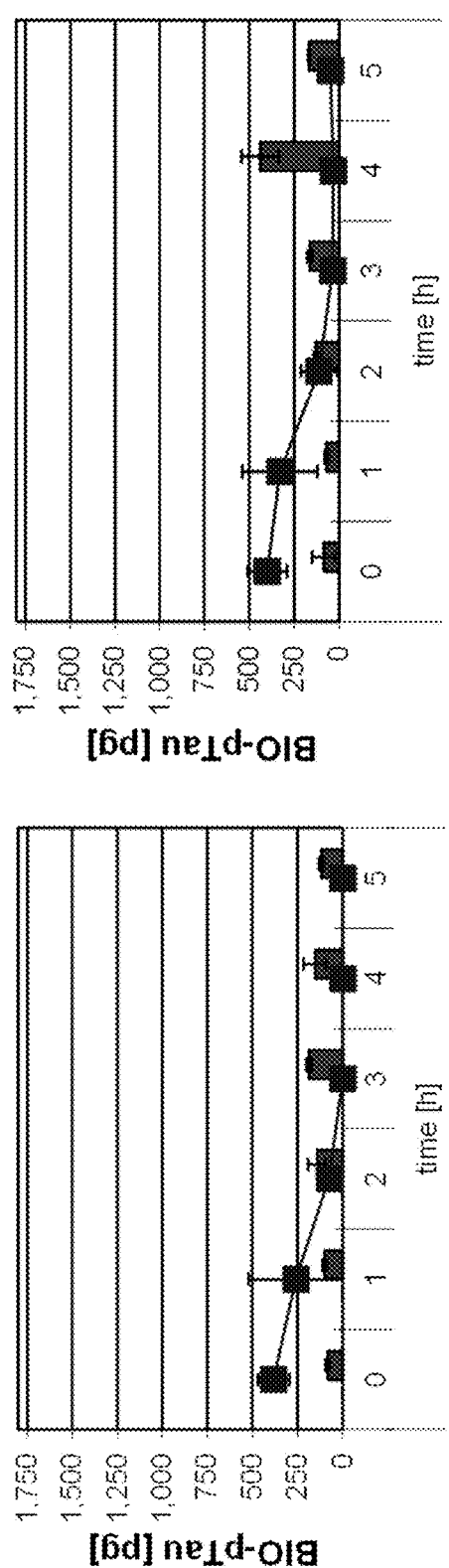
Figure 60:
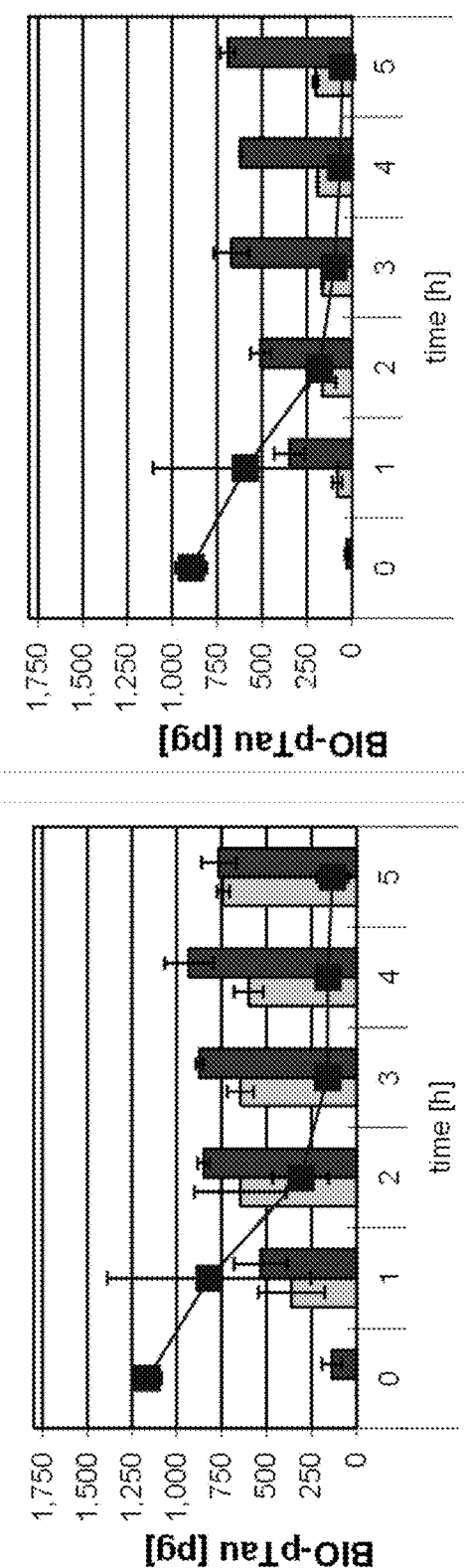

FIG. 60: Complexes of biotin-labelled anti-pTau antibody and anti-CD33/biotin bispecific antibody (upper left panel) and free biotin-labelled anti-pTau antibody (upper right panel) are not effectively endocytosed (cell lysate, line), and not transported into the basolateral (left column, light grey) or apical (right column, black) compartments (loading 3.8 μg/ml).

Complexing biotin-labelled anti-pTau antibody with either anti-TfR/biotin bispecific antibody 1 (lower left panel) or anti-TfR/biotin bispecific antibody 2 (lower right panel) mediates effective endocytosis (cell lysate, line) and subsequent transport of biotin-labelled anti-pTau antibody into the basolateral (left column, light grey) as well as back into the apical (right column, black) compartment (loading 3.8 μg/ml).

Figure 61:
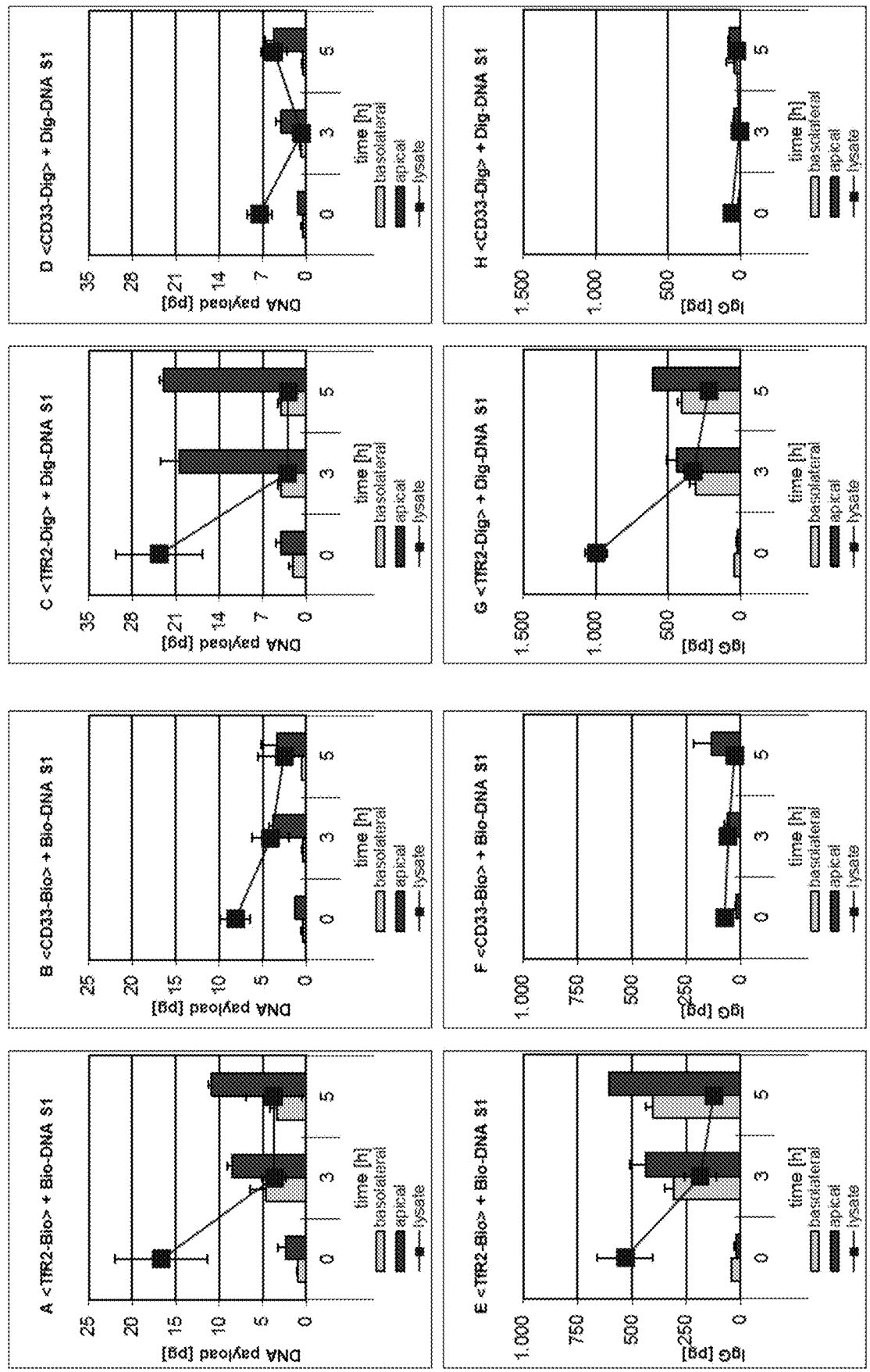

FIG. 61: Transwell assay of transcytosis and release from endothelial cells of haptenylated payloads and of hapten-binding bispecific antibody blood brain barrier-shuttle modules; using bispecific antibodies with reduced affinity towards TfR (TfR2) and non-binding bispecific antibodies (anti-CD33) and using 34mer oligonucleotide payload (oligonucleotide S1)

A, B, C, D: qPCR quantification of DNA payload
E, F, G, H: ELISA quantification of blood brain barrier-shuttle module (bispecific antibody)
A, E: anti-TfR2-Bio+Bio-DNA oligonucleotide S1
B, F: anti-CD33-Bio+Bio-DNA oligonucleotide S1
C, G: anti-TfR2-Dig+Dig-DNA oligonucleotide S1
D, H: anti-CD33-Dig+Dig-DNA oligonucleotide S1.

Figure 62:
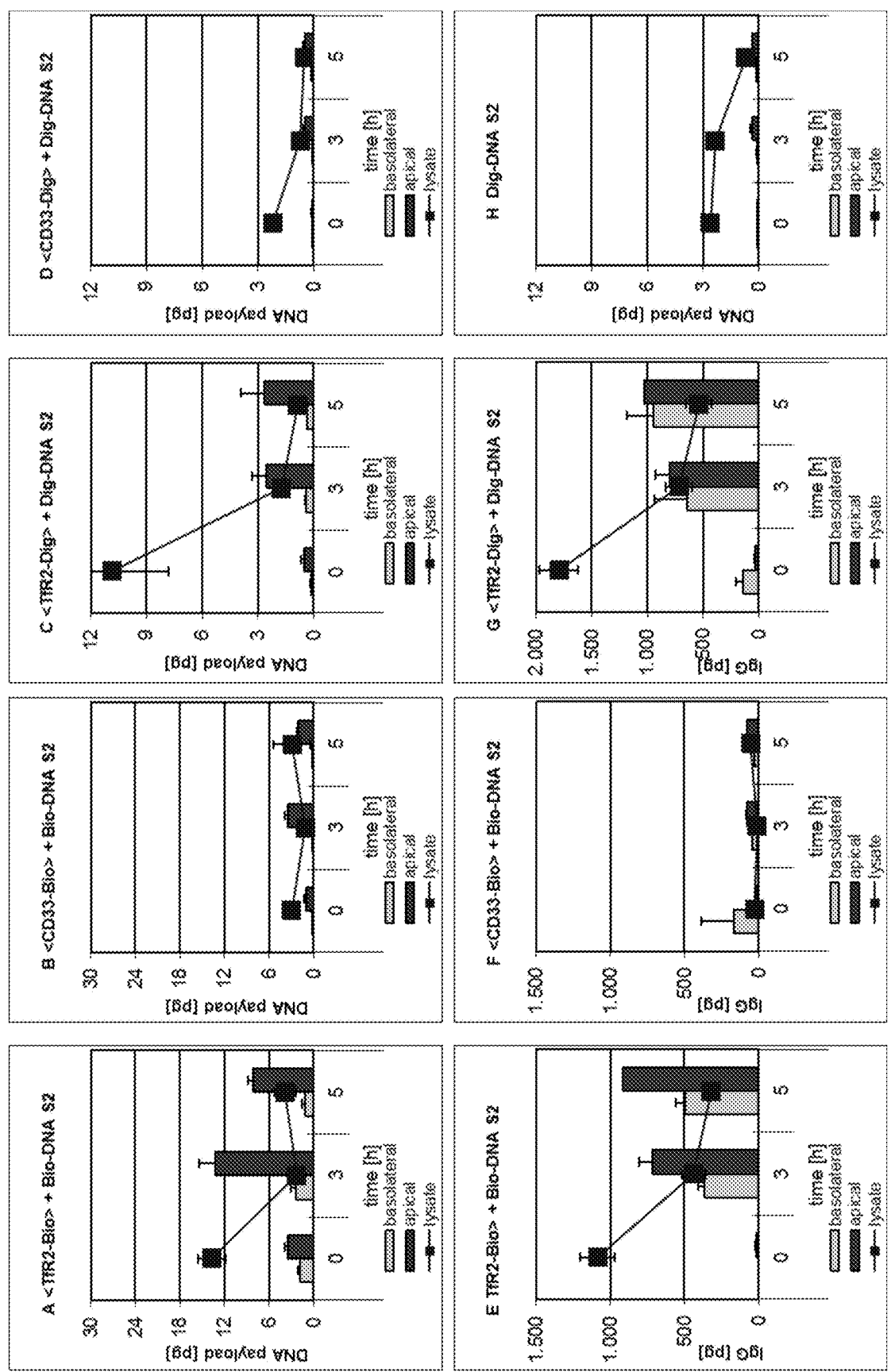

FIG. 62: Transwell assay of transcytosis and release from endothelial cells of haptenylated payloads and of hapten-binding bispecific antibody blood brain barrier-shuttle modules; using bispecific antibodies with reduced affinity towards TfR (TfR2) and non-binding bispecific antibodies (anti-CD33) and using 28mer oligonucleotide payload (oligonucleotide S2)

A, B, C, D, H: qPCR quantification of oligonucleotide payload

E, F, G: ELISA quantification of blood brain barrier-shuttle module (bispecific antibody)
A, E: anti-TfR2-Bio+Bio-DNA oligonucleotide S2
B, F: anti-CD33-Bio+Bio-DNA oligonucleotide S2
C, G: anti-TfR2-Dig+Dig-DNA oligonucleotide S2
D: anti-CD33-Dig+Dig-DNA oligonucleotide S2
H: Dig-DNA oligonucleotide S2 payload only.

Figure 63:
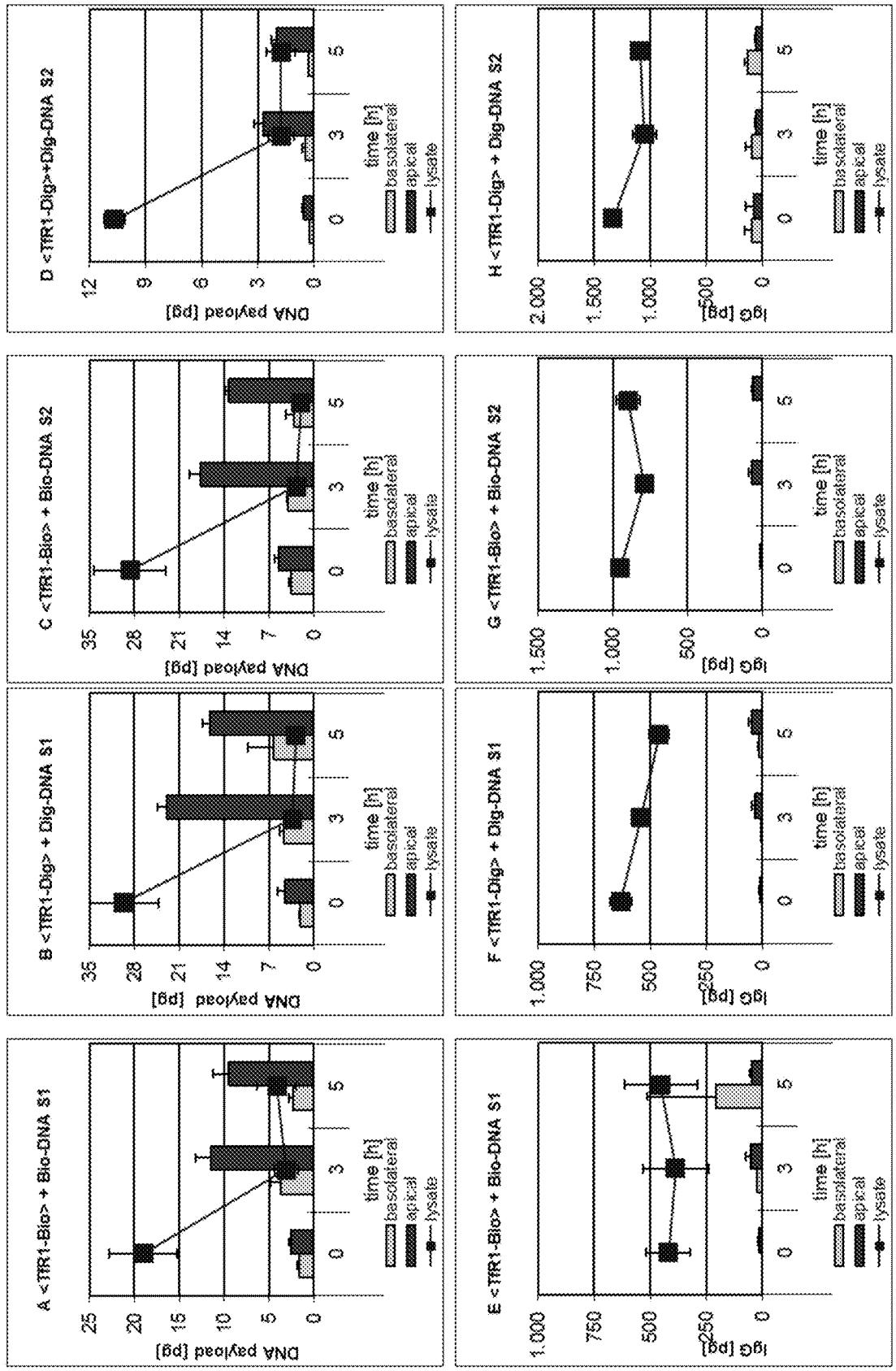

FIG. 63: Transwell assay of transcytosis and release from endothelial cells of haptenylated payloads and of hapten-binding bispecific antibody blood brain barrier-shuttle modules; using bispecific antibodies with high affinity towards TfR (TfR1) and using 34mer oligonucleotide payload (oligonucleotide S1) or 28mer oligonucleotide payload (oligonucleotide S2)

A, B, C, D: qPCR quantification of DNA payload
E, F, G, H: ELISA quantification of blood brain barrier-shuttle module (bispecific antibody)
A, E: anti-TfR1-Bio+Bio-DNA oligonucleotide S1
B, F: anti-TfR1-Dig+Dig-DNA oligonucleotide S1
C, G: anti-TfR1-Bio+Bio-DNA oligonucleotide S2
D, H: anti-TfR1-Dig+Dig-DNA oligonucleotide S2.

DETAILED DESCRIPTION OF THE INVENTION

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "amino acid" denotes the group of carboxy α-amino acids, either occurring naturally, i.e. which directly or in form of a precursor can be encoded by a nucleic acid, or occurring non-naturally. The individual naturally occurring amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophane (Trp, W), tyrosine (Tyr, Y), and valine (Val, V). Examples of non-naturally occurring amino acids include, but are not limited to, Aad (alpha-Aminoadipic acid), Abu (Aminobutyric acid), Ach (alpha-aminocyclohexane-carboxylic acid), Acp (alpha-aminocyclopentane-carboxylic acid), Acpc (1-Aminocyclopropane-1-carboxylic acid), Aib (alpha-aminoisobutyric acid), Aic (2-Aminoindane-2-carboxylic acid; also called 2-2-Aic), 1-1-Aic (1-aminoindane-1-carboxylic acid), (2-aminoindane-2-carboxylic acid), Allylglycine (AllylGly), Alloisoleucine (allo-Ile), Asu (alpha-Aminosuberic acid, 2-Aminooctanedioc acid), Bip (4-phenyl-phenylalanine-carboxylic acid), BnHP ((2S,4R)-4-Hydroxyproline), Cha (beta-cyclohexylalanine), Cit (Citrulline), Cyclohexylglycine (Chg), Cyclopentylalanine, beta-Cyclopropyl alanine, Dab (1,4-Diaminobutyric acid), Dap (1,3-Diaminopropionic acid), p (3,3-diphenylalanine-carboxylic acid), 3,3-Diphenylalanine, Di-n-propylglycine (Dpg), 2-Furylalanine, Homocyclohexylalanine (HoCha), Homocitrulline (HoCit), Homocycloleucine, Homoleucin (HoLeu), Homoarginine (HoArg), Homoserine (HoSer), Hydroxyproline, Lys(Ac), (1) Nal (1-Naphtyl Alanine), (2) Nal (2-Naphtyl Alanine), 4-MeO-Apc (1-amino-4-(4-methoxyphenyl)-cyclohexane-1-carboxylic acid), Nor-leucine (Nle), Nva (Norvaline), Omathine, 3-Pal (alpha-amino-3-pyridylalanine-carboxylic acid), 4-Pal (alpha-amino-4-pyridylalanine-carboxylic acid), 3,4,5,F3-Phe (3,4,5-Trifluoro-phenylalanine), 2,3,4,5,6,F5-Phe (2,3,4,5,6-Pentafluoro-phenylalanine), Pqa (4-oxo-6-(1-piperazinyl)-3 (4H)-quinazoline-acetic acid (CAS 889958-08-1)), Pyridylalanine, Quinolylalanine, Sarcosine (Sar), Thiazolylalanine, Thienylalanine, Tic (alpha-amino-1,2,3,4,tetrahydroisoquinoline-3-carboxylic acid), Tic(OH), Tle (tertbutyl-Glycine), and Tyr(Me).

The term "amino acid sequence variant" refers to polypeptides having amino acid sequences that differ to some extent from a native/parent/wild-type amino acid sequence. Ordinarily, amino acid sequence variants will possess at least about 70% sequence identity with the native/parent/wild-type amino acid sequence. In one embodiment the variant has about 80% or more sequence identity with native/parent/wild-type amino acid sequence. In one embodiment the variant has about 90% or more sequence identity with the native/parent/wild-type amino acid sequence. In one embodiment the variant has about 95% or more sequence identity with the native/parent/wild-type amino acid sequence. In one embodiment the variant has about 98% or more sequence identity with the native/parent/wild-type amino acid sequence. The amino acid sequence variants possess substitutions, deletions, and/or insertions at certain positions within the amino acid sequence of the native/parent/wild-type amino acid sequence. Amino acids can be designated by the conventional names, one-letter and three-letter codes.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and specificity.

The term "antibody fragment" denotes a molecule other than an intact antibody that comprises a portion of an intact antibody that specifically binds the antigen to which the intact antibody also specifically binds. Examples of antibody fragments include but are not limited to Fv, Fab, Fab', Fab'-SH, F(ab')2, diabodies, linear antibodies, single-chain antibody molecules (e.g. scFv), single-chain Fab fragments (scFab), single heavy chain antibodies (VHH), and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "biotin", short "BI", denotes 5-[(3aS,4S,6aR)-2-oxohexahydro-1H-thieno[3,4-d]imidazol-4-yl]pentanoic acid. Biotin is also known as vitamin H or coenzyme R.

The term "biotinylated payload" denotes a conjugated entity comprising a biotin moiety, optionally a linker and a payload. The linker can be any linker, such as e.g. a peptidic linker or a chemical linker.

The term "bispecific antibodies" denotes antibodies which have two different (antigen/hapten) binding specificities. In one embodiment bispecific antibodies as reported herein are specific for two different antigens, i.e. a hapten and a non-hapten antigen.

The term "bromodeoxyuridine", short "BrdU", denotes 5-bromo-2'-desoxyuridine. Bromodeoxyuridine is also known as broxuridine, BudR, BrdUrd.

The term "bromodeoxyuridinylated payload" denotes a conjugated entity comprising a bromodeoxyuridine moiety, optionally a linker and a payload. The linker can be any linker, such as e.g. a peptidic linker or a chemical linker.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. A cytotoxic agent is a specific payload. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof, and the various antitumor or anticancer agents disclosed below.

The term "digoxigenin", short "DIG", denotes 3-[(3S,5R, 8R,9S,10S,12R,13S,14S,17R)-3,12,14-trihydroxy-10,13-dimethyl-1,2,3,4,5,6,7,8,9,11,12,15,16,17-tetradecahydro-cyclopenta[a]-phenanthren-17-yl]-2H-furan-5-one (CAS number 1672-46-4). Digoxigenin (DIG) is a steroid found exclusively in the flowers and leaves of the plants *Digitalis purpurea, Digitalis orientalis* and *Digitalis lanata* (foxgloves) (Polya, G., Biochemical targets of plant bioactive compounds, CRC Press, New York (2003) p. 847).

The term "digoxigenylated payload" denotes a conjugated entity comprising a digoxigenin moiety, optionally a linker and a payload. The linker can be any linker, such as e.g. a peptidic linker or a chemical linker.

The term "effector functions" denotes those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. An Fc-region without effector function (=effector-less Fc-region) comprises mutations in the amino acid sequence that abolish the binding of the Fc-region to C1q or the Fcγ-receptors.

The term "effective amount" of an agent, e.g., a pharmaceutical formulation, denotes an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The term "fluorescein", short "FLUO", denotes 6-hydroxy-9-(2-carboxyphenyl)-(3H)-xanthen-3-on, alternatively 2-(6-hydroxy-3-oxo-(3H)-xanthen-9-yl)-benzoic acid. Fluorescein is also known as resorcinolphthalein, C.I. 45350, solvent yellow 94, D & C yellow no. 7, angiofluor, Japan yellow 201, or soap yellow.

The term "fluoresceinylated payload" denotes a conjugated entity comprising a fluorescein moiety, optionally a linker and a payload. The linker can be any linker, such as e.g. a peptidic linker or a chemical linker.

The term "framework", short "FR", denotes heavy and light chain variable domain amino acid residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "artificial cysteine residue" denotes a cysteine amino acid residue which has been engineered into a (parent) antibody or (parent) polypeptide, which has a thiol functional group (SH), and which is not paired as an intramolecular disulfide bridge. Nevertheless, the artificial cysteine residue can be paired as intermolecular disulfide bridge, e.g. with glutathione.

The term "full length antibody" denotes an antibody having a structure substantially similar to a native antibody structure or having heavy chains that contain an Fc-region as defined herein. Native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "full length antibody" is an antibody comprising a VL and VH domain, as well as a light chain constant domain (CL) and heavy chain constant domains, CH1, CH2 and CH3. The constant domains may be native sequence constant domains (e.g., human native sequence constant domains) or an amino acid sequence variant thereof. The full length antibody may have one or more "effector functions" which refer to those biological activities attributable to the Fc constant region (a native sequence Fc-region or amino acid sequence variant Fc-region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B-cell receptor and BCR.

The term "hapten" denotes a small molecule that can elicit an immune response only when attached to a large carrier such as a protein. Exemplary haptens are aniline, o-, m-, and p-aminobenzoic acid, quinone, histamine-succinyl-glycine (HSG), hydralazine, halothane, indium-DTPA, fluorescein, biotin, digoxigenin, theophylline, bromodeoxyuridine and dinitrophenol. In one embodiment the hapten is biotin or digoxigenin or theophylline or fluorescein or bromodeoxyuridine.

The term "haptenylated payload" denotes a hapten which is (covalently) conjugated to a payload. Activated hapten derivatives can be used as starting materials for the formation of such conjugates. In one embodiment the hapten is conjugated (in one embodiment via its 3-hydroxy group) to the payload via a linker. In one embodiment the linker comprises a) one or more (in one embodiment three to six) methylene-carboxy-methyl groups (—$CH_2$—C(O)—), and/or b) from 1 to 10 (in one embodiment from 1 to 5) amino acid residues (in one embodiment selected from glycine, serine, glutamate, β-alanine, γ-aminobutyric acid, ε-aminocaproic acid or lysine), and/or c) one or more (in one embodiment one or two) compounds having the structural formula NH2-[(CH$_2$)$_n$O]$_x$CH$_2$—CH$_2$—COOH in which n is 2 or 3 and x is 1 to 10, in one embodiment 1 to 7. The last element results (at least partly) in a linker (part) of the formula —NH—[(CH$_2$)$_n$O]$_x$CH2—CH$_2$—C(O)—. One example of such a compound is e.g. 12-amino-4,7,10-trioxadodecanoic acid (results in a TEG (triethylenglycol) linker). In one embodiment the linker further comprises a maleimido group. The linker has a stabilizing and solubilizing effect since it contains charges or/and can form hydrogen bridges. In addition it can sterically facilitate the binding of the anti-hapten antibody to the haptenylated payload. In one embodiment the linker is conjugated to a side chain of an amino acid of the payload (in one embodiment a polypeptide) (e.g. conjugated to a lysine or cysteine side chain via an amino or thiol group). In one embodiment the linker is conjugated to the amino terminus or the carboxy terminus of the payload (in one embodiment a polypeptide). The conjugation position of the linker to the payload is typically chosen to be in a region where the conjugation to the linker does not affect the biological activity of the payload. Therefore the attachment position of the linker depends on the nature of the payload and the relevant structure elements which are responsible for the biological activity of the payload. The biological activity of the payload to which the hapten attached can be tested before and after conjugation in an in vitro assay.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
  (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
  (b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
  (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "monospecific antibody" denotes an antibody that has one or more binding sites each of which has the same binding specificity, i.e. binds to the same antigen or hapten.

A "naked antibody" refers to an antibody that is not conjugated to a heterologous moiety (e.g., a cytotoxic moiety) or radiolabel. The naked antibody may be present in a pharmaceutical formulation.

The term "package insert" is used to refer to instructions customarily included in commercial packages of therapeutic products, that contain information about the indications, usage, dosage, administration, combination therapy, contraindications and/or warnings concerning the use of such therapeutic products.

The term "payload" denotes any molecule or combination of molecules that can be conjugated to a hapten. The term "payload" further denotes a moiety whose biological activity is desired to be delivered (in)to and/or localize at a cell or tissue. Payloads include, but are not limited to labels, chemotherapeutic agents, anti-angiogenic agents, cytotoxins (e.g. Pseudomonas exotoxin, ricin, abrin, Diphtheria toxin, and the like), cytokines, prodrugs, enzymes, growth factors, transcription factors, drugs, radionuclides, ligands, antibodies or fragments thereof, liposomes, nanoparticles, viral particles, cytokines, and the like.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamylamines including altretamine, triethylenemelamine, trietylenephosphoramide, triethylenethiophosphoramide and trimethylomelamine; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitroureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-II; 35 topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

An "anti-angiogenic agent" refers to a compound which blocks, or interferes with to some degree, the development of blood vessels. The anti-angiogenic agent may, for instance, be a small molecule or an antibody that binds to a growth factor or growth factor receptor involved in promoting angiogenesis. The anti-angiogenic factor is in one embodiment an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and —P; mullerian-inhibiting substance; mouse gonadotropin-associated peptide; inhibin; activin; vascular endothelial growth factor; integrin; thrombopoietin (TPO); nerve growth factors such as NGF-p; platelet growth factor; transforming growth factors (TGFs) such as TGF-a and TGF-p; insulin-like growth factor-I and -II; erythropoietin (EPO); osteoinductive factors; interferons such as interferon-a, -P, and -y; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-10, IL-11, IL-12; a tumor necrosis factor such as TNF-α or TNF-P; and other polypeptide factors including LIF and kit ligand (KL). As used herein, the term cytokine includes proteins from natural sources or from recombinant cell culture and biologically active equivalents of the native sequence cytokines.

The term "fMLP" denotes the tripeptide consisting of N-formylmethionine, leucine and phenylalanine. In one embodiment the effector moiety is fMLP or a derivative thereof.

The term "prodrug" refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, Vol. 14, 615th Meeting Belfast (1986) pp. 375-382 and Stella, et al., "Prodrugs: A Chemical Approach to Targeted Drug Delivery", Directed Drug Delivery, Borchardt, et al., (eds.), pp. 247-267, Humana Press (1985). The prodrugs that can be used as effector moiety include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described herein.

The term "cytotoxin" refers to a substance that inhibits or prevents a cellular function and/or causes cell death or destruction. Cytotoxins include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

All polypeptide sequences are written according to the generally accepted convention whereby the alpha-N-terminal amino acid residue is on the left and the alpha-C-terminal amino acid residue is on the right. As used herein, the term "N-terminus" refers to the free alpha-amino group of an amino acid in a polypeptide, and the term "C-terminus" refers to the free a-carboxylic acid terminus of an amino acid in a polypeptide. A polypeptide which is N-terminated with a group refers to a polypeptide bearing a group on the alpha-amino nitrogen of the N-terminal amino acid residue. An amino acid which is N-terminated with a group refers to an amino acid bearing a group on the alpha-amino nitrogen.

Unless indicated otherwise by a "D" prefix, e.g., D-Ala or N-Me-D-Ile, or written in lower case format, e.g., a, i, 1, (D versions of Ala, Ile, Leu), the stereochemistry of the alpha-carbon of the amino acids and aminoacyl residues in polypeptides described in this specification and the appended claims is the natural or "L" configuration. The Cahn-Ingold-Prelog "R" and "S" designations are used to specify the stereochemistry of chiral centers in certain acyl substituents at the N-terminus of the polypeptides. The designation "R,S" is meant to indicate a racemic mixture of the two enantiomeric forms. This nomenclature follows that described in Cahn, R. S., et al., Angew. Chem. Int. Ed. Engl. 5 (1966) 385-415.

The term "single-chain Fv", short "scFv", denotes an antibody fragment that comprise the VH and VL domains of antibody, wherein these domains are present in a single polypeptide chain. In one embodiment, the Fv polypeptide further comprises a polypeptide linker between the VH and VL domains which enables the scFv to form the desired structure for antigen binding. For a review of scFv, see Plueckthun in The Pharmacology of Monoclonal Antibodies, vol. 113, Rosenburg and Moore (Eds), Springer-Verlag, New York, pp. 269-315 (1994).

The term "theophylline", short "THEO", denotes 1,3-dimethyl-7H-purine-2,6-dione. Theophylline is also known as dimethylxanthine.

The term "theophyllinylated payload" denotes a conjugated entity comprising a theophylline moiety, optionally a linker and a payload. The linker can be any linker, such as e.g. a peptidic linker or a chemical linker.

The term "treatment" (and grammatical variations thereof such as "treat" or "treating") denotes a clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "x-valent", e.g. "mono-valent" or "bi-valent" or "tri-valent" or "tetra-valent", denotes the presence of a specified number of binding sites, i.e. "x", in an antibody molecule. As such, the terms "bivalent", "tetravalent", and "hexavalent" denote the presence of two binding site, four binding sites, and six binding sites, respectively, in an antibody molecule. The bispecific antibodies as reported herein are at least "bivalent" and may be "trivalent" or "multivalent" (e.g. "tetravalent" or "hexavalent"). In one embodiment the bispecific antibody as reported herein is bivalent, trivalent, or tetravalent. In one embodiment the bispecific antibody is bivalent. In one embodiment the bispecific antibody is trivalent. In one embodiment the bispecific antibody is tetravalent.

In certain aspects and embodiments the antibodies as reported herein have two or more binding sites and are bispecific. That is, the antibodies may be bispecific even in cases where there are more than two binding sites (i.e. that the antibody is trivalent or multivalent). The term bispecific antibodies includes, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for a hapten, a second binding site is specific for a non-hapten antigen, and vice versa.

The term "variable region" denotes the domain of an antibody heavy or light chain that is involved in binding the antibody to its antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector" denotes a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Conjugates as Reported Herein

Herein is reported a blood brain barrier-shuttle module (BBB-shuttle module) that is a bispecific antibody with a first binding specificity for a hapten and a second binding specificity for a blood brain barrier receptor (BBBR). Such a BBB-shuttle module recognizes a transcytoseable cell surface target on the blood brain barrier (such as TfR, LRPs or other targets, BBBR) and simultaneously binds to a haptenylated payloads.

It has been found that no further requirements with respect to binding valency, antibody format, BBBR binding affinities have to be met.

It has further been found that it is not required that the bispecific antibody-based shuttle module as reported herein is released from the endothelial cells of the blood brain barrier in order to mediate transcytosis of the haptenylated payload. Instead, the haptenylated payload, which is complexed by/bound to the bispecific antibody-based shuttle module upon binding to the BBBR, is released from the bispecific antibody-based shuttle module within the BBB cell, i.e. in the intracellular vesicular system, is separated from the shuttle module, and subsequently is exocytosed from the BBB cell into the brain leaving the bispecific antibody behind in the BBB cell.

The bispecific antibody-based shuttle module as reported herein is very variable in terms of binding specificity valency as well as affinity of the BBBR binding specificity. Simultaneously it enables payload release from the shuttle module.

Non-Covalent Complexes

The bispecific antibody as reported herein is used as a haptenylated payload delivery vehicle for a therapeutic or diagnostic payload. The therapeutic or diagnostic payload is conjugated with the hapten and thus complexed by the hapten-binding site of the bispecific antibody as reported herein. This complex is defined and stable and specifically delivers the haptenylated payload to a target cell or tissue. Since the haptenylated therapeutic or diagnostic payload is complexed in a non-covalent manner by the bispecific antibody, the haptenylated payload is on the one hand bound to its delivery vehicle (=bispecific antibody) during its time in the circulation but can also on the other hand be efficiently released after internalization or transcytosis. The conjugation with the hapten can be effected without interfering with the activity of the therapeutic or diagnostic payload. The bispecific antibody does not contain an unusual covalent addition and therefore obviates any risk of immunogenicity. Therefore this simple complexation procedure can be used for any payload in combination with only one anti-hapten antibody; for example peptides, proteins, small molecules, imaging reagents and nucleic acids. Complexes of haptenylated diagnostic or therapeutic payloads with the bispecific antibody as reported herein containing hapten-specific binding sites confers benign biophysical behavior and improved PK parameters to the diagnostic or therapeutic payload, e.g. to diagnostic or therapeutic polypeptide or small molecules. Furthermore, such complexes are capable to target the delivery load to cells or tissues which display the antigen that is recognized by the bispecific antibody's second binding specificity.

Specific targeting and delivery of nucleic acids to and into target tissues and target cells is a mayor task. For therapeutic applications, homogenous defined entities are desired. Antibody or antibody-fragment-mediated nucleic acid delivery has been shown in some examples (e.g. Lieberman et al., Nat. Biotechnol. 23 (2005) 709). Of particular interest is the specific targeting and delivery of double stranded RNA molecules (dsRNA) to and into target tissues and target cells. Double-stranded ribonucleic acid (dsRNA) molecules have been shown to block gene expression in a highly conserved regulatory mechanism known as RNA interference (RNAi). DsRNAs can be conjugated to antibodies with good stability to assure specific targeting and avoid systemic non-specific release. On the other hand, the dsRNA has to be released at or within target cells to enable entry into the cell.

The bispecific antibody as reported herein can be used as delivery vehicle for nucleic acids (DNA or RNA). Thus this invention provides a specific delivery platform for targeted gene therapy, targeted RNAi and targeted LNA delivery.

In one embodiment a complex of a haptenylated nucleic acid and a bispecific antibody as reported herein are used for specific targeted delivery of nucleic acids to cells or tissue. The nucleic acid retains their functionality despite being haptenylated, as well as while being complexed by the antibody. In addition, the blood brain barrier receptor binding site of the bispecific antibody retains its binding specificity and affinity in the presence of complexed haptenylated nucleic acid. The complexes of haptenylated nucleic acids with the bispecific antibody as reported herein can be used to target the nucleic acids specifically to cells that express the blood brain barrier receptor. Thereby, the cells that are recognized by the blood brain barrier receptor or the brain after transcytosis are selectively addressed by the nucleic acids, activities caused by the nucleic acids (e.g. RNAi or nucleic acid mediated cytotoxicity) are therefore enhanced in the blood brain barrier receptor expressing cells or the brain. In one embodiment, these activities are further enhanced by additionally applying targeted endosome modulating agents. The nucleic acids are not only specifically delivered to antigen expressing cells but also become internalized into the target cells. Since the haptenylated nucleic acids are coupled in a non-covalent manner to the bispecific antibody as reported herein the payload (i.e. nucleic acids) can be released after internalization or transcytosis.

In one preferred embodiment the nucleic acid is DNA. In one preferred embodiment the nucleic acid is dsRNA. In one preferred embodiment the nucleic acid is LNA.

To mediate their activity (for example the specific destruction of mRNAs by siRNAs), therapeutic or diagnostic nucleic acids have to access the cytoplasm of their target cells. One important factor for delivery of specific nucleic acid activity is that the molecules are not only delivered to cells, but also that a sufficient amount of the nucleic acids has to be transferred into the cytoplasm of these cells. For that, these molecules have to penetrate a biological membrane at least once. Since biologics do not pass easily across membranes, this process is a bottleneck that must be overcome for effective delivery of nucleic acid activity. Means to overcome this bottleneck can be membrane penetration, protein translocation across membranes, or endosome-escape or vesicular-escape mechanisms that may involve membrane disrupting processes.

In one embodiment the bispecific antibodies as reported herein or the non-covalent complexes of the bispecific antibody as reported herein with haptenylated nucleic acids are used as a nucleic acid delivery module to which a modulator of endosome functionality, or with endosome escape/disruption modules are linked. In one embodiment the endosome escape module comprises a peptide.

In one embodiment the endosome escape module comprises Dynamic Poly Conjugates (DPCs). DPCs are chemical entities that upon cell binding and internalization cause endosome escape of siRNAs (Rozema, D. B., et. al., Proc. Natl. Acad. Sci. USA 104(2007) 12982-12987). Such DPCs are composed of PBAVE (polymers of butyl-aminovinyl ethers) scaffolds to which PEG molecules are attached reversibly using a bifunctional maleamate linkage. For the latter, carboxylated dimethyl maleic acid (CDM) can be applied. The PEG units are used to shield the endosomolytic positive charges of the PBAVE. Also linked to the PBAVE is the siRNA cargo (e.g. via a reversible disulfide linkage). The resulting delivery vehicles are called siRNA Dynamic Poly Conjugates because siRNA, shielding groups (and additional targeting ligands) are conjugated to a polymer in a reversible manner. The endosomolytic properties of such DPCs which cause the cytoplasmic delivery of siRNA are induced by its chemical environment: The decrease in pH within maturing endolysomes induces release of the CDM-PEG, exposing positive charges of PBAVE which in turn mediates endosomolysis.

Therefore, in one embodiment the endosomolytic features of DPCs with the specific targeting properties of the bispecific haptenylated payload delivery system are combined.

In one embodiment the non-covalent complex of the bispecific antibody as reported herein and the haptenylated nucleic acid is used for imaging analyses. In this embodiment, the nucleic acids are simultaneously conjugated to the hapten and a detectable label. Thereby it is possible to visualize the localization of nucleic acids targeted to blood brain barrier receptor expressing cells by microscopy or other imaging technologies. In one embodiment the detectable label is a fluorescence label. In one embodiment the localization of nucleic acids is visualized in cells, i.e. in vitro. In another embodiment the localization of nucleic acids is visualized in vivo.

Due to their chemical and physical properties, such as molecular weight and domain architecture including secondary modifications, the downstream processing of antibodies is very complicated. For example, are not only for formulated drugs but also for intermediates in downstream processing (DSP) concentrated solutions required to achieve low volumes for economic handling and application storage.

But with increasing concentration of the antibody a tendency to form aggregates can be observed. These aggregated antibodies have impaired characteristics compared to the isolated antibody. Aggregation of the antibodies as reported herein can be reduced by the introduction of disulfide bonds between the heavy and light chain variable domains of the single chain antibodies connected to the monospecific bivalent parent antibody. This improved stability is not only useful during the production process but also for the storage of the antibodies. In one embodiment the disulfide bond between the variable domains of the single chain antibodies comprised in the bispecific antibody as reported herein is independently for each single chain antibody selected from:

i) heavy chain variable domain position 44 to light chain variable domain position 100,
ii) heavy chain variable domain position 105 to light chain variable domain position 43, or
iii) heavy chain variable domain position 101 to light chain variable domain position 100.

In one embodiment the disulfide bond between the variable domains of the single chain antibodies comprised in the bispecific antibody as reported herein is between heavy chain variable domain position 44 and light chain variable domain position 100.

In one embodiment the disulfide bond between the variable domains of the single chain antibodies comprised in the bispecific antibody as reported herein is between heavy chain variable domain position 105 and light chain variable domain position 43.

Covalent Conjugates

It has been found that by the covalent coupling of a haptenylated payload to an anti-hapten antibody a stabilization and PK-property improvement of the payload can be achieved.

Covalent conjugates of a haptenylated payload and an anti-hapten antibody may confer benign biophysical behavior and improved PK properties to the polypeptide. Furthermore, in case a bispecific antibody is used, the conjugates can be used to target the polypeptide to cells which display the antigen that is recognized by the second binding specificity of the bispecific antibody. Such conjugates are composed of one anti-hapten binding specificity and one (non-hapten) antigen binding specificity. The stoichiometric ratio of antibody to haptenylated payload depends on the format of the bispecific antibody and can be 1:1, 1:2, 2:1, 2:2, 2:4 and 4:2 (antibody: hapten-polypeptide).

It is desired that the payload retains good biological activity despite being conjugated the hapten, as well as being conjugated to the antibody. It is also desired (in case of bispecific targeting modules) that the cell surface target binding site of the bispecific antibody retains its binding specificity and affinity in the presence of the covalently conjugated haptenylated payload.

The reactive group in the haptenylated payload may be any reactive group, such as e.g. a maleimide, e.g. N-ethyl maleimide (NEM), a iodoacetamide, a pyridyl disulfide, or other reactive conjugation partner (see e.g. Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labeling: A Practical Approach, Academic Press, London; Means (1990) Bioconjugate Chem. 1:2; Hermanson, G. in Bioconjugate Techniques (1996)Academic Press, San Diego, pp. 40-55 and 643-671).

The reactive group on the antibody is limited to those that can be selectively, i.e. position specifically, generated. Therefore, it is limited to the side chain groups of the amino acid residues cysteine, serine, asparagine, glutamine, tyrosine, lysine, arginine, aspartic acid, and glutamic acid.

For the formation of a covalent conjugate between the antibody and the haptenylated payload both compounds have to be modified by the introduction of a reactive group. Upon binding of the haptenylated payload by the antibody the two reactive groups are brought in close proximity allowing the formation of a covalent bond. In one embodiment the modification is the introduction of a thiol functionality in each of the compounds. In one embodiment the thiol compound is a cysteine residue.

The position comprising the functional group must simultaneously meet two requirements: (i) the coupling positions should be in proximity to the binding region of the anti-hapten binding specificity of the antibody to utilize the hapten positioning effect for directed coupling, and (ii) the mutation and coupling position must be positioned in a manner that hapten binding by itself is not affected. These requirements for finding a suitable position are de facto 'contradicting' each other because requirement (i) is best served by a position close to the binding site, while requirement (ii) is most safely achieved by positions that are distant from the binding site.

Despite these virtually excluding requirements, positions were identified that can be mutated without affecting hapten positioning, and which nevertheless simultaneously allow directed covalent coupling.

The first position is located at position VH52b or at position VH53, respectively, according to the Kabat numbering of the heavy chain variable domain. If the antibody has a short VH CDR2, which does not have intermittent residues, such as 52a, 52c, 52c, and 52d, the position is 53 (numbering and alignment according to the numbering scheme and rules of Kabat for the antibody heavy chain variable domain). If the antibody has a long VH CDR2 comprising residues 52a and 52b, and optionally further residues as 52c and 52d, etc. the position is 52b (numbering and alignment according to the numbering scheme and rules of Kabat for the antibody heavy chain variable domain).

It has been found that any payload can be used in the haptenylated payload (in case of a haptenylated payload selected from the group consisting of biotinylated payloads, theophyllinylated payloads, digoxigenylated payloads, and fluoresceinylated payloads) upon derivatization with a universal linker which comprises the functional group for the formation of the covalent bond between the haptenylated payload and an amino acid residue in the heavy chain CDR2 of the antibody. The location of the functional group in the universal linker has the advantage that it is not necessary to re-engineer the synthesis and the position of the functional group in the heavy chain CDR2 of the antibody if the payload is changed.

It has further been found that any payload can be used in the helicarylated payload upon derivatization of the helicar amino acid sequence with a cysteine comprising the functional group for the formation of the covalent disulfide bond between the helicarylated payload and the cysteine residue in the light chain CDR2 of the antibody. The location of the cysteine residue (thiol functional group) in the helicar motif amino acid sequence has the advantage that it is not necessary to re-engineer the synthesis and the position of the cysteine residue in the light chain CDR2 of the antibody if the payload is changed.

The second position is located at position VH28 according to the Kabat numbering.

For example, in the anti-digoxigenin antibody structure, the hapten is bound in a deep pocket formed by hydrophobic residues. A fluorescent digoxigenin-Cy5 conjugate was used in this crystallographic study, wherein the fluorophore as well as the linker between digoxigenin and Cy5 were not visible in the structure due to a high flexibility and resulting disorder in the crystal. However, the linker and Cy5 are attached to O32 of digoxigenin which points into the direction of the CDR2 of the heavy chain. The distance between O32 of digoxigenin to the Cα of the amino acid residue in position 52b according to Kabat is about 10.5 Å.

It has been found that the positions are "universal" position, i.e. the position is applicable to any (anti-hapten) antibody or any helicarylated payload, respectively, and, thus, it is not required to start from scratch every time a new covalent complex has to be generated e.g. by providing the crystal structure and determining the appropriate position that enables hapten-positioned covalent coupling.

The antibodies modified as reported herein retain the hapten (antigen) binding capability of their parent (i.e. wild-type) antibody counterparts. Thus, the engineered antibody is capable of binding, in one embodiment it is capable of specifically binding, to haptens (antigens).

The terms "binding site that specifically binds to" or "an antibody that specifically binds to" denote that the molecule comprising the binding site or an antibody can form a complex with a further molecule in a specific manner. The binding can be detected in an in vitro assay, such as in a plasmon resonance assay (BIAcore, GE-Healthcare Uppsala, Sweden). The affinity of the complex formation is defined by the terms ka (rate constant for the association of the compounds to form the complex), $k_D$ (dissociation constant, dissociation of the complex), and $K_D$ ($k_D$/ka). Binding or specifically binding means a binding affinity ($K_D$) of about $10^{-7}$ M or less.

It has been found that the formation of a covalent bond between a cysteine-modified antibody and a cysteine-modified haptenylated payload bearing the cysteine residue in the linker between the hapten and the payload or within the hapten or within the payload takes place upon binding of the antibody to the haptenylated payload without the requirement of the addition of reducing and/or oxidizing agents if the formed bond is a disulfide bond. Thus, the disulfide bridge between the two compounds is formed spontaneously upon formation of the non-covalent complex. Therefore, a method for the formation of a covalent complex as reported herein simply requires the mixing of the two compounds. The only pre-requisite for the formation of the disulfide bond is a proper orientation of the two compounds with respect to each other.

Replacement of the amino acid residue at position VH52b and VH53, respectively, (according to the Kabat numbering scheme) with a Cys residue resulted in antibody derivatives with heavy chain variable region sequences that are listed in SEQ ID NO: 20 and 28 for anti-digoxigenin antibody-VH52bC, in SEQ ID NO: 84 and 92 for anti-theophylline antibody-VH53C, in SEQ ID NO: 52 and 60 for anti-biotin antibody-VH53C, in SEQ ID NO: 108 for anti-fluorescein antibody-VH52bC, and in SEQ ID NO: 226 for anti-bromodeoxyuridine antibody-VH53C.

Replacement of the heavy chain variable domain amino acid residue at position VH28 (according to the Kabat numbering scheme) with a Cys residue resulted in antibody derivatives with heavy chain variable region sequences that are listed in SEQ ID NO: 116, 124, 132, 140, 148, 156, and 164, respectively.

A further position that was identified as modification point is the position VH28 according to the Kabat numbering.

Replacement of the amino acid at position VH28 according to Kabat with Cys generated antibody derivatives with heavy chain variable region sequences that are listed is SEQ ID NO: 124 and 132 for anti-digoxigenin antibody-VH28C, in SEQ ID NO: 156 and 164 for anti-theophylline antibody-VH28C, in SEQ ID NO: 140 and 148 for anti-biotin antibody-VH28C, in SEQ ID NO: 116 for anti-fluorescein antibody-VH28C, and in SEQ ID NO: 227 for anti-bromodeoxyuridine antibody-VH28C.

ESI-MS analyses demonstrate that covalent antibody conjugation of haptenylated payload (payload=therapeutic peptide) result in a conjugate of defined size which is larger than non-complexed antibody or non-complexed peptide.

TABLE 1

TIC table.

| sample | Notes | LC MW$_{calc}$ | LC MW$_{exp}$ | HC MW$_{calc}$ | HC MW$_{exp}$ | Conjugate MW$_{calc}$ | Conjugate MW$_{exp}$ |
|---|---|---|---|---|---|---|---|
| humanized anti-digoxigenin antibody | 1); 2); 3) | 23371 | 23371 | 49635 | 49634 | n.a. | n.a. |
| humanized anti-digoxigenin antibody-VH52bC | 1); 2); 3) | 23371 | 23371 | 49681 | 49680 | n.a. | n.a. |
| Ac-PYY[PEG3-Cys(SS-R)-4Abu-Dig] R = humanized anti-digoxigenin antibody VH52bC | 1); 2); 3) | 23371 | 23371 | 49681 | 49680 | 152227 | 152233 |
| chimeric anti-biotin antibody | 2); 3) | 23429 | 23429 | 49312 | 49311 | n.a. | n.a. |
| chimeric anti-biotin antibody VH53C | 2); 3) | 23429 | 23429 | 49344 | 49343 | n.a. | n.a. |

TABLE 1-continued

TIC table.

| sample | Notes | LC MW$_{calc}$ | LC MW$_{exp}$ | HC MW$_{calc}$ | HC MW$_{exp}$ | Conjugate MW$_{calc}$ | Conjugate MW$_{exp}$ |
|---|---|---|---|---|---|---|---|
| humanized anti-biotin antibody | 1); 2); 3) | 23465 | 23464 | 49218 | 49217 | n.a. | n.a. |
| humanized anti-biotin antibody VH53C | 1); 2); 3) | 23465 | 23465 | 49250 | 49250 | n.a. | n.a. |
| Ac-PYY[PEG3-Cys(SS-R)-βAla-Biot R = chimeric anti-biotin antibody VH53C | 2); 3) | 23429 | 23429 | 49344 | 49344 | 151233 | 151238 |
| Ac-PYY[PEG3-Cys(SS-R)-PEG2-Biot R = chimeric anti-biotin antibody VH53C | 2); 3) | 23429 | 23429 | 49344 | 49344 | 151381 | 151385 |
| Ac-PYY[PEG3-Cys(SS-R)-βAla-Biot R = humanized anti-biotin antibody VH53C | 1); 2); 3) | 23465 | 23465 | 49250 | 49250 | 151118 | 151124 |
| Ac-PYY[PEG3-Cys(SS-R)-PEG2-Biot R = humanized anti-biotin antibody VH53C | 1); 2); 3) | 23465 | 23465 | 49250 | 49250 | 151266 | 151272 |
| anti-fluorescein antibody | 2); 3) | 23958 | 23958 | 49150 | 49149 | n.a. | n.a. |
| anti-fluorescein antibody VH52bC | 2); 3) | 23958 | 23957 | 49124 | 49124 | n.a. | n.a. |
| anti-fluorescein antibody VH28C | 2); 3) | 23958 | 23957 | 49152 | 49151 | n.a. | n.a. |
| Ac-PYY[PEG3-Cys(SS-R)-PEG2-Fluo R = anti-fluorescein antibody VH52bC | 2); 3) | 23958 | 23957 | 49124 | 49125 | 152271 | 152265 |
| Ac-PYY[PEG3-Cys(SS-R)-PEG2-Fluo R = anti-fluorescein antibody VH28C | 2); 3) | 23958 | 23958 | 49152 | 49152 | 152324 | 152319 |

1) HC w N-terminal pyro-glutamic acid
2) HC w/o C-terminal Lys
3) HC w N -> D at Glycosylation site due to deglycosylation
4) LC w N-terminal pyro-glutamic acid The results of the in vivo experiments show that hapten- and TfR-binding bispecific BBB-shuttle vehicles bind the haptenylated payload antibody and enable transport of the payload across the BBB. The results of these experiments also show that the payload can become released from the shuttle vehicle and subsequently bind to and accumulate on its target in the brain.

Antibody Affinity

In certain embodiments, the antibody as reported herein itself or the antibody in the complex as reported herein has a dissociation constant (Kd) of ≤10 nM, ≤1 nM, ≤0.1 nM, ≤0.01 nM, or ≤0.001 nM (e.g. of about $10^{-8}$ M or less, e.g. from about $10^{-8}$ M to about $10^{-13}$ M, e.g., from about $10^{-9}$ M to about $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (about 0.2 μM) before injection at a flow rate of 5 l/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen, Y. et al., J. Mol. Biol. 293 (1999) 865-881. If the on-rate exceeds 106 M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Antibody Fragments

In certain embodiments, an antibody provided herein or in a conjugate as reported herein is an antibody fragment. Antibody fragments include, but are not limited to, Fab, Fab', Fab'-SH, F(ab')2, Fv, and scFv fragments and conjugates thereof, and other fragments described below as long as the fragments are bivalent and bispecific or are combined to form a bivalent bispecific antibody fragment fusion polypeptide. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

Chimeric and Humanized Antibodies

In certain embodiments, an antibody provided herein or the antibody in a conjugate as reported herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

Human Antibodies

In certain embodiments, an antibody provided herein or the antibody in a conjugate as reported herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention or antibodies in the conjugate as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example:

U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Antibody Formats

The above outlined antibodies and antibody fragments can be combined in multiple ways to generate different antibody formats.

For example, one or more scFv antibody fragments can be fused to the C-terminus of one or more polypeptide chains of a complete antibody. Especially to each heavy chain C-terminus or to each light chain C-terminus a scFv antibody fragment can be fused.

For example, one or more antibody Fab fragments can be fused to the C-terminus of one or more polypeptide chains of a complete antibody. Especially to each heavy chain C-terminus or to each light chain C-terminus an antibody Fab fragment can be fused.

For example, one scFv and one antibody Fab fragment can be fused to the N-termini of an antibody Fc-region.

For example one scFv or antibody Fab fragment can be fused to an N-terminus of an antibody Fc-region and one scFv or antibody Fab fragment can be fused to the C-terminus of the respective other chain of an antibody Fc-region.

Multispecific Antibodies

A wide variety of recombinant antibody formats have been developed, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Leger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N. and Leger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent FV antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

In certain embodiments, an antibody provided herein or the antibody in a conjugate as reported herein is a multispecific antibody, e.g. a bispecific antibody. Multispecific antibodies are monoclonal antibodies that have binding specificities for at least two different sites. In certain embodiments, one of the binding specificities is for a hapten and the other is for any other (non-hapten) antigen. Bispecific antibodies may also be used to localize cytotoxic agents to cells. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

In one embodiment the CH3 domains of the heavy chains of the bispecific antibody are altered by the "knob-into-holes" technology which is described in detail with several examples in e.g. WO 96/027011, WO 98/050431, Ridgway J. B., et al., Protein Eng. 9 (1996) 617-621, Merchant, A. M., et al., Nat Biotechnol 16 (1998) 677-681. In this method the interaction surfaces of the two $CH_3$ domains are altered to increase the heterodimerization of both heavy chains containing these two $CH_3$ domains. Each of the two $CH_3$ domains (of the two heavy chains) can be the "knob", while the other is the "hole". The introduction of a disulfide bridge stabilizes the heterodimers (Merchant, A. M, et al., Nature Biotech 16 (1998) 677-681, Atwell, S., et al. J. Mol. Biol. 270 (1997) 26-35) and increases the yield.

In one embodiment of all aspects the bispecific antibody is characterized in that the $CH_3$ domain of one heavy chain and the $CH_3$ domain of the other heavy chain each meet at an interface which comprises an original interface between the antibody $CH_3$ domains, wherein said interface is altered to promote the formation of the bispecific antibody, wherein the alteration is characterized in that a) the $CH_3$ domain of one heavy chain is altered, so that within the original interface the $CH_3$ domain of one heavy chain that meets the original interface of the $CH_3$ domain of the other heavy chain within the bispecific antibody, an amino acid residue is replaced with an amino acid residue having a larger side chain volume, thereby generating a protuberance within the interface of the $CH_3$ domain of one heavy chain which is positionable in a cavity within the interface of the $CH_3$ domain of the other heavy chain and b) the $CH_3$ domain of the other heavy chain is altered, so that within the original interface of the second $CH_3$ domain that meets the original interface of the first $CH_3$ domain within the bispecific antibody an amino acid residue is replaced with an amino acid residue having a smaller side chain volume, thereby generating a cavity within the interface of the second $CH_3$ domain within which a protuberance within the interface of the first $CH_3$ domain is positionable.

Thus, the antibodies as reported herein are in one embodiment characterized in that the $CH_3$ domain of the first heavy chain of the full length antibody and the $CH_3$ domain of the second heavy chain of the full length antibody each meet at an interface which comprises an alteration in the original interface between the antibody $CH_3$ domains, wherein i) in the $CH_3$ domain of the first heavy chain an amino acid residue is replaced with an amino acid residue having a larger side chain volume, thereby generating a protuberance within the interface of the $CH_3$ domain of one heavy chain which is positionable in a cavity within the interface of the $CH_3$ domain of the other heavy chain and wherein ii) in the $CH_3$ domain of the second heavy chain an amino acid residue is replaced with an amino acid residue having a smaller side chain volume, thereby generating a cavity within the interface of the second $CH_3$ domain within which a protuberance within the interface of the first $CH_3$ domain is positionable.

In one embodiment the amino acid residue having a larger side chain volume is selected from the group consisting of arginine (R), phenylalanine (F), tyrosine (Y), tryptophane (W).

In one embodiment the amino acid residue having a smaller side chain volume is selected from the group consisting of alanine (A), serine (S), threonine (T), valine (V).

In one embodiment both $CH_3$ domains are further altered by the introduction of cysteine (C) as amino acid in the corresponding positions of each $CH_3$ domain such that a disulfide bridge between both $CH_3$ domains can be formed.

In one preferred embodiment, the multispecific antibody comprises the amino acid T366W mutation in the first CH3 domain of the "knobs chain" and the amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681) e.g. by introducing the amino acid Y349C mutation into the CH3 domain of the "hole chain" and the amino acid E356C mutation or the amino acid S354C mutation into the CH3 domain of the "knobs chain".

In one embodiment the bispecific antibody comprises Y349C, T366W mutations in one of the two CH3 domains and E356C, T366S, L368A, Y407V mutations in the other of the two CH3 domains. In one embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering according to EU index of Kabat; (Kabat, E. A., et al., Sequences of Proteins of Immunological Interest, 5th ed., Public Health Service, National Institutes of Health, Bethesda, Md. (1991))). Further knobs-in-holes technologies as described by EP 1 870 459 A1, can be used alternatively or additionally. Thus another example for the bispecific antibody are R409D, K370E mutations in the CH3 domain of the "knobs chain" and D399K, E357K mutations in the CH3 domain of the "hole chain" (numbering according to EU index of Kabat; (Kabat, E. A., et al., Sequences of Proteins of Immunological Interest, 5th ed., Public Health Service, National Institutes of Health, Bethesda, Md. (1991)).

In one embodiment the bispecific antibody comprises a T366W mutation in the CH3 domain of the "knobs chain" and T366S, L368A, Y407V mutations in the CH3 domain of the "hole chain" and additionally R409D, K370E mutations in the CH3 domain of the "knobs chain" and D399K, E357K mutations in the CH3 domain of the "hole chain".

In one embodiment the bispecific antibody comprises Y349C, T366W mutations in one of the two CH3 domains and S354C, T366S, L368A, Y407V mutations in the other of the two CH3 domains or the bispecific antibody comprises Y349C, T366W mutations in one of the two CH3 domains and S354C, T366S, L368A, Y407V mutations in the other of the two CH3 domains and additionally R409D, K370E mutations in the CH3 domain of the "knobs chain" and D399K, E357K mutations in the CH3 domain of the "hole chain". Such knob and hole mutations in the CH3 domain are typically used in human heavy chain constant regions of SEQ ID NO: 169, SEQ ID NO: 170, SEQ ID NO: 171, or SEQ ID NO: 172 (human IgG1 subclass allotypes (Caucasian and Afro-American or mutants L234A/L235A, and L234A/L235A/P329G), SEQ ID NO: 173, SEQ ID NO: 174, or SEQ ID NO: 175 (human IgG4 subclass or mutants S228P, L235E, and S228P/L235E/P329G) (numbering according to the EU index of Kabat et al., Sequences of Proteins of Immunological Interest, 5th ed., Public Health Service, National Institutes of Health, Bethesda, Md. (1991).

In one embodiment the bispecific antibody comprises human heavy chain constant regions of SEQ ID NO: 169, SEQ ID NO: 170, SEQ ID NO: 171, or SEQ ID NO: 172, SEQ ID NO: 173, SEQ ID NO: 174, or SEQ ID NO: 175 further including such "knob" and "hole" mutations in the CH3 domain (e.g. Y349C, T366W mutations in one of the two CH3 domains and S354C, T366S, L368A, Y407V mutations in the other of the two CH3 domains) (numbering according to the EU index of Kabat et al., Sequences of Proteins of Immunological Interest, 5th ed., Public Health Service, National Institutes of Health, Bethesda, Md. (1991).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to a hapten as well as another, different antigen (see US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one preferred embodiment, the multispecific antibody (which comprises a CH3 domain in each heavy chain) comprises the amino acid S354C, T366W mutations in one of the two CH3 domains and the amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459 A1, is used. This approach is based on the introduction of substitutions/mutations of charged amino acids with the opposite charge at specific amino acid positions in the CH3/CH3 domain interface between both heavy chains. In one preferred embodiment the multispecific antibody comprises the amino acid R409D, K370E mutations in the CH3 domain of the first heavy chain (of the multispecific antibody) and the amino acid D399K, E357K mutations in the seconds CH3 domain of the second heavy chain (of the multispecific antibody) (numbering according to Kabat).

In another embodiment the multispecific antibody comprises the amino acid T366W mutation in the CH3 domain of the "knobs chain" and the amino acid T366S, L368A, Y407V mutations in the CH3 domain of the "hole chain" and additionally the amino acid R409D, K370E mutations in the CH3 domain of the "knobs chain" and the amino acid D399K, E357K mutations in the CH3 domain of the "hole chain".

In another embodiment the multispecific antibody comprises the amino acid S354C, T366W mutations in one of the two CH3 domains and the amino acid Y349C, T366S, L368A, Y407V mutations in the other of the two CH3 domains or the multispecific antibody comprises the amino acid Y349C, T366W mutations in one of the two CH3 domains and the amino acid S354C, T366S, L368A, Y407V mutations in the other of the two CH3 domains and additionally the amino acid R409D, K370E mutations in the CH3 domain of the "knobs chain" and the amino acid D399K, E357K mutations in the CH3 domain of the "hole chain".

In one embodiment the heterodimerization approach described in WO2013/157953 is used. In one embodiment the first CH3 domain comprises the amino acid T366K mutation and the second CH3 domain comprises the amino acid L351D mutation. In a further embodiment the first CH3 domain further comprises the amino acid L351K mutation. In a further embodiment the second CH3 domain further comprises an amino acid mutation selected from Y349E, Y349D and L368E (preferably L368E).

In one embodiment the heterodimerization approach described in WO2012/058768 is used. In one embodiment the first CH3 domain comprises the amino acid L351Y, Y407A mutations and the second CH3 domain comprises the amino acid T366A, K409F mutations. In a further embodiment the second CH3 domain comprises a further amino acid mutation at position T411, D399, S400, F405, N390 or K392 e.g. selected from a) T411N, T411R, T411Q, T411K, T411D, T411E or T411W, b) D399R, D399W, D399Y or D399K, c) S400E, S400D, S400R or S400K, F405I, F405M, F405T, F405S, F405V or F405W, N390R, N390K or N390D, K392V, K392M, K392R, K392L, K392F or K392E. In a further embodiment the first CH3 domain comprises the amino acid L351Y, Y407A mutations and the second CH3 domain comprises the amino acid T366V, K409F mutations. In a further embodiment the first CH3 domain comprises the amino acid Y407A mutation and the second CH3 domain comprises the amino acid T366A, K409F mutations. In a further embodiment the second CH3 domain further comprises the amino acid K392E, T411E, D399R and S400R mutations.

In one embodiment the heterodimerization approach described in WO2011/143545 is used e.g. with the amino acid modification at a position selected from the group consisting of 368 and 409.

In one embodiment the heterodimerization approach described in WO2011/090762 is used, which also uses the knobs-into-holes technology described above. In one embodiment the first CH3 domain comprises the amino acid T366W mutation and the second CH3 domain comprises the amino acid Y407A mutation. In one embodiment the first CH3 domain comprises the amino acid T366Y mutation and the second CH3 domain comprises the amino acid Y407T mutation.

In one embodiment the multispecific antibody is of IgG2 isotype and the heterodimerization approach described in WO2010/129304 is used.

In one embodiment the heterodimerization approach described in WO2009/089004 is used. In one embodiment the first CH3 domain comprises the substitution of the amino acid residue K392 or N392 with a negative-charged amino acid (e.g. glutamic acid (E), or aspartic acid (D), preferably K392D or N392D) and the second CH3 domain comprises the substitution of the amino acid residue D399, E356, D356 or E357 with a positive-charged amino acid (e.g. Lysine (K) or arginine (R), preferably D399K, E356K, D356K, or E357K and more preferably D399K and E356K). In a further embodiment the first CH3 domain further comprises substitution of the amino acid residue K409 or R409 with a negative-charged amino acid (e.g. glutamic acid (E), or aspartic acid (D), preferably K409D or R409D). In a further embodiment the first CH3 domain further or alternatively comprises substitution of the amino acid residue K439 and/or K370 with a negative-charged amino acid (e.g. glutamic acid (E), or aspartic acid (D)).

In one embodiment the heterodimerization approach described in WO2007/147901 is used. In one embodiment the first CH3 domain comprises the amino acid K253E, D282K, and K322D mutations and the second CH3 domain comprises the amino acid D239K, E240K, and K292D mutations.

In one embodiment the heterodimerization approach described in WO2007/110205 is used.

In one embodiment the first binding specificity of the bispecific antibody is to a hapten and the second binding specificity is to a non-hapten antigen. In one embodiment the non-hapten antigen is selected from the leukocyte markers, CD2, CD3, CD4, CD5, CD6, CD7, CD8, CD11a,b,c, CD13, CD14, CD18, CD19, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CD56, CD58, CD69, CD72, CTLA-4, LFA-1 and TCR; the histocompatibility antigens, MHC class I or II, the Lewis Y antigens, SLex, SLey, SLea, and SLeb; the integrins, VLA-1, VLA-2, VLA-3, VLA-4, VLA-5, VLA-6, αVβ3, and LFA-1, Mac-1, and p150,95, αVβ1, gpIIbIIIa, αR β3, α6β4, αVβ 5, αVβ6, and αV 62 7; the selectins, L-selectin, P-selectin, and E-selectin and their counter receptors VCAM-1, ICAM-1, ICAM-2, and LFA-3; the interleukins, IL-1, IL-2, IL-3, IL-4, IL-5, IL-6, IL-7, IL-8, IL-9, IL-10, IL-11, IL-12, IL-13, IL-14, and IL-15; the interleukin receptor is selected from the group consisting of IL-1R, IL-2R, IL-3R, IL-4R, IL-5R, IL-6R, IL-7R, IL-8R, IL-9R, IL-10R, IL-11R, IL-12R, IL-13R, IL-14R, and IL-15R; the chemokine is selected from the group consisting of PF4, RANTES, MIP 1α, MCP 1, NAP-2, Groα, Groβ3, and IL-8; the growth factor is selected from the group consisting of TNFalpha, TGFbeta, TSH, VEGF/VPF, VEGFA, VEGFB, VEGF111, VEGF121, VEGF165, VEGF189, VEGF206, PTHrP, EGF family, PDGF family, endothelin, Fibrosin (FSF-1), human Laminin, and gastrin releasing peptide (GRP), PLGF, HGH, HGHR; the growth factor receptor is selected from the group consisting of TNFalphaR, RGFbetaR, TSHR, VEGFR/VPFR, EGFR, PTHrPR, PDGFR family, EPO-R, GCSF-R and other hematopoietic receptors; the interferon receptor is selected from the group consisting of IFNCαR, IFNβR, and IFNλR; the Ig and its receptor is selected from the group consisting of IgE, FcγRI, and FcγRII; the tumor antigen is selected from the group consisting of her2-neu, mucin, CEA and endosialin; the allergen is selected from the group consisting of house dust mite antigen, lol pl (grass) antigens, and urushiol; the viral polypeptide is selected from the group consisting of CMV glycoproteins B, H, and gCIII, HIV-1 envelope glycoproteins, RSV envelope glycoproteins, HSV envelope glycoproteins, HPV envelope glycoproteins, Hepatitis family surface antigens; the toxin is selected from the group consisting of *Pseudomonas* endotoxin and osteopontin/uropontin, snake venom, spider venom, and bee venom conotoxin; the blood factor is selected from the group consisting of complement C3b, complement C4a, complement C4b-9, Rh factor, fibrinogen, fibrin, and myelin associated growth inhibitor; and the enzyme is selected from the group consisting of cholesterol ester transfer polypeptide, membrane bound matrix metalloproteases, and glutamic acid decarboxylase (GAD).

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. Heavy chain CDR3 and light chain CDR3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein or comprised in a conjugate as reported herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

In one preferred embodiment the antibody comprises in both heavy chains the mutations L234A, L235A and P329G (numbering according to EU index).

d) Cysteine Engineered Antibody Variants

In certain embodiments, it may be desirable to create cysteine engineered antibodies, e.g., "thioMAbs," in which one or more residues of an antibody are substituted with cysteine residues.

In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Haptenylated Compounds

The hapten in a conjugate as reported herein may be conjugated, if it is not by itself one of the molecules, to a therapeutic agent (drug), a cytotoxic agent (e.g. a toxin such as doxorubicin or pertussis toxin), a fluorophores such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent. Such a conjugate is denoted as haptenylated compound. The conjugation can be either directly or via an intervening linker.

a) Therapeutic Moieties

The drug moiety (D) of the hapten-drug conjugate (ADC, haptenylated drug) can be any compound, moiety or group which has a cytotoxic or cytostatic effect. Drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC 1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The haptenylated compound can be a haptenylated label. Any label moiety which can be covalently attached to the hapten can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & I T Van Vunakis), Academic Press, New York, 73 (1981) 147-166.

Examples of enzyme-substrate combinations (U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

Antibody Conjugates

The antibody in a conjugate as reported herein may be further conjugated, if it is not by itself one of the molecules, to a therapeutic agent (drug), a cytotoxic agent (e.g. a toxin such as doxorubicin or pertussis toxin), a fluorophores such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

Immunoconjugates

The invention also provides immunoconjugates comprising an antibody as reported herein or a conjugate as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M. et al., Bioorg. & Med. Chem. Letters 12 (2002) 1529-1532; King, H. D. et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein or a complex as reported herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Linker

The term "linker" denotes a bifunctional or multifunctional moiety which can be used to conjugate (link) the antigen (e.g. a hapten) to other moieties, such as detectable labels or drugs. Antigen (hapten) conjugates can be conveniently prepared using a linker having reactive functionality for binding to the drug, to the antigen (hapten) and to the anti-hapten antibody.

In one embodiment, a linker has a reactive site which has an electrophilic group that is reactive to a nucleophilic group present on the anti-hapten antibody. A cysteine thiol group on the antibody for example is reactive with an electrophilic group on a linker and forms a covalent bond to a linker. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, alpha-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

The linker may comprise amino acid residues which link the antigen (hapten) to the payload. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or a-amino acids, such as e.g. β-alanine, or co-amino acids such as 4-amino-butyric acid.

In another embodiment, the linker has a reactive functional group which has a nucleophilic group that is reactive to an electrophilic group present on the antigen (hapten) or the antibody (anti-hapten antibody). Useful electrophilic groups include, but are not limited to, aldehyde and ketone carbonyl groups. The heteroatom of a nucleophilic group of a linker can react with an electrophilic group on the hapten or the antibody and form a covalent bond to an antigen (hapten) or the antibody. Useful nucleophilic groups on a linker include, but are not limited to, hydrazide, oxime, amino, hydrazine, thiosemicarbazone, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate ($SO_3^-$) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a drug or label as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, $BM(PEO)_3$, and $BM(PEO)_4$, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys(Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and haptenylated compounds including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

III. Nucleic Acid

The DNA encoding the amino acid sequence variant of the antibody as reported herein or as comprised in a conjugate as reported herein can be prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such modified engineered antibodies. General guidance can be found in Sambrook et al., Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

IV. Expression and Purification

Antibodies may be produced using recombinant methods and compositions, e.g., as described in U.S. Pat. No. 4,816, 567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody as reported herein, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

V. Methods and Compositions for Diagnostics and Detection

In certain embodiments, any of the antibodies, especially the bispecific antibodies, and conjugates as reported herein is useful for detecting the presence of one or more target molecules in a biological sample. The term "detecting" as used herein encompasses quantitative or qualitative detection. In one embodiment a biological sample comprises a cell or tissue.

In one embodiment, an antibody or conjugate as reported herein for use in a method of diagnosis or detection is provided. In certain embodiments, the method comprises contacting the biological sample with an antibody or conjugate as reported herein under conditions permissive for binding of the antibody or the conjugate to the target, and detecting whether a complex is formed between the antibody or the conjugate and the target. Such method may be an in vitro or in vivo method.

In certain embodiments, labeled antibodies or conjugates are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazindiones, horseradish peroxidase (HRP), alkaline phosphatase, 3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

VI. Pharmaceutical Formulations

Pharmaceutical formulations of an antibody or conjugate as reported herein are prepared by mixing such antibody or conjugate having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody or conjugate, which matrices are in the form of shaped articles, e.g. films, or microcapsules.

The formulations to be used for in vivo administration are generally sterile. Sterility may be readily accomplished, e.g., by filtration through sterile filtration membranes.

VII. Therapeutic Methods and Compositions

Any of the antibodies or conjugates reported herein may be used in therapeutic methods.

In one aspect, an antibody or a conjugate as reported herein for use as a medicament is provided. In further aspects, an antibody or a conjugate as reported herein for use in treating a disease is provided. In certain embodiments, an antibody or a conjugate as reported herein for use in a method of treatment is provided. In certain embodiments, the invention provides an antibody or a conjugate as reported herein for use in a method of treating an individual comprising administering to the individual an effective amount of the antibody or the conjugate as reported herein. In one such embodiment, the method further comprises administering to the individual an effective amount of at least one additional therapeutic agent, e.g., as described below. An "individual" according to any of the above embodiments may be a human.

In a further aspect, the invention provides for the use of an antibody or a conjugate as reported herein in the manufacture or preparation of a medicament. In one embodiment, the medicament is for treatment of a disease. In a further embodiment, the medicament is for use in a method of treating a disease comprising administering to an individual having a disease an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a disease. In one embodiment, the method comprises administering to an individual having such a disease an effective amount of an antibody or a conjugate as reported herein. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the antibodies or conjugates as reported herein, e.g., for use in any of the above therapeutic methods. In one embodiment, a pharmaceutical formulation comprises any of the antibodies or conjugates as reported herein and a pharmaceutically acceptable carrier. In another embodiment, a pharmaceutical formulation comprises any of the antibodies or conjugates as reported herein and at least one additional therapeutic agent, e.g., as described below.

Antibodies and conjugates as reported herein can be used either alone or in combination with other agents in a therapy. For instance, an antibody or conjugate as reported herein may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies and conjugates as reported herein can also be used in combination with radiation therapy.

An antibody or conjugate as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or conjugates as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or conjugate need not be, but is optionally formulated with one or more agents currently used to prevent or treat the disorder in question. The effective amount of such other agents depends on the amount of antibody or conjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or conjugate as reported herein (when used alone or in combination with one or more other additional therapeutic agents) will depend on the type of disease to be treated, the type of antibody or conjugate, the severity and course of the disease, whether the antibody or conjugate is administered for preventive or therapeutic purposes, previous therapy, the patient's clinical history and response to the antibody or conjugate, and the discretion of the attending physician. The antibody or conjugate is suitably administered to the patient at one time or over a series of treatments. Depending on the type and severity of the disease, about 1 µg/kg to 15 mg/kg (e.g. 0.5 mg/kg-10 mg/kg) of antibody or conjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or conjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an antibody or a conjugate as reported herein.

VIII. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or a complex as reported herein. The label or package insert indicates that the composition is used for treating the condition of choice. Moreover, the article of manufacture may comprise (a) a first container with a composition contained therein, wherein the composition comprises an antibody or a complex as reported herein; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an antibody or a conjugate as reported herein.

IX. Specific Embodiments

1. A covalent conjugate comprising
   i) a bispecific antibody, which has a first binding specificity, which specifically binds to a haptenylated payload, and a second binding specificity, which specifically binds to a blood brain barrier receptor, and
   ii) a haptenylated payload,
   wherein the haptenylated payload is specifically bound by the first binding specificity,
   wherein the covalent conjugate has a covalent bond between the haptenylated payload and the first binding specificity that specifically binds to the haptenylated payload, and
   wherein the haptenylated payload is selected from the group consisting of biotinylated payloads, theophyllinylated payloads, digoxigenylated payloads, carboranylated payloads, fluoresceinylated payloads, helicarylated payloads and bromodeoxyuridinylated payloads.

2. A non-covalent complex comprising a bispecific antibody, which has a first binding specificity that specifically binds to a haptenylated payload and a second binding specificity that specifically binds to a blood brain barrier receptor and a haptenylated payload, wherein the haptenylated payload is specifically bound by the first binding specificity.

3. A covalent conjugate comprising a bispecific antibody, which has a first binding specificity that specifically binds to a haptenylated payload and a second binding specificity that specifically binds to a blood brain barrier receptor and a haptenylated payload, wherein the haptenylated payload is specifically bound by the first binding specificity, and which has a covalent bond between a haptenylated payload and a first binding specificity that specifically binds to the haptenylated payload.

4. The complex or the conjugate according to any one of items 1 to 3, wherein the haptenylated payload is selected from the group comprising biotinylated payloads, theophyllinylated payloads, digoxigenylated payloads, carboranylated payloads, fluoresceinylated payloads, helicarylated payloads and bromodeoxyuridinylated payloads.

5. The complex or the conjugate according to any one of items 1 to 4, wherein the hapten is a derivative or analogue of a nucleotide or a nucleosides. In one embodiment the hapten is a derivatives or analogues of an amino acid.

6. The complex or the conjugate according to any one of items 1 to 5, wherein the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

7. The complex or the conjugate according to any one of items 1 to 6, wherein the bispecific antibody is a full length antibody comprising two binding sites.

8. The complex or the conjugate according to any one of items 1 to 7, wherein the bispecific antibody is a full length antibody to which one or two scFvs or scFabs have been fused and that comprises three or four binding sites.

9. The complex or the conjugate according to any one of items 1 to 8, wherein the bispecific antibody is an antibody fragment. In one embodiment the antibody fragment is selected from F(ab')2 and diabodies.

10. The complex or the conjugate according to any one of items 1 to 9, wherein the bispecific antibody is a humanized or a human antibody.

11. The complex or the conjugate according to any one of items 1 to 10, wherein the bispecific antibody is free of effector function.

12. The complex or the conjugate according to any one of items 1 to 11, wherein the bispecific antibody has no functional Fc-region.
13. The complex or the conjugate according to any one of items 1 to 12, wherein the bispecific antibody has no Fc-region.
14. The complex or the conjugate according to any one of items 1 to 13, wherein the bispecific antibody has an Fc-region of the human IgG1 subclass with the mutations L234A, L235A and P329G, wherein the positions are determined according to the Fc-region numbering of Kabat (Kabat EU index).
15. The complex or the conjugate according to any one of items 1 to 14, wherein the bispecific antibody has an Fc-region of the human IgG4 subclass with the mutations S228P, L235E and P329G, wherein the positions are determined according to the Fc-region numbering of Kabat (Kabat EU index).
16. The complex or the conjugate according to any one of items 1 to 15, wherein the bispecific antibody comprises
    a) one binding site for the haptenylated payload and one binding site for the blood brain barrier receptor, or
    b) two binding sites for the haptenylated payload and one binding site for the blood brain barrier receptor, or
    c) one binding site for the haptenylated payload and two binding sites for the blood brain barrier receptor, or
    d) two binding sites for the haptenylated payload and two binding sites for the blood brain barrier receptor.
17. The complex or the conjugate according to any one of items 1 to 16, wherein the bispecific antibody comprises two binding sites for the haptenylated payload and two binding sites for the blood brain barrier receptor.
18. The complex or the conjugate according to any one of items 1 to 17, wherein the haptenylated payload comprises between the hapten and the payload a linker.
19. The complex or the conjugate according to item 18, wherein the linker is a peptidic linker.
20. The complex or the conjugate according to item 18, wherein the linker is a chemical linker (non-peptidic linker).
21. The complex or the conjugate according to any one of items 1 to 20, wherein the bispecific antibody and the haptenylated payload each comprise a functional group whereby upon binding of the haptenylated payload by the bispecific antibody a covalent bond is formed between the haptenylated payload and the bispecific antibody.
22. The complex or the conjugate according to any one of items 1 to 21, wherein the bispecific antibody comprises a functional group at an amino acid residue in the CDR2 of the antibody, whereby the CDR2 is determined according to Kabat.
23. The complex or the conjugate according to item 22, wherein the functional group at an amino acid residue in the CDR2 of the antibody is a thiol group.
24. The complex or the conjugate according to any one of items 1 to 23, wherein the bispecific antibody comprises a cysteine amino acid residue in the CDR2 of the antibody.
25. The complex or the conjugate according to any one of items 1 to 24, wherein the haptenylated payload comprises a functional group in the hapten or if present in the linker between the hapten and the payload.
26. The complex or the conjugate according to item 25, wherein the functional group is a thiol, or a maleimide, or a haloacetyl.
27. The complex or the conjugate according to any one of items 25 to 26, wherein the functional group in the hapten or if present in the linker is a thiol group.
28. The complex or the conjugate according to any one of items 1 to 27, wherein the covalent bond is between a cysteine residue in the CDR2 of the antibody and the thiol group in the haptenylated payload.
29. The complex or the conjugate according to item 28, wherein the covalent bond is a disulfide bond.
30. The complex or the conjugate according to any one of items 28 to 29, wherein the covalent bond is a disulfide bond and it is formed without the addition of redox active agents.
31. The complex or the conjugate according to any one of items 1 to 30, wherein the CDR2 is the heavy chain CDR2 in case of a haptenylated payload selected from the group consisting of biotinylated payloads, theophyllinylated payloads, digoxigenylated payloads, and fluoresceinylated payloads.
32. The complex or the conjugate according to item 31, wherein the cysteine residue in the heavy chain CDR2 of the antibody is at position 52, or position 52a, or position 52b, or position 52c, or position 52d, or position 53 according to the heavy chain variable domain numbering of Kabat.
33. The complex or the conjugate according to any one of items 31 to 32, wherein the cysteine residue in the heavy chain CDR2 of the antibody is at position 52a, or position 52b, or position 52c, or position 53 according to the heavy chain variable domain numbering of Kabat.
34. The complex or the conjugate according to any one of items 31 to 33, wherein the cysteine residue in the heavy chain CDR2 of the antibody is at position 52b or at position 53 according to the heavy chain variable domain numbering of Kabat.
35. The complex or the conjugate according to any one of items 1 to 30, wherein the CDR2 is the light chain CDR2 in case of a helicarylated payload.
36. The complex or the conjugate according to item 35, wherein the cysteine residue in the light chain CDR2 of the antibody is at position 51 or at position 55 according to the light chain variable domain numbering of Kabat.
37. The complex or the conjugate according to any one of items 35 to 36, wherein the cysteine residue in the light chain CDR2 of the antibody is at position 55 according to the light chain variable domain numbering of Kabat.
38. The complex or the conjugate according to any one of items 1 to 37, wherein exactly one covalent bond is formed per CDR2.
39. The complex or the conjugate according to any one of items 1 to 38, wherein the payload is selected from a binding moiety, a labeling moiety, and a biologically active moiety.
40. The complex or the conjugate according to any one of items 1 to 39, wherein the biologically active moiety is selected from the group comprising antibodies, antibody fragments, antibody conjugates polypeptides, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), locked nucleic acids (LNAs), ribozymes, and small molecules, or active fragments of any of the foregoing.
41. The complex or the conjugate according to any one of items 1 to 40, wherein the payload is a nucleic acid or nucleic acid derivative.

42. The complex or the conjugate according to any one of items 1 to 41, wherein the nucleic acid is an iRNA or a LNA.
43. The complex or the conjugate according to any one of items 1 to 42, wherein the payload is a polypeptide.
44. The complex or the conjugate according to any one of items 1 to 43, wherein the payload is a small molecule (non-polypeptide biologically active moiety).
45. The complex or the conjugate according to any one of items 1 to 44, wherein the biologically active moiety is a polypeptide.
46. The complex or the conjugate according to item 45, wherein the polypeptide is consisting of 5 to 500 amino acid residues.
47. The complex or the conjugate according to any one of items 45 to 46, wherein the polypeptide comprises 10 to 450 amino acid residues.
48. The complex or the conjugate according to any one of items 45 to 47, wherein the polypeptide comprises 15 to 400 amino acid residues.
49. The complex or the conjugate according to any one of items 45 to 48, wherein the polypeptide comprises 18 to 350 amino acids residues.
50. The complex or the conjugate according to any one of items 1 to 49, wherein the bispecific antibody comprises a first binding specificity that specifically binds to a digoxigenylated payload (anti-digoxigenin binding specificity; anti-DIG binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).
51. The complex or the conjugate according to any one of items 1 to 50, wherein the bispecific antibody has two binding specificities that specifically bind to the digoxigenylated payload (two anti-digoxigenin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).
52. The complex or the conjugate according to any one of items 1 to 51, wherein the binding specificity that specifically binds to a digoxigenylated payload is a pair of an antibody heavy chain variable domain and an antibody light chain variable domain comprising (a) a heavy chain CDR1 comprising the amino acid sequence of SEQ ID NO: 01, (b) a heavy chain CDR2 comprising the amino acid sequence of SEQ ID NO: 02, (c) a heavy chain CDR3 comprising the amino acid sequence of SEQ ID NO: 03, (d) a light chain CDR1 comprising the amino acid sequence of SEQ ID NO: 05, (e) a light chain CDR2 comprising the amino acid sequence of SEQ ID NO: 06, and (f) a light chain CDR3 comprising the amino acid sequence of SEQ ID NO: 07.
53. The complex or the conjugate according to any one of items 1 to 52, wherein the binding specificity that specifically binds to a digoxigenylated payload is a humanized binding specificity.
54. The complex or the conjugate according to any one of items 1 to 53, wherein the binding specificity that specifically binds to a digoxigenylated payload comprises CDRs as in any of the above embodiments and an acceptor human framework (e.g. a human immunoglobulin framework or a human consensus framework).
55. The complex or the conjugate according to any one of items 1 to 54, wherein the binding specificity that specifically binds to a digoxigenylated payload is a pair of an antibody heavy chain variable domain and an antibody light chain variable domain comprising (a) a heavy chain CDR1 comprising the amino acid sequence of SEQ ID NO: 09 or 25, (b) a heavy chain CDR2 comprising the amino acid sequence of SEQ ID NO: 10 or 26, (c) a heavy chain CDR3 comprising the amino acid sequence of SEQ ID NO: 11 or 27, (d) a light chain CDR1 comprising the amino acid sequence of SEQ ID NO: 13 or 29, (e) a light chain CDR2 comprising the amino acid sequence of SEQ ID NO: 14 or 30, and (f) a light chain CDR3 comprising the amino acid sequence of SEQ ID NO: 15 or 31.
56. The complex or the conjugate according to any one of items 1 to 55, wherein the binding specificity that specifically binds to a digoxigenylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 04 or 12 or 20 or 28.
57. The complex or the conjugate according to any one of items 1 to 56, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin.
58. The complex or the conjugate according to any one of items 1 to 57, wherein a total of 1 to 10 amino acids have been substituted, inserted and/or deleted in SEQ ID NO: 01 or 09 or 17 or 25.
59. The complex or the conjugate according to any one of items 1 to 58, wherein substitutions, insertions, or deletions occur in regions outside the CDRs (i.e., in the FRs).
60. The complex or the conjugate according to any one of items 1 to 59, wherein the anti-digoxigenin antibody comprises the VH sequence in SEQ ID NO: 01 or 09 or 17 or 25, including post-translational modifications of that sequence.
61. The complex or the conjugate according to any one of items 1 to 60, wherein the binding specificity that specifically binds to a digoxigenylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 08 or 16 or 24 or 32.
62. The complex or the conjugate according to any one of items 1 to 61, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin.
63. The complex or the conjugate according to any one of items 1 to 62, wherein a total of 1 to 10 amino acids have been substituted, inserted and/or deleted in SEQ ID NO: 08 or 16 or 24 or 32, optionally the substitutions, insertions, or deletions occur in regions outside the CDRs (i.e., in the FRs).
64. The complex or the conjugate according to any one of items 1 to 63, wherein the anti-digoxigenin antibody comprises the VL sequence in SEQ ID NO: 08 or 16 or 24 or 32, including post-translational modifications of that sequence.

65. The complex or the conjugate according to any one of items 1 to 49, wherein the bispecific antibody comprises a first binding specificity that specifically binds to a biotinylated payload (anti-biotin binding specificity; anti-BI binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

66. The complex or the conjugate according to any one of items 1 to 49 and 65, wherein the bispecific antibody has two binding specificities that specifically bind to the biotinylated payload (two anti-biotin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

67. The complex or the conjugate according to any one of items 1 to 49 and 65 to 66, wherein the binding specificity that specifically binds to a biotinylated payload is a pair of an antibody heavy chain variable domain and an antibody light chain variable domain comprising (a) a heavy chain CDR1 comprising the amino acid sequence of SEQ ID NO: 33, (b) a heavy chain CDR2 comprising the amino acid sequence of SEQ ID NO: 34, (c) a heavy chain CDR3 comprising the amino acid sequence of SEQ ID NO: 35, (d) a light chain CDR1 comprising the amino acid sequence of SEQ ID NO: 37, (e) a light chain CDR2 comprising the amino acid sequence of SEQ ID NO: 38, and (f) a light chain CDR3 comprising the amino acid sequence of SEQ ID NO: 39.

68. The complex or the conjugate according to any one of items 1 to 49 and 65 to 67, wherein the binding specificity that specifically binds to a biotinylated payload is a humanized binding specificity.

69. The complex or the conjugate according to any one of items 1 to 49 and 65 to 68, wherein the binding specificity that specifically binds to a biotinylated payload comprises CDRs as in any of the above embodiments and an acceptor human framework (e.g. a human immunoglobulin framework or a human consensus framework).

70. The complex or the conjugate according to any one of items 1 to 49 and 65 to 69, wherein the binding specificity that specifically binds to a biotinylated payload is a pair of an antibody heavy chain variable domain and an antibody light chain variable domain comprising (a) a heavy chain CDR1 comprising the amino acid sequence of SEQ ID NO: 41 or 57, (b) a heavy chain CDR2 comprising the amino acid sequence of SEQ ID NO: 42 or 58, (c) a heavy chain CDR3 comprising the amino acid sequence of SEQ ID NO: 43 or 59, (d) a light chain CDR1 comprising the amino acid sequence of SEQ ID NO: 45 or 61, (e) a light chain CDR2 comprising the amino acid sequence of SEQ ID NO: 46 or 62, and (f) a light chain CDR3 comprising the amino acid sequence of SEQ ID NO: 47 or 64.

71. The complex or the conjugate according to any one of items 1 to 49 and 65 to 70, wherein the binding specificity that specifically binds to a biotinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 36 or 44 or 52 or 60.

72. The complex or the conjugate according to any one of items 1 to 49 and 65 to 71, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

73. The complex or the conjugate according to any one of items 1 to 49 and 65 to 72, wherein a total of 1 to 10 amino acids have been substituted, inserted and/or deleted in SEQ ID NO: 36 or 44 or 52 or 60, optionally the substitutions, insertions, or deletions occur in regions outside the CDRs (i.e., in the FRs).

74. The complex or the conjugate according to any one of items 1 to 49 and 65 to 73, wherein the anti-biotin antibody comprises the VH sequence in SEQ ID NO: 36 or 44 or 52 or 60, including post-translational modifications of that sequence.

75. The complex or the conjugate according to any one of items 1 to 49 and 65 to 74, wherein the binding specificity that specifically binds to a biotinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 40 or 48 or 56 or 64.

76. The complex or the conjugate according to any one of items 1 to 49 and 65 to 75, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

77. The complex or the conjugate according to any one of items 1 to 49 and 65 to 76, wherein a total of 1 to 10 amino acids have been substituted, inserted and/or deleted in SEQ ID NO: 40 or 48 or 56 or 64, optionally the substitutions, insertions, or deletions occur in regions outside the CDRs (i.e., in the FRs).

78. The complex or the conjugate according to any one of items 1 to 49 and 65 to 77, wherein the anti-biotin antibody comprises the VL sequence in SEQ ID NO: 40 or 48 or 56 or 64, including post-translational modifications of that sequence.

79. The complex or the conjugate according to any one of items 1 to 49, wherein the bispecific antibody comprises a first binding specificity that specifically binds to a theophyllinylated payload (anti-theophylline binding specificity; anti-THEO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

80. The complex or the conjugate according to any one of items 1 to 49 and 79, wherein the bispecific antibody has two binding specificities that specifically bind to the theophyllinylated payload (two anti-theophylline binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).
81. The complex or the conjugate according to any one of items 1 to 49 and 79 to 80, wherein the binding specificity that specifically binds to a theophyllinylated payload is a pair of an antibody heavy chain variable domain and an antibody light chain variable domain comprising (a) a heavy chain CDR1 comprising the amino acid sequence of SEQ ID NO: 65, (b) a heavy chain CDR2 comprising the amino acid sequence of SEQ ID NO: 66, (c) a heavy chain CDR3 comprising the amino acid sequence of SEQ ID NO: 67, (d) a light chain CDR1 comprising the amino acid sequence of SEQ ID NO: 69, (e) a light chain CDR2 comprising the amino acid sequence of SEQ ID NO: 70, and (f) a light chain CDR3 comprising the amino acid sequence of SEQ ID NO: 71.
82. The complex or the conjugate according to any one of items 1 to 49 and 79 to 81, wherein the binding specificity that specifically binds to a theophyllinylated payload is a humanized binding specificity.
83. The complex or the conjugate according to any one of items 1 to 49 and 79 to 82, wherein the binding specificity that specifically binds to a theophyllinylated payload comprises CDRs as in any of the above embodiments and an acceptor human framework (e.g. a human immunoglobulin framework or a human consensus framework).
84. The complex or the conjugate according to any one of items 1 to 49 and 79 to 83, wherein the binding specificity that specifically binds to a theophyllinylated payload is a pair of an antibody heavy chain variable domain and an antibody light chain variable domain comprising (a) a heavy chain CDR1 comprising the amino acid sequence of SEQ ID NO: 73 or 89, (b) a heavy chain CDR2 comprising the amino acid sequence of SEQ ID NO: 74 or 90, (c) a heavy chain CDR3 comprising the amino acid sequence of SEQ ID NO: 75 or 91, (d) a light chain CDR1 comprising the amino acid sequence of SEQ ID NO: 77 or 93, (e) a light chain CDR2 comprising the amino acid sequence of SEQ ID NO: 78 or 94, and (f) a light chain CDR3 comprising the amino acid sequence of SEQ ID NO: 79 or 95.
85. The complex or the conjugate according to any one of items 1 to 49 and 79 to 84, wherein the binding specificity that specifically binds to a theophyllinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 76 or 84 or 92.
86. The complex or the conjugate according to any one of items 1 to 49 and 79 to 85, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.
87. The complex or the conjugate according to any one of items 1 to 49 and 79 to 86, wherein a total of 1 to 10 amino acids have been substituted, inserted and/or deleted in SEQ ID NO: 68 or 76 or 84 or 92, optionally the substitutions, insertions, or deletions occur in regions outside the CDRs (i.e., in the FRs).
88. The complex or the conjugate according to any one of items 1 to 49 and 79 to 87, wherein the anti-theophylline antibody comprises the VH sequence in SEQ ID NO: 68 or 76 or 84 or 92 including post-translational modifications of that sequence.
89. The complex or the conjugate according to any one of items 1 to 49 and 79 to 88, wherein the binding specificity that specifically binds to a theophyllinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 72 or 80 or 88 or 96.
90. The complex or the conjugate according to any one of items 1 to 49 and 79 to 89, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.
91. The complex or the conjugate according to any one of items 1 to 49 and 79 to 90, wherein a total of 1 to 10 amino acids have been substituted, inserted and/or deleted in SEQ ID NO: 72 or 80 or 88 or 96, optionally the substitutions, insertions, or deletions occur in regions outside the CDRs (i.e., in the FRs).
92. The complex or the conjugate according to any one of items 1 to 49 and 79 to 91, wherein the anti-theophylline antibody comprises the VL sequence in SEQ ID NO: 72 or 80 or 88 or 96, including post-translational modifications of that sequence.
93. The complex or the conjugate according to any one of items 1 to 49, wherein the bispecific antibody comprises a first binding specificity that specifically binds to a fluoresceinylated payload (anti-fluorescein binding specificity; anti-FLUO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).
94. The complex or the conjugate according to any one of items 1 to 49 and 93, wherein the bispecific antibody has two binding specificities that specifically bind to the fluoresceinylated payload (two anti-fluorescein binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).
95. The complex or the conjugate according to any one of items 1 to 49 and 93 to 94, wherein the binding specificity that specifically binds to a fluoresceinylated payload is a pair of an antibody heavy chain variable domain and an antibody light chain variable domain comprising (a) a heavy chain CDR1 comprising the amino acid sequence of SEQ ID NO: 97, (b) a heavy chain CDR2 comprising the amino acid sequence of SEQ ID NO: 98, (c) a heavy chain CDR3 comprising the amino acid sequence of SEQ ID NO: 99, (d) a light chain CDR1 comprising the amino acid sequence of SEQ ID NO: 101, (e) a light chain CDR2 comprising the amino acid sequence of SEQ ID NO: 102, and (f) a light chain CDR3 comprising the amino acid sequence of SEQ ID NO: 103.

96. The complex or the conjugate according to any one of items 1 to 49 and 93 to 95, wherein the binding specificity that specifically binds to a fluoresceinylated payload is a humanized binding specificity.

97. The complex or the conjugate according to any one of items 1 to 49 and 93 to 96, wherein the binding specificity that specifically binds to a fluoresceinylated payload comprises CDRs as in any of the above embodiments and an acceptor human framework (e.g. a human immunoglobulin framework or a human consensus framework).

98. The complex or the conjugate according to any one of items 1 to 49 and 93 to 97, wherein the binding specificity that specifically binds to a fluoresceinylated payload is a pair of an antibody heavy chain variable domain and an antibody light chain variable domain comprising (a) a heavy chain CDR1 comprising the amino acid sequence of SEQ ID NO: 105 or 113, (b) a heavy chain CDR2 comprising the amino acid sequence of SEQ ID NO: 106 or 114, (c) a heavy chain CDR3 comprising the amino acid sequence of SEQ ID NO: 107 or 115, (d) a light chain CDR1 comprising the amino acid sequence of SEQ ID NO: 109 or 117, (e) a light chain CDR2 comprising the amino acid sequence of SEQ ID NO: 110 or 118, and (f) a light chain CDR3 comprising the amino acid sequence of SEQ ID NO: 111 or 119.

99. The complex or the conjugate according to any one of items 1 to 49 and 93 to 98, wherein the binding specificity that specifically binds to a fluoresceinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 108 or 116.

100. The complex or the conjugate according to any one of items 1 to 49 and 93 to 99, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

101. The complex or the conjugate according to any one of items 1 to 49 and 93 to 100, wherein a total of 1 to 10 amino acids have been substituted, inserted and/or deleted in SEQ ID NO: 108 or 116, optionally the substitutions, insertions, or deletions occur in regions outside the CDRs (i.e., in the FRs).

102. The complex or the conjugate according to any one of items 1 to 49 and 93 to 101, wherein the anti-fluorescein antibody comprises the VH sequence in SEQ ID NO: 108 or 116, including post-translational modifications of that sequence.

103. The complex or the conjugate according to any one of items 1 to 49 and 93 to 102, wherein the binding specificity that specifically binds to a fluoresceinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 112 or 120.

104. The complex or the conjugate according to any one of items 1 to 49 and 93 to 103, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

105. The complex or the conjugate according to any one of items 1 to 49 and 93 to 104, wherein a total of 1 to 10 amino acids have been substituted, inserted and/or deleted in SEQ ID NO: 112 or 120, optionally the substitutions, insertions, or deletions occur in regions outside the CDRs (i.e., in the FRs).

106. The complex or the conjugate according to any one of items 1 to 49 and 93 to 105, wherein the anti-fluorescein antibody comprises the VL sequence in SEQ ID NO: 112 or 120, including post-translational modifications of that sequence.

107. The complex or the conjugate according to any one of items 1 to 49, wherein the bispecific antibody comprises a first binding specificity that specifically binds to a bromodeoxyuridinylated payload (anti-bromodeoxyuridine binding specificity; anti-BrdU binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

108. The complex or the conjugate according to any one of items 1 to 49 and 107, wherein the bispecific antibody has two binding specificities that specifically bind to the bromodeoxyuridinylated payload (two anti-bromodeoxyuridine binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

109. The complex or the conjugate according to any one of items 1 to 49 and 107 to 108, wherein the binding specificity that specifically binds to a bromodeoxyuridinylated payload is a pair of an antibody heavy chain variable domain and an antibody light chain variable domain comprising (a) a heavy chain CDR1 comprising the amino acid sequence of SEQ ID NO: 214, (b) a heavy chain CDR2 comprising the amino acid sequence of SEQ ID NO: 216, (c) a heavy chain CDR3 comprising the amino acid sequence of SEQ ID NO: 218, (d) a light chain CDR1 comprising the amino acid sequence of SEQ ID NO: 219, (e) a light chain CDR2 comprising the amino acid sequence of SEQ ID NO: 220, and (f) a light chain CDR3 comprising the amino acid sequence of SEQ ID NO: 221.

110. The complex or the conjugate according to any one of items 1 to 49 and 107 to 109, wherein the binding specificity that specifically binds to a bromodeoxyuridinylated payload is a humanized binding specificity.

111. The complex or the conjugate according to any one of items 1 to 49 and 107 to 110, wherein the binding specificity that specifically binds to a bromodeoxyuridinylated payload comprises CDRs from a non-human antibody and an acceptor human framework (e.g. a human immunoglobulin framework or a human consensus framework).

112. The complex or the conjugate according to any one of items 1 to 49 and 107 to 111, wherein the binding specificity that specifically binds to a bromodeoxyuridinylated payload is a pair of an antibody heavy chain variable domain and an antibody light chain variable domain comprising (a) a heavy chain CDR1 comprising the amino acid sequence of SEQ ID NO: 214 or 215, (b) a heavy chain CDR2 comprising the amino acid sequence of SEQ ID NO: 216 or 217, (c) a heavy chain CDR3 comprising the amino acid sequence of SEQ ID NO: 218, (d) a light chain CDR1 comprising the amino acid sequence of SEQ ID NO: 219, (e) a light chain CDR2 comprising the amino acid sequence of SEQ ID NO: 220, and (f) a light chain CDR3 comprising the amino acid sequence of SEQ ID NO: 221.

113. The complex or the conjugate according to any one of items 1 to 49 and 107 to 112, wherein the binding specificity that specifically binds to a bromodeoxyuridinylated payload is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 222 or 224.

114. The complex or the conjugate according to any one of items 1 to 49 and 107 to 113, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

115. The complex or the conjugate according to any one of items 1 to 49 and 107 to 114, wherein a total of 1 to 10 amino acids have been substituted, inserted and/or deleted in SEQ ID NO: 222 or 224, optionally the substitutions, insertions, or deletions occur in regions outside the CDRs (i.e., in the FRs).

116. The complex or the conjugate according to any one of items 1 to 49 and 107 to 115, wherein the anti-bromodeoxyuridine antibody comprises the VH sequence in SEQ ID NO: 223 or 225, including post-translational modifications of that sequence.

117. The complex or the conjugate according to any one of items 1 to 49 and 107 to 116, wherein the binding specificity that specifically binds to a bromodeoxyuridinylated payload is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 223 or 225.

118. The complex or the conjugate according to any one of items 1 to 49 and 107 to 117, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

119. The complex or the conjugate according to any one of items 1 to 49 and 107 to 118, wherein a total of 1 to 10 amino acids have been substituted, inserted and/or deleted in SEQ ID NO: 223 or 225, optionally the substitutions, insertions, or deletions occur in regions outside the CDRs (i.e., in the FRs).

120. The complex or the conjugate according to any one of items 1 to 49 and 107 to 119, wherein the anti-bromodeoxyuridine antibody comprises the VL sequence in SEQ ID NO: 223 or 225, including post-translational modifications of that sequence.

121. The complex or the conjugate according to any one of items 1 to 38, 40, 43 and 45 to 120, wherein the payload is a haptenylated full length antibody or a haptenylated antibody fragment.

122. The complex or the conjugate according to any one of items 1 to 38, 40, 43 and 45 to 121, wherein the haptenylated payload is a haptenylated full length anti-alpha synuclein antibody.

123. The complex or the conjugate according to any one of items 1 to 38, 40, 43 and 45 to 121, wherein the haptenylated payload is a haptenylated anti-alpha synuclein antibody fragment that specifically binds to alpha-synuclein.

124. The complex or the conjugate according to any one of items 121 to 123, wherein the hapten is biotin.

125. The complex or the conjugate according to any one of items 1 to 38, 40, 43 and 45 to 124, wherein the antibody comprises in the heavy chain variable domain the HVRs of SEQ ID NO: 243 to 245 and in the light chain variable domain the HVRs of SEQ ID NO: 246 to 248.

126. The complex or the conjugate according to any one of items 1 to 38, 40, 43 and 45 to 125, wherein the antibody comprises in the heavy chain variable domain the HVRs of SEQ ID NO: 249, 250 and 245 and in the light chain variable domain the HVRs of SEQ ID NO: 251 to 253.

127. The complex or the conjugate according to any one of items 1 to 38, 40, 43 and 45 to 126, wherein the antibody comprises a heavy chain variable domain consisting of SEQ ID NO: 254 and a light chain variable domain consisting of SEQ ID NO: 255.

128. The complex or the conjugate according to any one of items 1 to 38, 40, 43 and 45 to 127, wherein the antibody has been obtained by humanizing an antibody comprising a heavy chain variable domain consisting of SEQ ID NO: 254 and a light chain variable domain consisting of SEQ ID NO: 255.

129. The complex or the conjugate according to any one of items 1 to 38, 40, 43 and 45 to 128, wherein the antibody is a humanized antibody and comprises in the heavy chain variable domain the HVRs of SEQ ID NO: 243 to 245 and in the light chain variable domain the HVRs of SEQ ID NO: 246 to 248, wherein in each HVR up to 3 amino acid residues can be changed.

130. The complex or the conjugate according to any one of items 1 to 38, 40, 43 and 45 to 129, wherein the antibody is a humanized antibody and comprises in the heavy chain variable domain the HVRs of SEQ ID NO: 249, 250 and 245 and in the light chain variable domain the HVRs of SEQ ID NO: 251 to 253, wherein in each HVR up to 3 amino acid residues can be changed.

131. The complex or the conjugate according to any one of items 1 to 38, 40, 43 and 45 to 130, wherein the antibody is a humanized antibody and the heavy chain variable domain is derived from a heavy chain variable domain consisting of SEQ ID NO: 254 and a light chain variable domain is derived from a light chain variable domain consisting of SEQ ID NO: 255.

132. The complex or the conjugate according to any one of items 1 to 38, 40, 43 and 45 to 131, wherein the antibody binds to the same epitope as an antibody comprising in the heavy chain the HVRs of SEQ ID NO: 256 to 258 and in the light chain the HVRs of SEQ ID NO: 259 to 261.

133. The complex or the conjugate according to any one of items 1 to 38, 40, 43 and 45 to 132, wherein the antibody binds to the same epitope as an antibody comprising in the heavy chain the HVRs of SEQ ID NO: 262, 263 and 258 and in the light chain the HVRs of SEQ ID NO: 264 to 266.

134. The complex or the conjugate according to any one of items 1 to 38, 40, 43 and 45 to 133, wherein the antibody comprises a heavy chain variable domain consisting of SEQ ID NO: 267 and a light chain variable domain consisting of SEQ ID NO: 268.

135. The complex or the conjugate according to any one of items 1 to 38, 40, 43 and 45 to 134, wherein the antibody has been obtained by humanizing an antibody comprising a heavy chain variable domain consisting of SEQ ID NO: 267 and a light chain variable domain consisting of SEQ ID NO: 268.

136. The complex or the conjugate according to any one of items 1 to 38, 40, 43 and 45 to 135, wherein the antibody is a humanized antibody and comprises in the heavy chain variable domain the HVRs of SEQ ID NO: 256 to 258 and in the light chain variable domain the HVRs of SEQ ID NO: 259 to 261, wherein in each HVR up to 3 amino acid residues can be changed.

137. The complex or the conjugate according to any one of items 1 to 38, 40, 43 and 45 to 136, wherein the antibody is a humanized antibody and comprises in the heavy chain variable domain the HVRs of SEQ ID NO: 262, 263 and 258 and in the light chain variable domain the HVRs of SEQ ID NO: 264 to 266, wherein in each HVR up to 3 amino acid residues can be changed.

138. The complex or the conjugate according to any one of items 1 to 38, 40, 43 and 45 to 137, wherein the antibody is a humanized antibody and the heavy chain variable domain is derived from a heavy chain variable domain consisting of SEQ ID NO: 267 and a light chain variable domain is derived from a light chain variable domain consisting of SEQ ID NO: 268.

139. The complex or the conjugate according to any one of items 1 to 38, 40, 43 and 45 to 138, wherein the antibody binds to the same epitope as an antibody comprising in the heavy chain the HVRs of SEQ ID NO: 269 to 271 and in the light chain the HVRs of SEQ ID NO: 272 to 274.

140. The complex or the conjugate according to any one of items 1 to 38, 40, 43 and 45 to 139, wherein the antibody binds to the same epitope as an antibody comprising in the heavy chain the HVRs of SEQ ID NO: 269, 275 and 271 and in the light chain the HVRs of SEQ ID NO: 276 to 278.

141. The complex or the conjugate according to any one of items 1 to 38, 40, 43 and 45 to 140, wherein the antibody comprises a heavy chain variable domain consisting of SEQ ID NO: 279 and a light chain variable domain consisting of SEQ ID NO: 280.

142. The complex or the conjugate according to any one of items 1 to 38, 40, 43 and 45 to 141, wherein the antibody has been obtained by humanizing an antibody comprising a heavy chain variable domain consisting of SEQ ID NO: 279 and a light chain variable domain consisting of SEQ ID NO: 280.

143. The complex or the conjugate according to any one of items 1 to 38, 40, 43 and 45 to 142, wherein the antibody is a humanized antibody and comprises in the heavy chain variable domain the HVRs of SEQ ID NO: 269 to 271 and in the light chain variable domain the HVRs of SEQ ID NO: 272 to 274, wherein in each HVR up to 3 amino acid residues can be changed.

144. The complex or the conjugate according to any one of items 1 to 38, 40, 43 and 45 to 143, wherein the antibody is a humanized antibody and comprises in the heavy chain variable domain the HVRs of SEQ ID NO: 269, 275 and 271 and in the light chain variable domain the HVRs of SEQ ID NO: 276 to 278, wherein in each HVR up to 3 amino acid residues can be changed.

145. The complex or the conjugate according to any one of items 1 to 38, 40, 43 and 45 to 144, wherein the antibody is a humanized antibody and the heavy chain variable domain is derived from a heavy chain variable domain consisting of SEQ ID NO: 279 and a light chain variable domain is derived from a light chain variable domain consisting of SEQ ID NO: 280.

146. The complex or the conjugate according to any one of items 1 to 38, 40, 43 and 45 to 121, wherein the haptenylated payload is a haptenylated full length anti-human Tau(pS422) antibody.

147. The complex or the conjugate according to any one of items 1 to 38, 40, 43 and 45 to 121 and 146, wherein the haptenylated payload is a haptenylated anti-human Tau (pS422) antibody fragment that specifically binds to human Tau phosphorylated at the serine at position 422.

148. The complex or the conjugate according to any one of items 146 to 147, wherein the hapten is biotin.

149. The complex or the conjugate according to any one of items 1 to 38, 40, 43 and 45 to 121 and 146 to 148, wherein the anti-human Tau(pS422) antibody comprises
a) in the heavy chain variable domain the HVRs of SEQ ID NO: 230, 239 and 232, or
b) in the heavy chain variable domain the HVRs of SEQ ID NO: 230, 231 and 232.

150. The complex or the conjugate according to any one of items 1 to 38, 40, 43 and 45 to 121 and 146 to 149, wherein the antibody further comprises
a) in the light chain variable domain the HVRs of SEQ ID NO: 234, 235 and 236, or
b) in the light chain variable domain the HVRs of SEQ ID NO: 233, 229 and 236.

151. The complex or the conjugate according to any one of items 1 to 38, 40, 43 and 45 to 121 and 146 to 150, wherein the antibody comprises
a) in the heavy chain variable domain the HVRs of SEQ ID NO: 230, 239 and 232, and in the light chain variable domain the HVRs of SEQ ID NO: 234, 235 and 236, or
b) in the heavy chain variable domain the HVRs of SEQ ID NO: 230, 231 and 232, and in the light chain variable domain the HVRs of SEQ ID NO: 233, 229 and 236, or
c) in the heavy chain variable domain the HVRs of SEQ ID NO: 230, 231 and 232, and in the light chain variable domain the HVRs of SEQ ID NO: 234, 235 and 236.

152. The complex or the conjugate according to any one of items 1 to 38, 40, 43 and 45 to 121 and 146 to 151, wherein the antibody comprises
a) a heavy chain variable domain of SEQ ID NO: 241 and a light chain variable domain of SEQ ID NO: 238, or
b) a heavy chain variable domain of SEQ ID NO: 240 and a light chain variable domain of SEQ ID NO: 237, or
c) a heavy chain variable domain of SEQ ID NO: 240 and a light chain variable domain of SEQ ID NO: 238, or
d) a heavy chain variable domain of SEQ ID NO: 242 and a light chain variable domain of SEQ ID NO: 238.

153. The complex or the conjugate according to any one of items 1 to 38, 40, 43 and 45 to 121, wherein the haptenylated payload is a haptenylated full length anti-Abeta antibody.

154. The complex or the conjugate according to any one of items 1 to 38, 40, 43 and 45 to 121 and 154, wherein the haptenylated payload is a haptenylated anti-Abeta antibody fragment that specifically binds to human Abeta.

155. The complex or the conjugate according to any one of items 153 to 154, wherein the hapten is biotin.

156. The complex or the conjugate according to any one of items 1 to 38, 40, 43 and 45 to 121 and 153 to 155, wherein anti-Abeta antibody comprises in the heavy chain variable domain the HVRs of SEQ ID NO: 281, 282 and 283.

157. The complex or the conjugate according to any one of items 1 to 38, 40, 43 and 45 to 121 and 153 to 156, wherein the antibody further comprises in the light chain variable domain the HVRs of SEQ ID NO: 284, 285 and 286.

158. The complex or the conjugate according to any one of items 1 to 38, 40, 43 and 45 to 121 and 153 to 157, wherein the antibody comprises in the heavy chain variable domain the HVRs of SEQ ID NO: 281, 282 and 283 and in the light chain variable domain the HVRs of SEQ ID NO: 284, 285 and 286.

159. The complex or the conjugate according to any one of items 1 to 38, 40, 43 and 45 to 121 and 153 to 158, wherein the antibody comprises
a) a heavy chain variable domain of SEQ ID NO: 287 and a light chain variable domain of SEQ ID NO: 290, or
b) a heavy chain variable domain of SEQ ID NO: 288 and a light chain variable domain of SEQ ID NO: 291, or
c) a heavy chain variable domain of SEQ ID NO: 289 and a light chain variable domain of SEQ ID NO: 292.

160. A pharmaceutical formulation comprising the complex or the conjugate according to any one of items 1 to 159 and a pharmaceutically acceptable carrier.

161. The complex or the conjugate according to any one of items 1 to 159 for use as a medicament.

162. The conjugate according to any one of items 1 to 159 for the treatment of cancer or a neurological disorder.

163. Use of the complex or the conjugate according to any one of items 1 to 159 in the manufacture of a medicament.

164. The use according to item 163, wherein the medicament is for the treatment of cancer.

165. The use according to item 163, wherein the medicament is for the treatment of a neurological disorder.

166. The use according to item 165, wherein the neurological disorder is selected from Alzheimer's disease (AD) (including, but not limited to, mild cognitive impairment and prodromal AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer (e.g. cancer affecting the CNS or brain), and traumatic brain injury.

167. The use of the complex or the conjugate according to any one of items 1 to 159 as diagnostic agent.

168. The use of the complex or the conjugate according to any one of items 1 to 159 to increase the stability of a payload.

169. The use of the complex or the conjugate according to any one of items 1 to 159 to increase the activity of a payload.

170. The use of the complex or the conjugate according to any one of items 1 to 159 to increase the in vivo half-life of a payload.

171. The use of the complex or the conjugate according to any one of items 1 to 159 in the treatment of a disease.

172. A method of treating an individual having a disease comprising administering to the individual an effective amount of the complex or the conjugate according to any one of items 1 to 159.

173. A method of treating a disease in an individual comprising administering to the individual an effective amount of the complex or the conjugate according to any one of items 1 to 159.

174. The use or method according to any one of items 171 to 173, wherein the disease is cancer.

175. The use or the method according to any one of items 171 to 173, wherein the disease is a neurological disorder.

176. The use or the method according to item 175, wherein the neurological disorder is selected from Alzheimer's disease (AD) (including, but not limited to, mild cognitive impairment and prodromal AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer (e.g. cancer affecting the CNS or brain), and traumatic brain injury.

177. The use of the complex or the conjugate according to any one of items 1 to 159 for targeted delivery of a haptenylated payload across the blood brain barrier.

178. The use according to item 177, wherein the use is for the targeted delivery of the free (i.e. isolated) haptenylated payload across the blood brain barrier.

179. The use of the complex according to any one of items 1 to 2 and 4 to 159 for targeted delivery of a haptenylated payload across the blood brain barrier and release of the haptenylated payload in the blood brain barrier or the brain.

180. The use according to item 179, wherein the delivery of the haptenylated payload is higher compared to the delivery in the absence of the bispecific antibody or the complex.

181. The use according to item 180, wherein the delivery is two-fold higher.

182. The use according to any one of items 180 to 181, wherein the delivery is 10-fold higher.

183. The use according to any one of items 179 to 182, wherein the haptenylated payload has a higher biological activity in the absence of the bispecific antibody or complex than in the presence of the bispecific antibody or complex.

184. The use according to item 183, wherein the biological activity is two-fold higher in the absence of the bispecific antibody or complex.

185. The use according to any one of items 183 to 184, wherein the biological activity is ten-fold higher in the absence of the bispecific antibody or complex.

The disclosure of all references cited herein is herewith incorporated by reference.

The following examples, figures and sequences are provided to aid the understanding of the present invention, the true scope of which is set forth in the appended claims. It is understood that modifications can be made in the procedures set forth without departing from the spirit of the invention.

EXAMPLES

Example 1

Isolation and Characterization of cDNAs Encoding the VH and VL Domains of a Murine Anti-Digoxigenin Antibody and a Murine Anti-Biotin Antibody of IgG1 Class with Kappa Light Chain from Mouse Hybridoma The isolation and characterization of cDNAs encoding the VH and VL domains of anti-digoxigenin antibodies, the RNA preparation, generation of DNA fragments, the cloning of the DNA fragments into plasmids and the determination of the DNA- and amino acid sequences were described in WO 2011/003557 and WO 2011/003780, respectively.

The protein and (DNA) sequence information of the VH and VL domains of the murine hapten-binding antibodies were obtained directly from hybridoma clones. The experimental steps performed subsequently were (i) the isolation of RNA from antibody producing hybridoma cells, (ii) conversion of this RNA into cDNA, the transfer into VH and VL harboring PCR fragments, and (iii) integration of these PCR fragments into plasmids vectors for propagation in $E.$ $coli$ and determination of their DNA (and deduced protein) sequences.

RNA Preparation from Hybridoma Cells:

RNA was prepared from $5 \times 10^6$ antibody expressing hybridoma cells applying the RNAeasy-Kit (Qiagen). Briefly, the sedimented cells were washed once in PBS and sedimented and subsequently resuspended for lysis in 500 µl RLT-buffer (+B-ME). The cells were completely lysed by passing through a Qiashredder (Qiagen) and then subjected to the matrix-mediated purification procedure (ETOH, RNAeasy columns) as described in the manufacturer's manual. After the last washing step, RNA was recovered from the columns in 50 µL RNAse-free water. The concentration of the recovered RNA was determined by quantifying A260 and A280 of 1:20 diluted samples. The integrity (quality, degree of degradation) of the isolated RNA samples was analyzed by denaturing RNA gel electrophoresis on Formamide-Agarose gels (see Maniatis Manual). Discrete bands representing the intact 18s and 28 s ribosomal RNAs were obtained and intactness (and approx. 2:1 intensity ratios) of these bands indicated a good quality of the RNA preparations. The isolated RNAs from hybridoma were frozen and stored at −80° C. in aliquots.

Generation of DNA Fragments Encoding VH and VH by RACE PCR, Cloning of these DNA Fragments into Plasmids and Determination of their DNA- and Amino Acid Sequences The cDNA for subsequent (RACE-) PCR reactions were prepared from RNA preparations by applying the technologies as described in International patent application WO 2012/093068. Subsequently, the VH and VL-encoding PCR fragments were isolated by agarose gel extraction and subsequent purification by standard molecular biology techniques. PWO-generated purified PCR fragments were inserted into the vector pCR bluntII topo by applying the pCR bluntII topo Kit (Invitrogen) exactly following the manufacturer's instructions. The Topo-ligation reactions were transformed into $E.$ $coli$ Topo10-one-shot competent cells. Thereafter, $E.$ $coli$ clones that contained vectors with either VL- or VH containing inserts were identified as colonies on LB-Kanamycin agar plates. Plasmids were prepared from these colonies and the presence of the desired insert in the vector was confirmed by restriction digestion with EcoRI. Because the vector backbone contains EcoRI restriction recognition sites flanking each side of the insert, plasmids harboring inserts were defined by having EcoRI-releasable inserts of approx. 800 bp (for VL) or 600 bp (for VH). The DNA sequence and the deduced protein sequence of the VL and VH were determined by automated DNA sequencing on multiple clones for VH and VL.

The murine VL sequence of the anti-biotin antibody is depicted in SEQ ID NO: 40. The murine VH sequence of the anti-biotin antibody is depicted in SEQ ID NO: 36.

The murine VL sequence of the anti-digoxigenin antibody is depicted in SEQ ID NO: 08. The murine VH sequence of the anti-digoxigenin antibody is depicted in SEQ ID NO: 04.

Example 2

Isolation and Characterization of cDNAs Encoding the VH and VL Domains of a Murine Anti-Theophylline Antibody of IgG1 Class with Kappa Light Chain from Mouse Hybridoma The sequences of the anti-theophylline antibody were obtained as outlined in Example 1.

The murine VL sequence of the anti-theophylline antibody is depicted in SEQ ID NO: 72. The murine VH sequence of the anti-theophylline antibody is depicted in SEQ ID NO: 68.

Example 3

Humanization of the VH and VL Domains of Murine Anti-Digoxigenin Antibody and Anti-Biotin Antibody The generation of humanized variants of the digoxigenin-binding antibody has been described in detail in WO 2011/003557 and WO 2011/003780. The murine biotin-binding antibody muM33 was humanized in a similar manner as follows:

The generation and characterization of encoding sequences and amino acid sequences that comprise the VH and VL domains of a murine anti-biotin antibody of the IgG1 class with kappa light chain from mouse hybridoma are described in WO 2011/003557 and WO 2011/003780. Based on this information, a corresponding humanized anti-biotin antibody was generated (huM33) based on the human germline framework IGHV1-69-02 and IGKV1-27-01 combination. For VL, it was not necessary to integrate any backmutation in the framework of the human IGKV1-27-01 and the human J element of the IGKJ2-01 germline. The humanized VH is based on the human IGHV1-69-02 germline and the human J element of the IGHJ4-01-3 germline. Two backmutations in framework region 1 at position 24 (A24S) and in framework region 3 at position 73 (K73T) were introduced. The amino acid sequence of the humanized VH is depicted in SEQ ID NO: 44 and the amino acid sequence of the humanized VL is shown in SEQ ID NO: 48.

Example 4

Humanization of the VH and VL Domains of the Murine Anti-Theophylline Antibody

The murine theophylline-binding antibody was humanized as follows: a humanized anti-theophylline antibody was generated based on the human germline framework IGHV4-31-02 and IGKV2-30-01 combination. The humanized VH is based on the human IGHV4-31-02 germline and the human J element of the IGHJ4-01-3 germline. One backmutations in framework region 3 at position 71 (V71R) was introduced. The humanized VL is based on the human IGHV2-30-01 germline and the human J element of the IGKJ2-01 germline. One backmutations in framework region 2 at position 46 (R46L) was introduced. The amino acid sequence of the humanized VH is depicted in SEQ ID NO: 76 and the amino acid sequence of the humanized VL is shown in SEQ ID NO: 80.

Example 5

Crystallization and X-Ray Structure Determination of the Binding Region of the Murine Anti-Digoxigenin Fv Region in the Presence of Digoxigenin, and of the Binding Region of the Murine Anti-Biotin Fv Region in the Presence of Biotin The determination of the structure of the Fab fragment of the digoxigenin-binding antibody has been described in detail in WO 2011/003557 and WO 2011/003780, also published (3RA7) in Metz, S. et al., Proc. Natl. Acad. Sci. USA 108 (2011) 8194-8199.

The structure of the murine anti-biotin antibody was determined. Therefore, Fab fragments were generated by protease digestion of the purified IgGs and subsequently purified, applying well known state of the art methods (papain digestion).

For crystallization of the apo Fab fragment (purified Fabs) in 20 mM His-HCl, 140 mM NaCl, pH 6.0 were concentrated to 13 mg/ml. Crystallization droplets were set up at 21° C. by mixing 0.2 µl of protein solution with 0.2 µL reservoir solution in vapor diffusion sitting drop experiments. Crystals appeared out of 0.1 M Tris pH 8.5, 0.01 M cobalt chloride, 20% polyvinylpyrrolidone K15 within 5 days and grew to a final size of 0.3 mm×0.06 mm×0.03 mm within 8 days.

Crystals were harvested with 15% Glycerol as cryoprotectant and then flash frozen in liquid N2. Diffraction images were collected with a Pilatus 6M detector at a temperature of 100K at the beam line X10SA of the Swiss Light Source and processed with the programs XDS (Kabsch, W., J. Appl. Cryst. 26 (1993) 795-800) and scaled with SCALA (obtained from BRUKER AXS), yielding data to 2.22 Å resolution. This Fab fragment crystal belongs to monoclinic space group P21 with cell dimensions of a=90.23 Å b=118.45 Å c=96.79 Å and β=117.53° and contains four Fab molecules per crystallographic asymmetric unit (see Table 3).

Standard crystallographic programs from the CCP4 software suite were used to solve the structure by molecular replacement with the PDB entry 3PQP as search model, to calculate the electron density, and to refine the x-ray structure (CCP4, Collaborative Computational Project, Acta Crystallogr. D, 760-763 (1994)). The structural models were rebuilt into the electron density using COOT (Emsley, P., et al. Acta Crystallogr. D Biol. Crystallogr. 60 (2010) 486-501). Coordinates were refined with REFMAC5 (Murshudov, G. N., et al. Acta Crystallogr. D Biol. Crystallogr. 53 (1997) 240-55) and with autoBUSTER (Global Phasing Ltd.).

For the crystallization of Fab-fragment in complex with a biotin-derivative, apo Crystals of the Fab fragment used for soaking experiments were derived out of 0.8 M Succinic Acid within 3 days after screening and grew to a final size of 0.25 mm×0.04 mm×0.04 mm within 5 days. Biocytinamid was dissolved at 100 mM in water. Subsequently, the compound was diluted to 10 mM working concentration in crystallization solution and applied to the crystals in the crystallization droplet. Crystals were washed three times with 2 µl of 10 mM compound solution and were finally incubated for 16 h with biocytinamid at 21° C.

Crystals were harvested with 15% glycerol as cryoprotectant and then flash frozen in liquid N2. Diffraction images were collected with a Pilatus 6M detector at a temperature of 100 K at the beam line X10SA of the Swiss Light Source and processed with the programs XDS (Kabsch, W., J. Appl. Cryst. 26 (1993) 795-800) and scaled with SCALA (obtained from BRUKER AXS), yielding data to 2.35 Å resolution. This Fab fragment crystal belongs to monoclinic space group P21 with cell dimensions of a=89.09 Å b=119.62 Å c=96.18 Å and 3=117.15° and contains four Fab molecules per crystallographic asymmetric unit (see Table 4).

Standard crystallographic programs from the CCP4 software suite were used to solve the structure by molecular replacement with the coordinates of the apo Fab fragment as search model, to calculate the electron density, and to refine the x-ray structure to a resolution of 2.5 Å (CCP4). The structural models were rebuilt into the electron density using COOT Emsley, P., Lohkamp, B., Scott, W. G. & Cowtan, K. Features and development of COOT. Acta Crystallogr. D Biol. Crystallogr. 60, 486-501 (2010)). Coordinates were refined with REFMAC5 (Murshudov, G. N., et al. Acta Crystallogr. D Biol. Crystallogr. 53, 240-255 (1997)) and with autoBUSTER (Global Phasing Ltd.).

TABLE 3

Data collection and structure refinement statistics for monoclinic muM33 Fab fragment apo-crystal

| Data Collection | |
| --- | --- |
| Wavelength (Å) | 1.0 |
| Resolution[1] (Å) | 2.22 (2.34-2.22) |
| Unique reflections[1] | 77716 (11301) |
| Completeness (%)[1] | 98.0 (100) |
| $R_{merge}$ (%)[1,2] | 6.4 (44.4) |
| <I/σ>[1] | 8.3 (1.7) |
| Unit Cell (Space group C2) | a = 90.23 Å b = 118.45 Å |
| | c = 96.73 Å and β = 117.53° |
| Refinement | |
| Resolution (Å) | 2.2 (2.28-2.22) |
| $R_{cryst}$[1,3] | 20.66 (21.84)) |
| $R_{free}$[1,4] | 25.23 (26.47) |

TABLE 3-continued

Data collection and structure refinement statistics for monoclinic muM33 Fab fragment apo-crystal

| | |
| --- | --- |
| Number of Atoms in refinement | 13314 |
| R.m.s. deviations from ideality Bond lengths (Å)/angles (°) | 0.01/1.21 |
| Main chain dihedral angles (%) Most favored/allowed/generous/disallowed[5] | 90.4/9.1/0.3/0.2 |

[1]Values in parentheses refer to the highest resolution bins.
[2]$R_{merge} = \Sigma|I - <I>|/\Sigma I$ where I is intensity.
[3]$R_{cryst} = \Sigma|F_o - <F_c>|/\Sigma F_o$ where $F_o$ is the observed and $F_c$ is the calculated structure factor amplitude.
[4]$R_{free}$ was calculated based on 5% of the total data omitted during refinement.
[5]Calculated with PROCHECK [Laskowski, R.A., et al., J. Appl. Crystallogr. 26, 283-291 (1993)].

TABLE 4

Data collection and structure refinement statistics for monoclinic muM33 Fab fragment biocytinamid complex crystal

| Data Collection | |
| --- | --- |
| Wavelength (Å) | 1.0 |
| Resolution[1] (Å) | 2.35 (2.45-2.35) |
| Unique reflections[1] | 74645 (8714) |
| Completeness (%)[1] | 99.9 (99.9) |
| $R_{merge}$ (%)[1,2] | 6.30 (65.00) |
| <I/σ>[1] | 10.29 (1.18) |
| Unit Cell (Space group C2) | a = 89.09 Å b = 119.62 Å |
| | c = 96.18 Å and β = 117.15° |
| Refinement | |
| Resolution (Å) | 2.5 (2.565-2.500) |
| $R_{cryst}$[1,3] | 20.92 (36.86)) |

TABLE 4-continued

Data collection and structure refinement statistics for monoclinic muM33 Fab fragment biocytinamid complex crystal

| | |
|---|---|
| $R_{free}^{1,4}$ | 27.56 (47.5) |
| Number of Atoms in refinement | 13656 |
| R.m.s. deviations from ideality Bond lengths (Å)/angles (°) | 0.009/1.43 |
| Main chain dihedral angles (%) Most favored/allowed/generous/disallowed[5] | 87.5/12.0/0.2/0.3 |

[1]Values in parentheses refer to the highest resolution bins.
[2]$R_{merge} = \Sigma|I - <I>|/\Sigma I$ where I is intensity.
[3]$R_{cryst} = \Sigma|F_o - <F_c>|/\Sigma F_o$ where $F_o$ is the observed and $F_c$ is the calculated structure factor amplitude.
[4]$R_{free}$ was calculated based on 5% of the total data omitted during refinement.
[5]Calculated with PROCHECK [Laskowski, R.A., MacArthur, MW., Moss, D.S. & Thornton, J.M.
PROCHECK: a program to check the stereochemical quality of protein structure. J. Appl. Crystallogr. 26, 283-291 (1993)].

The result of the experimental structure determination is shown in FIG. 33. The crystal form of the complex contained four independent biocytinamid:anti-biotin Fab complexes in the asymmetric unit, with biocytinamid bound similarly by all Fab molecules. Biocytinamid is bound in a pocket formed by CDRs 1 and 3 of the heavy chain and all 3 light chain CDRs. The binding pocket of the ligand is defined by residues ASN29, ASP31, THR32, PHE33, GLN35, TRP99 and TRP106 from the heavy chain and ASN31, TYR32, LEU33, SER34, TYR49, SER50, PHE91 and TYR96 from the light chain. The biotin head group forms hydrogen bonds with residues of CDR2 and CDR1 at one end of the pocket: N3 of biocytinamid is interacting with the hydroxyl-oxygen of Ser50 whereas O22 is in contact with the backbone-amide nitrogen of the same residue. In addition, O22 of biocytinamid is also hydrogen-bonded to the hydroxyl-group oxygen of Ser34. In addition to that, hydrophobic interactions are observed between biocytinamid and the aromatic side chains lining the binding pocket. The amide bond at the end of the $(CH_2)_4$ aliphatic tail of biotin stacks onto PHE33 of heavy chain CDR1 and is stabilized by an additional hydrogen bond to the backbone amide nitrogen of PHE33 and to Asp31. This positions the amide nitrogen, which is the site of linkage to the active entity, in a way that atoms that are following the nitrogen are pointing away from the binding pocket towards the solvent.

The results of the experimental determination of the binding region at a resolution of 2.5 Å enables the characterization of the binding mode of the ligand to its antibody, which is a prerequisite for detailed modeling and further improvement via protein engineering of recombinant biotin binding modules.

Example 6

Definition and Generation of Anti-Hapten Antibody with Introduced Functionalities for Covalent Conjugation Derivatization of the humanized VH and VL sequences of the anti-hapten antibody described above was done to generate compounds that permit covalent coupling of antigens/haptens to the antibody at a defined position.

The experimentally determined structure of an anti-digoxigenin Fab-fragment bound to digoxigenin (3RA7) (Metz, S. et al., Proc. Natl. Acad. Sci. USA 108 (2011) 8194-8199) was used to identify positions in which alterations enable a site-directed coupling reaction to occur between the antibody and its complexed antigen/hapten. The structure of the anti-biotin Fab-fragment bound to biocytinamid (see Example 5) was used to confirm the correct position of the introduced cysteine residue for the biotin-binding antibody fragment and provide the proof of the general applicability of the identified position(s).

The positions to be mutated must simultaneously meet two requirements: (i) the coupling positions should be in proximity to the binding region to utilize the antigen/hapten positioning effect for directed coupling, and (ii) the mutation and coupling position must be positioned in a manner that antigen/hapten binding by itself is not affected. These requirements for finding a suitable position are de facto 'contradicting' each other because requirement (i) is best served by a position close to the binding site, while requirement (ii) is most safely achieved by positions that are distant from the binding site.

Despite these virtually excluding requirements, we were able to identify positions that can be mutated without affecting hapten positioning, and which nevertheless simultaneously allow directed covalent coupling of a haptenylated compound.

The first position is located at position VH52b or VH53 according to the Kabat numbering depending on the actual length of the CDR2 of the respective antibody. In the anti-digoxigenin antibody structure, the hapten is bound in a deep pocket formed by hydrophobic residues. A fluorescent digoxigenin-Cy5 conjugate was used in this crystallographic study, wherein the fluorophore as well as the linker between digoxigenin and Cy5 were not visible in the structure due to a high flexibility and resulting disorder in the crystal. However, the linker and Cy5 are attached to O32 of digoxigenin which points into the direction of the CDR2 of the heavy chain. The distance between O32 (see above) of digoxigenin to the Cα of the amino acid residue in position 52b according to Kabat numbering is 10.5 Å.

Replacement of the amino acid at position VH52b/VH53 with Cys generated antibody derivatives with heavy chain variable region sequences that are listed as SEQ ID NO: 20 and 28 for anti-digoxigenin antibody-VH52bC, SEQ ID NO: 84 and 92 for anti-theophylline antibody-VH53C, SEQ ID NO: 52 and 60 for anti-biotin antibody-VH53C, and SEQ ID NO: 108 for anti-fluorescein antibody-VH52bC.

A further position that was identified as modification point is the position VH28 according to the Kabat numbering.

In consequence, we introduced a cysteine at Kabat position VH28. Replacement of the amino acid at position VH28 with Cys generated antibody derivatives with heavy chain variable region sequences that are listed as SEQ ID NO: 124 and 132 for anti-digoxigenin antibody-VH28C, SEQ ID NO: 156 and 164 for anti-theophylline antibody-VH28C, SEQ ID NO: 140 and 148 for anti-biotin antibody-VH28C, and SEQ ID NO: 116 for anti-fluorescein antibody-VH28C.

It has been found that one of these positions is a 'universal' position, i.e. this position is applicable to any antibody and, thus, it is not required to start from scratch every time a new antibody has to be modified by providing the crystal structure and determining the appropriate position that enables hapten-positioned covalent coupling.

The mutation VH52bC or VH53C, respectively, according to Kabat heavy chain variable region numbering could be used for each hapten-binding antibody (anti-hapten antibody). Even though the antibodies and structures of their binding pockets are quite diverse, it has been shown that the VH52bC/VH53C mutation can be used for covalent attachment of antigens/haptens to antibodies that bind digoxigenin, biotin, fluorescein, as well as theophylline.

Binding entities that are composed of these sequences could be expressed and purified with standard Protein A- and size exclusion chromatography (see Example 7). The resulting molecules were fully functional and retained affinity towards their cognate haptens in the same manner as their unmodified parent molecules. This was demonstrated by Surface-Plasmon-Resonance (SPR) experiments (see Example 9).

Example 7

Composition, Expression and Purification of Recombinant Anti-Hapten Antibodies

Murine and humanized anti-hapten antibody variable regions were combined with constant regions of human origin to form mono- or bispecific chimeric or humanized antibodies.

The generation of monospecific humanized anti-hapten antibodies and bispecific humanized anti-hapten antibodies that specifically bind a hapten as well as a different non-hapten target (e.g. receptor tyrosine kinases or IGF-1R) required (i) design and definition of amino acid and nucleotide sequences for such molecules, (ii) expression of these molecules in transfected cultured mammalian cells, and (iii) purification of these molecules from the supernatants of transfected cells. These steps were performed as previously described in WO 2012/093068.

In general, to generate a humanized antibody of the IgG class that has the binding specificity of the (original) murine anti-hapten antibody, the humanized VH sequence was fused in frame to the N-terminus of CH1-hinge-CH2-CH3 of a human Fc-region of the subclass IgG1. Similarly, the humanized VL sequence was fused in frame to the N-terminus of human CLkappa constant region.

To generate bispecific antibody derivatives that contain the hapten-binding specificity as well as specificities to other targets, the anti-hapten antibody, a scFv or Fab fragment was fused in frame to the C-terminus of the heavy chain of previously described antibodies. In many cases, the applied anti-hapten scFv was further stabilized by introduction of a VH44-VL 100 disulfide bond which has been previously described (e.g. Reiter, Y., et al., Nature biotechnology 14 (1996) 1239-1245).

Expression Plasmids

Expression plasmids comprising expression cassettes for the expression of the heavy and light chains were separately assembled in mammalian cell expression vectors.

Thereby the gene segments encoding the individual elements were joined as outlined above.

General information regarding the nucleotide sequences of human light and heavy chains from which the codon usage can be deduced is given in: Kabat, E. A., et al., Sequences of Proteins of Immunological Interest, 5th ed., Public Health Service, National Institutes of Health, Bethesda, Md. (1991), NIH Publication No 91-3242.

The transcription unit of the K-light chain is composed of the following elements:
the immediate early enhancer and promoter from the human cytomegalovirus (hCMV),
a synthetic 5'-UT including a Kozak sequence,
a murine immunoglobulin heavy chain signal sequence including the signal sequence intron,
the cloned variable light chain cDNA arranged with a unique BsmI restriction site at the 5' end and a splice donor site and a unique NotI restriction site at the 3' end,
the genomic human K-gene constant region, including the intron 2 mouse Ig-K enhancer (Picard, D., and Schaffner, W. Nature 307 (1984) 80-82), and
the human immunoglobulin K-polyadenylation ("poly A") signal sequence.

The transcription unit of the γ1-heavy chain is composed of the following elements:
the immediate early enhancer and promoter from the human cytomegalovirus (hCMV),
a synthetic 5'-UT including a Kozak sequence,
a modified murine immunoglobulin heavy chain signal sequence including the signal sequence intron,
the cloned monospecific variable heavy chain cDNA or the cloned bispecific fusion scFv-variable heavy chain cDNA arranged with a unique BsmI restriction site at the 5' and a splice donor site and a unique NotI restriction site at the 3' end,
the genomic human γ1-heavy gene constant region, including the mouse Ig-enhancer (Neuberger, M. S., EMBO J. 2 (1983) 1373-1378), and
the human γ1-immunoglobulin polyadenylation ("polyA") signal sequence.

Beside the κ-light chain or γ1-heavy chain expression cassette these plasmids contain
a hygromycin resistance gene,
an origin of replication, oriP, of Epstein-Barr virus (EBV),
an origin of replication from the vector pUC18 which allows replication of this plasmid in E. coli, and
a β-lactamase gene which confers ampicillin resistance in E. coli.

Recombinant DNA Techniques

Cloning was performed using standard cloning techniques as described in Sambrook et al., 1999 (supra). All molecular biological reagents were commercially available (if not indicated otherwise) and were used according to the manufacturer's instructions.

DNA that contains coding sequences, mutations or further genetic elements was synthesized by Geneart A G, Regensburg.

DNA sequences were determined by double strand sequencing performed at SequiServe (SequiServe GmbH, Germany).

DNA and Protein Sequence Analysis and Sequence Data Management

The Vector NTI Advance suite version 9.0 was used for sequence creation, mapping, analysis, annotation, and illustration.

Expression of Anti-Hapten Antibodies and Derivatives The anti-hapten antibodies were expressed by transient transfection of human embryonic kidney 293 (HEK293) cells in suspension. For that, light and heavy chains of the corresponding mono- or bispecific antibodies were constructed in expression vectors carrying prokaryotic and eukaryotic selection markers as outlined above. These plasmids were amplified in E. coli, purified, and subsequently applied for transient transfections. Standard cell culture techniques were used for handling of the cells as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The cells were cultivated in appropriate expression medium at 37° C./8% $CO_2$. On the day of transfection the cells were seeded in fresh medium at a density of 1-2×10$^6$ viable cells/ml. The DNA-complexes with transfection reagents were prepared in Opti-MEM I medium (Invitrogen, USA) comprising 250 μg of heavy and light chain plasmid DNA in a 1:1 molar ratio for a 250 ml final transfection volume. The monospecific or bispecific antibody containing cell culture supernatants were clarified 7 days after transfection by centrifugation at 14,000 g for 30 minutes and filtration through a sterile filter (0.22 μm). Supernatants were stored at −20° C. until purification.

To determine the concentration of antibodies and derivatives in the cell culture supernatants, affinity HPLC chromatography was applied. For that, the cell culture supernatant containing mono- or bispecific antibody or derivatives thereof that bind to protein-A was applied to an Applied Biosystems Poros A/20 column in a solution comprising 200 mM $KH_2PO_4$, 100 mM sodium citrate, at pH 7.4. Elution from the chromatography material was performed by applying a solution comprising 200 mM NaCl, 100 mM citric acid, at pH 2.5. An UltiMate 3000 HPLC system (Dionex) was used. The eluted protein was quantified by UV absorbance and integration of peak areas. A purified IgG1 antibody served as a standard.

Purification of Anti-Hapten Antibodies that Bind Digoxigenin, Fluorescein, Theophylline or Biotin Seven days after transfection the HEK 293 cell supernatants were harvested. The recombinant antibody (or -derivatives) contained therein were purified from the supernatant in two steps by affinity chromatography using protein A-Sepharose™ affinity chromatography (GE Healthcare, Sweden) and Superdex200 size exclusion chromatography. Briefly, the antibody containing clarified culture supernatants were applied on a MabSelectSuRe protein A (5-50 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. The antibodies (or -derivatives) were eluted with 50 mM citrate buffer, pH 3.2. The protein containing fractions were neutralized with 0.1 ml 2 M Tris buffer, pH 9.0. Then, the eluted protein fractions were pooled, concentrated with an Amicon Ultra centrifugal filter device (MWCO: 30 K, Millipore) and loaded on a Superdex200 HiLoad 26/60 gel filtration column (GE Healthcare, Sweden) equilibrated with 20 mM histidine, 140 mM NaCl, at pH 6.0. The protein concentration of purified antibodies and derivatives was determined by determining the optical density (OD) at 280 nm with the OD at 320 nm as the background correction, using the molar extinction coefficient calculated on the basis of the amino acid sequence according to Pace et. al., Protein Science 4 (1995) 2411-2423. Monomeric antibody fractions were pooled, snap-frozen and stored at −80° C. Part of the samples was provided for subsequent protein analytics and characterization.

The homogeneity of the antibodies was confirmed by SDS-PAGE in the presence and absence of a reducing agent (5 mM 1,4-dithiothreitol) and staining with Coomassie brilliant blue. The NuPAGE® Pre-Cast gel system (Invitrogen, USA) was used according to the manufacturer's instruction (4-20% Tris-Glycine gels).

Under reducing conditions, polypeptide chains related to the IgG were identified after SDS-PAGE at apparent molecular sizes analogous to the calculated molecular weights. Expression levels of all constructs were analyzed by protein A. Average protein yields were between 6 mg and 35 mg of purified protein per liter of cell-culture supernatant in such non-optimized transient expression experiments.

Example 8

Generation of Haptenylated Compounds

For the generation of compounds for non-covalent complexation as well as for conjugation (covalent complexation) it is necessary (i) to couple the hapten via suitable linkers to the compound (=payload), and (ii) to assure that the coupling occurs in a manner that allows the compound to retain its functionality.

a) Hapten-Polypeptide Conjugates:

Any polypeptide can be derivatized N- or C-terminal or in a side-chain position by the hapten bearing linker as long as a reactive residue, such as a cysteine residue, can be introduced into the linker between polypeptide and hapten. Especially the polypeptide can comprise non-natural amino acid residues.

Exemplary haptenylated compounds are listed in the following Table 5.

TABLE 5

| compound | FIG. |
|---|---|
| Ac-PYY(PEG3-Cys-4Abu-$NH_2$) | 10 |
| Ac-Ile-Lys(N-propyl-($OCH_2CH_2$)$_3$-Cys-4Abu-$NH_2$)-Pqa-Arg-His-Tyr-Leu-Asn-Trp-Val-Thr-Arg-Gln-(NMe)Arg-Tyr-$NH_2$ | |
| DIG-3-cme-eda-Cy5 | 11 |
| DIG-maleiimid-Cy5 | 12 |
| DIG-eda-Cy5 | 13 |
| DIG-Ahx-Cys-Cy5 | 14 |
| DIG-Cys-MR121 | 15 |
| Ac-PYY(PEG3-Dig) | 16 |
| Ac-Ile-Lys(N-(Digoxigenin-3-carboxlmethyl-N-12-amino-4,7,10-trioxadodecanoic acid)-Pqa-Arg-His-Tyr-Leu-Asn-Trp-Val-Thr-Arg-Gln-(NMe)Arg-Tyr-$NH_2$ | |
| Ac-PYY(PEG3-Cys-4Abu-Dig) | 17 |
| Ac-Ile-Lys(N-(Digoxigenin-3-carboxlmethyl-N-4-amino-butyric acidyl-N-Cysteinyl-N-12-amino-4,7,10-trioxododecanoic acid)-Pqa-Arg-His-Tyr-Leu-Asn-Trp-Val-Thr-Arg-Gln-(NMe)Arg-Tyr-$NH_2$ | |
| PEG3-PYY(PEG3-Cys-4Abu-Dig) | 18 |
| 3,6,9-trioxo-decanoic acidyl-Ile-Lys(N-propyl-($OCH_2CH_2$)$_3$-Cys-Abu-Dig-3cme)-Pqa-Arg-His-Tyr-Leu-Asn-Trp-Val-Thr-Arg-Gln-(NMe)Arg-Tyr-$NH_2$ | |
| Dy636-eda-Btn | 19 |
| Dy636-Ser-Btn | 20 |
| Dy636-Cys-Btn | 21 |
| Cy5-Cys-Btn | 22 |
| Cy5-Ser-Btn | 23 |
| Ac-PYY(PEG2-Btn) | 24 |
| Ac-Ile-Lys(N-carboxymethyl-($OCH_2CH_2$)$_2$—NH-Btn)-Pqa-Arg-His-Tyr-Leu-Asn-Trp-Val-Thr-Arg-Gln-(NMe)Arg-Tyr-$NH_2$ | |
| Ac-PYY(PEG3-Cys-ß-Ala-Btn) | 25 |
| Ac-Ile-Lys(N-carboxymethyl-($OCH_2CH_2$)$_3$—NH-Cys-ß-Ala-Btn)-Pqa-Arg-His-Tyr-Leu-Asn-Trp-Val-Thr-Arg-Gln-(NMe)Arg-Tyr-$NH_2$ | |
| Ac-PYY(PEG3-Ser-PEG2-Btn) | 26 |
| Ac-Ile-Lys(N-carboxymethyl-($OCH_2CH_2$)$_3$—NH-Ser-carboxymethyl-($OCH_2CH_2$)$_2$-NH-Btn)-Pqa-Arg-His-Tyr-Leu-Asn-Trp-Val-Thr-Arg-Gln-(NMe)Arg-Tyr-$NH_2$ | |
| Ac-PYY(PEG3-Cys-PEG2-Btn) | 27 |
| Ac-Ile-Lys(N-carboxymethyl-($OCH_2CH_2$)$_3$—NH-Cys-carboxymethyl-($OCH_2CH_2$)$_2$—NH-Btn)-Pqa-Arg-His-Tyr-Leu-Asn-Trp-Val-Thr-Arg-Gln-(NMe)Arg-Tyr-$NH_2$ | |

TABLE 5-continued

| compound | FIG. |
|---|---|
| Ac-PYY(PEG3-Cys-4-Abu-5-Fluo)<br>Ac-Ile-Lys(N-carboxymethyl-(OCH$_2$CH$_2$)$_3$—NH-Cys-4Abu-5-Fluo)-Pqa-Arg-His-Tyr-Leu-Asn-Trp-Val-Thr-Arg-Gln-(NMe)Arg-Tyr-NH$_2$ | 28 |
| Ac-PYY(PEG3-Cys-PEG2-5-Fluo)<br>Ac-Ile-Lys(N-carboxymethyl-(OCH$_2$CH$_2$)$_3$—NH-Cys-carboxymethyl-(OCH$_2$CH$_2$)$_2$—NH-5-Fluo)-Pqa-Arg-His-Tyr-Leu-Asn-Trp-Val-Thr-Arg-Gln-(NMe)Arg-Tyr-NH$_2$ | 29 |

Abbreviations:
4Abu = 4-Amino-butyric acid
Ahx = Aminohexanoic acid
Btn = biotinyl
cme = carboxymethyl
Cy5 = Indodicarbocyanine, Cyanin-5
Dadoo = 1,8-Diamino-3,6-dioxo-octane
DCM = dichloromethane
Dig(OSu) = Digoxigenin-3-carboxylmethyl-N-hydroxysuccinimide
Dy636 = Fluorophore
eda = ethylenediamine
Fluo = 5-Carboxy-fluorescein
HATU = 0-(7-Aza-1H-benzotriazole-1-yl)-1,1,3,3-tetramethyluronium hexafluorophosphate
HFIP = 1,1,1,3,3,3,-hexafluoro-2-propanol
Mmt = 4-Methoxytrityl
MR121 = Oxazine fluorophore
MTBE = tert. Butyl-methyl-ether
NMM = N-Methyl-morpholine
NMP = N-Methyl-2-pyrrolidone
PEG2 = 8-amino-3,6-dioxa-octanoic acid
PEG3 = 12-amino-4,7,10-trioxadodecanoic acid
O$_2$O$_c$ = 8-amino-3,6-dioxa-octanoic acid
Pip = piperidine
Pqa = 4-oxo-6-piperazin-1-yl-4H-quinazolin-3-yl)-acetic acid
TBTU = 2-(1H-Benzotriazole-1-yl)-1,1,3,3-tetramethyluronium tetrafluoroborate
TCEP = Tris(2-chloroethyl)phosphate
TFE = 2,2,2,Trifluoroethanole
TIS = Triisopropylsilane A scheme of the coupling procedure and the employed reagents is shown in FIGS. 30, 31 and 32.

An exemplary polypeptide that has been used herein was a neuropeptide-2 receptor agonist derivative. This polypeptide is a Peptide Tyrosine Tyrosine or Pancreatic Peptide YY short PYY(3-36) analog as reported in WO 2007/065808. It was digoxigenylated via the amino acid residue lysine in position 2. The digoxigenylated PYY polypeptide is termed DIG-PYY in the following text irrespective of the side-chain linking the polypeptide to the digoxigenin residue.

Other exemplary compounds are the non-peptide fluorescent dyes Cy5, Dy636 and MR121. These compounds can be coupled to the digoxigenin or biotin containing linker systems via NHS-ester chemistry.

i) General Method for the Generation of the PYY(3-36)-Derived Polypeptide Conjugation Precursor Standard protocol for PYY derivatives on an automated multiple synthesizer:
Synthesizer: Multiple Synthesizer SYRO I (MultiSynTech GmbH, Witten) with vortex stirring system
Resin: 200 mg TentaGel S RAM (0.25 mmol/g), RAPP Polymere, Tubingen, 10 ml plastic syringe with a Teflon frit as reaction vessel
Stock solutions:
Fmoc amino acids: 0.5 M in DMF or NMP
Deblocking reagent: 30% piperidine in DMF
Activator: 0.5 M TBTU and HATU, respectively
Base: 50% NMM in NMP
Coupling:
Fmoc amino acid: 519 µl
Base: 116 µl
Activator: 519 µl
Reaction time: double coupling: 2×30 min
Fmoc-deblock:
Deblocking reagent: 1200 µl
Reaction time: 5 min+12 min
Washing:
Solvent: 1200 µl
Volume: 1300 µl
Reaction time: 5×1 min
Final cleavage:
Cleavage reagent: 8 ml TFA/thioanisol/thiocresol/TIS (95:2, 5:2, 5:3)
Reaction time: 4 h
Work-up: The cleavage solution was filtered and concentrated to 1-2 ml and the peptide precipitated by addition of MTBE. The white solid was collected by centrifugation, washed 2 times with MTBE and dried.

Ac-IK-Pqa-R(Pbf)H(Trt)Y(tBu)LN(Trt)W(Boc)VT(But)R(Pbf)Q(Trt)-MeArg(Mtr)-Y(tBu)-TentaGel S RAM resin (SEQ ID NO: 176)

The PYY(3-36)-polypeptide derivative (termed PYY) was obtained by automated solid-phase synthesis of the resin-bound peptide sequence Ac-IK(Mmt)-Pqa-R(Pbf)H(Trt)Y(tBu)LN(Trt)W(Boc)VT(tBu)R(Pbf)Q(Trt)-MeArg(Mtr)-Y(tBu)-TentaGel-RAM resin. Peptide synthesis was performed according in a Multiple Synthesizer SYRO I (MultiSynTech GmbH, Witten) with vortex stirring system using Fmoc chemistry. Employing a TentaGel RAM resin (loading: 0.25 mmol/g; Rapp Polymers, Germany), the peptide sequence was assembled in iterative cycles by sequential coupling of the corresponding Fmoc-amino acids (scale: 0.05 mmol). In every coupling step, the N-terminal Fmoc-group was removed by treatment of the resin (5 min+12 min) with 30% piperidine in Dimethylformamide (DMF). Couplings were carried out employing Fmoc-protected amino acids (0.25 mmol) activated by TBTU (0.25 mmol) at positions 1, 13, 14 and 15 and NMM 50% in NMP (double coupling 2×30 min vortex). At all other positions HATU (0.25 mmol) and NMM 50% in NMP was used as activator. Between each coupling step the resin was washed 5×1 min with DMF. After synthesis of the linear precursor, acetylation was performed by reaction with DMF/DIPEA/Ac$_2$O in 15 min and washing with DMF yielding Ac-IK(Mmt)-Pqa-R(Pbf)H(Trt)Y(tBu)LN(Trt)W(Boc)VT(But)R(Pbf)Q(Trt)-MeArg(Mtr)-Y(tBu)-TentaGel S RAM resin.

For the removal of the Mmt group, the peptide was treated with DCM/HFIP/TFE/TIS (6.5:2:1:0.5), 2×1 h, yielding the partial deblocked precursor Ac-IK-Pqa-R(Pbf)H(Trt)Y(tBu)LN(Trt)W(Boc)VT(But)R(Pbf)Q(Trt)-MeArg(Mtr)-Y(tBu)-TentaGel S RAM resin after washing with DMF.

Ac-PYY(PEG3-Dig)/Ac-IK(PEG3-Dig)-Pqa-RHYLN-WVTRQ-MeArg-Y-NH2 (SEQ ID NO: 177)

Syntheses see also WO 2012/093068.

Figure 2A:
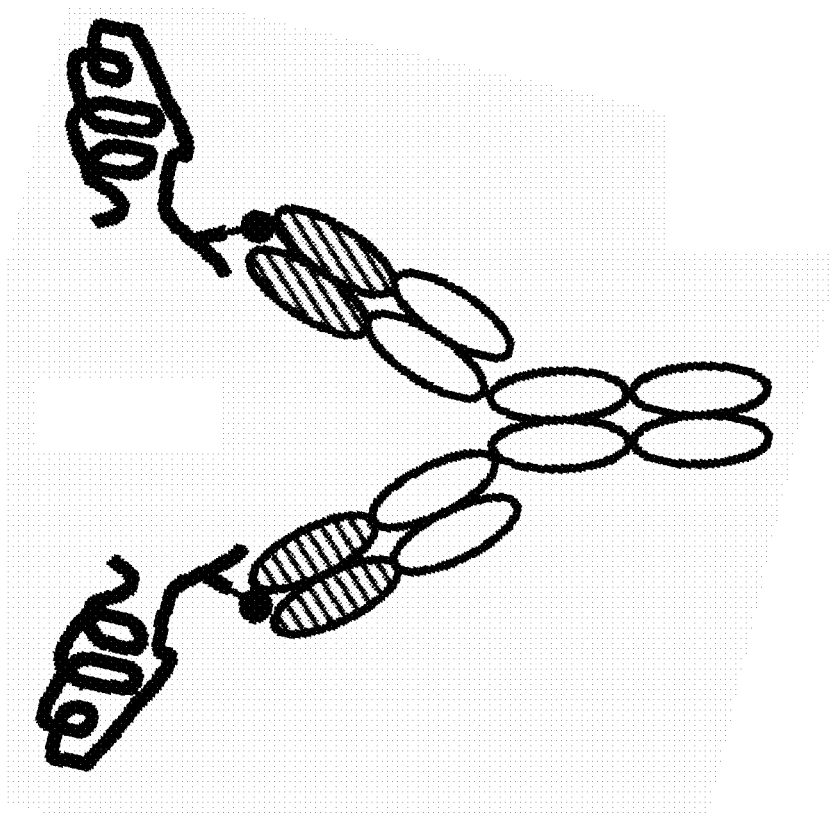
FIGS. 2A-2C: Scheme of a complex of a monospecific bivalent anti-digoxigenin antibody and a digoxigenin-Cy5 conjugate (FIG. 2A) and of a complex of a monospecific bivalent anti-digoxigenin antibody and a digoxigenin-polypeptide conjugate (FIG. 2B). Scheme of a complex of a bispecific tetravalent anti-digoxigenin antibody and a digoxigenin-polypeptide conjugate (FIG. 2C).
Figure 2B:
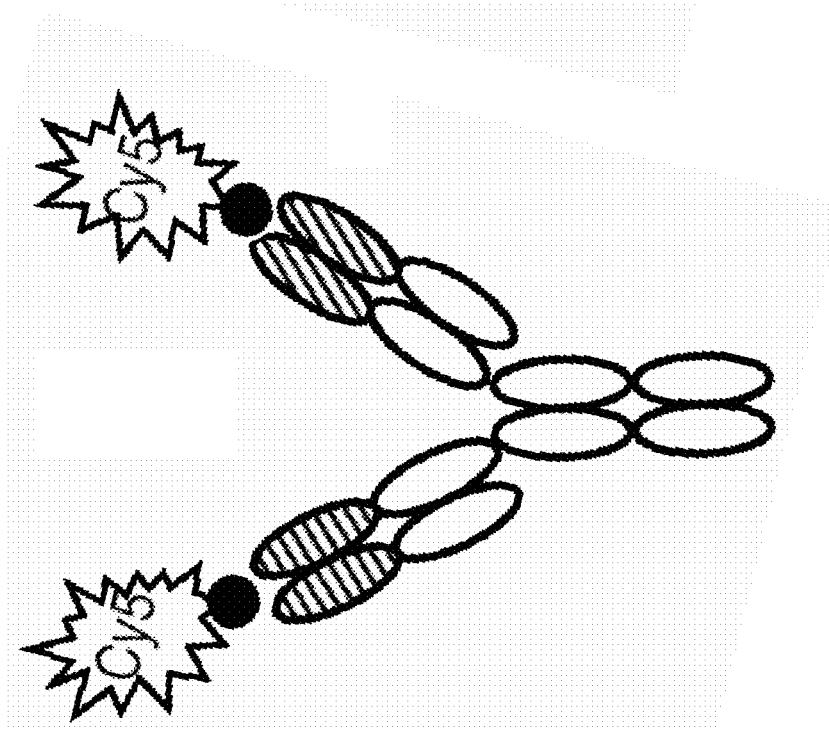
Figure 2C:
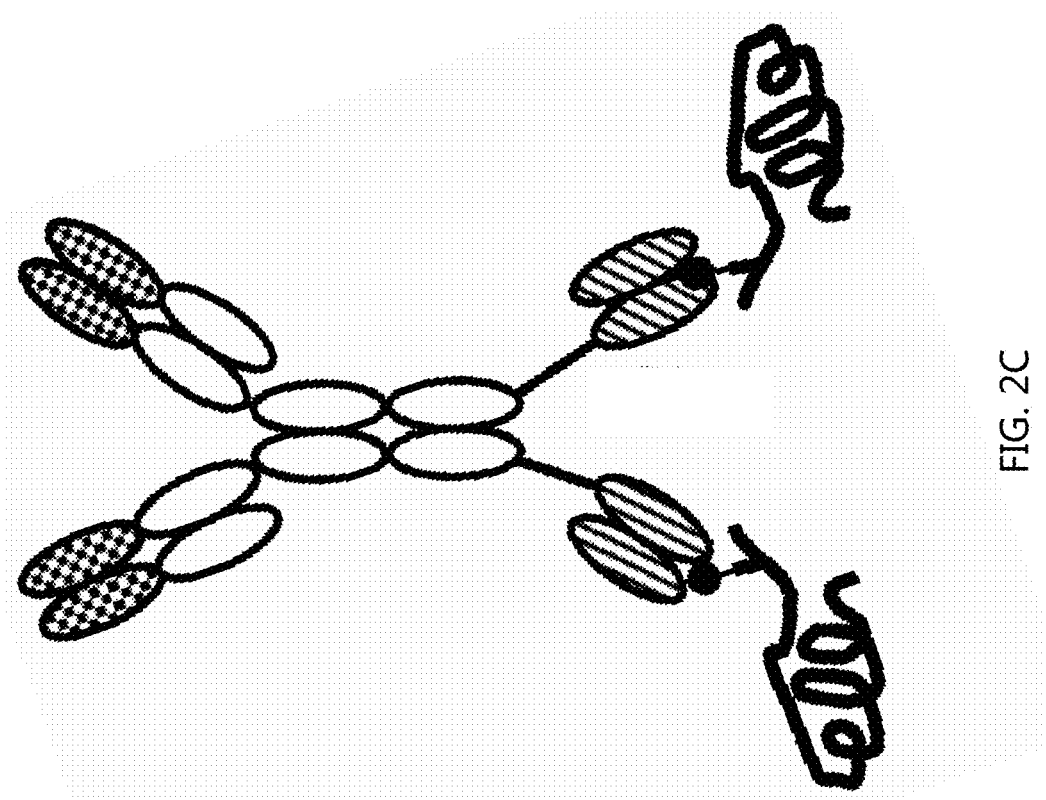
Figure 3:
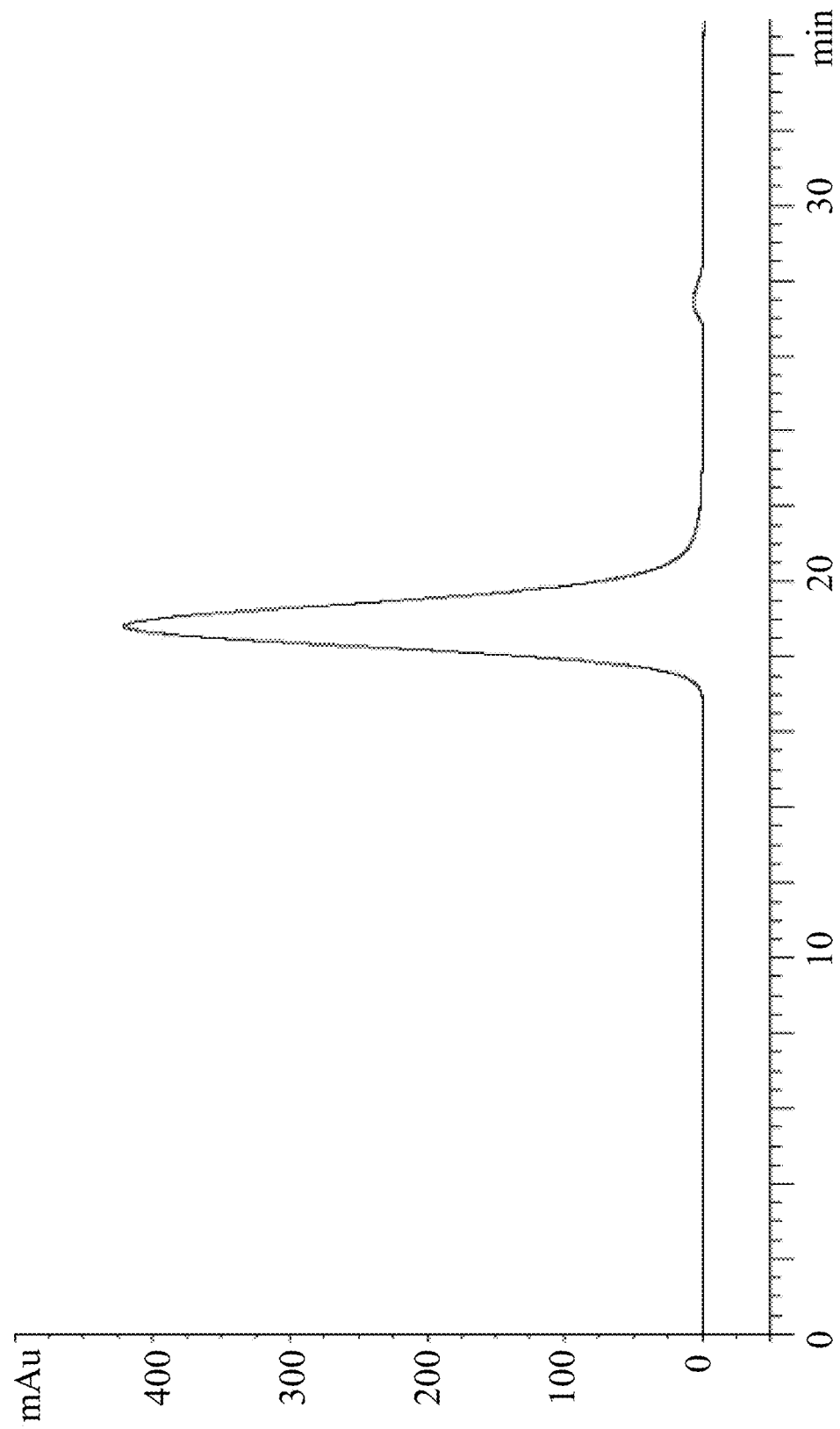
FIG. 3: Size exclusion chromatogram (recorded at 280 nm) of a complex comprising an anti-digoxigenin antibody and digoxigenin which is conjugated to a peptide (DIG-PYY) showing a single peak of a complex of defined size.
Figure 4B:
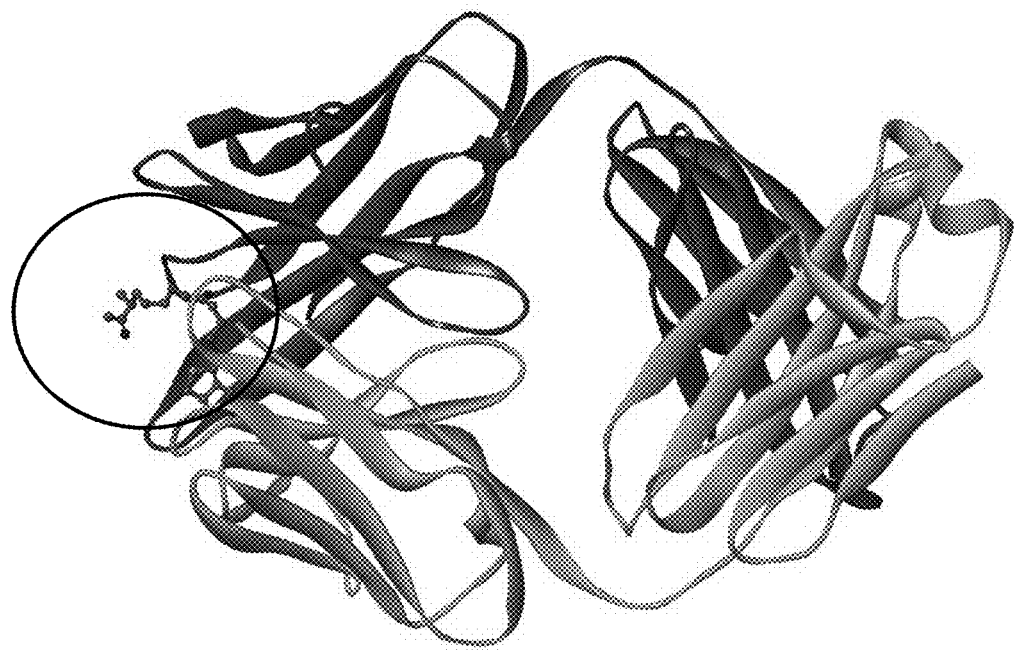
FIGS. 4A-4B.
Figure 4A:

To a solution of peptide Ac-IK(H2N-TEG)-Pqa-RHYL-NWVTRQ(N-methyl)RY (100 mg, 40.6 µmol) in water (5 mL) was added Digoxigenin-3-carboxy-methyl-N-hydroxysuccinimide (26.6 mg, 48.8 µmol) dissolved in NMP (1 mL). Triethylamine (13.6 L, 97.6 µmol) was added and the mixture was tumbled for 2 h at room temperature. Subsequently, additional Digoxigenin-3-carboxy-methyl-N-hydroxysuccinimide (13.3 mg, 24.4 µmol) dissolved in NMP (0.5 mL), and triethylamine (6.8 µL, 48.8 µmol) were added and the solution was tumbled for 15 h. The crude product was purified by preparative reversed phase HPLC employing an acetonitrile/water gradient containing 0.1% TFA (Merck Chromolith prep RP-18e column, 100×25 mm) to furnish the Dig-PYY peptide (29 mg, 10.0 µmol, 25%) as a colorless solid. For analytical characterization of the peptide derivative we applied the following conditions an d received the following data: Analytical HPLC: $t_R$=11.3 min (Merck Chromolith Performance RP-18e, 100×4.6 mm, water+0.1% TFA-acetonitrile/water+0.1% TFA 80:20, 25 min); ESI-MS (positive ion mode): m/z: calcd. for $C_{140}H_{207}N_{35}O_{32}$: 2892.4; found: 964.9 [M+2H]$^{2+}$, calcd: 965.1. Until the point of complexation to the antibody, we stored the digoxigenylated peptide as lyophilisate at 4° C. FIG. 2C shows the structure of DIG-moPYY.

ii) Generation of the Digoxigenylated PYY(3-36)-Derived Polypeptides with a Cysteine Containing Linker
Ac-IK(PEG3-Cys-4Abu-NH2)-Pqa-RHYLNWVTRQ-MeArg-Y-NH2 (SEQ ID NO: 178)

Starting with the precursor Ac-IK-Pqa-R(Pbf)H(Trt)Y(tBu)LN(Trt)W(Boc)VT(But)R(Pbf)Q(Trt)-MeArg(Mtr)-Y(tBu)-TentaGel S RAM resin (SEQ ID NO: 176) the peptide synthesis was continued with following steps:

Manual double coupling with 66.5 mg (3 eq.) Fmoc-12-amino-4,7,10-trioxadodecanoic acid (PEG3-spacer), 57.0 mg (3 equiv.) HATU and 16.7 µl (3 equiv.) NMM in 1.2 ml DMF for 2×30 min. After washings with DMF (5×1 min) the Fmoc-group was cleaved with 30% Pip/DMF and the resin was washed with DMF using the standard protocol.

The following double couplings of Fmoc-Cys(Trt)-OH and Fmoc-4-Abu-OH were performed automatically in the SYRO 1 synthesizer by means of the protocol as described in the standard protocol for PYY derivatives on an automated multiple synthesizer. Finally the resin was washed with DMF, EtOH, MTBE and dried.

Cleavage from the resin was performed with 8 ml TFA/thioanisol/thiocresol/TIS (95:2.5:2.5:3) for 4 h. The cleavage solution was filtered and concentrated to 1-2 ml and the peptide precipitated by addition of MTBE. The white solid was collected by centrifugation, washed 2 times with MTBE and dried.

The crude product was purified by preparative reversed phase HPLC giving a colorless solid. Yield: 28.0 mg.
Purification Protocol
  HPLC: Shimadzu LC-8A with UV-Vis-detector SPD-6A
  Solvent A: 0.05% TFA in water
  Solvent B: 0.05% TFA in 80% acetonitrile/water
  Column: UltraSep ES, RP-18, 10 µm, 250×20 mm (SEP-SERV, Berlin)
  Flow: 15 ml/min
  Detection: 230 nm
  Gradient: 20-50% B in 30 min
Analytical Data:
  HPLC: Shimadzu LC-9A with photodiode array-detector SPD-M6A
  Solvent A: 0.05% TFA in water
  Solvent B: 0.05% TFA in 80% acetonitrile/water
  Column: UltraSep ES, RP-18, 7 µm, 250×3 mm (SEPS-ERV, Berlin)
  Flow: 0.6 ml/min
  Gradient: 5-80% B in 30 min
  MS: Shimadzu time-of-flight mass spectrometer AXIMA Linear (MALDI-TOF), molecular weights are calculated as average mass
  m/z: calc. for $C_{122}H_{185}N_{37}O_{28}S$=2650.13; found: 2650.3.
Ac-IK(PEG3-Cys-4Abu-Dig)-Pqa-RHYLNWVTRQ-MeArg-Y-NH2 (SEQ ID NO: 179)

To a solution of 15 mg of peptide Ac-IK(PEG3-Cys-4Abu-NH2)-Pqa-RHYLNWVTRQ-MeArg-Y-amide (SEQ ID NO: 180) in 50 µl DMSO, 250 µl PBS buffer pH 7.4 was added and the solution stirred overnight. The dimer formation was controlled by HPLC. After 18 h app. 90% of the dimer was formed.

To this solution was added 7.3 mg Digoxigenin-3-carboxy-methyl-N-hydroxysuccinimide (Dig-OSu) dissolved in 100 µl DMF and the mixture was stirred for 5 h at room temperature. Subsequently, additional 16.9 mg Dig-OSu dissolved in 100 µl DMF was added and stirred for 2 h. Further amount of 6.9 mg in 100 µl DMF was added and stirred for 18 h. For the reduction of the dimer TCEP was added, stirred for 3 h and the solution was used directly for purification by means of preparative reversed phase HPLC.
Analytical data:
Conditions were the same as described for SEQ ID NO: 178
Gradient for preparative HPLC: 38-58% B in 30 min.
Yield: 5.3 mg
m/z: calc. for $C_{147}H_{219}N_{37}O_{34}S$=3080.7; found: 3079.8.
PEG3-IK(PEG3-Cys-4Abu-Dig)-Pqa-RHYLNWVTRQ-MeArg-Y-NH2 (SEQ ID NO: 180)

Automated solid-phase synthesis of resin-bound PYY sequence:
PEG2-IK(ivDde)-Pqa-R(Pbf)H(Trt)Y(tBu)LN(Trt)W(Boc)VT(tBu)R(Pbf)Q(Trt)-MeArg(Mtr)-Y(tBu)-TentaGel-RAM resin (SEQ ID NO: 181)

The peptide synthesis was performed according to established protocols (FastMoc 0.25 mmol) in an automated Applied Biosystems ABI 433A peptide synthesizer using Fmoc chemistry. Employing a TentaGel RAM resin (loading: 0.18 mmol/g; Rapp Polymers, Germany), the peptide sequence was assembled in iterative cycles by sequential coupling of the corresponding Fmoc-amino acids (scale: 0.25 mmol). In every coupling step, the N-terminal Fmoc-group was removed by treatment of the resin (3×2.5 min) with 20% piperidine in N-methyl pyrrolidone (NMP). Couplings were carried out employing Fmoc-protected amino acids (1 mmol) activated by HBTU/HOBt (1 mmol each) and DIPEA (2 mmol) in DMF (45-60 min vortex). At positions 2, 3, and 14, respectively, the amino acid derivatives Fmoc-Lys(ivDde)-OH, Fmoc-Pqa-OH, and Fmoc-N-Me-Arg(Mtr)-OH were incorporated into the synthesis sequence. After every coupling step, non-reacted amino groups were capped by treatment with a mixture of Ac$_2$O (0.5 M), DIPEA (0.125 M) and HOBt (0.015 M) in NMP (10 min vortex). Between each step, the resin was extensively washed with N-methyl pyrrolidone and DMF. Incorporation of sterically hindered amino acids was accomplished in automated double couplings. For this purpose, the resin was treated twice with 1 mmol of the activated building block without a capping step in between coupling cycles. After completion of the target sequence, the N-terminal Fmoc-group was removed with 20% piperidine in NMP and 2-[2-(methoxyethoxy)-ethoxy]acetic acid (4 mmol) was coupled after activation with HBTU/HOBt (2 mmol each) and DIPEA (4 mmol). Subsequently, the resin was transferred into a fritted solid-phase reactor for further manipulations.
PEG2-IK(PEG3-Cys-Abu-NH2)-Pqa-RHYLNWVTRQ-MeArg-Y-NH2 (SEQ ID NO: 182)

For the removal of the ivDde group, the peptide resin (PEG2-IK(ivDde)-Pqa-R(Pbf)H(Trt)Y(tBu)LN(Trt)W(Boc)VT(tBu)R(Pbf)Q(Trt)-MeArg(Mtr)-Y(tBu)-TentaGel-RAM resin; SEQ ID NO: 181) was swelled with DMF for 30 min, and was subsequently treated with a 2% solution of hydrazine hydrate in DMF (60 mL) for 2 h. After washing the resin extensively with isopropanol and DMF, a solution of Fmoc-12-amino-4,7,10-trioxadodecanoic acid (PEG3-spacer) (887 mg, 2 mmol), HBTU (2 mmol), HOBt (2 mmol) and a 2 M diisopropylethyl amine (2 mL, 4 mmol) in DMF (3 mL) was added, and the mixture was shaken for 3 h. The resin was washed with DMF and the Fmoc-group was cleaved with a mixture 20% pyridine in DMF. Subsequently, the resin was treated with a mixture of Fmoc-Cys(Trt)-OH (1.2 g; 2 mmol), HBTU/HOBt (2 mmol each) and DIPEA (4 mmol) for 2 h. The resin was washed with DMF and the Fmoc-group was cleaved with a mixture 20% pyridine in DMF and Fmoc-4-aminobutyric acid (0.65 g, 2 mmol) activated with HBTU/HOBt (2 mmol each) and DIPEA (4 mmol) was coupled (2 h). The N-terminal Fmoc-group was removed with 20% piperidine in NMP and the resin washed repeatedly with DMF. Subsequently, the resin was treated with a mixture of trifluoroacetic acid, water and triisopropylsilane (19 mL:0.5 mL:0.5 mL) for 2.5 h. The cleavage solution was filtered and the peptide was precipitated by addition of cold (0° C.) diisopropyl ether (300 mL) to furnish a colorless solid, which was repeatedly washed with diisopropyl ether. The crude product was re-dissolved in a mixture of acetic acid/water and lyophilized and purified by preparative reversed phase HPLC employing an acetonitrile/water gradient containing 0.1% TFA (Merck Chromolith prep RP-18e column, 100×25 mm).

Analytical HPLC: tR=8.6 min (Merck Chromolith Performance RP-18e, 100×4.6 mm, water+0.1% TFA→acetonitrile/water+0.1% TFA 80:20, 25 min); ESI-MS (positive ion mode): m/z: calcd. for $C_{127}H_{195}N_{37}O_{31}S$: 2768.3; found: 1385.0 $[M+2H]^{2+}$, calcd: 1385.1; 923.7 $[M+3H]^{3+}$, calcd: 923.8; 693.1 $[M+4H]^{4+}$, calcd: 693.1.

PEG2-IK(PEG3-Cys-4Abu-Dig)-Pqa-RHYLNWVTRQ-MeArg-Y-NH2 (PEG2-PYY(PEG3-Cys-4Abu-Dig) (SEQ ID NO: 183)

To a solution of peptide PEG2-IK(PEG3-Cys-Abu-NH2)-Pqa-RHYLNWVTRQ-MeArg-Y-NH2 (SEQ ID NO: 182, 4.1 mg, 1.48 µmol) in DMF (3 mL) was added Digoxigenin-3-carboxy-methyl-N-hydroxysuccinimide (0.81 mg, 1.48 µmol) dissolved in NMP (1 mL). Triethylamine (0.41 µl, 97.6 µmol) in DMF was added and the mixture was tumbled for 2 h at room temperature. The crude product was purified by preparative reversed phase HPLC employing an acetonitrile/water gradient containing 0.1% TFA (Merck Chromolith prep RP-18e column, 100×25 mm) to furnish the PEG3-Cys-4Abu-Dig peptide (1.2 mg, 0.375 µmol, 25%) as a colorless solid.

Analytical HPLC: tR=10.2 min (Merck Chromolith Performance RP-18e, 100×4.6 mm, water+0.1% TFA→acetonitrile/water+0.1% TFA 80:20, 25 min); ESI-MS (positive ion mode): m/z: calcd for $C_{152}H_{229}N_{37}O_{37}S$: 3198.8; found: 1067.3 [M+3H]3+, calcd: 1067.3.

iii) Generation of PYY(3-36)-Derived Polypeptides with Biotin or with Biotin and Cysteine Containing Linker:
Ac-IK(PEG2-Biotin)-Pqa-RHYLNWVTRQ-MeArg-Y-amide/Ac-PYY(PEG2-Biot) (SEQ ID NO: 184)

Starting with the common precursor peptide resin (SEQ ID NO: 176), the peptide was coupled manually 2 times with 57.8 mg (3 equiv.) Fmoc-8-amino-dioxaoctanoic acid (PEG2 spacer), 48.2 mg (3 equiv.) TBTU and 33.3 µl (6 equiv.) NMM in 1.2 ml DMF, 30 min each and washed with DMF. The Fmoc-group was cleaved with 30% Pip/DMF using the standard protocol described for SEQ ID NO: 176, the resin was washed with DMF and treated for 2 h with a biotin-OBt solution in NMP (48.9 mg biotin (4 equiv.), 64.2 mg TBTU (4 equiv.) and 44.4 µl NMM (8 equiv.) in 1.2 ml NMP, pre-activation 3 min). After washing with DMF, EtOH and MTBE the peptide resin was dried.

Final cleavage was performed as described above. The crude product was purified by preparative reversed phase HPLC employing a gradient of 22-52% B in 30 min giving a solid. Yield: 42 mg.

Purification Protocol
HPLC: Shimadzu LC-8A with UV-Vis-detector SPD-6A
Solvent A: 0.05% TFA in water
Solvent B: 0.05% TFA in 80% acetonitrile/water
Column: UltraSep ES, RP-18, 10 m, 250×20 mm (SEPSERV, Berlin)
Flow: 15 ml/min
Detection: 230 nm Analytical Data:
HPLC: Shimadzu LC-9A with photodiode array-detector SPD-M6A
Solvent A: 0.05% TFA in water
Solvent B: 0.05% TFA in 80% acetonitrile/water
Column: UltraSep ES, RP-18, 7 µm, 250×3 mm (SEPSERV, Berlin)
Flow: 0.6 ml/min
Gradient: 5-80% B in 30 min
MS: Shimadzu time-of-flight mass spectrometer AXIMA Linear (MALDI-TOF), molecular weights are calculated as average mass
m/z: calc. for $C_{122}H_{181}N_{37}O_{27}S=2630.10$; found: 2631.5.

Ac-IK(PEG3-Cys-B-Ala-Biotin)-Pqa-RHYLNWVTRO-MeArg-Y-NH2/Ac-PYY(PEG3-Cys-B-Ala-Biot) (SEQ ID NO: 185)

Starting with the precursor Ac-IK-Pqa-R(Pbf)H(Trt)Y(tBu)LN(Trt)W(Boc)VT(But)R(Pbf)Q(Trt)-MeArg(Mtr)-Y(tBu)-TentaGel S RAM resin (SEQ ID NO: 176) the peptide was coupled manually 2 times 30 min with 66.5 mg (3 equiv.) Fmoc-12-amino-4,7,10-trioxadodecanoic acid (PEG3-spacer), 57.0 mg (3 equiv.) HATU and 16.7 µl (3 equiv.) NMM in 1.2 ml DMF. After washing with DMF the Fmoc-group was cleaved with 30% Pip/DMF and the resin was washed with DMF using the standard protocol.

Following double couplings of Fmoc-Cys(Trt)-OH and Fmoc-B-Ala-OH performed automatically in the SYRO 1 synthesizer by means of the standard protocol, a solution of biotin-OBt in NMP (prepared from 48.9 mg biotin (4 equiv.), 64.2 mg TBTU (4 equiv.) and 44.4 µl NMM (8 equiv.) in 1.2 ml NMP, pre-activation 3 min) was added manually and stirred at room temperature. After 2 h the resin was washed with DMF, EtOH, MTBE and dried.

Final cleavage was performed as described above. The crude product was purified by preparative reversed phase HPLC as described for SEQ ID NO: 184 giving a colorless solid. Yield: 41.4 mg Analytical Data:
Gradient for preparative HPLC: 28-58% B in 30 min.
m/z: calc. for $C_{131}H_{197}N_{39}O_{30}S_2=2862.4$; found: 2862.4.

Ac-IK(PEG3-Cys-PEG2-Biotin)-Pqa-RHYLNWVTRO-MeArg-Y-NH2/Ac-PYY(PEG3-Cys-PEG2-Biot) (SEQ ID NO: 186)

Starting with the precursor Ac-IK-Pqa-R(Pbf)H(Trt)Y(tBu)LN(Trt)W(Boc)VT(But)R(Pbf)Q(Trt)-MeArg(Mtr)-Y(tBu)-TentaGel S RAM resin (SEQ ID NO: 176) the peptide synthesis was continued with following steps:
double coupling with Fmoc-PEG3-OH (by means of the standard protocol),
double coupling of Fmoc Cys(Trt)-OH (by means of the standard protocol),
double coupling of Fmoc-PEG2-OH with 57.8 mg (3 equiv.) Fmoc-8-amino-dioxaoctanoic acid (PEG2 spacer), 48.2 mg (3 equiv.) TBTU and 33.3 µl (6 equiv.) NMM in 1.2 ml DMF, 2×30 min and biotinylation with a solution of 48.9 mg biotin (4 equiv.), 64.2 mg TBTU (4 equiv.) and 44.4 μl NMM (8 equiv.) in 1.2 ml NMP, (pre-activation 3 min), single coupling 2 h.

Cleavage from the resin, purification and analysis was performed as described in for SEQ ID NO: 184. Yield: 47.7 mg Analytical data:

The same conditions as for SEQ ID NO: 184. Gradient for preparative HPLC: 25-45% B in 30 min.

m/z: calc. for C134H203N3903252=2936.5; found: 2937.8.

iv) Generation of PYY(3-36)-Derived Polypeptides with a Fluorescein or with a Fluorescein and Cysteine Containing Linker Ac-IK(PEG3-Cys-4-Abu-5-Fluo)-Pqa-RHYLNWVTRO-MeArg-Y-NH2/Ac-PYY(PEG3-Cys-4-Abu-5-Fluo) (SEQ ID NO: 187)

Starting with the precursor Ac-IK-Pqa-R(Pbf)H(Trt)Y (tBu)LN(Trt)W(Boc)VT(But)R(Pbf)Q(Trt)-MeArg(Mtr)-Y (tBu)-TentaGel S RAM resin (SEQ ID NO: 176) the peptide synthesis was continued analogously to SEQ ID NO: 179. For labeling a solution of 54.2 mg 5-Carboxyfluorescein, 33.1 mg HOBt and 35.6 μl DIC in DMF was added and stirred for 18 h at room temperature.

Cleavage from the resin, purification and analysis was performed as described in for SEQ ID NO: 179. Yield: 41.6 mg Analytical Data:

Gradient for preparative HPLC: 29-49% B in 30 min.

m/z: calc. for C143H195N37O34S=3008.44; found: 3007.2.

Ac-IK(PEG3-Cys-PEG2-5-Fluo)-Pqa-RHYLNWVTRQ-MeArg-Y-NH2/Ac-PYY(PEG3-Cys-PEG2-5-Fluo) (SEQ ID NO: 188)

Starting with the precursor Ac-IK-Pqa-R(Pbf)H(Trt)Y (tBu)LN(Trt)W(Boc)VT(But)R(Pbf)Q(Trt)-MeArg(Mtr)-Y (tBu)-TentaGel S RAM resin (SEQ ID NO: 176) the peptide synthesis was continued with following steps:

double coupling with Fmoc-PEG3-OH (by means of the standard protocol), double coupling of Fmoc Cys(Trt)-OH (by means of the standard protocol), double coupling Fmoc-PEG2-OH (see SEQ ID NO: 186).

For the labeling the peptide resin was stirred for 18 h with a solution of 56.7 mg 5-Carboxyfluorescein, 34.6 mg HOBt and 37.3 μl DIC in DMF. Cleavage from the resin, purification and analysis were performed as described in SEQ ID NO; 185. Yield: 41.7 mg Analytical Data:

Gradient for preparative HPLC: 34-64% B in 30 min.

m/z: calc. for C145H199N37O36S1=3068.5; found: 3069.2.

b) Hapten-labeled fluorescent dyes:

i) Generation of digoxigenvlated Cy5

Syntheses see WO 2012/093068.

ii) Generation of Dig-Cys-MR121

In an Erlenmeyer flask 1,2-Diamino-propane trityl resin (250 mg, 0.225 mmol, loading 0.9 mmol/g) was swelled with DMF (5 mL) for 30 min. Subsequently, a solution of Fmoc-Cys(Trt)-OH (395 mg, 0.675 mmol) in DMF (2 mL) and a solution of HATU (433 mg, 1.2375 mmol) and HOAt (164 mg, 1.2375 mmol) in DMF (8 mL) were added to the resin. To this suspension was added DIPEA (385 μL, 2.25 mmol) and the mixture was swirled for 16 h at ambient temperature, filtered, and washed repeatedly with DMF. After the coupling step, non-reacted amino groups were capped by treatment with a mixture of Ac$_2$O (20%) in DMF followed by a washing step with DMF. Removal of the N-terminal Fmoc group was accomplished by treatment of the resin with piperidine (20%) in DMF for 2 h. Afterwards, the resin was washed thoroughly with DMF and isopropanol, and again DMF and was then treated with a solution of MR121 (25 mg, 0.05 mmol) in 1% DIPEA in DMF (10 mL) for 16 h. After filtration and washing with DMF, the resin was treated with a mixture of trifluoroacetic acid, water and triisopropylsilane (9 mL:9 mL:1 mL) for 3 h. The cleavage solution was filtered, concentrated under reduced pressure, and the resulting solid was purified by preparative reversed phase HPLC employing an acetonitrile/water gradient containing 0.1% TFA (Merck Chromolith prep RP-18e column, 100×25 mm) and lyophilized. Analytical HPLC: $t_R$=7.7 min (Merck Chromolith Performance RP-18e, 100×4.6 mm, water+0.1% TFA→acetonitrile/water+0.1% TFA 80:20, 25 min. Subsequently, a portion of this intermediate (10.0 mg, 17.6 μmol) was dissolved in DMF (1 mL) and a solution of Digoxigenin-3-carboxy-methyl-N-hydroxysuccinimide (9.6 mg, 17.6 μmol) in DMF (1 mL) and 1% triethylamine in DMF (2 mL) were added and the mixture was tumbled for 16 h. The solution was concentrated afterwards, and the target compound was purified by preparative reversed phase HPLC employing an acetonitrile/water gradient containing 0.1% TFA (Merck Chromolith prep RP-18e column, 100×25 mm). Yield: 1.0 mg. Analytical HPLC: $t_R$=10.1 min (Merck Chromolith Performance RP-18e, 100×4.6 mm, water+0.1% TFA→acetonitrile/water+0.1% TFA 80:20, 25 min. ESI-MS (positive ion mode): m/z: calcd for [M]: 996.3; found: 995.8 [M]$^{1+}$.

iii) Generation of DIG-Cys-Ahx-Cy5

In an Erlenmeyer flask 1,2-Diamino-propane trityl resin (250 mg, 0.225 mmol, loading 0.9 mmol/g) was swelled with DMF (5 mL) for 30 min. Subsequently, a solution of Fmoc-Cys(Trt)-OH (395 mg, 0.675 mmol) in DMF (2 mL) and a solution of HATU (433 mg, 1.2375 mmol) and HOAt (164 mg, 1.2375 mmol) in DMF (8 mL) were added to the resin. To this suspension was added DIPEA (385 μL, 2.25 mmol) and the mixture was swirled for 16 h at ambient temperature, filtered, and washed repeatedly with DMF. After the coupling step, non-reacted amino groups were capped by treatment with a mixture of Ac$_2$O (20%) in DMF followed by a washing step with DMF. Removal of the N-terminal Fmoc group was accomplished by treatment of the resin with piperidine (20%) in DMF. Afterwards, the resin was washed thoroughly with DMF and isopropanol, and again DMF and was then treated with a solution of Cy5-Mono NHS-ester (25 mg, 0.0316 mmol) in 1% DIPEA in DMF (10 mL) for 16 h. After filtration and washing with DMF, the resin was treated with a mixture of trifluoroacetic acid, water and triisopropylsilane (9 mL:9 mL:1 mL) for 3 h. The cleavage solution was filtered, concentrated under reduced pressure, and the resulting solid was re-dissolved in water and lyophilized. Purification of the intermediate was accomplished by preparative reversed phase HPLC employing an acetonitrile/water gradient containing 0.1% TFA (Merck Chromolith prep RP-18e column, 100×25 mm) resulting in a blue solid after lyophilization. Analytical HPLC: $t_R$=6.2 min (Merck Chromolith Performance RP-18e, 100×4.6 mm, water+0.1% TFA→acetonitrile/water+0.1% TFA 80:20, 25 min. Subsequently, a portion of this intermediate (6.5 mg, 7.9 μmol) was dissolved in DMF (1 mL) and a solution of Dig-Amcap-OSu (5.2 mg, 7.9 μmol) in DMF (1 mL) and 1% triethylamine in DMF (2 mL) were added and the mixture was tumbled for 16 h. The solution was concentrated afterwards, and the target compound was purified by preparative reversed phase HPLC employing an acetonitrile/water gradient containing 0.1% TFA (Merck Chromolith prep RP-18e column, 100×25 mm). Yield: 3 mg. Analytical HPLC: $t_R$=8.7 min (Merck Chromolith Performance RP-18e, 100×4.6 mm, water+0.1% TFA→acetonitrile/water+0.1% TFA 80:20, 25 min. ESI-MS (positive ion mode): m/z: calcd for [M]: 1360.0; found: 1360.7 [M+H]$^{1+}$.

iv) Generation of Biotin-eda-Dy636

To a solution of biotin-ethylenediamine hydrobromide (2.14 mg, 5.83 µmol) in 0.1 M K$_3$PO$_4$ buffer (pH 8.0, 500 µL) was added a solution of Dy636-OSu (5 mg, 5.83 µmol) in 0.1 M K$_3$PO$_4$ buffer (pH 8.0, 500 µL) and the resulting mixture was tumbled for 2 h at ambient temperature, filtered, and the target compound was isolated by preparative reversed phase HPLC employing an acetonitrile/water gradient containing 0.1% TFA (Merck Chromolith prep RP-18e column, 100×25 mm). After lyophilization the Dy636-Ethylendiamin-Bi conjugate was obtained as a colorless solid (2.8 mg, 48% %). Analytical HPLC: $t_R$=8.5 min (Merck Chromolith Performance RP-18e, 100×4.6 mm, water+0.1% TFA→acetonitrile/water+0.1% TFA 80:20, 25 min); ESI-MS (positive ion mode): m/z: calcd for $C_{50}H_{65}N_6O_{10}S_3$: 1006.3; found: 1007.3 [M+H]$^+$.

v) Generation of Biotin-Ser-Dy636

Step 1: Biotin-O$_2$Oc-Ser-O$_2$Oc-DADOO-NH$_2$

On an O-bis-(aminoethyl)ethylene glycol trityl resin (176 mg, 0.125 mmol, loading 0.71 mmol/g, Novabiochem) Fmoc-O$_2$Oc-OH, Fmoc-Ser(tBu)-OH, Fmoc-O$_2$Oc-OH (all Iris Biotech), and DMTr-D-Biotin (Roche) were coupled consecutively. Peptide synthesis was performed according to established protocols (FastMoc 0.25 mmol) in an automated Applied Biosystems ABI 433A peptide synthesizer using Fmoc chemistry (as described for SEQ ID NO: 180).

After synthesis, the resin was washed thoroughly with DMF, methanol, dichloromethane, and dried under vacuum. Then, the resin was placed into an Erlenmeyer flask and treated with a mixture of trifluoroacetic acid, water and triisopropylsilane (9.5 mL:250 µL: 250 µL) for 2 h at room temperature. The cleavage solution was filtered and the peptide was precipitated by addition of cold (0° C.) diisopropyl ether (80 mL) to furnish a colorless solid, which was repeatedly washed with diisopropyl ether. The crude product was re-dissolved in water, lyophilized and subsequently purified by preparative reversed phase HPLC employing an acetonitrile/water gradient containing 0.1% TFA (Merck Chromolith prep RP-18e column, 100×25 mm) resulting in a colorless solid after lyophilization. Yield: 56 mg (60%). Analytical HPLC: $t_R$=4.5 min (Merck Chromolith Performance RP-18e, 100×3 mm, water+0.1% TFA→acetonitrile/water+0.1% TFA 80:20, 25 min. ESI-MS (positive ion mode): m/z: calcd for [M]: 751.9; found: 752.4 [M+H]+; 376.9 [M+2H]$^{2+}$.

Step 2: Biotin-O$_2$Oc-Ser-O$_2$Oc-DADOO-Dy-636 (Bi-Ser-Dy-636)

The peptide (5.3 mg, 7.0 µmol) was dissolved in 200 mM potassium phosphate buffer, pH 7.5 (583 µL). Dy-636 NHS-ester (4 mg, 4.7 µmol, Dyomics) was dissolved in water (583 µL) and added to the peptide solution. The reaction solution was stirred for 2 hours at room temperature and was subsequently purified by preparative reversed phase HPLC employing an acetonitrile/water gradient containing 0.1% TFA (Merck Chromolith prep RP-18e column, 100×25 mm) resulting in a blue solid after lyophilization. Yield: 3.9 mg (55%). Analytical HPLC: $t_R$=8.3 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 1472.8; found: 1472.8 [M+H]+; 737.0 [M+2H]$^{2+}$.

vi) Generation of Biotin-Cys-Dy636

Step 1: Biotin-O$_2$Oc-Cys-O$_2$Oc-DADOO-NH2

On an O-bis-(aminoethyl)ethylene glycol trityl resin (352 mg, 0.25 mmol, loading 0.71 mmol/g, Novabiochem) Fmoc-O$_2$Oc-OH, Fmoc-Cys(Trt)-OH, Fmoc-O$_2$Oc-OH (all Iris Biotech), and DMTr-D-Biotin (Roche) were coupled consecutively. Peptide synthesis was performed according to established protocols (FastMoc 0.25 mmol) in an automated Applied Biosystems ABI 433A peptide synthesizer using Fmoc chemistry (as described in for SEQ ID NO: 180).

After synthesis, the resin was washed thoroughly with DMF, methanol, dichloromethane, and dried under vacuum. Then, the resin was placed into an Erlenmeyer flask and treated with a mixture of trifluoroacetic acid, water and triisopropylsilane (9.5 mL:250 µL: 250 µL) for 2 h at room temperature. The cleavage solution was filtered and the peptide was precipitated by addition of cold (0° C.) diisopropyl ether (100 mL) to furnish a colorless solid, which was repeatedly washed with diisopropyl ether. The crude product was re-dissolved in water, lyophilized and subsequently purified by preparative reversed phase HPLC employing an acetonitrile/water gradient containing 0.1% TFA (Merck Chromolith prep RP-18e column, 100×25 mm) resulting in a colorless solid after lyophilization. Yield: 79 mg (41%). Analytical HPLC: $t_R$=5.3 min (Merck Chromolith Performance RP-18e, 100×3 mm, water+0.1% TFA→acetonitrile/water+0.1% TFA 80:20, 25 min. ESI-MS (positive ion mode): m/z: calcd for [M]: 767.9; found: 768.4 [M+H]+; 384.8 [M+2H]$^{2+}$.

Step 2: Biotin-O$_2$Oc-Cys(TNB)-O$_2$Oc-DADOO-NH$_2$

The peptide (30 mg, 39 µmol) was dissolved in 100 mM potassium phosphate buffer, pH 7.5 (4 mL) and 5,5'-dithiobis(2-nitrobenzoic acid) (77 mg, 195 µmol) was added. The mixture was stirred for 30 minutes at room temperature and subsequently purified by preparative reversed phase HPLC employing an acetonitrile/water gradient containing 0.1% TFA (Merck Chromolith prep RP-18e column, 100×25 mm) resulting in a yellow solid after lyophilization. Yield: 31 mg (83%). Analytical HPLC: $t_R$=5.4 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 965.1; found: 965.4 [M+H]+; 483.3 [M+2H]$^{2+}$.

Step 3: Biotin-O$_2$Oc-Cys(TNB)-O$_2$Oc-DADOO-Dy-636

The TNB protected peptide (1.35 mg, 1.4 µmol) was dissolved in 200 mM potassium phosphate buffer, pH 7.5 (291 µL). Dy-636 NHS-ester (1 mg, 1.2 µmol, Dyomics) was dissolved in water (291 µL) and added to the peptide solution. The reaction solution was stirred for 1 hour at room temperature and was subsequently purified by preparative reversed phase HPLC employing an acetonitrile/water gradient containing 0.1% TFA (Merck Chromolith prep RP-18e column, 100×25 mm) resulting in a blue solid after lyophilization. Yield: 1 mg (50%). Analytical HPLC: $t_R$=9.0 min (Merck Chromolith Performance RP-18e, 100×3 mm, water+0.025% TFA-acetonitrile/water+0.023% TFA 80:20, 25 min. ESI-MS (positive ion mode): m/z: calcd for [M]: 1686.0; found: 1686.7 [M+H]+; 844.2 [M+2H]$^{2+}$.

Step 4: Biotin-O$_2$Oc-Cys-O$_2$Oc-DADOO-Dy-636 (Bi-Cys-Dy-636)

The TNB protected and dye labeled peptide (1 mg, 0.6 µmol) was dissolved in a mixture of 200 mM potassium phosphate buffer, pH 7.5 (250 µL) and water (192 µL). 100 mM tris(2-carboxyethyl)phosphine hydrochloride solution (58 µL) was added and the reaction mixture was stirred for 30 minutes at room temperature. Purification was performed by preparative reversed phase HPLC employing an acetonitrile/water gradient containing 0.1% TFA (Merck Chromolith prep RP-18e column, 100×25 mm) resulting in a blue solid after lyophilization. Yield: 0.7 mg (79%). Analytical HPLC: $t_R$=8.6 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 1488.9; found: 1488.6 [M+H]+; 745.1 [M+2H]$^{2+}$.

vii) Generation of Biotin-Cys-Cy5
Step 1: Biotin-O$_2$Oc-Cys-O$_2$Oc-DADOO-NH2

On an O-bis-(aminoethyl)ethylene glycol trityl resin (352 mg, 0.25 mmol, loading 0.71 mmol/g, Novabiochem) Fmoc-O2Oc-OH, Fmoc-Cys(Trt)-OH, Fmoc-O2Oc-OH (all Iris Biotech), and DMTr-D-Biotin (Roche) were coupled consecutively. Peptide synthesis was performed according to established protocols (FastMoc 0.25 mmol) in an automated Applied Biosystems ABI 433A peptide synthesizer using Fmoc chemistry (as described for SEQ ID NO: 180).

After synthesis, the resin was washed thoroughly with DMF, methanol, dichloromethane, and dried under vacuum. Then, the resin was placed into an Erlenmeyer flask and treated with a mixture of trifluoroacetic acid, water and triisopropylsilane (9.5 mL:250 µL:250 µL) for 2 h at room temperature. The cleavage solution was filtered and the peptide was precipitated by addition of cold (0° C.) diisopropyl ether (100 mL) to furnish a colorless solid, which was repeatedly washed with diisopropyl ether. The crude product was re-dissolved in water, lyophilized and subsequently purified by preparative reversed phase HPLC employing an acetonitrile/water gradient containing 0.1% TFA (Merck Chromolith prep RP-18e column, 100×25 mm) resulting in a colorless solid after lyophilization. Yield: 79 mg (41%). Analytical HPLC: $t_R$=5.3 min (Merck Chromolith Performance RP-18e, 100×3 mm, water+0.1% TFA→acetonitrile/water+0.1% TFA 80:20, 25 min. ESI-MS (positive ion mode): m/z: calcd for [M]: 767.9; found: 768.4 [M+H]+; 384.8 [M+2H]$^{2+}$.

Step 2: Biotin-O$_2$Oc-Cys(TNB)-O$_2$Oc-DADOO-NH2

The peptide (30 mg, 39 µmol) was dissolved in 100 mM potassium phosphate buffer, pH 7.5 (4 mL) and 5,5'-dithiobis(2-nitrobenzoic acid) (77 mg, 195 µmol) was added. The mixture was stirred for 30 minutes at room temperature and subsequently purified by preparative reversed phase HPLC employing an acetonitrile/water gradient containing 0.1% TFA (Merck Chromolith prep RP-18e column, 100×25 mm) resulting in a yellow solid after lyophilization. Yield: 31 mg (83%). Analytical HPLC: $t_R$=5.4 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 965.1; found: 965.4 [M+H]+; 483.3 [M+2H]$^{2+}$.

Step 3: Biotin-O$_2$Oc-Cys(TNB)-O$_2$Oc-DADOO-Cy5

The TNB protected peptide (9.9 mg, 10.3 µmol) was dissolved in 200 mM potassium phosphate buffer, pH 7.5 (1026 µL). Cy5-Mono NHS-ester (6.5 mg, 8.2 µmol, GE Healthcare) was dissolved in water (1026 µL) and added to the peptide solution. The reaction solution was stirred for 2 hours at room temperature and was subsequently purified by preparative reversed phase HPLC employing an acetonitrile/water gradient containing 0.1% TFA (Merck Chromolith prep RP-18e column, 100×25 mm) resulting in a blue solid after lyophilization. Yield: 10 mg (80%). Analytical HPLC: $t_R$=7.2 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 1603.9; found: 1604.9 [M+H]+; 803.1 [M+2H]$^{2+}$.

Step 4: Biotin-O$_2$Oc-Cys-O$_2$Oc-DADOO-Cy5 (Bi-Cys-Cy5)

The TNB protected and dye labeled peptide (10 mg, 6.1 µmol) was dissolved in a mixture of 200 mM potassium phosphate buffer, pH 7.5 (1522 µL) and water (1218 µL). 100 mM tris(2-carboxyethyl)phosphine hydrochloride solution (304 µL) was added and the reaction mixture was stirred for 30 minutes at room temperature. Purification was performed by preparative reversed phase HPLC employing an acetonitrile/water gradient containing 0.1% TFA (Merck Chromolith prep RP-18e column, 100×25 mm) resulting in a blue solid after lyophilization. Yield: 7.6 mg (86%). Analytical HPLC: $t_R$=6.4 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 1406.8; found: 1406.8 [M+H]+; 704.0 [M+2H]$^{2+}$.

viii) Generation of Biotin-Ser-Cy5
Step 1: Biotin-O$_2$Oc-Ser-O$_2$Oc-DADOO-NH2

On an O-bis-(aminoethyl)ethylene glycol trityl resin (176 mg, 0.125 mmol, loading 0.71 mmol/g, Novabiochem) Fmoc-O$_2$Oc-OH, Fmoc-Ser(tBu)-OH, Fmoc-O$_2$Oc-OH (all Iris Biotech), and DMTr-D-Biotin (Roche) were coupled consecutively. Peptide synthesis was performed according to established protocols (FastMoc 0.25 mmol) in an automated Applied Biosystems ABI 433A peptide synthesizer using Fmoc chemistry (as described for SEQ ID NO: 180).

After synthesis, the resin was washed thoroughly with DMF, methanol, dichloromethane, and dried under vacuum. Then, the resin was placed into an Erlenmeyer flask and treated with a mixture of trifluoroacetic acid, water and triisopropylsilane (9.5 mL:250 µL:250 µL) for 2 h at room temperature. The cleavage solution was filtered and the peptide was precipitated by addition of cold (0° C.) diisopropyl ether (80 mL) to furnish a colorless solid, which was repeatedly washed with diisopropyl ether. The crude product was re-dissolved in water, lyophilized and subsequently purified by preparative reversed phase HPLC employing an acetonitrile/water gradient containing 0.1% TFA (Merck Chromolith prep RP-18e column, 100×25 mm) resulting in a colorless solid after lyophilization. Yield: 56 mg (60%). Analytical HPLC: $t_R$=4.5 min (Merck Chromolith Performance RP-18e, 100×3 mm, water+0.1% TFA→acetonitrile/water+0.1% TFA 80:20, 25 min. ESI-MS (positive ion mode): m/z: calcd for [M]: 751.9; found: 752.4 [M+H]+; 376.9 [M+2H]$^{2+}$.

Step 2: Biotin-O$_2$Oc-Ser-O$_2$Oc-DADOO-Cy5 (Bi-Ser-Cy5)

The peptide (5.7 mg, 7.6 µmol) was dissolved in 200 mM potassium phosphate buffer, pH 7.5 (789 µL). Cy5-Mono NHS-ester (5 mg, 6.3 µmol, GE Healthcare) was dissolved in water (789 µL) and added to the peptide solution. The reaction solution was stirred for 2 hours at room temperature and was subsequently purified by preparative reversed phase HPLC employing an acetonitrile/water gradient containing 0.1% TFA (Merck Chromolith prep RP-18e column, 100×25 mm) resulting in a blue solid after lyophilization. Yield: 6 mg (58%). Analytical HPLC: $t_R$=6.1 min (Merck Chromolith Performance RP-18e, 100×3 mm, water+0.025% TFA→acetonitrile/water+0.023% TFA 80:20, 25 min. ESI-MS (positive ion mode): m/z: calcd for [M]: 1390.72; found: 1391.2 [M+H]$^+$.

Example 9

Binding of Recombinant Humanized Anti-Biotin Antibody to Biotin-Labeled Compound (Haptenylated Compound)

In order to determine whether the humanization procedure and the subsequent introduction of cysteine mutations resulted in derivatives that had retained full binding activity the following experiments were performed.

The binding properties of the recombinant anti-biotin antibody derivatives were analyzed by biolayer interferometry (BLI) technology using an Octet QK instrument (Fortebio Inc.). This system is well established for the study of molecule interactions. BLi-technology is based on the measurement of the interference pattern of white light reflected from the surface of a biosensor tip and an internal reference. Binding of molecules to the biosensor tip is resulting in a shift of the interference pattern which can be measured. To analyze if the humanization procedure described above diminished the ability of the anti-biotin antibody to bind to biotin, the properties of the chimeric and the humanized versions of the antibody in their ability to bind to a biotinylated protein were compared directly. Binding studies were performed by capturing anti-biotin antibody on anti-huIgG Fc antibody Capture (AHC) Biosensors (Fortebio Inc.). First, biosensors were incubated in an antibody solution with a concentration of 0.5 mg/ml in 20 mM histidine, 140 mM NaCl, pH 6.0 for 1 min. Thereafter, the biosensors were incubated for 1 min. in 1×PBS pH 7.4 to reach a stable baseline. Binding was measured by incubating the antibody-coated biosensors in a solution containing biotinylated protein with a concentration of 0.06 mg/ml in 20 mM histidine, 140 mM NaCl, pH 6.0 for 5 min. Dissociation was monitored for 5 min. in 1×PBS pH 7.4. The resulting binding curves for chimeric and humanized anti-biotin antibodies were compared directly.

The humanized version of the antibody showed equal or even better binding of the biotinylated antigen than the chimeric antibody. The same is true for the humanized antibody with the Cys mutation at Kabat position VH53. The biotinylated protein showed residual unspecific binding to the biosensors which was reduced when the biosensors were coated with Herceptin, which does not bind biotin. Thus, the functionality of the anti-biotin antibody was retained in its humanized variant (which is defined by the sequences as depicted in SEQ ID NO: 44 and 48, SEQ ID NO: 60 and 64).

Surface Plasmon Resonance

Surface plasmon resonance measurement was performed on a BIAcore® T200 instrument (GE Healthcare Biosciences AB, Sweden) at 25° C. Around 4300 resonance units (RU) of the capturing system (10 µg/ml Anti-human Capture (IgG Fc) from Human Antibody Capture Kit, BR-1008-39, GE Healthcare Biosciences AB, Sweden) were coupled on a CM3 chip (GE Healthcare, BR-1005-36) at pH 5.0 by using the standard amine coupling kit supplied by GE Healthcare (BR-1000-50). The running buffer for amine coupling was HBS-N (10 mM HEPES, pH 7.4, 150 mM NaCl, GE Healthcare, BR-1006-70). Running and dilution buffer for the followed binding study was PBS-T (10 mM phosphate buffered saline including 0.05% Tween 20) pH 7.4. The humanized anti-biotin antibody was captured by injecting a 2 nM solution for 60 sec at a flow rate of 5 µl/min. Biotinylated siRNA was diluted with PBS-T at concentrations of 0.14-100 nM (1:3 dilution series). Binding was measured by injecting each concentration for 180 sec at a flow rate of 30 µl/min, dissociation time 600 sec. The surface was regenerated by 30 sec washing with a 3 M $MgCl_2$ solution at a flow rate of 5 µl/min. The data were evaluated using BIAevaluation software (GE Healthcare Biosciences AB, Sweden). Bulk refractive index differences were corrected by subtracting the response obtained from an anti-human IgG Fc surface. Blank injections were also subtracted (=double referencing). For calculation of KD and kinetic parameters the Langmuir 1:1 model was used.

Kinetic binding analysis by surface plasmon resonance (SPR) was carried out for humanized anti-biotin antibody SEQ ID NO: 44 and 48 and humanized anti-biotin antibody VH53C SEQ ID NO: 60 and 64. Anti-biotin antibodies at a concentration of 2 nM were captured by anti-human IgG Fc antibody which was bound to a CM3 sensor chip. Binding of biotinylated siRNA (Mw: 13868 Da) was recorded at the concentrations 0.41, 1.23, 3.7, 11.1, 33.3, 100 and 300 nM. Measurements were carried out in duplicates. The calculated $K_D$ for humanized anti-biotin antibody and humanized anti-biotin antibody VH53C were 0.633 nM and 0.654 nM, respectively.

Example 10

Generation of Non-Covalent Complexes of Haptenylated Compounds with Anti-Hapten Antibodies General Method:

The generation of complexes of anti-hapten antibodies with haptenylated compounds (=haptens conjugated to a payload) shall result in defined complexes and it shall be assure that the compound (=payload) in these complexes retains its activity. For the generation of complexes of haptenylated compounds with the respective anti-hapten antibody the haptenylated compound was dissolved in H20 to a final concentration of 1 mg/ml. The antibody was concentrated to a final concentration of 1 mg/ml (4.85 µM) in 20 mM histidine buffer, 140 mM NaCl, pH=6.0. Haptenylated payload and antibody were mixed to a 2:1 molar ratio (compound to antibody) by pipetting up and down and incubated for 15 minutes at RT.

Alternatively, the haptenylated compound was dissolved in 100% DMF to a final concentration of 10 mg/ml. The antibody was concentrated to a final concentration of 10 mg/ml in 50 mM Tris-HCl, 1 mM EDTA, pH=8.2. Haptenylated compound and antibody were mixed to a 2.5:1 molar ratio (compound to antibody) by pipetting up and down and incubated for 60 minutes at RT and 350 rpm.

Exemplary Method for the Formation of Complexes of Haptenylated Fluorescent Dyes and Anti-Hapten Antibodies-Non-Covalent Digoxigenin-Cy5 Complex Humanized and murine anti-digoxigenin antibody or bispecific anti-digoxigenin antibody derivatives were used as antibody components. For the generation of complexes of digoxigenylated Cy5 with the anti-digoxigenin antibodies the Cy5-digoxigenin conjugate was dissolved in PBS to a final concentration of 0.5 mg/ml. The antibody was used in a concentration of 1 mg/ml (about M) in a buffer composed of 20 mM histidine and 140 mM NaCl, pH 6. Digoxigenylated Cy5 and antibody were mixed at a 2:1 molar ratio (digoxigenylated Cy5 to antibody). This procedure resulted in a homogenous preparation of complexes of defined composition.

The complexation reaction can be monitored by determining the fluorescence (650/667 nm) of the antibody-associated fluorophore on a size exclusion column. The results of these experiments demonstrate that complexation only occurs if the antibody contains binding specificities for digoxigenin. Antibodies without binding specificities for digoxigenin do not bind the digoxigenin-Cy5 conjugate. An increasing signal can be observed for bivalent anti-digoxigenin antibodies until a digoxigenin-Cy5 conjugate to antibody ratio of 2:1. Thereafter, the composition dependent fluorescence signals reach a plateau.

Exemplary Method for the Formation of Complexes of Haptenylated Fluorescent Dyes and Anti-Hapten Antibodies-Biotin-Cy5/Chimeric Anti-Biotin Antibody (Human IgG Subclass) Complex For the generation of complexes of biotin-derivatized-Cy5 (Biotin-Cys-Cy5) containing a cysteinylated linker, 0.16 mg of Biotin-Cys-Cy5 were dissolved in 100% DMF to a concentration of 10 mg/ml. 1 mg of the antibody was used in a concentration of 10.1 mg/ml (about 69 µM) in a buffer composed of 50 mM Tris-HCl, 1 mM EDTA, pH 8.2. Biotin-Cys-Cy5 and antibody were mixed at a 2.5:1 molar ratio (Biotin-Cys-Cy5 to antibody) and incubated for 60 min at RT, shaken at 350 rpm. The resulting conjugate was analyzed by SDS-PAGE as described in Example 11a. Detection of fluorescence was carried out as described in Example 11a.

Exemplary Method for the Formation of Conjugates of Biotinylated Fluorescent Dyes and Anti-Biotin Antibodies-Biotin-Ser-Cy5/Humanized Anti-Biotin Antibody:

For the generation of complexes of biotin-derivatized-Cy5 (Biotin-Ser-Cy5) containing a serine residue within the linker, 0.61 mg of Biotin-Ser-Cy5 were dissolved in 20 mM histidine, 140 mM NaCl, pH 6.0 to a concentration of 10 mg/ml. 18.5 mg of the humanized anti-biotin antibody was used in a concentration of 10 mg/ml (about 69 µM) in a buffer composed of 50 mM Tris-HCl, 1 mM EDTA, pH 8.2. Biotin-Ser-Cy5 and antibody were mixed at a 2.5:1 molar ratio (Biotin-Ser-Cy5 to antibody) and incubated for 60 min at RT, shaken at 350 rpm. The sample was then subjected to size exclusion chromatography using Superdex 200 16/60 high load prep grade column (GE Healthcare) with a flow rate of 1.5 ml/min and 20 mM histidine, 140 mM NaCl, pH 6.0 as the mobile phase. Peak fractions were collected and analyzed by SDS-PAGE for purity. The dye to antibody ratio was calculated by (1) measuring the absorbance of the samples at the wavelength 280 nm (protein) and 650 nm (Cy5); (2) using the formula: A650 of labeled protein/E (Cy5)*protein concentration (M)=moles dye per mole protein, where $c(Cy5)=250000\ M^{-1}\ cm^{-1}$, $A_{650}$ of the complex=47.0 and the protein concentration is 86.67 µM. The resulting ratio of dye to antibody molecule was 2.17 which indicates that all antibody paratopes are saturated with Biotin-Cy5 molecules.

Exemplary Method for the Formation of Complexes of Haptenylated Polypeptides and Anti-Hapten Antibodies—Digoxigenin-PYY(3-36)/Anti-Digoxigenin Antibody Complex For the generation of non-covalent complexes of digoxigenylated polypeptides with an anti-digoxigenin antibody the murine hybridoma-derived antibody (lyophilisate from 10 mM $KPO_4$, 70 mM NaCl; pH 7.5) was dissolved in 12 ml water and dialyzed against a solution comprising 20 mM histidine, 140 mM NaCl, pH 6.0 to yield 300 mg ($2\times10^{-6}$ mol) in 11 ml buffer (c=27.3 mg/ml). Digoxigenin-PYY(3-36) conjugate (11.57 mg, $4\times10^{-6}$ mol, 2 eq.) was added in 4 portions of 2.85 mg within 1 h and incubated for another hour at room temperature. After completion of the complexation reaction, the complexes were purified by size exclusion chromatography via a Superdex 200 26/60 GL column (320 ml) in 20 mM histidine, 140 mM NaCl, at pH 6.0 at a flow rate of 2.5 ml/min. The eluted complex was collected in 4 ml fractions, pooled and sterilized over a 0.2 µm filter to give 234 mg of the complex at a concentration of 14.3 mg/ml. In a similar manner, for generation of complexes of the humanized anti-digoxigenin antibody the antibody was adjusted to a concentration of 10.6 mg/ml (9.81 mg, $6.5\times10^{-8}$ mol in 0.93 ml) in 20 mM histidine, 140 mM NaCl, pH 6.0. 0.57 mg=$1.97\times10^{-7}$ mol=3.03 eq. of the digoxigenylated polypeptide (DIG-PYY) were added to the antibody solution as lyophilisate. Polypeptide and antibody were incubated for 1.5 hrs. at room temperature. The excess of polypeptide was removed by size exclusion chromatography via a Superose 6 10/300 GL column in 20 mM histidine, 140 mM NaCl, at pH 6.0 at a flow rate of 0.5 ml/min. The eluted complex was collected in 0.5 ml fractions, pooled and sterilized over a 0.2 µm filter to give 4.7 mg of the complex at a concentration of 1.86 mg/ml.

The resulting haptenylated polypeptide-anti-hapten antibody complex was defined as monomeric IgG-like molecule via the occurrence of a single peak in a size exclusion chromatography. The resulting complex was defined as monomeric IgG-like molecule, carrying two Digoxigenin-PYY derivatives per antibody molecule. The defined composition of these peptide complexes was confirmed by size exclusion chromatography, which also indicated the absence of protein aggregates. The defined composition (and 2:1 polypeptide to protein ratio) of these bispecific peptide complexes was further confirmed by SEC-MALLS (Size exclusion chromatography-Multi Angle Light Scattering). For SEC-MALLS analysis, 100-500 µg of the respective sample was applied to a Superdex 200 10/300 GL size exclusion column with a flow rate of 0.25-0.5 ml/min with 1×PBS pH 7.4 as mobile phase. Light scattering was detected with a Wyatt MiniDawn TREOS/QELS detector, the refractive index was measured with a Wyatt Optilab rEX-detector. Resulting data was analyzed using the software ASTRA (version 5.3.4.14). The results of SEC-MALLS analyses provide information about the mass, radius and size of the complex. These data were then compared with those of the corresponding non-complexed antibody. The results of these experiments demonstrate that exposure of Digoxigenylated-PYY to the anti-digoxigenin antibody results in complexes that contain two Digoxigenin-PYY derivatives per one antibody molecule. Thus, digoxigenylated PYY can be complexed with the anti-digoxigenin antibody at defined sites (binding region) and with a defined stoichiometry.

Characterization of the complex by surface plasmon resonance studies provided additional evidence that the complexation reaction generated defined and completely complexed molecules. The anti-digoxigenin antibody can be bound to the SPR chip which results in signal increases. Subsequent addition of digoxigenin-PYY conjugate results in further signal increases until all binding sites are completely occupied. At these conditions, addition of more Digoxigenin-PYY does not increase the signal further. This indicates that the complexing reaction is specific and that the signals are not caused by non-specific stickiness of the digoxigenylated polypeptide.

Exemplary Method for the Formation of Complexes of Haptenylated Polypeptides and Anti-Hapten Antibodies-Ac-PYY-PEG3-Cys-B-Ala-Biot/Chimeric Anti-Biotin Antibody Complex For the generation of non-covalent complexes of biotinylated-PYY-polypeptide containing a cysteinylated linker, 0.19 mg of Ac-PYY-PEG3-Cys-B-Ala-Biot were dissolved in 100% DMF to a concentration of 10 mg/ml. The antibody was used in a concentration of 10.7 mg/ml (about 73 µM) in a buffer composed of 50 mM Tris-HCl, 1 mM EDTA, pH 8.2. Ac-PYY-PEG3-Cys-B-Ala-Biot and antibody were mixed at a 2.5:1 molar ratio (Ac-PYY-PEG3-Cys-B-Ala-Biot to antibody) and incubated for 60 min at RT and 350 rpm. The resulting complex was defined as monomeric IgG-like molecule via the occurrence of a single peak in a size exclusion chromatography (95% monomer). The resulting complex was further analyzed by SDS-PAGE and subsequent Western Blot analysis. 10 µg of the complex were mixed with 4×LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 µm pore size, Invitrogen) for 40 min at 25V and 160 mA. The membrane was blocked in 1% (w/v) skim milk in 1×PBST (1×PBS+0.1% Tween20) for 1 h at RT. The membrane was washed 3× for 5 min in 1×PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Haptenylated Polypeptides and Anti-Hapten Antibodies-Ac-PYY-PEG3-Cys-PEG2-Biot)/Chimeric Anti-Biotin Antibody Complex For the generation of non-covalent complexes of biotinylated-PYY-polypeptide containing a cysteinylated linker, 0.16 mg of Ac-PYY-PEG3-Cys-PEG2-Biot were dissolved in 100% DMF to a concentration of 10 mg/ml. The antibody was used in a concentration of 10.7 mg/ml (about 73 µM) in a buffer composed of 50 mM Tris-HCl, 1 mM EDTA, pH 8.2. Ac-PYY-PEG3-Cys-PEG2-Biot and antibody were mixed at a 2.5:1 molar ratio (Ac-PYY-PEG3-Cys-PEG2-Biot to antibody) and incubated for 60 min at RT and 350 rpm. The resulting complex was defined as 63% monomeric IgG-like molecule and 37% dimeric soluble aggregates via size exclusion chromatography. The resulting complex was further analyzed by SDS-PAGE and subsequent Western Blot analysis. 10 µg of the complex were mixed with 4×LDS sample buffer (Invitrogen) and incubated at 95° C. for 5 min. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 µm pore size, Invitrogen) for 40 min at 25V and 160 mA. The membrane was blocked in 1% (w/v) skim milk in 1×PBST (1×PBS+0.1% Tween20) for 1 h at RT. The membrane was washed 3× for 5 min in 1×PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Haptenylated Polypeptides and Anti-Hapten Antibodies-Ac-PYY(PEG3-Cys-PEG2-5-Fluo)/Chimeric Anti-Fluorescein Antibody Complex For the generation of non-covalent complexes of fluorescein-conjugated-PYY-polypeptide containing a cysteinylated linker, 0.33 mg of Ac-PYY(PEG3-Cys-PEG2-5-Fluo were dissolved in 100% DMF to a concentration of 10 mg/ml. The antibody was used in a concentration of 9.99 mg/ml (about 68 µM) in a buffer composed of 50 mM Tris-HCl, 1 mM EDTA, pH 8.2. Ac-PYY(PEG3-Cys-PEG2-5-Fluo and antibody were mixed at a 2.5:1 molar ratio (Ac-PYY(PEG3-Cys-PEG2-5-Fluo) to antibody) and incubated for 60 min at RT and 350 rpm. The resulting complex was defined as 76% monomeric IgG-like molecule and 24% dimeric soluble aggregates via size exclusion chromatography. The resulting complex was further analyzed by SDS-PAGE and subsequent detection of fluorescein-related fluorescence in the polyacrylamide-gel. 8 µg of the complex were mixed with 4×LDS sample buffer (Invitrogen) and incubated at 95° C. for 5 min. Fluorescein-related fluorescence was recorded using a LumiImager F1 device (Roche) at an excitation wavelength of 645 nm.

Example 11

Generation of Defined Covalent Conjugates of Haptenylated Dyes or Polypeptides with an Anti-Hapten Antibody VH52bC/VH53C in the Presence of Redox Agents Exemplary Method for the Formation of Conjugates of Haptenylated Fluorescent Dyes and Anti-Hapten Antibodies-Dig-Cys-Ahx-Cy5/Anti-Digoxigenin Antibody VH52bC The generation of covalent conjugates of anti-hapten antibodies and haptenylated fluorescent dyes containing a cysteine-linker results in defined conjugates where a disulfide bridge is formed at a specific position between VH52bC in the CDR2 of the anti-hapten antibody and the cysteine in the linker between the hapten and the fluorescent dye. The conjugation reaction was carried out in the presence of redox reagents. Dig-Cys-Ahx-Cy5 was dissolved in 20 mM histidine, 140 mM NaCl, pH 6.0. Solubilization was facilitated by drop wise addition of 10% (v/v) acetic acid. The final concentration was adjusted to 0.4 mg/ml. The anti-digoxigenin antibody VH52bC in 20 mM histidine, 140 mM NaCl, pH 6.0 was brought to a concentration of 10 mg/ml. An anti-digoxigenin antibody was used as a control and was treated the same way as anti-digoxigenin antibody VH52bC. 4.7 nmol of each antibody was mixed with 2.5 molar equivalents of Dig-Cys-Ahx-Cy5. This was achieved by adding 11.7 nmol of this substance in 4 portions (2.9 nmol each) every 15 min. In between these additions, the samples were incubated at 25° C. while gently shaking. After addition of the last portion, 0.64 nmol of each antibody-Dig-Cys-Ahx-Cy5 complex was transferred to buffer containing the following redox reagents: 3 mM DTE (Dithioerythritol)+10 mM GSSG (oxidized Glutathione), 0.3 mM DTE+1 mM GSSG and 0.03 mM DTE+0.1 mM GSSG. All samples were incubated for 15 min in these conditions. After the incubation, samples were split into half (0.34 nmol each) and prepared for SDS gel electrophoresis. For this, 4×LDS sample buffer (Invitrogen) was added. For each sample also a reduced version was prepared by adding 10× NuPAGE sample reducing agent (Invitrogen). All samples were incubated at 70° C. for 5 min before electrophoresis on a 4-12% Bis-Tris polyacrylamide gel (NuPAGE, Invitrogen) with 1×MOPS buffer (Invitrogen). Cy5-related fluorescence in the gel was detected with a LumiImager F1 device (Roche) at an excitation wavelength of 645 nm. After detection of fluorescence, the gel was stained with SimplyBlue SafeStain (Invitrogen). Gels are shown in FIG. 8.

Site-specific disulfide bond formation was shown for anti-digoxigenin antibody VH52bC (FIG. 8, gels on top, lanes 1 A-C) with a low background fluorescence signal when anti-digoxigenin antibody without a cysteine in CDR2 was used (lanes 2 A-C). The background signals in the control reactions can be explained by coupling of Dig-Cys-Ahx-Cy5 to cysteines that are normally involved in the formation of antibody-interchain disulfide bonds. Increasing amounts of redox reagents substantially reduce disulfide bridges that connect antibody heavy and light chains, producing mainly ¾ antibodies (−1×LC), HC-dimers (−2×LC) and ½ antibodies (1×HC+1×LC). On the bottom of the gel fluorescence of Dig-Cys-Ahx-Cy5 that was not covalently linked to the antibody can be detected. The gels on the bottom of FIG. 8 show, that upon reduction of the samples, no Cy5-related fluorescence is detectable near the antibody heavy and light chains, indicating that the covalent linkage was indeed formed by a disulfide bridge. Coomassie stains of each gel show that the total amount of protein in each lane was equal.

Exemplary Method for the Formation of Conjugates of Haptenylated Fluorescent Dyes and Anti-Hapten Antibodies-Dig-Cys-Cy5/Anti-Digoxigenin Antibody VH52bC Dig-Cys-Cy5 was dissolved in 8.3 mM HCl, 10% (v/v) DMF to a final concentration of 3.25 mg/ml. The anti-digoxigenin antibody VH52bC antibody in 20 mM histidine, 140 mM NaCl, pH 6.0 was brought to a concentration of 15 mg/ml. anti-digoxigenin antibody was used as a control and was treated the same way as anti-digoxigenin antibody VH52bC. 13.3 nmol of each antibody was mixed with 2 molar equivalents of Dig-Cys-Cy5 at a final antibody concentration of 10 mg/ml in the presence of 1 mM GSH (reduced glutathione) and 5 mM GSSG (oxidized glutathione). This was achieved by adding 26.6 nmol of this substance in 2 portions every 5 min. In between these additions, the samples were incubated at RT while gently stirred. After addition of the last portion, the samples were incubated for 1 h at RT. The efficiency of the coupling reaction was evaluated by SDS-PAGE and subsequent recording of the Cy5-related fluorescence signal. 5, 10 and 20 μg of each sample were prepared for SDS-PAGE. For this, 4×LDS sample buffer (Invitrogen) was added. All samples were incubated at 70° C. for 5 min before electrophoresis on a 4-12% Bis-Tris polyacrylamide gel (NuPAGE, Invitrogen) with 1×MOPS buffer (Invitrogen). Cy5-related fluorescence in the gel was detected with a Lumilmager F1 device (Roche) at an excitation wavelength of 645 nm. After detection of fluorescence, the gel was stained with Simply-Blue SafeStain (Invitrogen).

Exemplary Method for the Formation of Conjugates of Haptenylated Polypeptides and Anti-Hapten Antibodies-PEG3-PYY(PEG3-Cys-4Abu-Dig)/Humanized Anti-Digoxigenin Antibody VH52bC For the generation of conjugates of digoxigenin-derivatized-PYY-polypeptide containing a cysteinylated linker, 1.4 mg of PEG3-PYY(PEG3-Cys-4Abu-Dig) were dissolved in 100% DMF to a concentration of 10 mg/ml. 1 mg of the antibody was used in a concentration of 10 mg/ml (about 68 μM) in a buffer composed of 5 mM Tris-HCl, 1 mM EDTA, 1 mM GSH, 5 mM GSSG, pH 8.2. PEG3-PYY(PEG3-Cys-4Abu-Dig) and antibody were mixed at a 2:1 molar ratio (PEG3-PYY(PEG3-Cys-4Abu-Dig) to antibody) and incubated for 60 min at RT, stirred at 100 rpm. The resulting conjugate was analyzed by mass spectrometry. 43% of the detected species was identified as antibody coupled to 2 polypeptide molecules, 46% was antibody coupled to 1 polypeptide molecule and 11% was identified as uncoupled antibody.

Example 12

Generation of Defined Covalent Conjugates of Haptenylated Dyes and Polypeptides with an Anti-Hapten Antibody VH52bC/VH53C in the Absence of Redox Agents For the generation of covalent anti-hapten antibody/haptenylated polypeptide or haptenylated dye disulfide-linked conjugates it is necessary to (i) couple the hapten (e.g. digoxigenin, fluorescein, biotin or theophylline) via a suitable reactive group (such as e.g. cysteine, maleimide) containing linkers to the polypeptide or dye that allows the polypeptide to be exposed above the antibody surface and hence to retain its activity, and (ii) generate covalent site specific conjugates of the haptenylated polypeptides with the anti-hapten antibody with a cysteine mutation (=antibody VH52bC/VH53C) in which the biological activity of the polypeptide is retained, and (iii) to carry out the reaction in the absence of a reducing agent in order to avoid the reduction of antibody interchain disulfide bridges.

General Method:

The generation of conjugates of anti-hapten antibodies with haptenylated compounds shall result in conjugates with defined stoichiometry and it shall be assured that the compound in these conjugates retains its activity. For the generation of conjugates of haptenylated compounds with the respective anti-hapten antibody the haptenylated compound was dissolved in 100% DMF to a final concentration of 10 mg/ml. The anti-hapten antibody VH52bC/VH53C was brought to a concentration of 10 mg/ml in 50 mM Tris-HCl, 1 mM EDTA, pH=8.2. Haptenylated compound and anti-hapten antibody VH52bC/VH53C were mixed in a 2.5:1 molar ratio (compound to antibody) by pipetting up and down and incubated for 60 minutes at RT and 350 rpm.

A polypeptide conjugated to the hapten via a cysteine containing linker is termed hapten-Cys-polypeptide or polypeptide-Cys-hapten in the following. The polypeptide may either have a free N-terminus or a capped N-terminus e.g. with an acetyl-group (Ac-polypeptide-Cys-hapten) or a PEG-residue (PEG-polypeptide-Cys-hapten).

A fluorescent dye conjugated to the hapten via a cysteine containing linker is termed dye-Cys-hapten or hapten-Cys-dye in the following.

Exemplary Method for the Formation of Conjugates of Haptenylated Fluorescent Dyes and Anti-Hapten Antibodies-Dig-Cys-Ahx-Cy5/Anti-Digoxigenin Antibody VH52bC Samples were prepared exactly as described in Example 11 a, with the difference that antibody-Dig-Cys-Ahx-Cy5 complexes were transferred to buffer containing either no redox compounds, 0.1 mM GSSG (oxidized glutathione) or 1 mM GSSG. The resulting fluorescence-scanned and Coomassie stained polyacrylamide gels are shown in FIG. 9. All three conditions show a similar specificity for site-specific disulfide bond formation (FIG. 9, top gels, lanes 1 A-C) with a low level of background reactions (FIG. 9, lanes 2 A-C). This confirms that formation of the disulfide bond can be accomplished without the need of reducing agents. This significantly stabilizes the antibody/reduces antibody disintegration, as only residual amounts of ¾ antibodies (−1× LC), HC-dimers (−2×LC) and ½ antibodies (1×HC+1×LC) are detected in comparison to Example 11.

Exemplary Method for the Formation of Conjugates of Haptenylated Fluorescent Dyes and Anti-Hapten Antibodies-Dig-Cys-Cy5/Anti-Digoxigenin Antibody VH52bC Samples were prepared exactly as described in Example 11b, with the difference that 13.3 nmol of antibody was mixed with 2 molar equivalents of Dig-Cys-Cy5 at a final antibody concentration of 10 mg/ml in the absence of redox reagents.

Exemplary Method for the Formation of Conjugates of Haptenylated Fluorescent Dyes and Anti-Hapten Antibodies-Biotin-Cys-Cy5/Chimeric Anti-Biotin Antibody VH53C For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the anti-biotin antibody VH53C was used in a concentration of 9.7 mg/ml (about 68 μM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 11a. Detection of fluorescence was carried out as described in Example 11a.

Exemplary Method for the Formation of Conjugates of Haptenylated Fluorescent Dyes and Anti-Hapten Antibodies-Biotin-Cys-Cy5/Humanized Anti-Biotin Antibody VH53C For the generation of conjugates of biotin-derivatized-Cy5 containing a cysteinylated linker, 0.16 mg of Biotin-Cys-Cy5 were dissolved in 100% DMF to a concentration of 10 mg/ml. 1 mg of the humanized anti-biotin antibody VH53C was used in a concentration of 7.4 mg/ml (about 51 µM) in a buffer composed of 50 mM Tris-HCl, 1 mM EDTA, pH 8.2. Biotin-Cys-Cy5 and antibody were mixed at a 2.5:1 molar ratio (Ac-Biotin-Cys-Cy5 to antibody) and incubated for 60 min at RT, shaken at 350 rpm. The resulting conjugate was analyzed by SDS-PAGE as described in Example 11a. Detection of fluorescence was carried out as described in Example 11a.

Exemplary Method for the Formation of Conjugates of Haptenylated Polypeptides and Anti-Hapten Antibodies-Ac-PYY(PEG3-Cys-4Abu-Dig)/Humanized Anti-Digoxigenin Antibody VH52bC For the generation of conjugates of digoxigenin-derivatized-PYY-polypeptide containing a cysteinylated linker, 2.4 mg of Ac-PYY(PEG3-Cys-4Abu-Dig) were dissolved in 20% acetate to a concentration of 5 mg/ml. 10 mg of the humanized anti-digoxigenin antibody VH52bC (68.4 nmol) was used in a concentration of 19.5 mg/ml (about 133 µM) in a buffer composed of 20 mM histidine, 140 mM NaCl, pH 6.0. Ac-PYY(PEG3-Cys-4Abu-Dig) and antibody were mixed at a 2:1 molar ratio (Ac-PYY(PEG3-Cys-4Abu-Dig) to antibody) and incubated for 60 min at RT, stirred at 100 rpm. The resulting conjugate was analyzed by mass spectrometry. 7.4% of the detected species was identified as antibody coupled to 2 peptide molecules, 40% was antibody coupled to 1 peptide molecule and 52% was identified as uncoupled antibody.

Exemplary Method for the Formation of Conjugates of Haptenylated Polypeptides and Anti-Hapten Antibodies-Ac-PYY(PEG3-Cys-βAla-Biot)/Chimeric Anti-Biotin Antibody VH53C For the generation of conjugates of biotin-derivatized-PYY-polypeptide containing a cysteinylated linker, 0.19 mg of Ac-PYY(PEG3-Cys-ßAla-Biot) were dissolved in 100% DMF to a concentration of 10 mg/ml. 1 mg of the chimeric anti-biotin antibody VH53C was used in a concentration of 9.7 mg/ml (about 67 µM) in a buffer composed of 50 mM Tris-HCl, 1 mM EDTA, pH 8.2. Ac-PYY[PEG3-Cys-βAla-Biot and antibody were mixed at a 2.5:1 molar ratio (Ac-PYY[PEG3-Cys-ßAla-Biot] to antibody) and incubated for 60 min at RT, shaken at 350 rpm. The resulting conjugate was analyzed by mass spectrometry. 87.7% of the detected species was identified as antibody coupled to 2 peptide molecules, 12.3% was identified as antibody coupled to 1 peptide molecule.

Exemplary Method for the Formation of Conjugates of Haptenylated Polypeptides and Anti-Hapten Antibodies-Ac-PYY(PEG3-Cys-PEG2-Biot)/Chimeric Anti-Biotin Antibody VH53C For the generation of conjugates of biotin-derivatized-PYY-polypeptide containing a cysteinylated linker, 0.16 mg of Ac-PYY(PEG3-Cys-PEG2-Biot) were dissolved in 100% DMF to a concentration of 10 mg/ml. 1 mg of the chimeric anti-biotin antibody VH53C was used in a concentration of 9.9 mg/ml (about 68 µM) in a buffer composed of 50 mM Tris-HCl, 1 mM EDTA, pH 8.2. Ac-PYY[PEG3-Cys-PEG2-Biot and antibody were mixed at a 2.5:1 molar ratio (Ac-PYY[PEG3-Cys-PEG2-Biot] to antibody) and incubated for 60 min at RT, shaken at 350 rpm. The resulting conjugate was analyzed by mass spectrometry. 100% of the detected species was identified as antibody coupled to 2 peptide molecules.

Exemplary Method for the Formation of Conjugates of Haptenylated Poly Peptides and Anti-Hapten Antibodies-Ac-PYY(PEG3-Cys-βAla-Biot)/Humanized Anti-Biotin Antibody VH53C For the generation of conjugates of biotin-derivatized-PYY-polypeptide containing a cysteinylated linker, 0.06 mg of Ac-PYY(PEG3-Cys-βAla-Biot) were dissolved in 100% DMF to a concentration of 10 mg/ml. 0.8 mg of the humanized anti-biotin antibody VH53C was used in a concentration of 9 mg/ml (about 62 µM) in a buffer composed of 50 mM Tris-HCl, 1 mM EDTA, pH 8.2. Ac-PYY[PEG3-Cys-βAla-Biot and antibody were mixed at a 2.5:1 molar ratio (Ac-PYY[PEG3-Cys-βAla-Biot] to antibody) and incubated for 60 min at RT, shaken at 350 rpm. The resulting conjugate was analyzed by mass spectrometry. 62.2% of the detected species was identified as antibody coupled to 2 peptide molecules, 33.9% was identified as antibody coupled to 1 peptide molecule and 3.9% was identified as uncoupled antibody.

Exemplary Method for the Formation of Conjugates of Haptenylated Polypeptides and Anti-Hapten Antibodies-Ac-PYY(PEG3-Cys-PEG2-Biot)/Humanized Anti-Biotin Antibody VH53C For the generation of conjugates of biotin-derivatized-PYY-polypeptide containing a cysteinylated linker, 0.08 mg of Ac-PYY(PEG3-Cys-PEG2-Biot) were dissolved in 100% DMF to a concentration of 10 mg/ml. 0.8 mg of the humanized anti-biotin antibody VH53C was used in a concentration of 9 mg/ml (about 62 µM) in a buffer composed of 50 mM Tris-HCl, 1 mM EDTA, pH 8.2. Ac-PYY[PEG3-Cys-PEG2-Biot and antibody were mixed at a 2.5:1 molar ratio (Ac-PYY[PEG3-Cys-PEG2-Biot] to antibody) and incubated for 60 min at RT, shaken at 350 rpm. The resulting conjugate was analyzed by mass spectrometry. 71.4% of the detected species was identified as antibody coupled to 2 peptide molecules, 26% was identified as antibody coupled to 1 peptide molecule and 2.5% was identified as uncoupled antibody.

Exemplary Method for the Formation of Conjugates of Haptenylated Polypeptides and Anti-Hapten Antibodies-Ac-PYY(PEG3-Cys-PEG2-Fluo)/Anti-Fluorescein Antibody VH52bC For the generation of conjugates of biotin-derivatized-PYY-polypeptide containing a cysteinylated linker, 0.33 mg of Ac-PYY[PEG3-Cys-PEG2-Fluo were dissolved in 100% DMF to a concentration of 10 mg/ml. 1 mg of the anti-fluorescein antibody VH52bC was used in a concentration of 9.3 mg/ml (about 63 µM) in a buffer composed of 50 mM Tris-HCl, 1 mM EDTA, pH 8.2. Ac-PYY[PEG3-Cys-PEG2-Fluo and antibody were mixed at a 2.5:1 molar ratio (Ac-PYY[PEG3-Cys-PEG2-Fluo] to antibody) and incubated for 60 min at RT, shaken at 350 rpm. The resulting conjugate was analyzed by mass spectrometry. 95% of the detected species was identified as antibody coupled to 2 peptide molecules, 5% was identified as antibody coupled to 1 peptide molecule.

Exemplary Method for the Formation of Conjugates of Haptenylated Polypeptides and Anti-Hapten Antibodies-Ac-PYY(PEG3-Cys-PEG2-Fluo)/Anti-Fluorescein Antibody VH28C For the generation of conjugates of biotin-derivatized-PYY-polypeptide containing a cysteinylated linker, 0.33 mg of Ac-PYY[PEG3-Cys-PEG2-Fluo were dissolved in 100% DMF to a concentration of 10 mg/ml. 1 mg of the anti-fluorescein antibody VH28C was used in a concentration of 9.5 mg/ml (about 63 µM) in a buffer composed of 50 mM Tris-HCl, 1 mM EDTA, pH 8.2. Ac-PYY[PEG3-Cys-PEG2-Fluo and antibody were mixed at a 2.5:1 molar ratio (Ac-PYY[PEG3-Cys-PEG2-Fluo] to antibody) and incubated for 60 min at RT, shaken at 350 rpm. The resulting conjugate was analyzed by mass spectrometry. 100% of the detected species was identified as antibody coupled to two peptide molecules.

Example 13

Generation of Covalent Theophylline-Anti-Theophylline Antibody Complexes

To evaluate the formation of covalent antibody complexes that utilize theophylline and theophylline-binding antibodies as hapten recognition system, Theophyllin-Cys-Cy5 was generated as fluorescent payload, applying generally the synthesis and purification technologies that have been described for Digoxigenin-Cys-Cy5 or Biotin-Cys-Cy5, with the exception that the hapten has been exchanged against theophylline (see Example 8 and FIGS. 13, 14 and 22). The composition of the Theophylline-Cys-Cy5 derivative that had been synthesized is shown in FIG. 43a). To demonstrate the formation of a covalent disulfide, theophylline-binding antibodies were generated which contained a designed Cys at position 54 or 55 of the heavy chain variable region (anti-theophylline antibody-Cys). The purity of these antibodies is shown exemplarily for the Y54C variant in FIG. 43b). These antibody derivatives were complexed with Theophylline-Cys-Cy5 and subsequently subjected to SDS-PAGE under non-reducing and reducing conditions as described in Example 12. Under non-reducing conditions, disulfide-linked anti-theophylline-antibody complexed Cy5 was detected by its H-chain associated fluorescence within the gel in the same manner as described in Example 12. This is depicted in FIG. 43c), which demonstrates that covalent complexes between antibody had been formed as a consequence of the simple loading reaction in the same manner as the disulfides that were observed when using Digoxigenin, Fluorescein or Biotin as hapten. These complexes dissociated as expected upon reduction, i.e. released the payload from the H-chain only when the disulfide became reduced (FIG. 43c)).

Example 14

Generation of Covalent Hapten-Antibody Complexes Under In-Vivo Like Conditions, and Evidence for Directed Disulfide-Formation In Vivo To evaluate the formation of covalent hapten-antibody complexes under in-vivo like conditions, anti-Biotin antibodies-Cys were incubated at 37° C. in murine serum with Biotin-Cys-Cy5 for 60 min. Subsequently, the antibody was captured from the murine serum by protein-A. Thereafter the captured antibodies were subjected to SDS-PAGE under non-reducing and reducing conditions as described in Example 12. Disulfide-linked antibody-complexed Cy5 was detected by its H-chain associated fluorescence within the gel in the same manner as described in Example 12. FIG. 44 demonstrates that covalent complexes between antibody form in serum at 37° C., i.e. under conditions that resemble the in-vivo conditions. These complexes dissociate as expected upon reduction, i.e. the payload is released from the H-chain only when the disulfide becomes reduced (FIG. 44). The observation that upon hapten-positioning a directed disulfide bond between antibody and payload can be formed even in the presence of serum is unexpected as serum contains a high amount of proteins, peptides and other compounds (which can interfere with disulfide-formation reactions). The observation that upon hapten-positioning a directed disulfide bond between antibody and payload can be formed in serum at 37° C. also opens the possibility to apply this PK-modulation system in a pre-targeting setting: separate application of antibody and hapten-payload, followed by in-vivo assembly of antibody complexes and subsequent disulfide formation.

To further evaluate potential in vivo 'pre-targeting' applications, the pharmacokinetics of Biotin-Cy5 was determined under pre-targeting conditions by the non-invasive optical imaging technology of the eye of animals as described in Example 19. In these experiments, the presence of Cy5 was determined non-invasive by optical imaging of the eye of animals, which revealed the fluorescence of Cy5 in the capillaries. The Cy5-mediated fluorescence values that we detected in the eye of mice 10 min. after injection of Biotin-Cy5 were set as 100% value, and fluorescence values measured at subsequent time points were expressed relative thereto. In this experiment, 1 mg antibody (either anti-Biotin antibody or anti-Biotin antibody-Cys (=Cys-mutant of anti-Biotin antibody)) was applied 24 hours before injection of Biotin-Cy5 and start of the eye imaging. The control group was not pre-injected with the anti-biotin antibody.

The results of these experiments are shown in FIG. 45: injection of Biotin-Cy5 into animals that did not receive pre-injected antibody was eliminated with a low serum half-life and low exposure levels (diamonds). The serum levels and half-life of Biotin-Cy5 that was injected into animals with 24 hours pre-injection of anti-Biotin antibody (without Cys mutation) were greatly increased. This shows that the antibody captures its antigen (with the payload) in the circulation, and prolongs the antigen's (and likewise of the conjugated payload) serum half-life. The relative serum level and half-life of Biotin-Cys-Cy5 that was injected into animals that were 24 hours pre-injected with the anti-Biotin antibody-Cys (i.e. an antibody containing the Cys mutation as reported herein for covalent payload coupling) were even further increased. In these samples, the relative Cy5 levels were not only higher than those of non-complexed compound, but also higher than the levels of complexed (but not disulfide-bonded) Cy5. Thus, hapten-complexed disulfide-linked payloads (which are formed under pre-targeting conditions in vivo) are more stable in the circulation, and can reach higher exposure levels, than non-covalent complexed payloads.

Example 15

Polypeptides in Conjugates and in Complexes with Anti-Hapten Antibody Retain Functionality We have previously shown that polypeptides which are part of non-covalent hapten-polypeptide conjugates and in complexes with anti-hapten antibodies retain functionality (WO2011/003557, WO 2011/003780 and WO 2012/093068). To demonstrate that coupled peptides retain functionality also upon covalent disulfide-coupling, the biological activity of anti-digoxigenin antibody complexed polypeptides and their disulfide-conjugates with anti-digoxigenin antibody VH52bC were compared.

The therapeutically desired functionality of PYY-derived peptides is binding to and interfering with the signaling of its cognate receptor NPY2. Signaling via the NPY2 receptor is involved in and/or regulates metabolic processes.

To evaluate whether complexation or SS-conjugation of the polypeptide Dig-PYY with the anti-digoxigenin antibody or the conjugation of the polypeptide Dig-Cys-PYY with the anti-digoxigenin antibody VH52bC, respectively, affect its activity, we evaluated its ability to inhibit the Forskolin stimulated cAMP accumulation in HEK293 cells expressing the NPY2 receptor (cAMP assay).

The following Table 6 shows the results of cAMP-assays that were performed to assess the biological activity of PYY(3-36), its Y2receptor specific modified analog moPYY, its antibody-complexed Dig-variant and its disulfide-conjugated Dig-Cys-derivative.

TABLE 6

| sample | day 1 $EC_{50}$ [nM] | day2 $EC_{50}$ [nM] |
|---|---|---|
| $PYY_{wt}$ | 0.09 | 0.1 |
| moPYY | 0.14 | 0.15 |
| moPYY(Cys-Dig)-disulfide conjugated-anti-digoxigenin antibody VH52bC | 5.38 | 5.33 |
| moPYY(Dig) - anti-digoxigenin antibody complex | 9.26 | 12.55 |

For the cAMP agonist assay, the following materials were used: 384-well plate; Tropix cAMP-Screen Kit; cAMP ELISA System (Applied Biosystems, cat. # T1505; CS 20000); Forskolin (Calbiochem cat. #344270); cells: HEK293/hNPY2R; growth medium: Dulbecco's modified eagle medium (D-MEM, Gibco); 10% Fetal bovine serum (FBS, Gibco), heat-inactivated; 1% Penicillin/Streptomycin (Pen 10000 unit/mL: Strep 10000 mg/mL, Gibco); 500 μg/mL G418 (Geneticin, Gibco cat. #11811-031); and plating medium: DMEM/F12 w/o phenol red (Gibco); 10% FBS (Gibco, cat. #10082-147), heat-inactivated; 1% Penicillin/ Streptomycin (Gibco, cat. #15140-122); 500 μg/mL G418 (Geneticin, Gibco, cat. #11811-031).

To perform the assay, on the first day, medium was discarded, and the monolayer cells were washed with 10 mL PBS per flask (T225). After decanting with PBS, 5 mL VERSENE (Gibco, cat #1504006) was used to dislodge the cells (5 min @ 37° C.). The flask was gently tapped and the cell suspension was pooled. Each flask was rinsed with 10 mL plating medium and centrifuged at 1000 rpm for 5 min. The suspension was pooled and counted. The suspension was resuspended in plating medium at a density of $2.0 \times 10^5$ cells/mL for HEK293/hNPY2R. 50 microliters of cells (HEK293/hNPY2R-10,000 cells/well) were transferred into the 384-well plate using Multi-drop dispenser. The plates were incubated at 37° C. overnight. On the second day, the cells were checked for 75-85% confluence. The media and reagents were allowed to come to room temperature. Before the dilutions were prepared, the stock solution of stimulating compound in dimethyl sulphoxide (DMSO, Sigma, cat # D2650) was allowed to warm up to 32° C. for 5-10 min. The dilutions were prepared in DMEM/F12 with 0.5 mM 3-Isobutyl-1-methylxanthine (IBMX, Calbiochem, cat #410957) and 0.5 mg/mL BSA. The final DMSO concentration in the stimulation medium was 1.1% with Forskolin concentration of 5 μM. The cell medium was tapped off with a gentle inversion of the cell plate on a paper towel. 50 μL of stimulation medium was placed per well (each concentration done in four replicates). The plates were incubated at room temperature for 30 min, and the cells were checked under a microscope for toxicity. After 30 min of treatment, the stimulation media was discarded and 50 μL/well of Assay Lysis Buffer (provided in the Tropix kit) was added. The plates were incubated for 45 min @ 37° C. 20 μL of the lysate was transferred from stimulation plates into the pre-coated antibody plates (384-well) from the Tropix kit. 10 μL of AP conjugate and 20 μL of anti-cAMP antibody were added. The plates were incubated at room temperature while shaking for 1 hour. The plates were then washed 5 times with Wash Buffer, 70 L per well for each wash. The plates were tapped to dry. 30 μL/well of CSPD/Sapphire-II RTU substrate/enhancer solution was added and incubated for 45 min @ RT (shake). Signal for 1 sec/well in a Luminometer (VICTOR-V) was measured.

The results of these assays (Table 6) show that the modified peptide derivative moPYY has a neglectable lower activity than the wild-type PYY. The $IC_{50}$ value of the cAMP assay was 0.09 nM for the wild-type PYY and 0.14 nM for the modified analog. Covalent disulfide-conjugation resulted to a slight reduction in biological activity. The $IC_{50}$ value was 5-36 nM for the conjugate. Surprisingly the covalent disulfide-conjugate is 2-fold more active than the non-covalent complex with an $IC_{50}$ value of 10.91 nM.

Example 16

Serum Stability of Complexes of Biotinylated Cy5 with Humanized Anti-Biotin Antibody in Comparison to Covalent Conjugates of Biotinylated Cy5 with Humanized Anti-Biotin Antibody VH53C The objective of the described peptide modification technology is to improve the therapeutic applicability of peptides. Major bottlenecks for therapeutic application of peptides are currently limited stability in vivo and/or short serum half-life and fast clearance. The PK parameters of antibody conjugates of fluorophores were determined in vivo and compare with the PK of non-covalent antibody-fluorophore complexes. Therefore, (i) the anti-biotin antibody VH53C was covalently conjugated to the biotinylated fluorophore Biot-Cys-Cy5, (ii) a non-covalent complex of the anti-biotin antibody with biotinylated fluorophore Biot-Cy5 was generated, (iii) the covalently conjugated and the non-covalently complexed compounds were administered to animals and (iv) the serum concentrations of the compounds over time in these animals were measured by determination of the fluorescence of Cy5 (A650), and that of the corresponding antibody by an ELISA method that specifically detects the humanized antibody.

Experimental Procedure

To analyze the influence on PK parameters of antibody-complexation or antibody-conjugation of a small fluorescent substrate, 13 nmol of Cy5-biotin/humanized anti-biotin antibody VH53C-conjugate, or of the corresponding antibody non-covalently complexed compound, or of the fluorescent compound alone, in 20 mM histidine/140 mM NaCl, pH 6.0 were administered to six female mice (strain NMRI) for each substance. About 0.1 ml blood samples were collected after the following time points: 0.08 h, 4 h and 48 h for Mouse 1, 2, and 3 in a first group, and 0.08 h, 24 h and 72 h for Mouse 1, 2 and 3 in a second group. Serum samples of about 50 μl were obtained after 1 h at RT by centrifugation (9300×g, 3 min, 4° C.). Serum samples were stored at −80° C.

To determine the amount of compound (fluorophore) in the serum at the given time points the fluorescent properties of Cy5 are used: Cy5 fluorescence in serum samples was measured in 120 μl quartz cuvettes at room temperature using a Cary Eclipse Fluorescence Spectrophotometer (Varian). Excitation wavelength was 640 nm, Emission was measured at 667 nm. Serum samples were diluted in 1×PBS to reach an appropriate range of Emission intensity. Blood serum of an untreated mouse in the same dilution in 1×PBS as the respective sample was used as a blank probe and did not show any fluorescence signal.

To determine the amount of human IgG antibody in the serum at the given time points, the following assay principle was used: human IgG1 antibodies in serum samples were captured on a solid phase (Maxisorb® microtiter plate, NUNC-Immuno™) coated with an anti-human kappa-chain monoclonal IgG antibody. Serum samples were diluted 1:10$^5$ and 1:10$^6$ and 100 μl of these dilutions were added to the wells. After incubation, wells were washed 3-times with 300 μl PBS/0.05% Tween 20 each. Detection of human IgG antibodies was carried out by first adding 100 μl of anti-human $C_H1$-domain IgG which is digoxigenylated at the C-terminus at a concentration of 0.25 g/ml. After washing 3-times with 300 μl of 1×PBS/0.05% Tween 20 each, 100 μl of anti-digoxigenin antibody Fab-fragment conjugated to horse-radish peroxidase (HRP) was added at a concentration of 25 mU/ml. Finally, per well 100 μl of ABTS® was added. After 30 min. incubation at ambient temperature, the extinction (OD) was measured at 405 nm and 492 nm [405/492] in a commercial microtiter plate ELISA Reader (e.g. Tecan Sunrise).

FIG. 34 shows the Bio-Cy5 serum levels as well as the serum levels of human IgG in mice treated with antibody-biotin-Cy5-complexes and -conjugates. The data are shown as relative (%) human IgG or fluorescence levels normalized to the (peak) serum levels 5 min. after injection. The relative human IgG serum levels of both antibody-hapten-complexes and -conjugates are in-line with the relative fluorescence measured for the antibody-hapten conjugates. Thus, the Biotin-Cys-Cy5 compound shows a similar in vivo stability as the antibody it is conjugated to, which means that antibody-hapten conjugates stay intact in vivo. This is clearly not the case for antibody-hapten complexes for which the relative Cy5-mediated fluorescence decreases faster than the relative human IgG serum levels. This means that the complexes release the payload over time in vivo.

In summary, the in vivo stability of haptenylated compounds is significantly increased when bound by an anti-hapten antibody. However, antibody-hapten complexes are not completely stable in vivo as the decrease of the hapten-Cy5 serum levels is faster than the decrease of antibody serum levels. This is not the case for antibody-hapten-Cy5 conjugates, which show a similar in vivo behavior as normal IgG antibodies.

Example 17

Serum Stability of Complexes of Digoxigenin-Cy5 with Humanized Anti-Digoxigenin Antibody in Comparison to Covalent Conjugates of Digoxigenin-Cys-Cy5 with Humanized Anti-Digoxigenin Antibody To analyze the influence of different haptens on the pharmacokinetics of antibody complexes or antibody conjugates, the PK parameters of anti-digoxigenin antibody complexed with Digoxigenin-Cy5 or covalently conjugated with Digoxigenin-Cys-Cy5 were determined in vivo. In the same manner as described for Biotin-Cy5 or Biotin-Cys-Cy5 (see Example 16), Digoxigenin-Cy5 or antibody-complexed or antibody-Cys-linked Digoxigenin-(Cys)-Cy5 was administered to female NMRI mice, followed by collection of blood at 0.08 h, 2 h, 4 h and 24 h. Digoxigenin-(Cys)-Cy5 levels were determined by measuring its fluorescence, and the corresponding antibody concentration was determined by ELISA as described in example 16. The data are shown in FIG. 41 as relative (%) human IgG or fluorescence levels normalized to the (peak) serum levels 5 min. after injection.

The results of these experiments demonstrate that for Digoxigenin-Cy5 less than 10% of the fluorescence that was applied (5 min. value) was detectable 2 hours after injection. At later time points, 4 hrs. and 24 hrs., respectively, after injection no uncomplexed Digoxigenin-Cy5 signals were detectable (see FIG. 41, grey triangles in both graphs). In contrast to non-complexed compound, antibody-complexed compound was detectable at much higher levels and at later time points (FIG. 41, upper graph). This indicates that antibody complexation significantly increases the serum half-life of the small compound Digoxigenin-Cy5. Furthermore, covalently linked payloads display a greater serum stability compared to the non-covalently linked complexes. A direct comparison of the Digoxigenin-Cy5 levels and antibody levels indicates loss of complexed payload from the antibody over time, with Cy5 levels decreasing faster than antibody levels. In contrast, covalently linked Digoxigenin-conjugates showed almost identical Cy5 and IgG serum half-lives (FIG. 41, lower graph). This indicates that the disulfide-linked payloads remain stably connected to the antibodies while the non-covalent complexes dissociate over time.

Example 18

Serum Stability of a Digoxigenylated Polypeptide Complexed with Humanized Anti-Digoxigenin Antibody To analyze the influence on PK parameters of antibody-complexation of a digoxigenylated polypeptide, 32.1 nmol of the polypeptide, or 32.1 nmol of a non-covalent complex between the digoxigenylated polypeptide and the corresponding anti-Digoxigenin antibody in 20 mM histidine/140 mM NaCl pH 6.0 was administered to 2 female mice (strain NMRI) each. About 0.1 ml blood samples were collected after the following time points: 0.08 h, 2 h and 24 h for Mouse 1 and 0.08 h, 4 h, and 24 h for Mouse 2. Serum samples of about 50 μl were obtained after 1 h at RT by centrifugation (9300×g, 3 min, 4° C.). Serum samples were stored at −80° C.

The determination of the amount of digoxigenylated peptide in the serum at the given time points was difficult compared to the detection of Dig-Cy5 as no direct means to detect the polypeptide in serum samples was available. Therefore, a Western Blot-related assay to detect digoxigenylated peptide in serum was established. In a first step, the serum samples were separated on reducing SDS-PAGE. Because sample preparation included exposure of the serum to high concentrations of SDS and reducing agents, complexed Dig-polypeptide conjugates can become released from the (completely denatured/unfolded) anti-digoxigenin antibody, whereas covalent conjugates remained bound. To mediate the release of the polypeptide from the non-covalent antibody complex and separate the individual components by SDS-PAGE, 2 μl of each serum sample was diluted in 18 μl 20 mM histidine/140 mM NaCl pH 6.0, mixed with 6.7 μl of 4×LDS sample buffer and 3 μl of 10× sample reducing agent (NuPAGE, Invitrogen) for 5 min at 95° C. As a control, 2 μl of serum of an untreated mouse of the same strain was used. Samples were applied to a 4-12% Bis-Tris Gel (NuPAGE, Invitrogen) which was run at 200 V/120 mA for 20 minutes using 1×MES (Invitrogen) as a running buffer. Subsequently, separated polypeptides were blotted onto a PVDF membrane (0.22 µm pore size, Invitrogen) using the XCell Sure Lock® Mini-Cell system (Invitrogen) for 40 min at 25 V/130 mA. Membranes were blocked in 1% skim milk in 1×PBS+1% Tween20 (PBST) for 1 h at RT. Digoxigenylated polypeptides were subsequently detected on the membrane with an anti-digoxigenin antibody. For that, anti-digoxigenin antibody was applied to the membranes in a concentration of 13 µg/ml in 10 ml of 1% skim milk/PBST for 2 h at RT. Membranes were washed for 3×5 min in 1×PBST. Anti-mouse IgG Fab-fragments coupled to POD from the LumiLightPLS Western Blotting Kit (Roche) was applied in a 1:25 dilution in 10 ml of 1% skim milk/PBST for 1 h at RT. Membranes were washed 3×5 min with 1×PBST. Detection was carried out by incubating the membranes in 4 ml LumiLight Western Blotting substrate for 5 min at RT. Chemiluminescence was detected with the Lumilmager F1 (Roche) with an exposure time of 20 min.

The results of these analyses are shown in FIGS. 35 A and B. The presence/amount of the digoxigenin polypeptide in murine serum at different time points has been determined. Mice that had received antibody complexed peptides (FIG. 35 left) showed strong signals at the earliest time point (5 min after administration). These signals were clearly assignable as shown by the size and location on the blot of the controls. In sera of mice that were treated with antibody-complexed polypeptide, polypeptide-associated signals were strongest at the early time points and decreased over time. Nevertheless, polypeptide was still detectable with good signals at all time points and even 24 hrs. after administration.

In mice that received non-complexed polypeptide, barely any signal associable to the small polypeptide was detectable even at the earliest time point. FIG. 35 shows at the right that under normal exposure conditions, no free polypeptide is visible on the blot. Contrast enhancement of the blot revealed the presence of some polypeptide 5 min after administration, however only in trace amounts. At later time points, no defined polypeptide band was detectable.

It can be seen that similar to non-complexed hapten-Cy5, non-complexed polypeptide has a very short half-life in the serum of mice. Mice that received the same polypeptides but in antibody complexed form, show presence of these polypeptides in the serum for an increased period of time. Twenty-four hours after injection polypeptide can still be determined in the serum of these mice.

Example 19

In Vivo Real-Time Measurement of Serum Half-Life and Exposure Levels of Covalently Linked Hapten-Antibody Conjugates and Non-Covalent Complexes To further analyze the pharmacokinetic properties of non-covalently complexed hapten compounds in comparison to covalently linked hapten compounds, the in vivo kinetics of an injected complex or conjugate between Biotin-Cy5 or Biotin-Cys-Cy5 and corresponding anti-Biotin antibody was determined through a non-invasive optical imaging technology, which revealed the Cy5 fluorescence in the capillaries of the eye of animals. Values were normalized to the 10 min value, which was set as 100%. The results of these experiments are shown in FIG. 42: non-complexed Biotin-Cy5 by itself has a short serum half-life and low exposure levels. Antibody-complexed Biotin-Cy5 which was not covalently linked was detectable at much higher levels and with an extended half-life. Covalently linked payload displayed an even greater serum stability, indicated by higher serum levels compared to the non-covalently linked complexes. These experiments confirm that covalently disulfide-linked payloads are more stable in the circulation, and can reach higher exposure levels, than non-covalently complexed payloads.

Example 20

Peptide-Complexation and Covalent Conjugation with Antibodies that Bind Different Haptens The application of hapten binding modules to couple haptenylated compounds (=payloads) to targeting vehicles is one technical possibility by which hapten-mediated delivery can be realized. The concept can be expanded to additional haptens or other entities that capture compounds and connect them to the targeting module. For example, for polypeptide delivery or stabilization, mono- or bispecific antibodies that bind digoxigenin or other haptens can be applied to stabilize and PK-optimize therapeutic polypeptides.

Prerequisites for application as polypeptide capturing modules are (i) that coupling of compounds to the hapten does not severely interfere with polypeptide activity and (ii) the possibility of effective binding/complexation of the antibody to haptenylated compounds.

Hapten-directed binding is a prerequisite for the efficient covalent coupling of haptenylated dyes or polypeptides with an anti-hapten cysteinylated antibody.

To show that affinity-driven complexation of haptenylated compounds with anti-hapten antibodies is a prerequisite for efficient disulfide-bond formation, Biotin-Cys-Cy5 was incubated with humanized anti-digoxigenin antibody and humanized anti-digoxigenin antibody VH53C.

Incubation of Biotin-Cys-Cy5 with humanized anti-biotin antibody and humanized anti-biotin antibody VH53C was carried out as a control reaction.

0.13 mg of Biotin-Cys-Cy5 were dissolved in 100% DMF to a concentration of 10 mg/ml. 0.7 mg of each antibody was used in a concentration of 6.7 mg/ml (about 46 µM) in a buffer composed of 50 mM Tris-HCl, 1 mM EDTA, pH 8.2. Biotin-Cys-Cy5 and antibodies were mixed at a 2.5:1 molar ratio (Ac-Biotin-Cys-Cy5 to antibody) and incubated for 60 min at RT, shaken at 350 rpm. The resulting complex/conjugate was further analyzed by SDS-PAGE and subsequent detection of Cy5-related fluorescence in the polyacrylamide-gel. 15 µg of the complex/conjugate were mixed with 4×LDS sample buffer (Invitrogen) and incubated at 95° C. for 5 min. Cy5-related fluorescence was recorded using a Lumilmager F1 device (Roche Diagnostics GmbH, Mannheim, Germany) at an excitation wavelength of 645 nm.

The non-reduced samples show covalent site-specific disulfide bond formation for humanized anti-biotin antibody VH53C (FIG. 36, lane 4) with very low background fluorescence signal when humanized anti-biotin antibody without a cysteine in CDR2 was used (FIG. 36, lane 3). Biotin-Cys-Cy5 was also covalently coupled to humanized anti-digoxigenin antibody VH52bC (FIG. 36, lane 2) with a low background signal when humanized anti-digoxigenin antibody was used (FIG. 36, lane 1), but with significantly lower efficiency. This can be deduced from the excess Biotin-Cys-Cy5 that is detected on the bottom of the gel (arrows). In the case of humanized anti-digoxigenin antibody VH52bC significantly more uncoupled Biotin-Cys-Cy5 can be detected (lane 2) than with humanized anti-biotin antibody VH53C (lane 4). Upon reduction of the samples, no Cy5-related fluorescence is detectable near the antibody heavy- and light-chains, indicating that the covalent linkage was indeed Example 21

Hapten-Directed Binding is a Prerequisite for the Efficient Covalent Coupling of Haptenylated Dyes or Polypeptides with an Anti-Hapten Cysteinylated Antibody To show that affinity-driven complexation of haptenylated compounds with anti-hapten antibodies is a prerequisite for efficient disulfide-bond formation, the non-haptenylated peptide Ac-PYY(PEG3-Cys-4Abu-NH2) (Biosynthan 1763.1, SEQ ID NO: 178) was incubated with humanized anti-digoxigenin antibody VH52bC and humanized anti-digoxigenin antibody. 1.4 mg of Ac-PYY(PEG3-Cys-4Abu-NH2) were dissolved in 100% DMF to a concentration of 10 mg/ml. 2 mg of each antibody was used in a concentration of 11-13 mg/ml (about 75-89 µM) in a buffer composed of 50 mM Tris-HCl, 1 mM EDTA, pH 8.2. Ac-PYY(PEG3-Cys-4Abu-NH2) and antibodies were mixed at a 2.1:1 molar ratio (Ac-PYY(PEG3-Cys-4Abu-NH2 to antibody)). The peptide was added in 3 portions while the solution was stirred at 500 rpm with a stirrer bar. Between each addition, samples were incubated for 5 min at 200 rpm. After addition of the last portion, samples were incubated for 1 h at RT and 200 rpm.

The resulting complex/conjugate was defined as 97% monomeric IgG-like molecule and 3% dimeric soluble aggregates for the Ac-PYY(PEG3-Cys-4Abu-NH2): humanized anti-digoxigenin antibody VH52bC conjugate and as 100% monomeric for the Ac-PYY(PEG3-Cys-4Abu-NH2): humanized anti-digoxigenin antibody complex via size exclusion chromatography. Furthermore, the resulting complex/conjugate was analyzed by mass spectrometry. For the Ac-PYY(PEG3-Cys-4Abu-NH2): humanized anti-digoxigenin antibody VH52bC conjugate 17% of the detected species was identified as antibody coupled to 2 peptide molecules, 51% was identified as antibody coupled to 1 peptide molecule and 32% was identified as antibody without coupled peptide. For the Ac-PYY(PEG3-Cys-4Abu-NH2): humanized anti-digoxigenin antibody complex 100% of the antibody was uncoupled.

Example 22

Disulfide Patterns that are Required for Formation of Properly Folded Functional Hapten-Binding Antibodies with a Cysteine Mutation for Covalent Payload Coupling Hapten-binding modules for covalent compound/payload coupling may be composed of 'standard' antibodies such as IgGs which contain extra cysteines that enable covalent attachment of haptenylated compounds/payloads. The method as reported herein introduces the required functionalities (cysteines) within folded domains, whose structure and sequence provide the basis for antibody functionality. Correct formation of defined disulfide bonds within as well as between the domains of antibodies is essential for the formation and maintenance of the correct structure and functionality. FIG. 37(A) shows the disulfide pattern that is required to form functional binding arms such as Fabs of unmodified antibodies, and FIG. 37(B) shows the disulfide pattern which is necessary to maintain structure and functionality of the VH52cB/VH53C mutated antibody derivative. To maintain the proper disulfide pattern, the additional cysteine that was introduced in the VH domain must be unoccupied and must not interfere or react with neighboring cysteines. FIG. 37(C) and 37(D) show that the additions of the extra cysteines generate possibilities to form incorrect disulfides within the VH domains during the biosynthesis of such molecules. The fact that the VH52bC/VH53C position is located within the VH domain (and quite close to other cysteines) aggravates the risk that incorrect disulfides may be formed during the biosynthesis of the heavy chain. Another potential problem is that VH and VL domains become assembled within the secretory pathway to one Fv fragment. The secretory pathway involves redox-shuffling conditions and disulfide forming and -shuffling enzymes. Therefore, the potential to introduce incorrect disulfides by addition of the VH52bC/VH53C mutation may 'spread' also to disulfides of the light chain (exemplarily shown in FIG. 37(E). This does further enhance the risk to obtain/generate improperly folded non-functional molecules. It is therefore quite surprising that—despite of these risks—good amounts of homogeneous functional antibody derivatives that contain the VH52bC/VH53C mutation could be expressed and obtained, and which are capable to covalently connect to haptenylated compounds/payloads.

Example 23

Composition and Generation of Anti-Hapten Disulfide-Stabilized Single-Chain Fv Fragments with a Cysteine Mutation for Covalent Coupling Hapten-binding modules for covalent compound/payload coupling can consist of 'standard' antibodies such as IgGs. Alternatively, they may be modified entities such as recombinant Fv or Fab fragments, or derivatives thereof. Single-chain Fv fragments are frequently applied as alternative to full lengths antibodies, especially in applications where small module size is required, or where additional binding modules are desired to generate bi- or multispecific antibody derivatives. One example for anti-hapten Fv-derived entities that have been generated is a disulfide-stabilized single-chain Fv which bind to and covalently connects digoxigenylated compounds/payloads. The disulfide-stabilized single-chain Fv with Dig-binding specificity was generated by connecting anti-digoxigenin antibody VH and VL domains via a flexible Gly and Ser rich linker to each other. These VH and VL domains harbored in addition cysteine mutations in positions 44 of VH and position 100 of VL (positions according to Kabat et al.). These additional cysteines form a stable intermolecular disulfide bond between VH and VL. This stabilizes the scFv, as previously described (e.g. Reiter, Y., et al., Nature Biotechnology 14 (1996) 1239-1245).

In addition to that, another cysteine was introduced into the VH at position 52b or 53, respectively, according to the Kabat numbering to add the covalent linkage functionality to the Fv fragment.

However, introducing such a mutation into disulfide-stabilized Fv fragments is far more challenging than placing them into full length antibodies. Single-chain Fv fragments are inherently less stable than full length IgGs or Fab fragments because they lack constant domains as stabilizing and heterodimerization forcing entities. Stability can be conferred by placing additional cysteine mutations into the Fvs such as the VH44-VL 100 disulfide. However, this stabilizing principle works only if the disulfide forms at the correct positions between correct cysteines. Thus, in addition to defined intradomain disulfides (one in VH and one in VL), one single defined correct interdomain disulfide needs to be formed. Disulfide connections between non-matching cysteines will generate misfolded instable and non-functional entities. Considering that a disulfide-stabilized Fv fragment contains 6 cysteines, 21 different disulfide connections can theoretically be formed—but only the right combination of 3 defined disulfides will form a functional stabilized dsscFv. This challenge is aggravated upon addition of another free cysteine into the VH domain. The stabilized dsscFv that is desired contains two defined intradomain disulfides (one each in VH and VL), one defined interdomain disulfide (between VH and VL), and furthermore one free cysteine for haptenylated compound/payload coupling (in VH at position 52b/53). Considering that a disulfide-stabilized Fv fragment with extra cysteine mutation for covalent coupling contains 7 cysteines, many different disulfide connections can theoretically be formed but only the right combination of the 3 defined disulfides, with the exact free cysteine position at VH52b/VH53 will result in a functional stabilized covalent coupling competent dsscFv. One additional challenge is the fact that the additional free cysteine (VH52b/VH53) is located in close proximity to the VH44 cysteine which is not a naturally occurring cysteine but a mutation introduced for disulfide stabilization. VH44C is necessary for forming the correct inter-domain disulfide bond, and this disulfide most likely without being bound by this theory forms after independent folding and assembly of VH and VL. Proximity of VH44C and VH52bC/VH53C aggravates the risk that the intradomain disulfide does not form in a correct manner. But it has been found that functional disulfide stabilized single-chain Fv modules that bind digoxigenin and that are simultaneously capable to covalently connect to digoxigenylated payloads can be produced. The composition of the disulfide-stabilized single-chain Fv molecule that contains the correct disulfides and the free cysteine in the correct position and its comparison to the undesired incorrectly folded molecules is shown in FIG. 38. The sequences that encode the light chain variable regions and the modified heavy chain variable regions of this Dig-binding dsscFv with the VH52bC mutation Fv antibody derivative are listed under SEQ ID NO: 190 (VH) and the corresponding VL under SEQ ID NO: 189. The successful generation of such dsscFv as modules for the generation of bispecific antibody derivatives is described in the Example 24 (below), as well as in FIG. 40(A), FIG. 40(B), and FIG. 40(C).

Example 24

Composition, Expression and Purification of Bispecific Anti-Hapten Antibody Derivatives for Targeted Delivery of Covalently Coupled Compounds/Payloads Bispecific antibodies were generated that contain hapten-binding antibody modules for covalent compound/payload coupling. These antibodies additionally contain binding modules that enable targeting to other antigens. Applications for such bispecific antibodies include specific targeting of haptenylated compounds/payloads to cells or tissues that carry the targeting antigen. One example for such molecules that was generated is a bispecific antibody with binding regions that recognize the tumor associated carbohydrate antigen LeY, and simultaneously with disulfide-stabilized Fvs which bind and covalently connect digoxigenylated compounds/payloads. Therefore, disulfide-stabilized single-chain Fvs were connected via flexible Gly and Ser rich connector peptides to the C-termini of the CH3 domains of a LeY antibody, resulting in tetravalent molecules with two LeY binding arms and additionally two digoxigenin binding entities. The digoxigenin-binding entities harbored a VH44-VL100 disulfide bond which has been previously described (e.g. Reiter, Y., et al., Nature Biotechnology 14 (1996) 1239-1245). The digoxigenin binding entity contained in addition the VH52bC mutation for covalent coupling. The sequences that encode the light chain and the modified heavy chain of this LeY-Dig antibody derivative are listed under SEQ ID NO: 191 and SEQ ID NO: 192. The composition of the LeY-Dig bispecific antibody derivative as delivery vehicle for covalently coupled compounds/payloads is shown schematically in FIG. 39.

The bispecific molecules were generated by molecular biology techniques, expressed by secretion from cultured cells, subsequently purified from culture supernatants in the same manner as described above. FIG. 40(A) shows the presence of modified H-chain and L-chain of this LeY-Dig (52bC) bispecific antibody in cell culture supernatants, visualized in Western Blot analyses that detect antibody L-chains and H chains. FIG. 40(B) demonstrates the homogeneity of these antibodies after purification by SDS-PAGE in the presence of a reducing agent. Staining of the SDS-PAGE with Coomassie brilliant blue visualizes polypeptide chains related to the IgG with the apparent molecular sizes analogous to their calculated molecular weights. FIG. 40(C) shows the SEC profile of the LeY-Dig(52bC) bispecific antibody after protein A purification, demonstrating homogeneity and lack of aggregates in the protein preparations. Thus, bispecific antibodies which contain targeting modules as well as modules for covalent coupling of haptenylated compounds/payloads can be generated and purified to homogeneity.

Example 25

X-Ray Structure Determination of Murine Anti-Biotin Antibody-Fab-Fragments in Complex with Biocytinamid The protein structure of murine anti-Biotin antibody Fab-fragment was determined in complex with biocytinamid. Therefore, crystals of the Fab-fragment were grown in 0.8 M Succinic Acid, followed by charging of the antibody crystals with Biocytinamid (diluted to 10 mM working concentration in crystallization solution, applied to the crystals in the crystallization droplet). Crystals were washed three times with 2 µl of 10 mM Biocytinamid solution and were finally incubated for 16 hrs. with Biocytinamid at 21° C., harvested with 15% Glycerol as cryoprotectant and flash frozen in liquid nitrogen. Processed diffraction images yielded a protein structure at 2.5 Å resolution. The structure and charge composition of the biotin-binding variable region is shown in FIG. 46: Biotin binds into a surface pocket which is flanked by charged regions that composed of amino acids from the CDR regions. The complexed hapten is positioned in close proximity to a negatively charged cluster of amino acids. Biotin which—as hapten—is derivatized for payload coupling at its carboxyl group binds with good efficacy as there is no charge repulsion at this position (due to the lack of the COOH group). In contrast, free (normal) biotin cannot bind efficient to the antibody because its carboxyl group would be in close proximity to this negative charge cluster, and hence becomes repulsed.

Example 26

Engineering of Blood Brain Barrier-Shuttle Modules

Hapten-binding bispecific blood brain barrier-shuttle modules were generated by fusing disulfide-stabilized hapten-binding single-chain Fvs to the C-termini of the CH3 domains of anti-TfR antibodies. Similar designs and technologies were applied as previously described (see e.g.

PCT/EP2013/064100). An example for the composition of these blood brain barrier-shuttle modules is shown in FIG. 47.

The blood brain barrier-shuttle modules recognize transcytoseable cell surface targets on endothelial cells of the blood brain barrier (blood brain barrier receptor). Exemplarily, we used two different antibodies that bind the transferrin receptor with different affinities. Antibody TfR1 binds to the transferrin receptor with high affinity and antibody TfR2 binds to the transferrin receptor with reduced affinity (see e.g. WO 2012/075037). The TfR-binding sites derived from these anti-TfR antibodies were set as unaltered Fab arms into a bispecific antibody to obtain a bivalent full-length IgG module. Disulfide-stabilized hapten-binding single-chain Fvs were fused via short GS-linker to the C-termini of the CH3 domain of the generated bispecific antibody. Exemplarily, as anti-hapten binding sites previously described entities that bind derivatives of digoxigenin (Dig) or Biotin (Bio) were used (for sequences see above).

Examples for the sequence composition of these shuttle vehicles are listed as SEQ ID NO: 193 (LC anti-TfR1 antibody), SEQ ID NO: 194 (HC anti-TfR1 antibody conjugated to scFv anti-digoxigenin antibody fragment), SEQ ID NO: 195 (HC anti-TfR1 antibody conjugated to scFv anti-biotin antibody fragment), SEQ ID NO: 196 (LC anti-TfR2 antibody), SEQ ID NO: 197 (HC anti-TfR2 antibody conjugated to scFv anti-digoxigenin antibody fragment), SEQ ID NO: 198 (HC anti-TfR2 antibody conjugated to scFv anti-biotin antibody fragment).

Example 27

Expression and Purification of Bispecific Antibodies (Blood Brain Barrier-Shuttle Modules)

The blood brain barrier-shuttle module bispecific antibodies were produced in mammalian cells in defined serum free media as previously described (see above). HEK293 suspension cells were transiently transfected with L- and H-chain encoding expression plasmids to generate cultures that express the blood brain barrier-shuttle module bispecific antibody.

To generate digoxigenylated payload binding blood brain barrier-shuttle modules that bind TfR with high affinity, expression plasmids containing SEQ ID NO: 193 encoding nucleic acid/expression cassette were co-transfected with expression plasmids containing SEQ ID NO: 194 encoding nucleic acid/expression cassette.

To generate biotinylated payload binding blood brain barrier-shuttle modules that bind TfR with high affinity, expression plasmids containing SEQ ID NO: 193 encoding nucleic acid/expression cassette were co-transfected with expression plasmids containing SEQ ID NO: 195 encoding nucleic acid/expression cassette.

To generate digoxigenylated payload binding blood brain barrier-shuttle modules that bind TfR with reduced affinity, expression plasmids containing SEQ ID NO: 196 encoding nucleic acid/expression cassette were co-transfected with expression plasmids containing SEQ ID NO: 197 encoding nucleic acid/expression cassette.

To generate biotinylated payload binding blood brain barrier-shuttle modules that bind TfR with reduced affinity, expression plasmids containing SEQ ID NO: 196 encoding nucleic acid/expression cassette were co-transfected with expression plasmids containing SEQ ID NO: 198 encoding nucleic acid/expression cassette.

Bispecific antibodies were purified from supernatants of HEK293 suspension cells that were transiently transfected with L- and H-chain encoding expression plasmids by protein A chromatography (see above). Subsequently, size exclusion chromatography (SEC) was applied to obtain bispecific antibodies free of aggregates or contaminants. Examples for the purity and composition of the purified blood brain barrier-shuttle modules are shown as SEC profiles and SDS PAGE in FIG. 48.

Example 28

Bispecific Hapten-Binding Blood Brain Barrier-Shuttle Modules Simultaneously Bind Haptenylated Payloads and Blood Brain Barrier Receptor To enable blood brain barrier-shuttle functionality of the bispecific antibodies, they must simultaneously bind to the blood brain barrier receptor on endothelial cells of the blood brain barrier, and to the haptenylated payloads to be shuttled. To evaluate this functionality of the hapten-binding bispecific antibodies as reported herein, simultaneous cell surface and payload binding was addressed by FACS analyses. For these analyses, cell binding of the blood brain barrier-shuttle module (=bispecific antibody) was detected by phytoerythrin-labeled IgG recognizing secondary antibodies. Simultaneous payload binding was detected by application of a haptenylated fluorescent payload (digoxigenylated Cy5; DIG-Cy5 (see above)). The results of the FACS analysis, using hCMEC/D3 cells as TfR expressing BBB-derived cell line and Dig-Cy5 as fluorescent payload are shown in FIG. 49: both transferrin receptor binding bispecific antibodies bind to hCMEC/D3 as shown by the anti-IgG-PE associated signals. Similarly, both bispecific antibodies also and simultaneously bind Dig-Cy5 as shown by cell-associated Cy5 attributable signals. A comparison of signal intensities between the (high affinity) TfR1 bispecific antibody and the (reduced affinity) TfR2 bispecific antibody indicates (as expected) higher signal intensity on cells with the high affinity compared to medium affinity bispecific antibody. A control bispecific antibody which recognizes an antigen that is not present in detectable amounts on hCMEC/D3 (CD33-Dig) does (as expected) not generate relevant signals with anti-IgG antibody nor with Dig-Cy5.

These results show that bispecific hapten-binding blood brain barrier-shuttle modules specifically bind to their targets on the surface of endothelial cells. Furthermore, these bispecific antibodies simultaneously bind haptenylated payloads and thereby can direct them to endothelial cells of the blood brain barrier.

Example 29

Receptor Binding Mode of the Blood Brain Barrier-Shuttle Module Influences Release from Brain Endothelial Cells We used brain endothelial cells (hCMEC/D3) to investigate cell binding and transcytosis of the shuttle modules as reported herein. Previous studies (Crepin et al., 2010; Lesley et al., 1989, WO 2012/075037, WO 2014/033074) reported that valency and affinity of TfR binding antibodies influence efficacy of binding to, transcytosis though, and release from endothelial cells of the blood brain barrier. To investigate cell binding and transcytosis in hCMEC/D3, hCMEC/D3 cells cultured on filter inserts were incubated apically with the bispecific antibody or parent antibody (without hapten-binding scFvs as controls) for 1 h at 37° C. Cell monolayers were washed at RT in serum-free medium apically (400 µl) and basolaterally (1600 µl) three times for 3-5 min. each. All wash volumes were collected to monitor efficiency of removal of the unbound ligand or antibody. Pre-warmed medium was added to the apical chamber and the filters transferred to a fresh 12 well plate (blocked overnight with PBS containing 1% BSA) containing 1600 µl pre-warmed medium. At this point, cells on some of the filters were lysed in 500 µl RIPA buffer (Sigma, Munich, Germany, # R0278) in order to determine specific uptakes. The remaining filters were incubated at 37° C., and samples of cells and of basolateral and apical media were collected at various time points to determine apical and/or basolateral release. The content of antibody in the samples was quantified using a highly sensitive IgG ELISA. The results of these analyses are shown in FIG. 50: high affinity bivalent anti-TfR antibodies (TfR1) become efficiently bound to the cells, but are not released to apical or basolateral compartments. In the same manner, bispecific antibodies that contain the high affinity TfR binding sites (TfR1-Dig, TfR1-Bio) become efficiently bound to the cells, but are not released to apical or basolateral compartments. In contrast, bivalent anti-TfR antibodies with reduced affinity (TfR2) become efficiently bound to the cells, and become subsequently released over time to apical or basolateral compartments. Bispecific antibodies that contain the reduced affinity bivalent TfR binding sites (TfR2-Dig, TfR2-Bio) also become efficiently bound to the cells and are released to apical or basolateral compartments to the same degree as the parent antibody. Control bispecific antibodies (CD33-Dig, CD33-Bio) that bind an antigen that is not present on hCMEC/D3 do not bind to these cells and are therefore also not released over time into apical or basolateral compartments.

Example 30

Figure 51A:
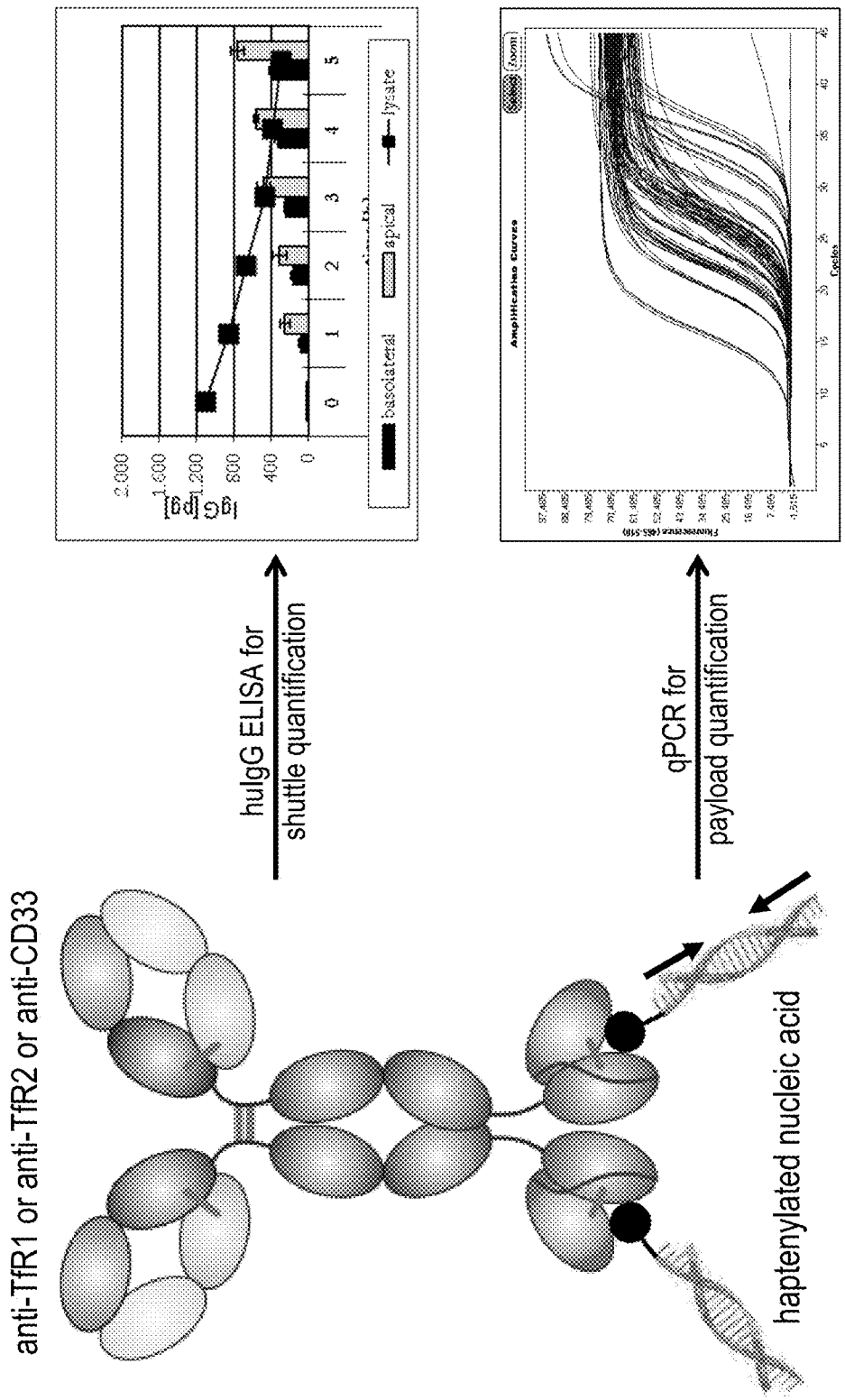
Figure 51B:
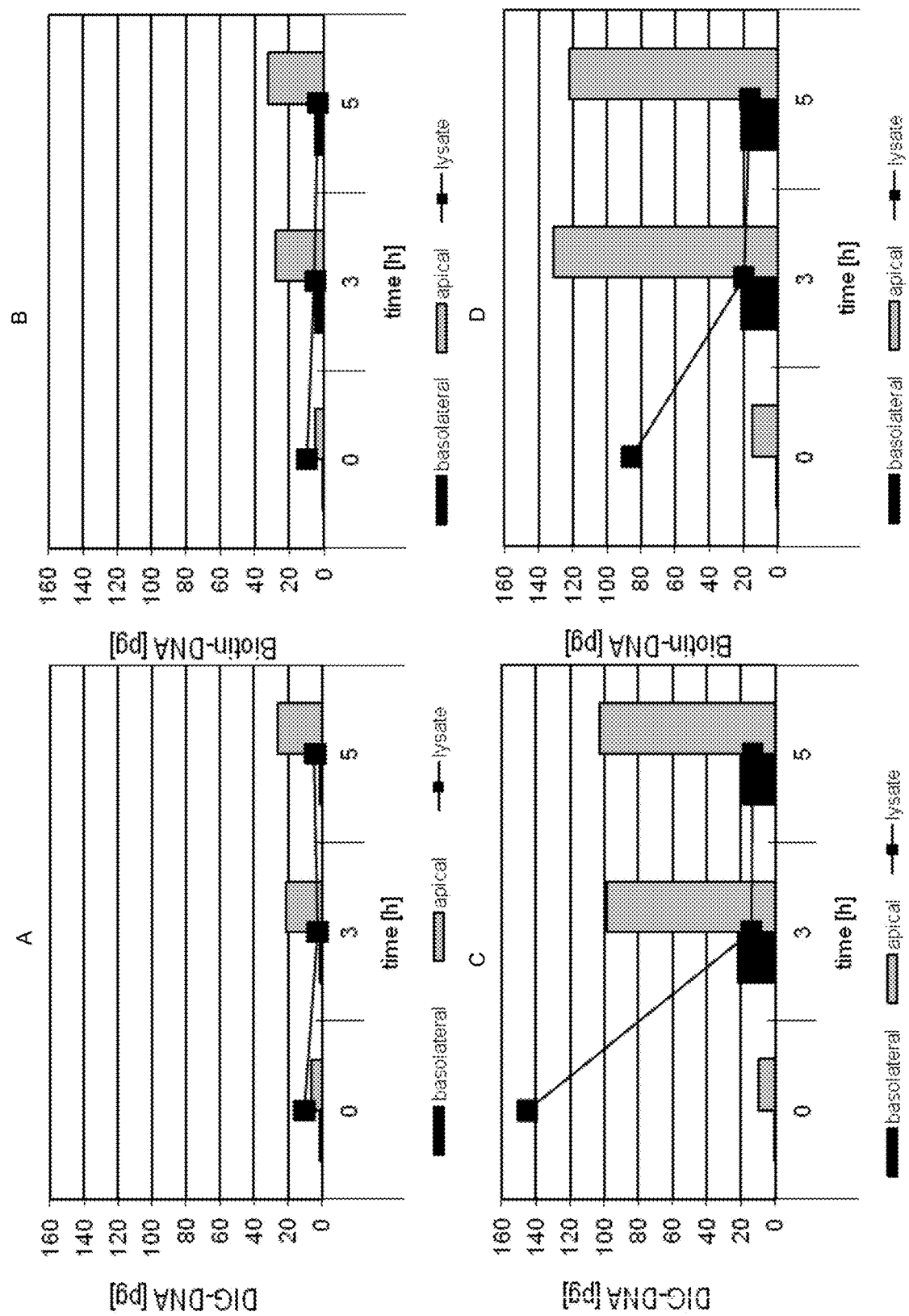

Blood Brain Barrier-Shuttle Modules with Reduced Affinity Towards TfR Shuttle Across Endothelial Cells and Support Transcytosis and Release of Haptenylated Payload Brain endothelial cells (hCMEC/D3) were used to investigate cell binding and transcytosis of haptenylated payloads that form non-covalent complexes with hapten-binding blood brain barrier-shuttle modules. To evaluate if payload transcytosis can be achieved via hapten-binding blood brain barrier-shuttle modules (bispecific antibodies) as reported herein for non-covalently complexed payloads, hCMEC/D3 cells in a trans-well system were exposed to haptenylated payload complexed by the bispecific antibody as reported herein (see previous examples for exemplary constructs) for one hour to allow TfR binding. Following removal of shuttle and payloads by washing (see Example 28), bound molecules, internalization, intracellular sorting, transcytosis and release of payload were monitored over time (0 to 5 hours after start of the experiment=washing step) in a similar manner as described in Example 28 for the shuttle modules. The payload that was used in the current example was mono-haptenylated DNA, which becomes upon incubation with bispecific antibodies as reported herein non-covalently complexed in a 2:1 (molar) ratio, as shown in FIG. 51A. Presence of the payload can be detected and quantified in cell extracts, apical and basolateral compartments by qPCR. Exemplarily, quantification of terminally mono-biotinylated or mono-digoxigenylated single-stranded DNA 50 mer (SEQ ID NO: 199) as payload using two PCR primers PrFor (SEQ ID NO: 200) and PrRev (SEQ ID NO: 201) on a Roche LightCycler is shown in FIG. 51A. The results of these analyses (FIG. 51B) demonstrate that the non-covalently attached haptenylated payload binds to cells, is internalized and subsequently becomes released into apical and basolateral compartments. Binding and subsequent release is mediated by the TfR-binding blood brain barrier-shuttle module because neither binding to cells nor release is detected if a CD33-binding control bispecific antibody is applied. Furthermore, neither binding to cells nor release is detected in cases where haptenylated payload without bispecific antibody is applied. Transcytosis of non-covalently complexed payload was observed for digoxigenin binding sites as well as for biotin binding sites comprising bispecific antibodies and the corresponding haptenylated payloads. This shows that different haptens can be used to design a non-covalent bispecific antibody blood brain barrier-shuttle module. Thus, payload transcytosis across the blood brain barrier can be achieved using hapten-binding bispecific antibodies for non-covalently complexed haptenylated payloads.

Example 31

Blood Brain Barrier-Shuttle Modules with Binding Sites with High Affinity Towards TfR Bind to but are not Released from Endothelial Cells, but Still Support Transcytosis and Release of Haptenylated Payload Brain endothelial cells (hCMEC/D3) were used to investigate cell binding and transcytosis of haptenylated payloads that can form non-covalent complexes with hapten-binding blood brain barrier-shuttle modules in the same manner as described in previous Example 30. HCMEC/D3 cells in a trans-well system were exposed to haptenylated payload complexed by the blood brain barrier-shuttle module (bispecific antibody) for 1 hour to allow TfR binding, internalization and intracellular sorting, and transcytosis. The payload was mono-haptenylated DNA, which becomes upon incubation with the bispecific antibody non-covalently complexed in a 2:1 (molar) ratio, as shown in FIG. 51A. Presence of mono-biotinylated or mono-digoxigenylated single-stranded DNA 50 mer payload (SEQ ID NO: 199) was quantified by qPCR in cell extracts, apical and basolateral compartments as described in previous Example 30.

The results of these analyses (FIG. 52) demonstrate that the non-covalent complexed haptenylated payload binds to cells, is internalized and subsequently becomes released into apical and basolateral compartments. This was a surprising finding since the bivalent high affinity shuttle module by itself is not released from the cells. Binding and subsequent payload release is mediated by the TfR-binding bispecific antibody blood brain barrier-shuttle module because neither binding to cells nor release is detected if a CD33-binding control bispecific antibody is applied. Furthermore, neither binding to cells nor release is detected in cases where haptenylated payload without bispecific antibody blood brain barrier-shuttle module is applied. Transcytosis and release of non-covalently complexed payload was observed for digoxigenin binding sites as well as biotin binding sites comprising bispecific antibodies and the corresponding haptenylated payloads. This indicates that different haptens can be used to design non-covalent complexes of haptenylated payload with bispecific antibody blood brain barrier-shuttle module. Payload transcytosis across cells that comprise the blood brain barrier can be achieved via haptenylated payloads non-covalently complexed by blood brain barrier-shuttle modules (bispecific antibody). Surprisingly, transcytosis does not rely on the release of the shuttle vehicle itself, because the payload becomes released even when applying shuttle modules that are not released.

Example 32

Haptenylated Payloads Separate from Blood Brain Barrier-Shuttle Modules within Vesicular Compartments Transcytosis assays with high affinity TfR binding site comprising blood brain barrier-shuttle modules that bind endothelial cells but are not released themselves from these cells (TfR1) showed a surprising result: haptenylated payloads were shuttled across cells and released into apical and basolateral compartments, even though the shuttle modules itself remained attached to cells/contained in the cell. Bispecific antibody mediated cell binding, uptake and distribution of payloads was analyzed by confocal microscopy. Therefore, brain endothelial cells (hCMEC/D3) were exposed to bispecific antibody-complexed haptenylated fluorescent payloads (hapten-Cy5 or hapten-DNA-Cy5) and analyzed by confocal fluorescence microscopy. Therefore, hCMEC/D3 cells were seeded onto microscopy grade glass coverslips and incubated with 50 nM bispecific antibody-complexed haptenylated fluorescent payloads for three hours at 37° C. in cell culture medium. Cells were then washed, fixed (4% paraformaldehyde) and the IgG part of the shuttle module was detected by counterstaining with anti-kappa light chain specific antibodies followed by secondary antibodies conjugated to ALEXA Fluor 488. Images were taken on a LEICA SP5x confocal microscope using a 100x/1.46NA objective lens using the appropriate bandpass filter settings for ALEXAFluor488 (IgG) and CY5 (hapten-DNA-CY5 payload). The results of these analyses are shown in FIG. 53. Complexes of high affinity bispecific antibodies with fluorescent labeled haptenylated payloads (DNA-Cy5) bind to TfR and initially locate on cell surfaces. Subsequently, they become co-internalized with their cognate receptors and appear within cells in vesicular compartments, i.e. endosomes and lysosomes. Shortly (three hours) after internalization, we observed a substantial separation of the fluorescence signals attributable to the shuttle module from those attributable to the haptenylated payloads. Thus, non-covalent complexes of blood brain barrier-shuttle modules as reported herein and haptenylated payloads can dissociate into different vesicular compartments inside the cell. Thereby, the payload becomes released from the shuttle module and can exit via transcytosis from endothelial cells even when the shuttle module remains bound to cells/retained in the cell. Intracellular separation of non-covalently complexed haptenylated payload was observed for digoxigenin-binding as well as biotin-binding blood brain barrier-shuttle modules (bispecific antibodies) and the corresponding haptenylated payloads. Thus, different haptens can be used to design non-covalent complexes of haptenylated payloads and blood brain barrier-shuttle modules that enable payload transcytosis.

Example 33

Helicar Motif Amino Acid Sequence Containing Peptide YY

Peptide YY is a short (36-amino acid) peptide released by cells in the ileum and colon in response to feeding. In humans it appears to reduce appetite. The most common form of circulating PYY is $PYY_{3-36}$, which binds to the Y2 receptor (Y2R) of the Y family of receptors. PYY is found in L cells in the mucosa of gastrointestinal tract, especially in ileum and colon. Also, a small amount of PYY, about 1-10%, is found in the esophagus, stomach, duodenum and jejunum. In the circulation, PYY concentration increases after food ingestion and decreases during fasting. PYY exerts its action through NPY receptors; it inhibits gastric motility and increases water and electrolyte absorption in the colon. PYY and PYY mimetics have been used to address obesity.

PYY was modified to comprise the helicar motif amino acid sequence and complexed by an anti-helicar motif amino acid sequence antibody in order to get advantage of the pharmacokinetic properties of the antibody and to avoid the intrinsic instability of the PYY.

Non-Covalent Complex Formation

The structural investigation of the $PYY_{3-36}$ peptide (Nygaard, R., et al., Biochem. 45 (2006) 8350-8357; SEQ ID NO: 211) reveals a helical motif (helicar-like motif amino acid sequence) for the central amino acids. As the N-terminal isoleucine and the modified C-terminus have been described as essential for the functional activity of the peptide, the central helix was modified in order to reflect the amino acids in the helicar motif amino acid sequence.

| PYY(3-36) (SEQ ID NO. 211) | 3  IKPEAPGEDASPEELNRYYASLRHYLNLVTRQRYNH2 | 36 |
|---|---|---|
| Helicar motif | AHLENEVARLKK | |
| PYY_helicar (SEQ ID NO: 212) | IKPEAPGEDASPEAHLANEVARLHYLNLVTRQRYNH2 (YNH2 = tyrosine amide) | |

| | binding [$K_d$] | soluble in PBS | |
|---|---|---|---|
| PYY(3-36) (SEQ ID NO: 211) | – | + | PYY wild-type |
| PYY_helicar (SEQ ID NO: 212) | 12 nM | + | helicar motif engineered PYY |

The full IgG1 anti-helicar motif amino acid sequence antibody was produced in HEK293 cells by transfecting two plasmids containing the variable regions of the heavy and the light chain inserted in a vector containing the constant human IgG1 and the constant human lambda domain, respectively. The anti-helicar motif amino acid sequence antibody (0019) was purified by standard procedures using protein A chromatography. A mass spectroscopy experiment confirmed the identity of antibody 0019.

The complex between antibody 0019 and the modified PYY peptide PYY_helicar was obtained in vitro by applying a small excess of the peptide to the antibody solution. The complex 0052 was formed. The stoichiometry of the complex was determined by SEC-MALLS analytical experiments to be 1.6 peptides complexed on one bivalent antibody.

The antibody 0019, the PYY(3-36) wild-type, the PYY_helicar and the complex 0052 were tested for their effect on to the Y2Receptor family.

| | NPY2R | NPY1R | NPY4R | NPY5R |
|---|---|---|---|---|
| Ac-Ile-Lys-Pqa-Arg-His-Tyr-Leu-Asn-Trp-Val-Thr-Arg-Gln-(NMe)-Arg-Try-NH2 * 4 HOAc | 1.0 nM | in-active | in-active | in-active |
| PYY_helicar (IKPEAPGEDASPEAHLANEVARLHYLNLVTRQRYNH2) (SEQ ID NO: 212) | 6.38 nM | in-active | in-active | in-active |
| PYY(3-36) (IKPEAPGEDASPEELNRYYASLRHYLNLVTRQRYNH2) (SEQ ID NO: 211) charge 1 | 0.05 nM | 168 nM | 162 nM | 170 nM |
| PYY(3-36) (IKPEAPGEDASPEELNRYYASLRHYLNLVTRQRYNH2) (SEQ ID NO: 211) charge 2 | 0.05 nM | 160 nM | 131 nM | 202 nM |
| anti-helicar motif amino acid sequence antibody (0019) | in-active | in-active | in-active | in-active |
| anti-helicar motif amino acid sequence antibody-PYY_helicar complex (0052) | 0.93 nM | in-active | in-active | in-active |

As demonstrated (Hoffmann, E., et al., J. Cont. Rel. 171 (2013) 48-56.) the peptides complexed by an antibody have a prolonged half-life in vivo. Moreover and surprisingly, the complex demonstrates a slightly better affinity for the NPY2R receptor compared to the non-complexed peptide; the antibody stabilizes the polypeptide and presents the peptide in its fixed biologically active conformation.

Covalent Complex Formation (Covalent Disulfide Bond)

In order to increase the in vitro and in vivo stability of the complex between the anti-helicar motif amino acid sequence antibody and the helicar motif amino acid sequence containing compound, the formation of a disulfide bridge upon binding has been used.

The first step is a specific recognition step (high affinity interaction), i.e. the formation of the helicar motif amino acid sequence containing compound-anti-helicar motif amino acid sequence antibody complex. This is followed in the second step by a spontaneous shuffling of a disulfide bridge to form the stability improved covalent complex.

As the 12-mer peptide (helicar motif amino acid sequence) is a relatively rigid entity (at least when complexed by a specific anti-helicar motif amino acid sequence antibody) it has been found that a structurally specific design for the disulfide bridge has to be used. As the complex formation and the thereafter effected covalent coupling is between two recombinantly produced entities, the artificial cysteine residues introduced for the formation of a covalent disulfide bond are not produced necessarily as free cysteine residues but are expressed in a reduced from, i.e. conjugated to a free cysteine or homo cysteine amino acid.

The position in the amino acid sequence of the anti-helicar motif amino acid sequence antibody variable domain where the artificial free cysteine residue is introduced is critical. A non-exposed cysteine in the antibody variable domain amino acid sequence has more probability to be expressed as a free cysteine (not conjugated), whereas an exposed cysteine residue close to the binding pocket can abolish the binding of the 12-mer peptide (helicar motif amino acid sequence) due to a steric hindrance induced by the cysteine conjugation to an additional moiety like a free cysteine.

a) Complexes with a Helicar Motif Amino Acid Sequence Containing Fluorescent Compound In order to identify a suitable position which has minimum risk of steric hindrance and strong affinity reduction, different positions for the introduction of the artificial cysteine residue in the helicar motif amino acid sequence have been tested. The cysteine residue has been introduced at the C-terminal end of the 12mer (helicar motif amino acid sequence) in order to have the major part of the paratope unchanged. The peptides have been synthesized and fused to a fluorescent motif.

```
wild-type:
AHLENEVARLKK              (SEQ ID NO: 202)

cysteine variant 1:
AHLENEVARCKK              (SEQ ID NO: 203)

->AHLENEVARCKK(5-Fluo)-OH cysteine variant 2:
AHLENEVARLCK              (SEQ ID NO: 204)

->AHLENEVARLCK(5-Fluo)-OH x TFA
```

On the antibody, a structural design has been done to allow the formation of the disulfide bridge for both designed peptides including each a cysteine in different 3D environment.

The 12-mer helical peptide AHLENEVARLKK (helicar motif amino acid sequence) is modeled into the VH and the VH domains. At the C-terminus of the peptide the residues L10 and K11 are identified as possible position and in the light chain variable domain the positions N55 and G51 according to the light chain numbering of Kabat are identified.

The heavy chain variable domain of the anti-helicar motif amino acid sequence antibody (0019) has the amino acid sequence:

```
                                      (SEQ ID NO: 205)
QAVVTQEPSL TVSPGGTVTL TCGSSTGAVT TSNYASWVQQ

KPGQAFTGLI GGTNNRAPWT PARFSGSLLG GKAALTLSGA

QPEDEAEYYC ALWYSNHWVF GGGTKLTVL.
```

The light chain variable domain of the anti-helicar motif amino acid sequence antibody (0019) has the amino acid sequence:

```
                                      (SEQ ID NO: 206)
DAVVTQESAL TTSPGETVTL TCRSSTGAVT TSNYASWVQE

KPDHLFTGLI GGTNNRAPGV PARFSGSLIG DKAALTITGA

QTEDEAIYFC ALWYSNHWVF GGGTKLTVL.
```

The light chain variable domain N55C variant of the anti-helicar motif amino acid sequence antibody (0155) has the amino acid sequence:

```
                                    (SEQ ID NO: 207)
DAVVTQESAL TTSPGETVTL TCRSSTGAVT TSNYASWVQE

KPDHLFTGLI GGTNCRAPGV PARFSGSLIG DKAALTITGA

QTEDEAIYFC ALWYSNHWVF GGGTKLTVL.
```

The light chain variable domain N51C variant of the anti-helicar motif amino acid sequence antibody (0157) has the amino acid sequence:

```
                                    (SEQ ID NO: 208)
DAVVTQESAL TTSPGETVTL TCRSSTGAVT TSNYASWVQE

KPDHLFTGLI CGTNNRAPGV PARFSGSLIG DKAALTITGA

QTEDEAIYFC ALWYSNHWVF GGGTKLTVL.
``` i) Covalent Conjugate of Helicar Motif Amino Acid Sequence Containing Compound with Antibody 0155

The bivalent antibody 0155 is expressed in HEK293 cells similarly to its parent molecule Y2R(bck)-0019 without free cysteine. The modified antibody is purified using the same protocol used for antibody 0019. The mass spectrometry analysis shows that the experimentally determined mass of the deglycosylated antibody is 142,001 Da. This exceeds the calculated mass by 259 Da. The reduced chains have the experimentally determined mass of 48,167 Da (complete heavy chain, calculated 48,168 Da, Cys=SH, C-Term=-K) and 22,720 Da (complete light chain, N55C, calculated 22,720 Da, Cys=SH). The sequences of the chains were confirmed after reduction.

Antibody 0155 was coupled to the helicar motif amino acid sequence cysteine variant 2 using a 2.5 molar excess of helicar motif amino acid sequence containing compound in 100% DMF to form the covalent complex 0156.

On the SDS page (denaturing condition, see FIG. 54) the fluorescence is seen only on the antibody 0155; in the reducing condition, only the small peptide is visible.

Results:

The covalent conjugation of the helicar motif amino acid sequence containing fluorescent compound to the anti-helicar motif amino acid sequence antibody was successful. A total of about 43% of the anti-helicar motif amino acid sequence antibody was covalently conjugated to two helicar motif amino acid sequences, about 40% of the anti-helicar motif amino acid sequence antibody was covalently conjugated to one helicar motif amino acid sequence, and about 17% of the anti-helicar motif amino acid sequence was not conjugated.

The conjugate comprising two helicar motif amino acid sequences is modified to about 50%. This species has not been taken into account for the quantification. As already determined for the starting material the antibody without helicar motif amino acid sequence contains two modifications of about 128 Da. The antibody conjugated to one helicar motif amino acid sequence has only one modification of about 128 Da.

ii) Covalent Conjugate of the Helicar Motif Amino Acid Sequence Containing Compound with Antibody 0157

Similarly to antibody 0155 is antibody 0157 expressed mostly as a cysteinylated form. The mass spectrometry analysis shows that the experimentally determined mass of the deglycosylated antibody is 141,863 Da. This exceeds the calculated mass by 3 Da. The antibody is mainly present as single or double homocysteinylated form. The reduced chains have the experimentally determined mass of 48,168 Da (complete heavy chain, calculated 48,168 Da, Cys=SH, C-Term=-K) and 22,777 Da (complete light chain, N51C, calculated 22,777 Da, Cys=SH). The sequences of the chains were confirmed after reduction.

The coupling of antibody 0157 with the helicar motif amino acid sequence cysteine variant 1 was not resulting in the expected covalent complex. The fluorescence is not seen in the expected lane but on the reference which should be negative in this experiment (see FIG. 55).

Antibody 0157 was incubated with helicar motif amino acid sequence cysteine variant 1. As control antibody 0019 was incubated with the same helicar motif amino acid sequence cysteine variant 1.

Results:

The covalent conjugation of the helicar motif amino acid sequence containing fluorescent compound to the anti-helicar motif amino acid sequence antibody was not successful. Without being bound by this theory it is assumed that in this case the antibody cysteinylation is too deep in the binding pocket to allow the helicar motif amino acid sequence containing fluorescent compound to bind efficiently and deliver the nucleophilic thiol group in an appropriate position to attack the C51.

b) Complexes with Helicar Motif Amino Acid Sequence Containing Recombinant Polypeptide The helicar based methodology becomes particularly attractive when considering the formation of a covalent complex with a recombinantly produced helicar motif amino acid sequence containing polypeptide.

As the conjugation of the antibody 0155 containing the VL-N55C mutation with the helicar motif amino acid sequence cysteine variant 1 (AHLENEVARLCK; SEQ ID NO: 203) has much better performed compared to the alternative (G51C on VL with helicar motif amino acid sequence cysteine variant 2 (AHLENEVARCKK; SEQ ID NO: 204)), the conjugation of 0155 with ahelicar motif amino acid sequence cysteine variant 1 containing polypeptide was further investigated. The polypeptide contained the helicar motif amino acid sequence cysteine variant 1 (AHLENEVARLCK; SEQ ID NO: 203) fused to the N-terminus.

The helicar motif amino acid sequence cysteine variant 1 containing *Pseudomonas* exotoxin molecule LR8M with the C-terminal lysine residue deleted (0236; SEQ ID NO: 213) has been produced in *E. coli* and purified using a combination of anion exchange chromatography and SEC (see e.g. WO 2011/032022).

Antibody 0155 is covalently conjugated with the helicar motif amino acid sequence cysteine variant 1 containing *Pseudomonas* exotoxin molecule LR8M with the C-terminal lysine residue deleted of SEQ ID NO: 213. The SEC chromatogram is shown in FIG. 56. The conjugation efficiency is analyzed by SDS-CE, Caliper, for the non reduced samples (see FIG. 57).

A total of about 4% of the anti-helicar motif amino acid sequence antibody was covalently conjugated to two polypeptide of SEQ ID NO: 213, about 41% of the anti-helicar motif amino acid sequence antibody was covalently conjugated to one polypeptide of SEQ ID NO: 213, and about 55% of the anti-helicar motif amino acid sequence was not conjugated.

In conclusion, the anti-helicar motif amino acid sequence monoclonal antibody can be used to complex peptides, small molecules with peptidic linker, and recombinant proteins via a high affinity recognition of a 12-mer helicar motif amino acid sequence. Peptides with propensity to fold as helix can be modified to mimic the original 12-mer helical motif amino acid sequence AHLENEVARLKK (SEQ ID NO: 202) and are thereafter complexable with the anti-helicar motif amino acid sequence monoclonal antibody. In addition to the high affinity complexation, covalent conjugation is enabled with a cysteine variant of SEQ ID NO: 202 containing a cysteine and a modified anti-helicar motif amino acid sequence antibody containing a cysteine in the CDRs via formation a stable disulfide bond. Recombinant proteins expressed by different system can be conjugated afterwards in vitro without particular reactions conditions but via spontaneous disulfide bridge shuffling.

Example 34

BrdU-Binding Bispecific Antibodies from Complexes with BrdU Containing Payloads SEC-MALLS analyses were applied to evaluate if and to what degree transferrin receptor (TfR)- and bromodeoxyuridine (BRU)-binding bispecific antibody (bsAb) are capable of binding to BRDU containing payloads. Therefore, BRDU-DNA was added to TfR-BRDU bsAb at a 2:1 stoichiometric ratio (350 μg; 2.5 mg/ml) and incubated for 30 min. at room temperature for formation of bsAb/payload-complexes. As control reagents we prepared free bispecific antibody (2.5 mg/ml) and free BRDU-DNA (3.2 mg/ml). BRDU-DNA (BRDU-ACC AAG CCT AGA GAG GAG CAA TAC AAC AGT ACA TAT CGC GTG GTA AGC GT; SEQ ID NO: 228) contained one BRDU per DNA molecule at the 5' end of the DNA. Complexes and control reagents were stored at −80° C. until analysis.

The hereby generated complexes and control reagents were subjected to SEC-MALLS analysis to identify and characterize free bispecific antibody, free payload and complexes of both. SEC-MALLS analysis was performed on a Dionex Ultimate 3000 HPLC equipped with Wyatt miniDawnTREOS/QELS and Optilab rEX detectors. Analytes were dissolved at 1 mg/ml in PBS buffer pH 7.4, applied to a Superdex200 10/300GL column at a flow rate of 0.5 ml/min and eluted with PBS buffer pH 7.4 for 60 min.

The results of these analyses (shown in FIG. 58) indicate that BRDU-containing DNA forms defined complexes with the bispecific antibody. These complexes elute from the column at a MW of 244.9 kDa (FIG. 58A) and display a hydrodynamic radius of 6.8 nm (FIG. 58B), allowing the calculation of a stoichiometric ratio of approximately two (1.8) DNA molecules per bispecific antibody molecule. In comparison to that, free bispecific antibody was detected at a MW of 215.4 kDa and its hydrodynamic radius was determined at 6.2 nm. Free BRDU-DNA was detected at a MW of 16.4 kDa.

Thus, it was shown that BRDU-containing DNA is effectively and stoichiometrically bound by the anti-TfR/BRDU bispecific antibody, resulting in complexes in a 2:1 molar ratio.

Example 35

Biotin-Binding Bispecific Antibodies Bind to Biotin-Containing IgGs

To analyze if and to what degree the TfR/biotin bispecific antibody is capable of binding to mono-biotinylated full length IgG, mono-biotinylated antibody of the IgG isotype specifically binding to pTau (biotin-labelled anti-pTau antibody, BIO-pTau) was added to anti-TfR/biotin bispecific antibody at a 2:1 stoichiometric ratio (300 μg, 1.3 mg/ml), and the mixture was incubated for 30 min. at room temperature (formation of bispecific antibody-payload complexes). Mono-biotinylated IgG was generated by producing IgG-derivatives with an Avi-tag at the C-terminus of one chain of a knob-into-hole heterodimeric antibody of the IgG isotype. The Avi-tag becomes enzymatically conjugated to one biotin in a defined manner.

As a control for the specificity of complex formation, an anti-TfR/digoxigenin bispecific antibody was mixed with BIO-pTau. As further control reagents aliquots of both free bispecific antibody and free BIO-pTau were prepared. Complexes and control reagents were stored at −80° C. until analysis.

The generated complexes were subjected to SEC-MALLS analysis to identify and characterize free bispecific antibody, free BIO-pTau and complexes thereof. SEC-MALLS analysis was performed on a Dionex Ultimate 3000 HPLC equipped with Wyatt miniDawnTREOS/QELS and Optilab rEX detectors. Analytes were dissolved at 1-2 mg/ml in PBS buffer pH 7.4, applied to a Superose 6 10/300GL column at a flow rate of 0.5 ml/min and eluted with PBS buffer pH 7.4 for 60 min.

The results of these analyses (shown in FIG. 59) indicate that BIO-pTau forms defined complexes with the bispecific antibody. These complexes elute from the column at a MW of 501 kDa (FIG. 59A) and display a hydrodynamic radius of 8.0 nm (FIG. 59B). In comparison to that, free bispecific antibody was detected at a MW of 205 kDa and its hydrodynamic radius was determined at 6.2 nm. Free BIO-pTau was detected at a MW of 150 kDa and its hydrodynamic radius was measured at 5.5 nm.

The complexes are specifically formed by interaction between biotin and the biotin-binding moiety of the bispecific antibody, because the digoxigenin-binding bispecific antibody does not form complexes with BIO-pTau (FIG. 59C).

Example 36

Transcytosis of Biotin-Labelled Anti-pTau Antibody

To analyze if and to what degree the anti-TfR/Biotin bispecific antibodies facilitate transcytosis of full length antibody payloads, complexes of anti-TfR/biotin bispecific antibody (anti-TfR/biotin bsAb-1 and anti-TfR/biotin bsAb-2) and BIO-pTau were formed as described in example 35 and subjected to a transcytosis assay as described above e.g. in Example 31. As control for non-specific transcytosis, complexes of anti-CD33/biotin bispecific antibody and BIO-pTau as well as free BIO-pTau were tested in parallel. Samples of the apical and basolateral compartments, and of the cell lysates were taken at 0, 1, 2, 3, 4 and 5 hours after loading of the cells. Loading concentration was always 3.8 μg/ml.

The amount of biotin-labelled anti-pTau antibody was measured by ELISA. Therefore pTau protein was coated onto NUNC Maxisorb White 384-well plates at 500 ng/ml, overnight at 2-8° C. or one hour at room temperature. Plates were blocked with PBS containing 2% BSA and 0.05% Tween 20 for at least one hour. Sample dilutions of up to 1/729 in PBS containing 0.5% BSA and 0.05% Tween 20 were applied for 1.5-2 hours, followed by Poly-HRP40-Streptavidin (Fitzgerald) for 30 min. and Super Signal ELISA Pico substrate (Thermo Scientific) for 10 min., all at room temperature. Standard dilutions of BIO-pTau antibody (100 ng/ml-0.5 pg/ml) were assayed on the same plate. Plates were washed with PBS containing 0.1% Tween 20 between consecutive incubation steps.

The results of these transcytosis assays (FIG. 60) show that complexing BIO-pTau to either anti-TfR/biotin bsAb-1 or anti-TfR/biotin bsAb-2 mediates effective endocytosis and subsequent transport of BIO-pTau into the basolateral as well as back into the apical compartment. In contrast, neither complexes of BIO-pTau to anti-CD33/biotin bispecific antibody nor free BIO-pTau are effectively endocytosed or transcytosed, indicating that the observed transcytosis is caused by specific binding of the anti-TfR/biotin bispecific antibody to the TfR on the surface of the cells.

Example 37

Hapten-Binding Blood Brain Barrier-Shuttle Enables Transcytosis and Release of Short Oligonucleotides In this Example it is shown that transcytosis of nucleic acids across endothelial cells that form the blood brain barrier can be achieved for small nucleic acids, such as antisense oligonucleotides or modified nucleic acid derivatives such as "locked" nucleic acids. Single-stranded nucleic acid payloads, which are smaller than the DNA fragments described in Examples 30 and 31, have been generated. These payloads, which were generated in hapten-coupled form, closely resemble therapeutic antisense oligonucleotides or locked nucleic acids, and can serve thereby as surrogate for said entities. Accurate detection of haptenylated (e.g. mono-biotinylated or mono-digoxigenylated) single-stranded 34mer or 28mer oligonucleotides (sequence S1 or S2, respectively) was achieved by qPCR assays similar to those described in Example 30. Specific detection was verified by analyzing serial dilutions of S1 and S2 DNAs in hCMEC/D3 media and in cell extracts, using the PCR primers PrFor (SEQ ID NO: 200) and PrRev (SEQ ID NO: 201). The conditions for the qPCR assay to detect presence of oligonucleotides S1 or S2 in apical or basolateral cell supernatant compartments or in cell extracts were as follows: Denaturation at 95° C. for 10 min.; 45 cycles of 95° C. for 10 sec., 54° C. for 15 sec., 72° C. for 10 sec.; followed by high resolution melting and cooling. The assays were carried out on a Roche Light Cycler 480 II.

Brain endothelial cells (hCMEC/D3) were used to investigate cell binding and transcytosis of haptenylated payloads that can form non-covalent complexes with hapten-binding blood brain barrier-shuttle modules in the same manner as described in Examples 30 and 31. HCMEC/D3 cells in a trans-well system were exposed to haptenylated payload complexed by the blood brain barrier-shuttle module (bispecific antibody) for 1 hour to allow TfR binding, internalization and intracellular sorting, and transcytosis. The payloads were mono-haptenylated oligonucleotides S1 or S2, which become upon incubation with the bispecific antibody non-covalently complexed in a 2:1 (molar) ratio, as shown in FIG. 51A. Presence of mono-biotinylated or mono-digoxigenylated oligonucleotide S1 or S2 was quantified by qPCR in cell extracts, apical and basolateral compartments as described in previous Examples 30 and 31. Presence of blood brain barrier-shuttle module (bispecific antibody) in the same extracts, apical and basolateral compartments was quantified by an ELISA specific for human IgG as described in Example 29.

The results of these analyses (FIG. 61 to 63) demonstrate that the non-covalently attached haptenylated payloads S1 and S2 bind to cells, are internalized and subsequently become released into apical and basolateral compartments. As was the case for the 50mer DNA payload in example 31, it was observed that the bivalent high affinity shuttle module which by itself is not released from the cells nevertheless facilitates the transcytosis of both payloads S1 and S2. Binding and subsequent release is mediated by the TfR-binding blood brain barrier-shuttle module because neither binding to cells nor release is detected if a CD33-binding control bispecific antibody is applied. Transcytosis of non-covalently complexed payloads S1 and S2 was observed for digoxigenin binding shuttles as well as for biotin binding shuttles comprising bispecific antibodies and the corresponding haptenylated payloads. On the contrary, neither significant specific binding to cells nor significant release is detected in cases where haptenylated payload without bispecific antibody is applied, or where haptenylated payload is applied together with a bispecific antibody which recognizes a non-corresponding hapten. This shows that short oligonucleotide-derived payloads are delivered across brain endothelial cells by a non-covalent bispecific antibody blood brain barrier-shuttle module. Thus, transcytosis of short nucleic acids such as antisense-oligonucleotides or "locked" nucleic acids across cells that form the blood brain barrier can be achieved via haptenylated payloads non-covalently complexed by blood brain barrier-shuttle modules (bispecific antibody). In the same manner as described in example 31, transcytosis of short nucleic acid derivatives does not rely on the release of the shuttle vehicle itself, because the payload becomes released from the shuttle entity even when applying shuttle modules that are not released.

Example 38

Evaluation of the In-Vivo Functionality of Hapten- and Transferrin-Receptor Binding Shuttle Vehicles for Payload Delivery Across the Blood Brain Barrier Animal experiments are applied to evaluate to what degree the bispecific hapten- and transferrin-receptor binding shuttle vehicles enable payload delivery across the blood brain barrier (BBB) in vivo. The payload to be transported and detected in the brain is a mono-biotinylated phospho-tau binding antibody derivative. The target of this antibody (the tau protein) is located in the brain. Because of that, the antibody needs to pass the blood-brain-barrier to access its target. This antibody is therefore applied as payload for the in vivo experiment. The shuttle vehicles that are combined with the payload are composed in the same or similar manner as those described and applied for the in-vitro experiment in Examples presented above, but have binding regions that bind to murine transferrin receptor instead of to the human counterpart. The reason for switching specificity is that the cultured BBB-transcytosis analysis system (transwell assays, see above) apply human cells with human TfR, while the animal experiments are performed in mice, which possess a murine TfR at the BBB.

The murine TfR-recognizing hapten (e.g. biotin)-binding shuttle vehicles are complexed with biotinylated pTau-binding antibodies and subsequently applied to TauPS2APP mice. Alternatively, murine TfR-recognizing hapten (e.g. biotin)-binding shuttle vehicles can also be injected into TauPS2APP mice followed subsequently by injection of biotinylated pTau-binding antibodies at later time points (=pre-targeting setting).

Groups of mice are treated on day-1 with a single dose of anti-CD4 to induce immunotolerance, followed subsequently by weekly i.v. injection of test substances for 10-12 weeks:

Group A: no treatment
Group B: (biotinylated) p-Tau binding antibody only
Group C: biotinylated p-Tau binding antibody complexed with bispecific anti-TfR/biotin antibody (shuttle vehicle)
Group D: p-Tau binding antibody covalently linked to an anti-TfR antibody Group A mice are sacrificed at day 0 to give a baseline group. The remaining groups receive weekly i.v. administrations of the respective compound for a total of 12 weeks and are sacrificed one week after the last administration.

To determine transfer of payload antibody across the BBB, each mouse brain is sagittally sectioned into two hemispheres and is used as follows:
(1) right hemisphere: immunohistochemistry of pTau-containing aggregates
(2) left hemisphere: preparation of brain homogenate for measurement of phospho-tau protein and total tau protein by specific AlphaLISAs.

The invention claimed is:

1. A method for producing a non-covalent conjugate, comprising the steps of:
   i) incubating a bispecific antibody which has a first binding specificity which specifically binds to a hapten of a haptenylated payload and a second binding specificity which specifically binds to a blood brain barrier receptor with the haptenylated payload to produce the non-covalent conjugate, and
   ii) isolating the non-covalent conjugate,
   wherein the non-covalent conjugate has a non-covalent bond between the haptenylated payload and the first binding specificity that specifically binds to the hapten of the haptenylated payload,
   wherein the hapten of the haptenylated payload is selected from the group consisting of biotin, theophylline, digoxigenin, fluorescein, and bromodeoxyuridine, and
   wherein the payload of the haptenylated payload is selected from the group consisting of a label, a chemotherapeutic agent, an anti-angiogenic agent, a cytotoxin, a cytokine, a prodrug, an enzyme, a growth factor, a transcription factor, a drug, a radionuclide, a ligand, an antibody or fragment thereof, a liposome, a nanoparticle, and a viral particle.

2. The method of claim 1, wherein the blood barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

3. The method of claim 1, wherein the blood brain barrier receptor is transferrin receptor or low density lipoprotein receptor-related protein 8.

4. The method of claim 1, wherein the bispecific antibody is free of effector function.

5. The method of claim 1, wherein the bispecific antibody comprises:
   a) one binding site for the hapten of the haptenylated payload and one binding site for the blood brain barrier receptor, or
   b) two binding sites for the hapten of the haptenylated payload and one binding site for the blood brain barrier receptor, or
   c) one binding site for the hapten of the haptenylated payload and two binding sites for the blood brain barrier receptor, or
   d) two binding sites for the hapten of the haptenylated payload and two binding sites for the blood brain barrier receptor.

6. The method of claim 1, wherein the bispecific antibody comprises a cysteine residue at an amino acid residue in the CDR2 of the antibody, whereby the CDR2 is determined according to Kabat numbering.

7. The method of claim 1, wherein the non-covalent bond is between a cysteine residue in the CDR2 of the antibody and a thiol group in the haptenylated payload.

8. The method of claim 7, wherein the CDR2 is the heavy chain CDR2 and the cysteine is at position 52b or 53 according to Kabat numbering.

9. A non-covalent conjugate, comprising:
i) a bispecific antibody, which has a first binding specificity, which specifically binds to a hapten of a haptenylated payload, and a second binding specificity, which specifically binds to a blood brain barrier receptor, and
ii) the haptenylated payload,
wherein the non-covalent conjugate has a non-covalent bond between the haptenylated payload and the first binding specificity that specifically binds to the hapten of the haptenylated payload,
wherein the hapten of the haptenylated payload is selected from the group consisting of biotin, theophylline, digoxigenin, fluorescein, and bromodeoxyuridine, and
wherein the payload of the haptenylated payload is selected from the group consisting of a label, a chemotherapeutic agent, an anti-angiogenic agent, a cytotoxin, a cytokine, a prodrug, an enzyme, a growth factor, a transcription factor, a drug, a radionuclide, a ligand, an antibody or fragment thereof, a liposome, a nanoparticle, and a viral particle.

10. The conjugate of claim 9, wherein the blood barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF).

11. The conjugate of claim 9, wherein the blood brain barrier receptor is transferrin receptor or low density lipoprotein receptor-related protein 8.

12. The conjugate of claim 9, wherein the bispecific antibody is free of effector function.

13. The conjugate of claim 9, wherein the bispecific antibody comprises:
a) one binding site for the hapten of the haptenylated payload and one binding site for the blood brain barrier receptor, or
b) two binding sites for the hapten of the haptenylated payload and one binding site for the blood brain barrier receptor, or
c) one binding site for the hapten of the haptenylated payload and two binding sites for the blood brain barrier receptor, or
d) two binding sites for the hapten of the haptenylated payload and two binding sites for the blood brain barrier receptor.

14. The conjugate of claim 9, wherein the bispecific antibody comprises a cysteine residue at an amino acid residue in the CDR2 of the antibody, whereby the CDR2 is determined according to Kabat numbering.

15. The conjugate of claim 9, wherein the non-covalent bond is between a cysteine residue in the CDR2 of the antibody and a thiol group in the haptenylated payload.

16. The conjugate of claim 9, wherein the CDR2 is the heavy chain CDR2 and the cysteine is at position 52b or 53 according to Kabat numbering.

17. A pharmaceutical formulation, comprising the conjugate of claim 9 and a pharmaceutically acceptable carrier.

* * * * *